(12) United States Patent
Trimpin

(10) Patent No.: US 8,853,621 B2
(45) Date of Patent: Oct. 7, 2014

(54) SYSTEMS AND METHODS EXTENDING THE LASERSPRAY IONIZATION MASS SPECTROMETRY CONCEPT FROM ATMOSPHERIC PRESSURE TO VACUUM

(75) Inventor: Sarah Trimpin, Detroit, MI (US)

(73) Assignee: Wayne State University, Detriot, MI (US)

( * ) Notice: Subject to any disclaimer, the term of this patent is extended or adjusted under 35 U.S.C. 154(b) by 0 days.

(21) Appl. No.: 13/881,684

(22) PCT Filed: Oct. 25, 2011

(86) PCT No.: PCT/US2011/057769
§ 371 (c)(1),
(2), (4) Date: Oct. 14, 2013

(87) PCT Pub. No.: WO2012/058248
PCT Pub. Date: May 3, 2012

(65) Prior Publication Data
US 2014/0027631 A1    Jan. 30, 2014

Related U.S. Application Data

(60) Provisional application No. 61/406,509, filed on Oct. 25, 2010, provisional application No. 61/422,016, filed on Dec. 10, 2010, provisional application No. 61/493,400, filed on Jun. 3, 2011.

(51) Int. Cl.
*H01J 49/40*   (2006.01)
*H01J 49/06*   (2006.01)
*H01J 49/00*   (2006.01)
*B01D 59/44*   (2006.01)
*G01N 27/62*   (2006.01)

(52) U.S. Cl.
USPC ...... 250/282; 250/287; 250/288; 315/111.81; 315/111.91; 435/6.1; 435/34; 435/183

(58) Field of Classification Search
USPC ............. 250/281, 282, 287, 28, 423 R, 423 P, 250/424, 425; 235/6.1, 6.11, 6.15, 7.01, 34, 235/91.1, 183; 315/111.81, 111.91
See application file for complete search history.

(56) References Cited

U.S. PATENT DOCUMENTS

| | | | |
|---|---|---|---|
| 6,248,998 B1* | 6/2001 | Okumoto et al. | ............ 250/288 |
| 2004/0051038 A1* | 3/2004 | Taniguchi | ................. 250/288 |
| 2007/0066769 A1 | 3/2007 | Venkataraman | |
| 2009/0008549 A1 | 1/2009 | Kim | |
| 2009/0140140 A1 | 6/2009 | Raznikov | |

(Continued)

OTHER PUBLICATIONS

Alves, S et al. "Gas-phase ionization/desolvation processes and their effect on protein charge state distribution under matrix-assisted laser desorption/ionization conditions," *Eur. J. Mass Spectrom.* 2006, 12, 369-383.

(Continued)

*Primary Examiner* — Bernard E Souw
(74) *Attorney, Agent, or Firm* — Lee & Hayes, PLLC; C. Rachal Winger

(57) ABSTRACT

Disclosed herein are systems and methods that allow analysis of macromolecular structures using laserspray ionization at intermediate pressure or high vacuum using commercially available mass spectrometers with or without modification and with the application of heat. The systems and methods produce multiply-charged ions for improved analysis in mass spectrometry.

18 Claims, 139 Drawing Sheets

(56) References Cited

U.S. PATENT DOCUMENTS

| | | | |
|---|---|---|---|
| 2010/0273666 A1* | 10/2010 | Bernatchez et al. | 506/8 |
| 2012/0085903 A1* | 4/2012 | Trimpin | 250/282 |
| 2013/0214154 A1* | 8/2013 | McEwen et al. | 250/288 |
| 2013/0306856 A1* | 11/2013 | Trimpin et al. | 250/282 |

OTHER PUBLICATIONS

Annan, R.S.and Carr, S.A. "Phosphopeptide analysis by matrix-assisted laser desorption time-of-flight mass spectrometry," Anal. Chem. 1996, 68, 3413-3421.

Batoy, S.M.A.B. et al. "Developments in MALDI Mass Spectrometry: The Quest for the Perfect Matrix," Applied Spectroscop Reviews 2008, 43, 485-550.

Beavis, R. C. and Chait, B. T. "Matrix-assisted laser-desorption mass spectrometry using 355 nm radiation," Rapid Commun. Mass Spectrom. 1989, 3, 436-439.

Beavis, R. C. et al. "alpha-Cyano-4-hydroxycinnamic acid as a matrix for matrixassisted laser desorption mass spectrometry," Org. Mass Spectrom. 1992, 27, 156-158.

Brown, R. S. et al. "Further studies of in-source fragmentation of peptides in matrix-assisted laser desorption-ionization," Int. J. Mass Spectrom. 1997, 169/170, 1-18.

Bush, M. F. et al. "Collision Cross Sections of Proteins and Their Complexes: A Calibration Framework and Database for Gas-Phase Structural Biology," Anal. Chem. 2010, 82, 9557-9565.

Cadene, M. and Chait, B.T. "A Robust, Detergent-Friendly Method for Mass Spectrometric Analysis of Integral Membrane Proteins," Anal. Chem. 2000, 72, 5655-5658.

Chang, W. C. et al. "Matrix-assisted laser desorption/ionization (MALDI) mechanism revisited," Analytica Chim. Acta 2007, 582, 1-9.

Chaurand, P. and Luetzenkirchen, F. "Peptide and protein identification by matrix-assisted laser desorption ionization (MALDI) and MALDI-post-source decay time-of-flight mass spectrometry," J. Am. Soc. Mass Spectrom. 1999, 10, 91-103.

Cohen, L. R. H. et al. "Analysis of quaternary protein ensembles by matrix assisted laser desorption/ionization mass spectrometry," J. Am. Soc. Mass Spectrom. 1997, 8, 1046-1052.

Colgrave, M. L. et al. "Nanoelectrospray ion mobility spectrometry and ion trap mass spectrometry studies of the non-covalent complexes of amino acids and peptides with polyethers," Int. J. Mass Spectrom. 2003, 229, 209-216.

Demirev, P. A. et al. "Top-Down Proteomics for Rapid Identification of Intact Microorganisms," S. Anal. Chem. 2005, 77, 7455-7461.

Djidja, M. et al. "Detergent addition to tryptic digests and ion mobility separation prior to MS/MS improves peptide yield and protein identification for in situ proteomic investigation of frozen and formalin-fixed paraffin-embedded adenocarcinoma tissue sections," Proteomics 2009, 9, 2750-2763.

Dole, M. et al. "Molecular Beams of Macroions," J. Chem. Phys. 1968, 49, 2240-2249.

Fenn, J. B. et al. "Electrospray ionization for mass spectrometry of large biomolecules," Science 1989, 246, 64-71.

Fenn, L. S. et al. "Characterizing ion mobility-mass spectrometry conformation space for the analysis of complex biological samples," Anal. Bioanal. Chem. 2009, 394, 235-244.

Fournier, F. et al. "Delayed extraction experiments using a repulsing potential before ion extraction: evidence of non-covalent clusters as ion precursor in UV matrix-assisted laser desorption/ionization. Part II—Dynamic effects with alpha-cyano-4-hydroxycinnamic acid matrix," J. Mass Spectrom. 2005, 40, 50-59.

Fournier, I. et al. "Delayed extraction experiments using a repulsing potential before ion extraction: evidence of non-covalent clusters as ion precursor in UV matrix-assisted laser desorption/ionization. Part II—Dynamic effects with alpha-cyano-4-hydroxycinnamic acid matrix," Int. J. Mass Spectrom. 2002, 213, 203-215.

Garrett, T. J. and Yost, R. A. "Analysis of intact tissue by intermediate-pressure MALDI on a linear ion trap mass spectrometer," Anal. Chem. 2006, 78, 2465-2469.

Handschuh, M. et al."Laser-induced molecular desorption and particle ejection from organic films," Appl Surf Sci. 1999, 137, 125-135.

Hoaglund, C. S. et al. "Three-dimensional ion mobility/TOFMS analysis of electrosprayed biomolecules," Anal. Chem. 1998, 70, 2236-2242.

Hortin, G.L. "The MALDI-TOF mass spectrometric view of the plasma proteome and peptidome," Clinical chemistry 2006, 52, 1223-1237.

Inutan, E. D. et al. "Laserspray Ionization, a New Method for Protein Analysis Directly from Tissue at Atmospheric Pressure with Ultrahigh Mass Resolution and Electron Transfer Dissociation," Mol. Cell. Proteomics 2011, 10, 1-8, DOI: 10.1074/mcp.M110.000760.

Inutan, E. D. and Trimpin, S. "Laserspray Ionization-Ion Mobility Spectrometry-Mass Spectrometry: Baseline Separation of Isomeric Amyloids Without the Use of Solvents Desorbed and Ionized Directly From a Surface," J. Proteome Res. 2010, 9, 6077-6081.

Inutan, E. D. et al. "Commercial intermediate pressure MALDI ion mobility spectrometry mass spectrometer capable of producing highly charged laserspray ionization ions," Anal. Chem. 2011, 83, 678-684.

Inutan, E. and Trimpin, S. "Laserspray ionization (LSI) ion mobility spectrometry (IMS) mass spectrometry," J. Am. Soc. Mass. Spectrom. 2010, 21, 1260-1264.

Iribarne, J. V. and Thomson, B. A. "On the evaporation of small ions from charged droplets," J. Chem. Phys. 1976, 64, 2287-2294.

Jackson, S. N. et al. "MALDI-ion mobility-TOFMS imaging of lipids in rat brain tissue," J. Mass Spectrom. 2007, 42, 1093-1098.

Jackson, S. N. et al. "Direct tissue analysis of phospholipids in rat brain using MALDI-TOFMS and MALDI-ion mobility-TOFMS," J. Am. Soc. Mass. Spectrom. 2005, 16, 133-138.

Jaskolla, T. W. and Karas, M. "Compelling evidence for Lucky Survivor and gas phase protonation: the unified MALDI analyte protonation mechanism," J. Am. Soc. Mass Spectrom. 2011, 22, 976-988.

Jones, M.D. et al. "Determination of disulfide bonds in highly bridged disulfide-linked peptides by matrix-assisted laser desorption/ionization mass spectrometry with postsource decay," Anal. Chem. 1998, 70, 136-143.

Karas, M. et al. "Matrix-Assisted Ultraviolet Laser Desorption of Non-Volatile Compounds," Int. J. Mass Spectrom. Ion Proc. 1987, 78, 53-68, DOI: 10.1016/0168-1176(87)87041-6.

Karas, M. et al. "Matrix Dependence of Metastable Fragmentation of Glycoproteins in MALDI TOF Mass Spectrometry," Anal. Chem. 1995, 67, 675-679.

Karas, M. et al. "Ionization in matrix-assisted laser desorption/ionization: singly charged molecular ions are the lucky survivors," J. Mass Spectrom. 2000, 35, 1-12.

Karas, M. and Hillenkamp, F. "Laser desorption ionization of proteins with molecular masses exceeding 10,000 daltons," Anal. Chem. 1988, 60, 2299-2301.

Karas, M. and Kruger, R. "Ion Formation in MALDI: The Cluster Ionization Mechanism," Chem. Rev. 2003, 103, 427-439.

Katta, V. et al. "Applications of In-Source Fragmentation of Protein Ions for Direct Sequence Analysis by Delayed Extraction MALDI-TOF Mass Spectrometry," Anal. Chem. 1998, 70, 4410-4416.

Kaufmann, R. et al. "Post-source decay and delayed extraction in matrix-assisted laser desorption/ionization-reflectron time-of-flight mass spectrometry. Are there trade-offs?," Rapid Commun. Mass Spectrom. 1996, 10, 1199-1208.

Kim, H. et al. "Experimental and theoretical investigation into the correlation between mass and ion mobility for choline and other ammonium cations in N2," Anal. Chem. 2008, 80, 1928-1936.

Knochenmuss, R. "Ion formation mechanisms in UV-MALDI," Analyst 2006, 131, 966-986.

Knochenmuss, R. and Zenobi, R. "MALDI ionization: the role of in-plume processes," Chem Rev. 2003, 103: 441-452.

Knochenmuss, R. and Zhigilei, L. V. "Molecular dynamics model of ultraviolet matrix-assisted laser desorption/ionization including ionization processes," J. Phys. Chem. B 2005, 109, 22947-22957.

Krause, J. et al. "Studies on the selection of new matrices for ultraviolet matrix-assisted laser desorption/ionization time-of-flight mass spectrometry," Rapid Commun. Mass. Spectrom. 1996, 10, 1927-1933.

(56) References Cited

OTHER PUBLICATIONS

Krutchinsky, A. N. and Chait, B. T. "On the nature of the chemical noise in MALDI mass spectra," *J. Am. Soc. Mass Spectrom.* 2002, 13, 129-134.

Laiko, V. V. et al. "Atmospheric pressure matrix-assisted laser desorption/ionization mass spectrometry," *Anal. Chem.* 2000, 72, 652-657.

Landgraf, R. R. et al. "Imaging of lipids in spinal cord using intermediate pressure matrix-assisted laser desorption-linear ion trap/Orbitrap MS," *Anal. Chem.* 2009, 81, 8488-8495.

Leary, J. A. et al. "Methodology for measuring conformation of solvent-disrupted protein subunits using T-WAVE ion mobility MS: an investigation into eukaryotic initiation factors," *J. Am. Soc. Mass. Spectrom.* 2009, 20, 1699-1706.

Lee, S. et al. "Determination of cross sections by overtone mobility spectrometry: evidence for loss of unstable structures at higher overtones," *J. Phys. Chem. B* 2010, 114, 12406-12415.

McCombie, G. and Knochenmuss, R. "Small-molecule MALDI using the matrix suppression effect to reduce or eliminate matrix background interferences," *Anal. Chem.* 2004, 76, 4990-4997.

McEwen, C. N. et al. "Laserspray ionization on a commercial atmospheric pressure-MALDI mass spectrometer ion source: selecting singly or multiply charged ions," *Anal. Chem.* 2010, 82, 4998-5001.

McEwen, C. N. et al. "New paradigm in ionization: multiply charged ion formation from a solid matrix without a laser or voltage," *Anal. Chem.* 2010, 82, 9164-9168.

McEwen, C. N. and Trimpin, S. "An alternative ionization paradigm for atmospheric pressure mass spectrometry: Flying elephants from Trojan horses," *Intern. J. Mass Spectrom.* 2011, 300, 167-172; 2010, DOI: 10.1016/j.ijms.2010.05.020.

McLean, J. A. et al. "Profiling and imaging of tissues by imaging ion mobility-mass spectrometry," *J. Mass Spectrom.* 2007, 42, 1099-1105.

Nguyen, S. et al. "Gas-phase ions of solute species from charged droplets of solutions." PNAS 2007, I(4), 1111-1117.

Niu, S. et al. "Direct comparison of infrared and ultraviolet wavelength matrix-assisted laser desorption/ionization mass spectrometry of proteins," *J. Am. Soc. Mass Spectrom.* 1998, 9, 1-7.

Nordhoff, E. et al. "Matrix-assisted laser desorption/ionization mass spectrometry of nucleic acids with wavelengths in the ultraviolet and infrared," *Rapid Commun. Mass Spectrom.* 1992, 6, 771-776.

Richards, A. L. et al. "Imaging mass spectrometry in transmission geometry," *Rapid Commun. Mass Spectrom.* 2011, 25, 815-820.

Richards, A. L. et al. "High-throughput analysis of peptides and proteins by laserspray ionization mass spectrometry," *Rapid Commun. Mass Spectrom.* 2011, 25, 247-250.

Ridenour, W. B. et al. "Structural characterization of phospholipids and peptides directly from tissue sections by MALDI traveling-wave ion mobility-mass spectrometry," *Anal. Chem.* 2010, 82, 1881-1889.

Scarff, C. A. et al. "Travelling wave ion mobility mass spectrometry studies of protein structure: biological significance and comparison with X-ray crystallography and nuclear magnetic resonance spectroscopy measurements," *Rapid Commun. Mass Spectrom.* 2008, 22, 3297-3304.

Schneider, B. B. et al. "AP and vacuum MALDI on a QqLIT instrument," *J. Am. Soc. Mass Spectrom.* 2005, 16, 176-182.

Schuerenberg, M. et al. "Matrix-assisted Laser Desorption/Ionization in Transmission Geometry: Instrumental Implementation and Mechanistic Implications," *Rapid Commun. Mass Spectrom.* 1996, 10, 1873-1880; DOI: 10.1002/(SICI)1097-0231(199612)10:15<1873::AID-RCM719>3.0.CO;2-3.

Senko, M.W. et al. "Collisional activation of large multiply charged ions using Fourier transform mass spectrometry," *Anal. Chem.* 1994, 66, 2801-2808.

Shvartsburg, A. A. et al. "Pendular proteins in gases and new avenues for characterization of macromolecules by ion mobility spectrometry," *Proc. Nat. Acad. Sci. of USA* 2009, 106, 6495-6500.

Smith, D. P. et al. "Monitoring copopulated conformational states during protein folding events using electrospray ionization-ion mobility spectrometry-mass spectrometry," *J. Am. Soc. Mass Spectrom.* 2007, 18, 2180-2190.

Tanaka, K. et al. "Protein and Polymer Analyses Up to M/Z 100 000 by Laser Ionization Time-Of-Flight Mass Spectrometry," *Rapid Commun. Mass Spectrom.* 1988, 2, 151-153.

Tao, L. et al. "A Collision Cross-Section Database of Singly-Charged Peptide Ions," *J. Am. Soc. Mass Spectrom.* 2007, 18, 1232-1238.

Trimpin, S. "A perspective on MALDI alternatives-total solvent-free analysis and electron transfer dissociation of highly charged ions by laserspray ionization," *J. Mass Spectrom.* 2010, 45, 471-485.

Trimpin, S. and Brizzard, B. "Analysis of insoluble proteins," *BioTechniques* 2009, 46, 409-419.

Trimpin, S. and Clemmer, D. E. "Ion mobility spectrometry/mass spectrometry snapshots for assessing the molecular compositions of complex polymeric systems," *Anal. Chem.* 2008, 80, 9073-9083.

Trimpin, S. et al. "Field-free transmission geometry atmospheric pressure matrix-assisted laser desorption/ionization for rapid analysis of unadulterated tissue samples," *Rapid Commun. Mass Spectrom.* 2009, 23, 3023-3027.

Trimpin, S. "High-throughput analysis of peptides and proteins by laserspray ionization mass spectrometry," *Rapid Commun. Mass Spectrom.* 2011, 25, 247-250.

Trimpin, S. "Imaging mass spectrometry in transmission geometry," *Rapid Commun. Mass Spectrom.* 2011, 25, 815-820.

Trimpin, S. et al. "Matrix-assisted laser desorption/ionization mass spectrometry method for selectively producing either singly or multiply charged molecular ions," *Anal. Chem.* 2010, 82, 11-15.

Trimpin, S. et al. "Laserspray ionization, a new atmospheric pressure MALDI method for producing highly charged gas-phase ions of peptides and proteins directly from solid solutions," *Mol. Cell. Proteomics* 2010, 9, 362-367.

Trimpin, S. et al. "Identification of endogenous phosphorylation sites of bovine medium and low molecular weight neurofilament proteins by tandem mass spectrometry," *Biochemistry* 2004, 43, 2091-2105.

Trimpin, S. et al. "Resolving oligomers from fully grown polymers with IMS-MS," *Anal. Chem.* 2007, 79, 7965-7974.

Trimpin, S. et al. "Investigations of theoretical principles for MALDI-MS derived from solvent-free sample preparation: Part I. Preorganization," *Int. J. Mass Spectrom.* 2006, 253, 13-21.

Vestal, M.L. "Modern MALDI time-of-flight mass spectrometry," *J. Mass Spectrom.* 2009, 44, 303-317.

Vinh, H. et al. "Sequencing branched peptides with CID/PSD MALDI-TOF in the low-picomole range: application to the structural study of the posttranslational polyglycylation of tubulin," *Anal. Chem.* 1997, 69, 3979-3985.

von Helden, G. et al. "Inclusion of a MALDI ion source in the ion chromatography technique: conformational information on polymer and biomolecular ions," *Int. J. Mass Spectrom. Ion Processes* 1995, 146/147, 349-364.

Wang, B. et al. "Producing highly charged ions without solvent using laserspray ionization: a total solvent-free analysis approach at atmospheric pressure," *Anal. Chem.* 2011, 83, 4076-4084; DOI:10.1021/ac2000576.

Weidner, S. M. and Trimpin, S. "Mass spectrometry of synthetic polymers," *Anal. Chem.* 2010, 82, 4811-4829.

Wenzel, T. et al. "2,5-Dihydroxyacetophenone: a matrix for highly sensitive matrix-assisted laser desorption/ionization time-of-flight mass spectrometric analysis of proteins using manual and automated preparation techniques," *Rapid Commun. Mass Spectrom.* 2006, 20, 785-789.

Williams, J. P. et al. "Use of ion mobility mass spectrometry and a collision cross-section algorithm to study an organometallic ruthenium anticancer complex and its adducts with a DNA oligonucleotide," *Rapid Commun. Mass Spectrom.* 2009, 23, 3563-3569.

Woods, A. S. et al. "Lipid/peptide/nucleotide separation with MALDI-ion mobility-TOF MS," *Anal. Chem.* 2004, 76, 2187-2195.

(56) References Cited

OTHER PUBLICATIONS

Wortmann, A. et al. "Investigation of the first shot phenomenon in MALDI mass spectrometry of protein complexes," *Analyst* 2007, 132, 199-207.

Zhigilei L. V. et al. "On the threshold behavior in laser ablation of organic solids," *Chem. Phys. Lett.* 1997, 276, 269-273.

Zhigilei, L. V. "Dynamics of the plume formation and parameters of the ejected clusters in short-pulse laser ablation," *Appl Phys A* 2003, 76, 339-350.

Zhigilei, L. V. and Garrison, B. J. "Microscopic mechanisms of laser ablation of organic solids in the thermal and stress confinement irradiation regimes," *J. Applied Phys 2000*, 88, 1281-1298.

Zydel, F. et al. "Laserspray ionization using an atmospheric solids analysis probe for sample introduction," *J. Am. Soc. Mass. Spectrom.* 2010, 21, 1889-1892.

International Search Report and Written Opinion for PCT/US2011/057769, Feb. 14, 2012.

\* cited by examiner

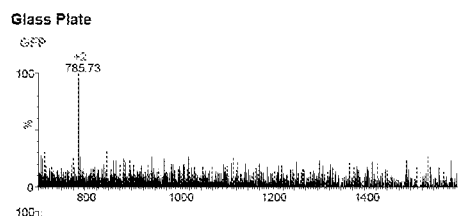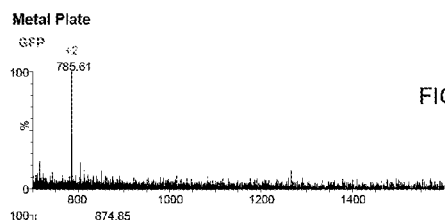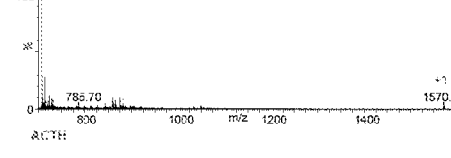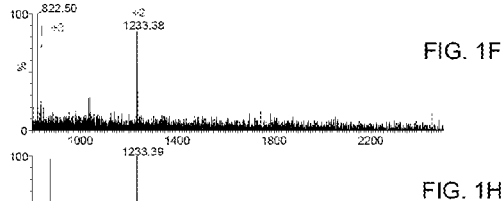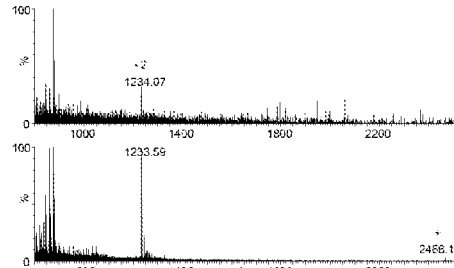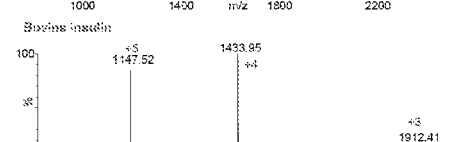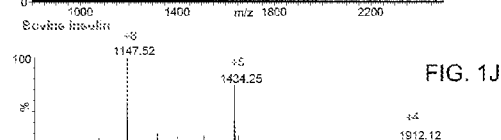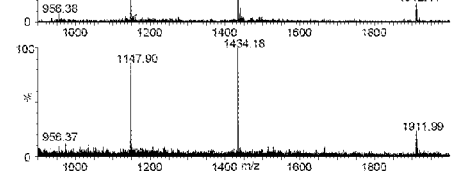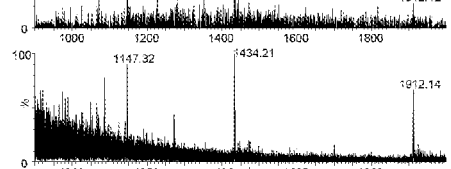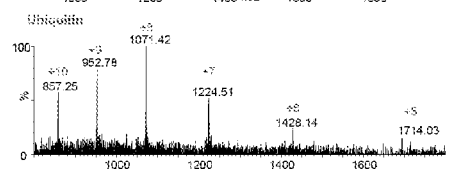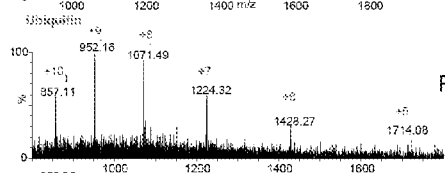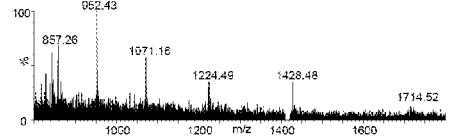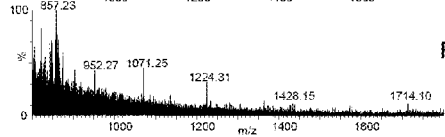

FIG. 3A
FIG. 3B
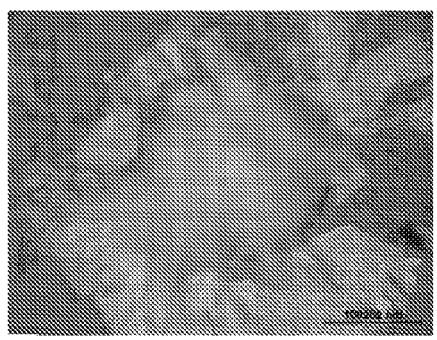
FIG. 3C
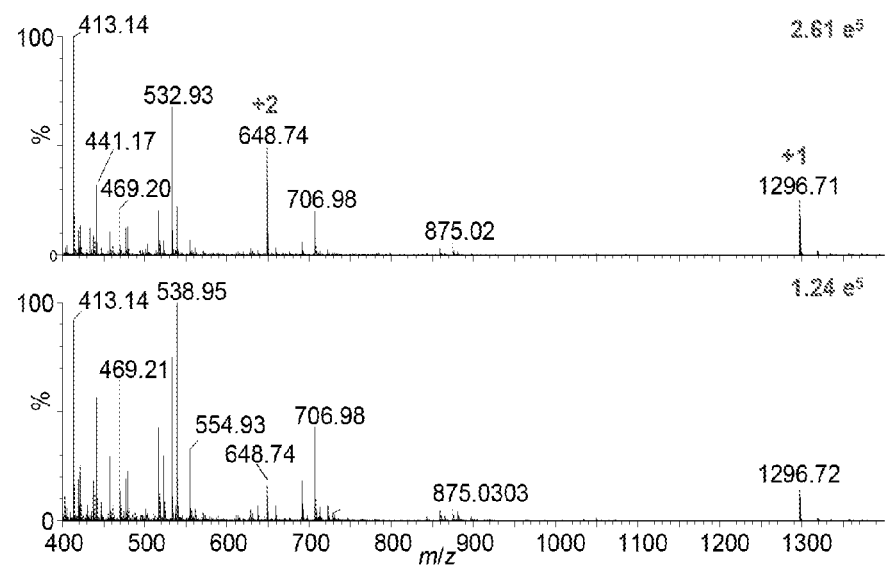
FIG. 3D

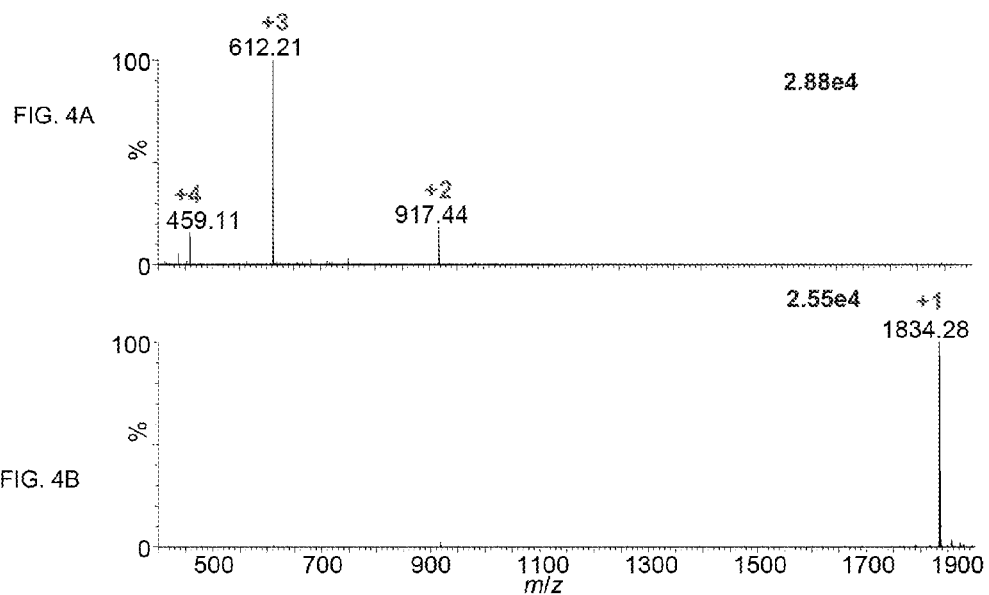

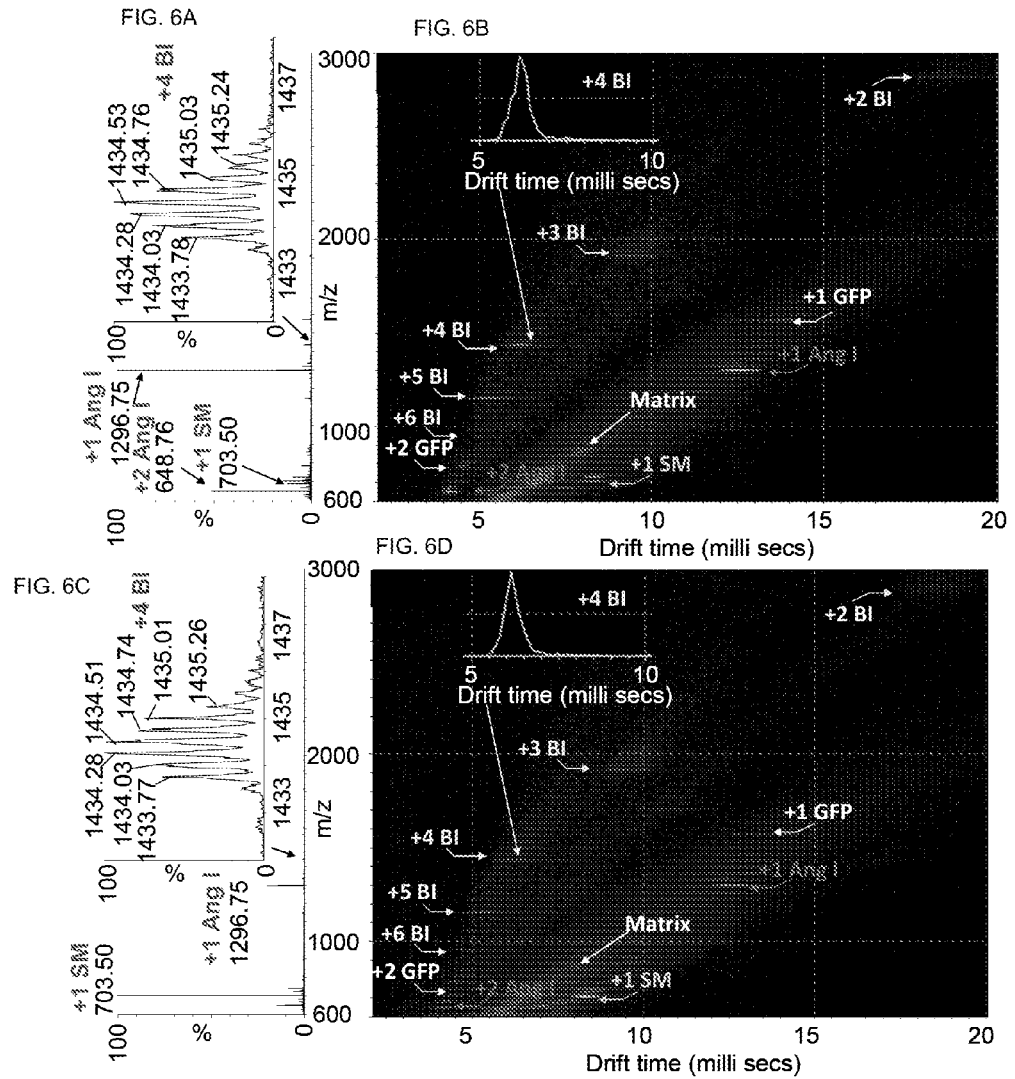

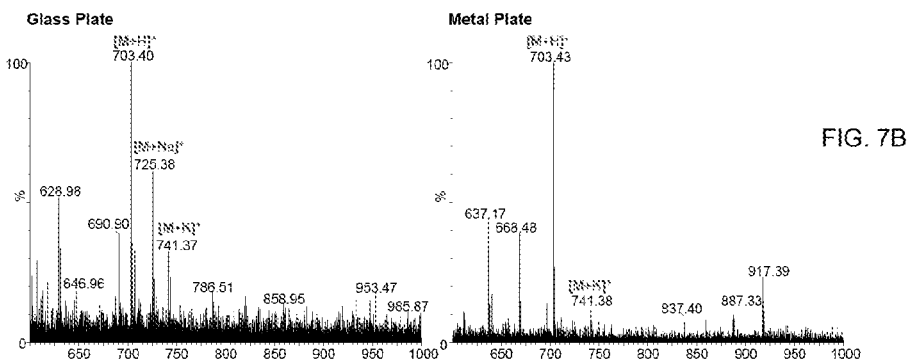
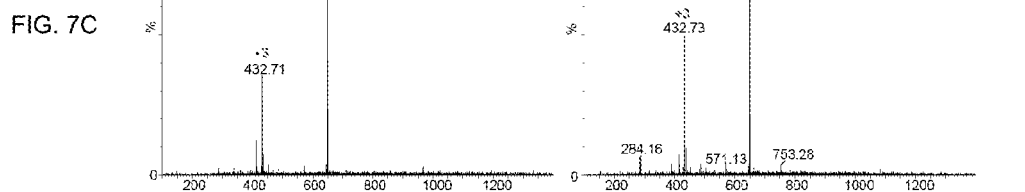
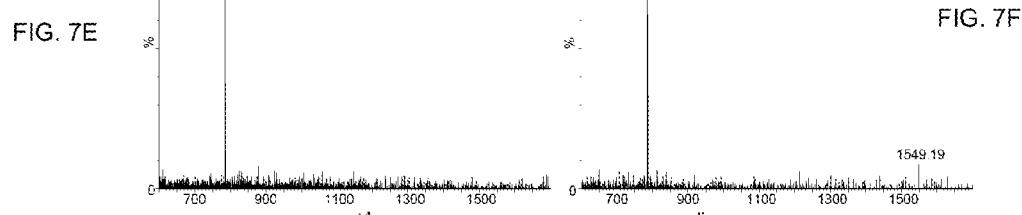
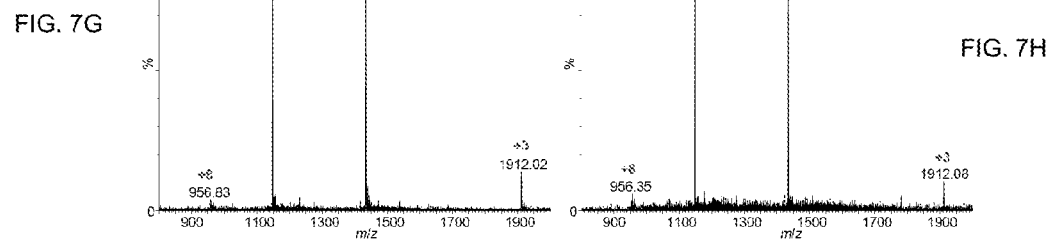
FIG. 7A FIG. 7B FIG. 7C FIG. 7D FIG. 7E FIG. 7F FIG. 7G FIG. 7H

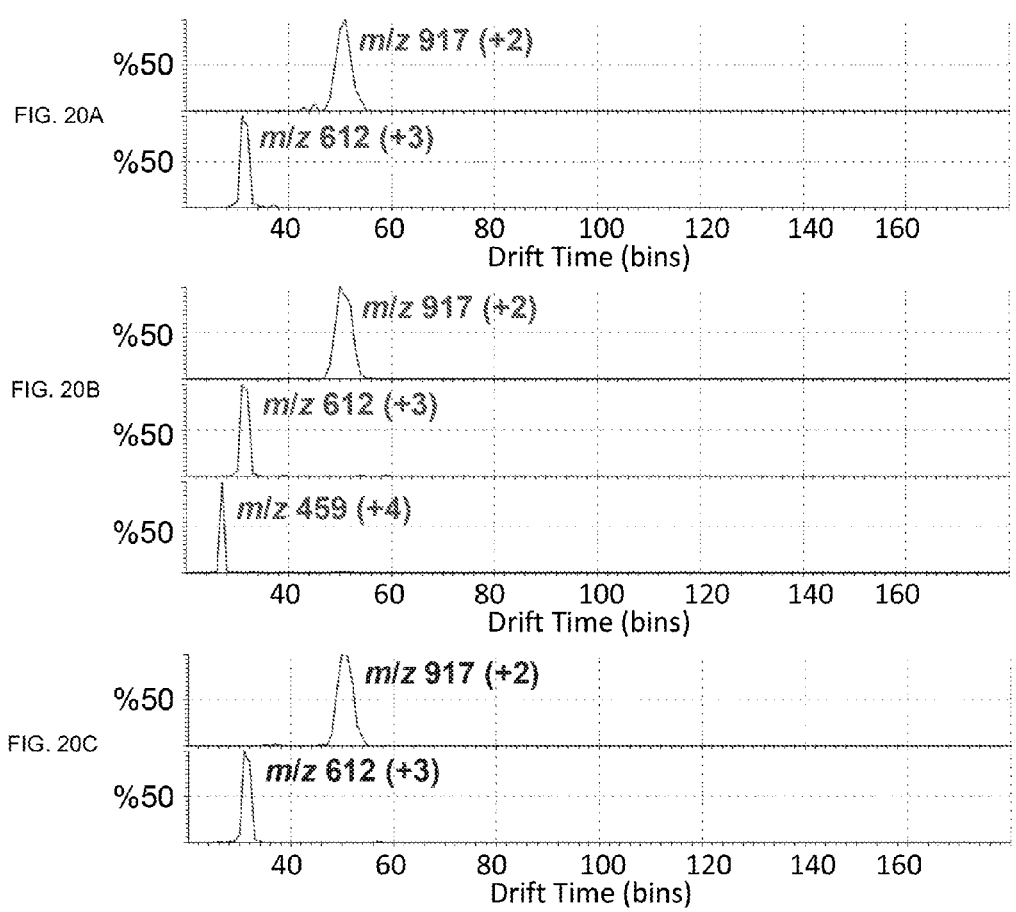

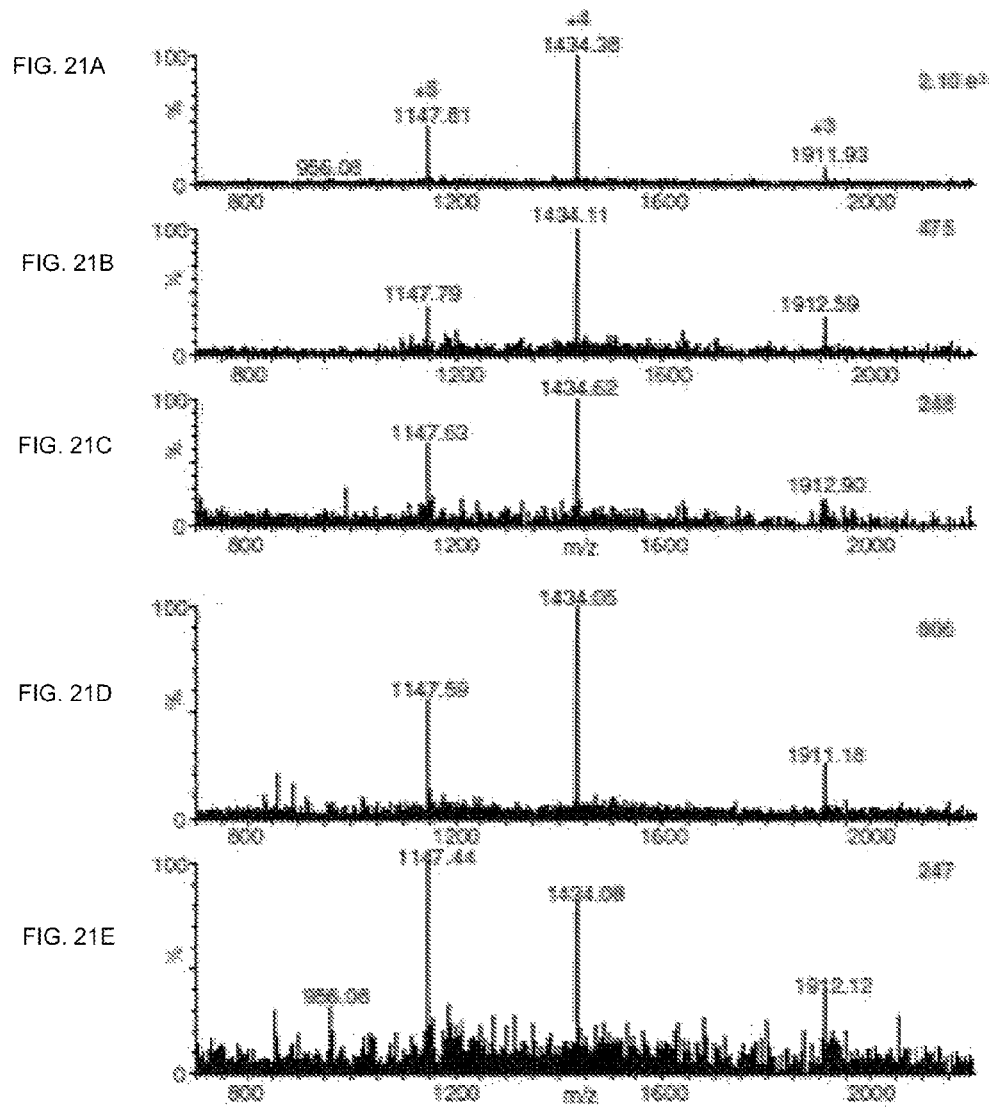

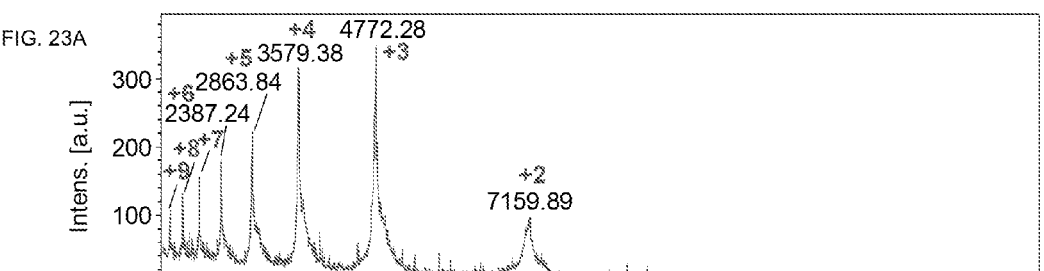
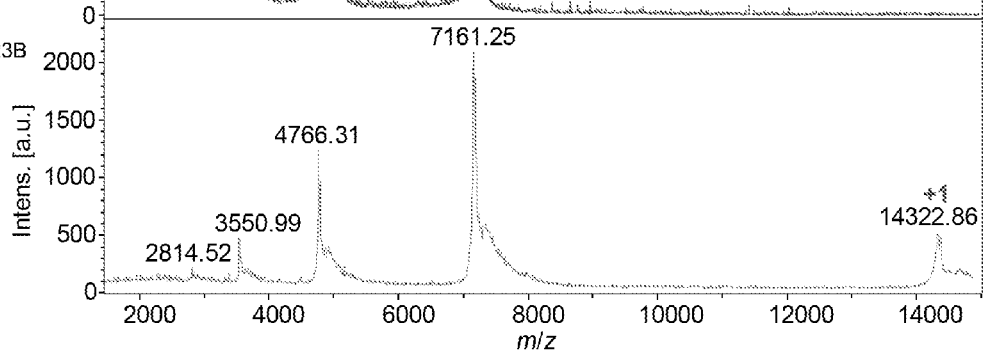

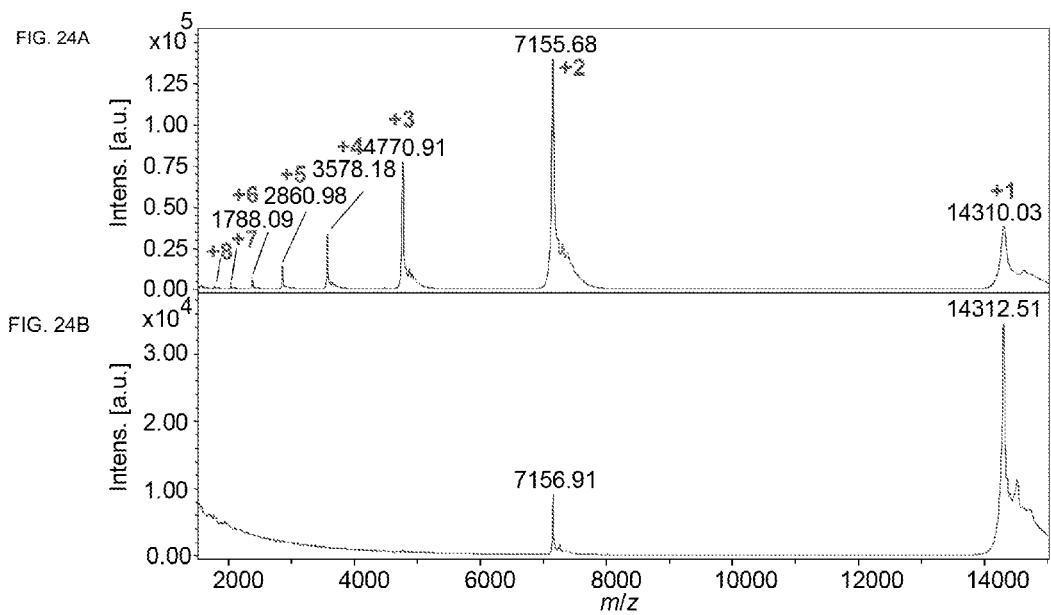

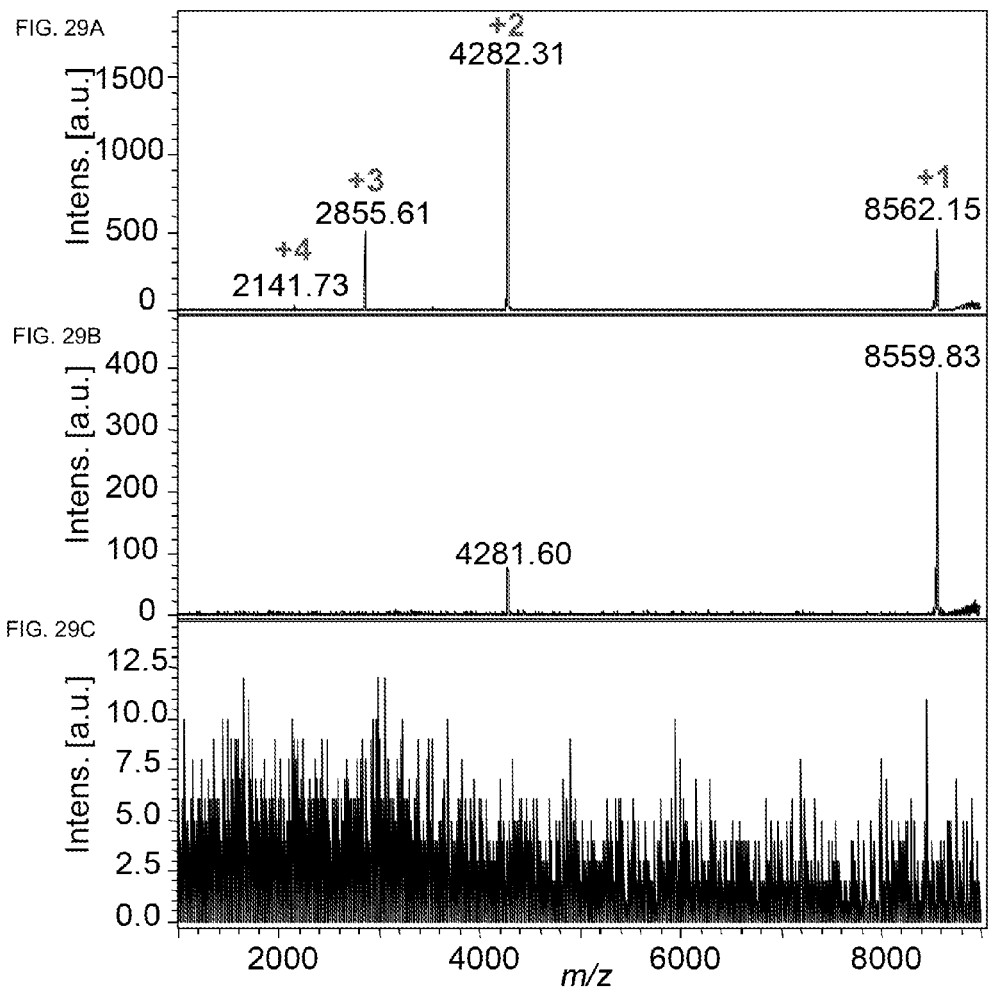

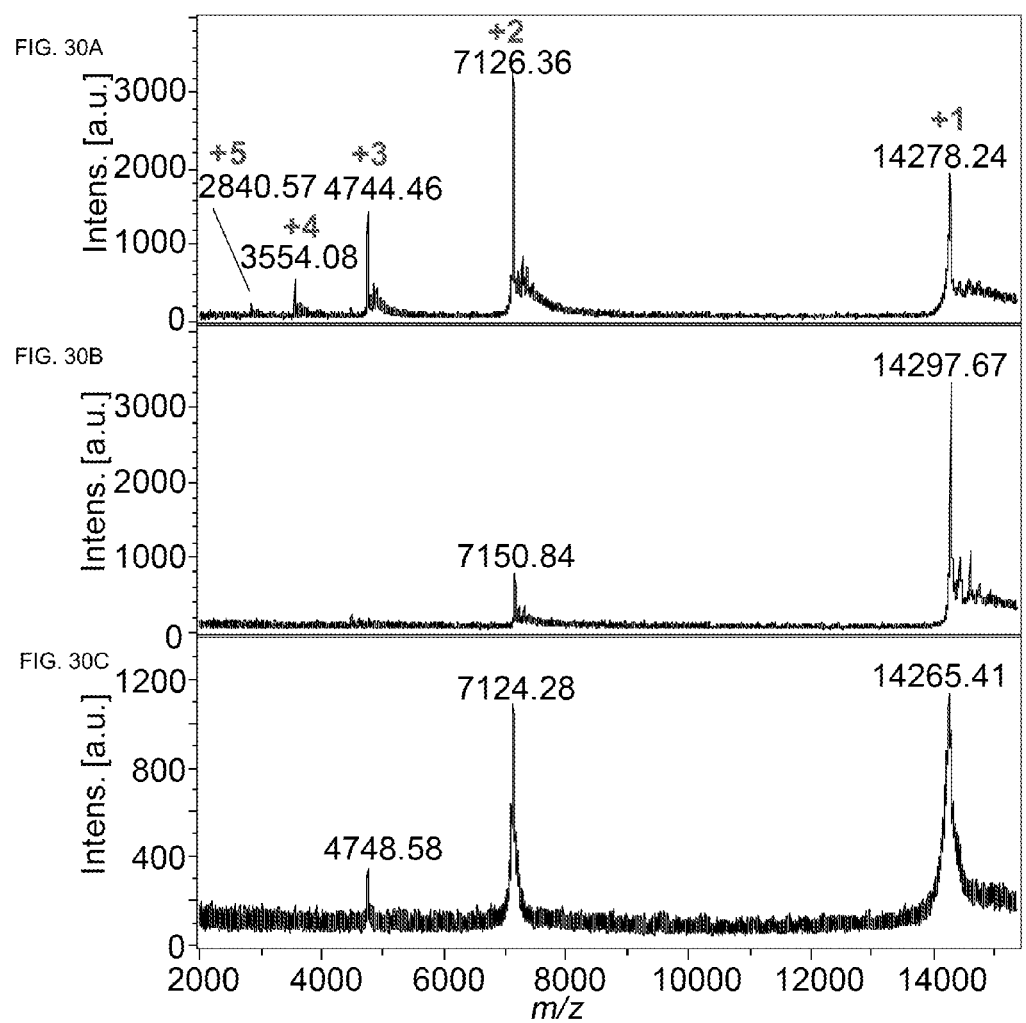

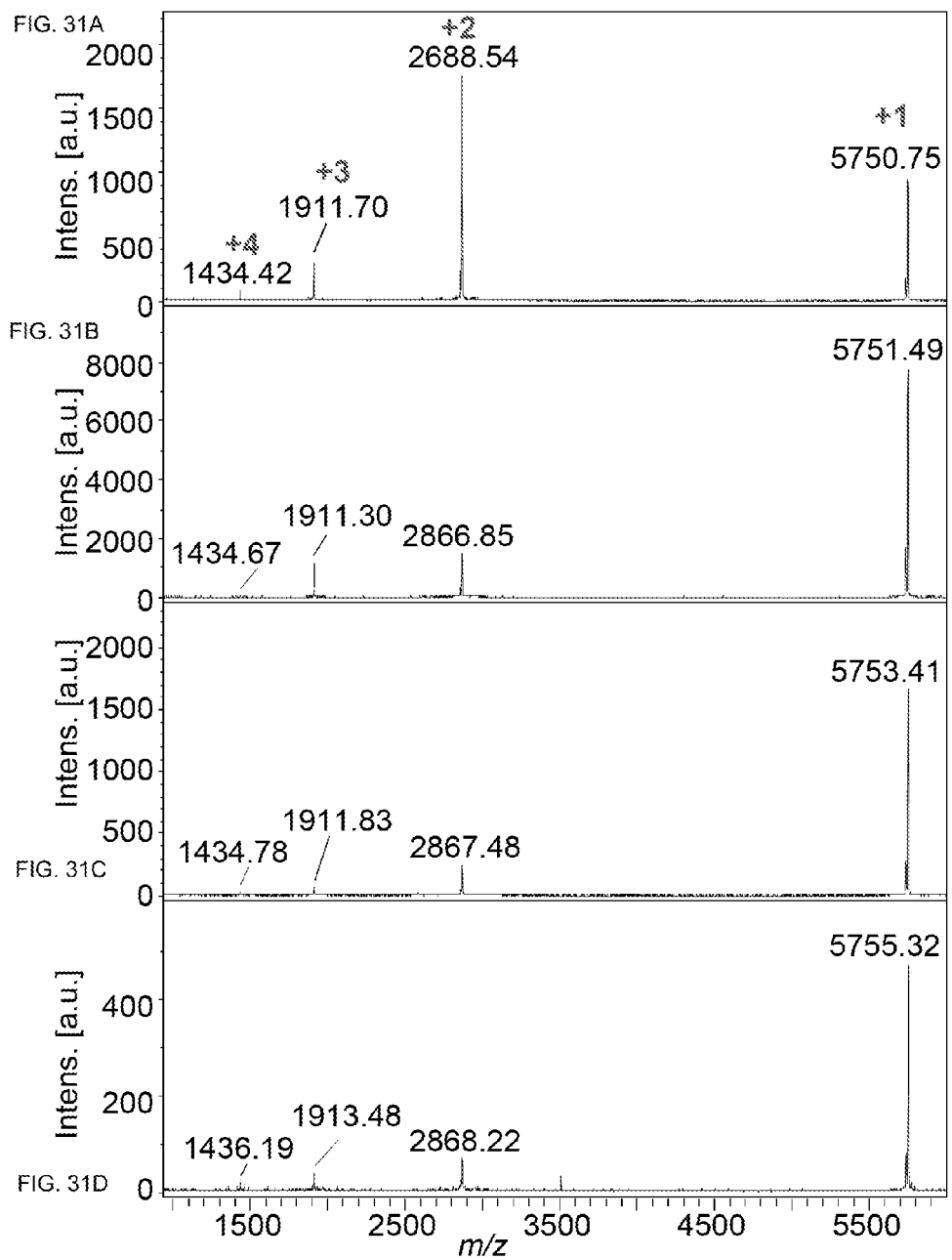

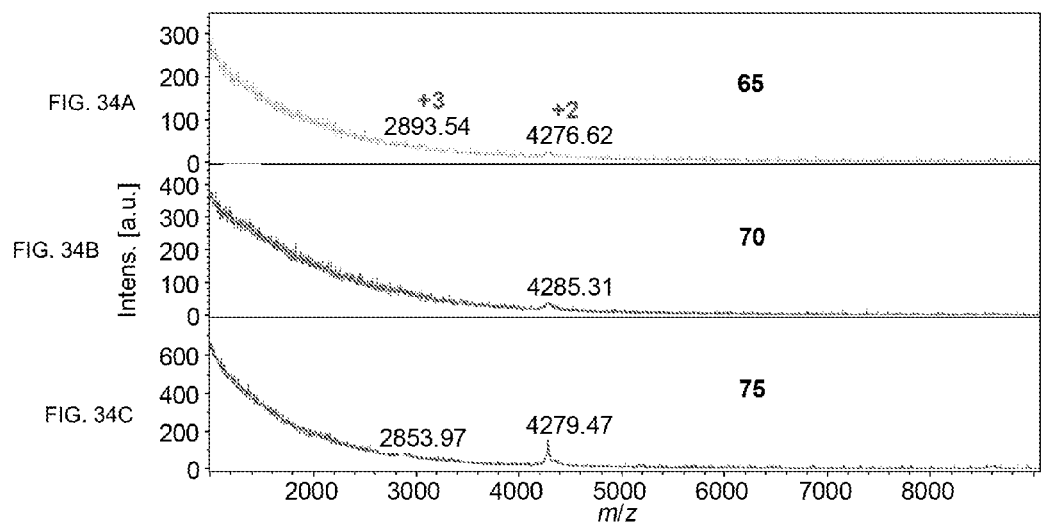

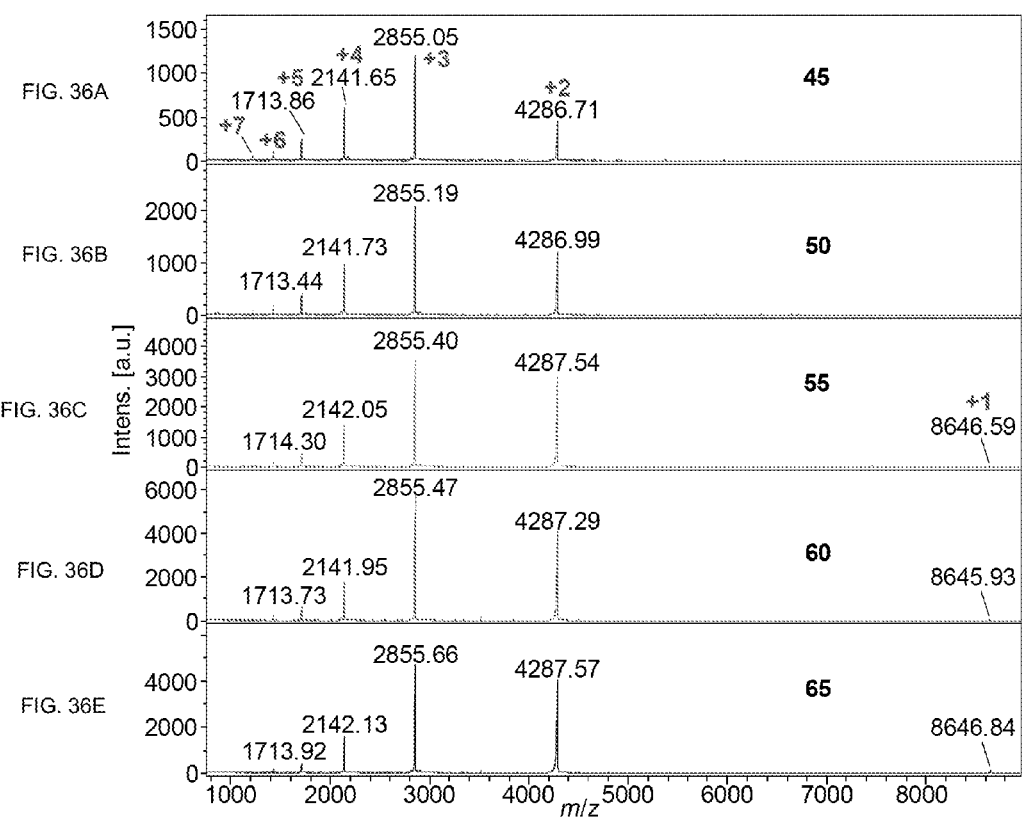

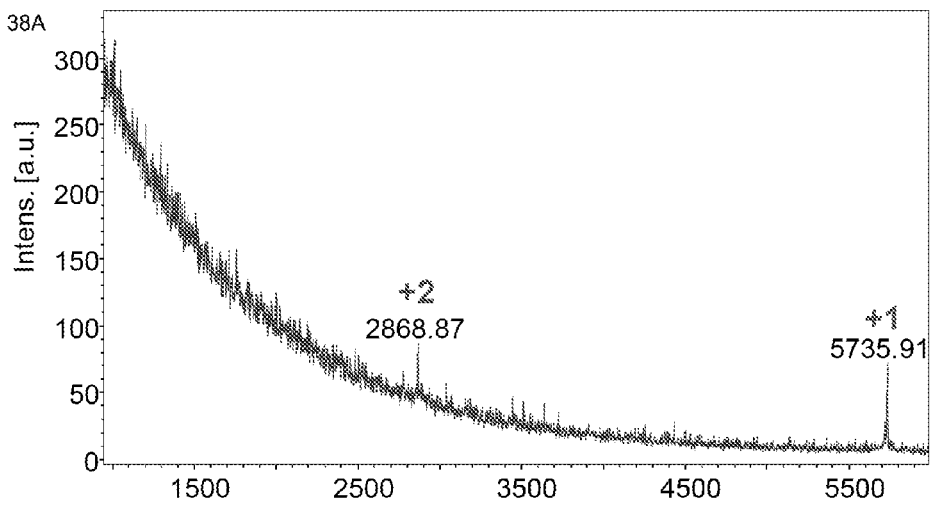
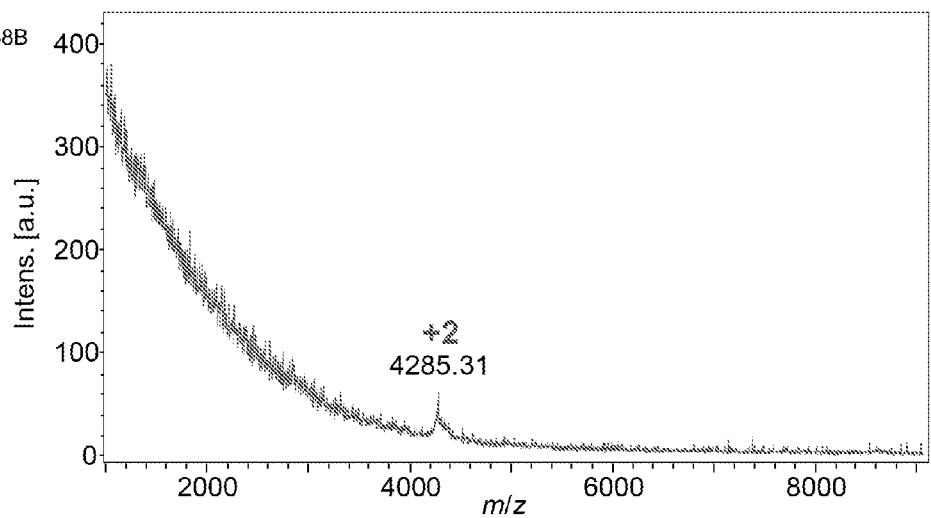

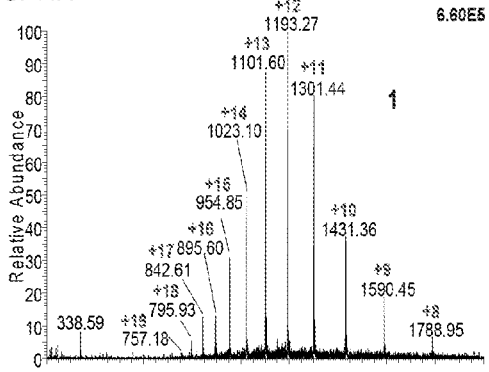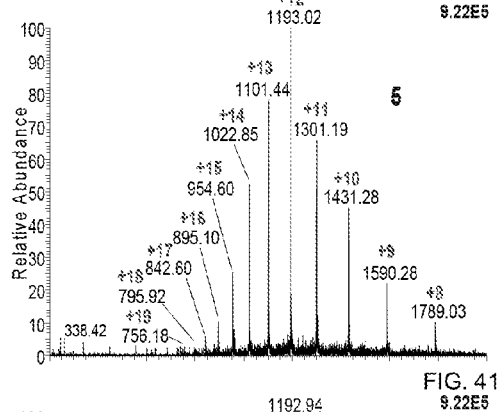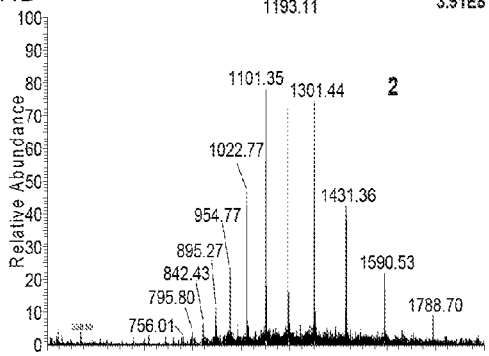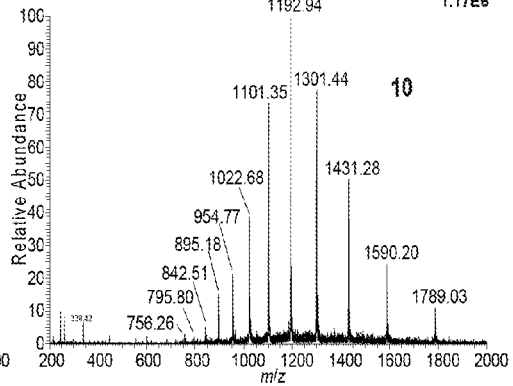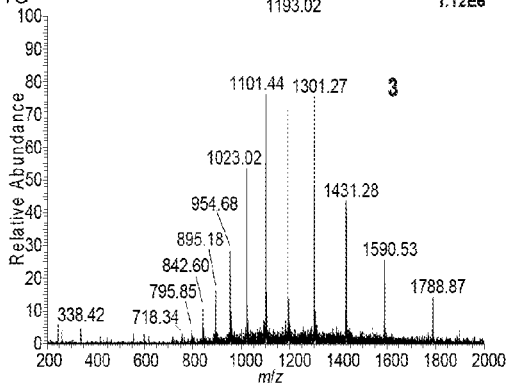

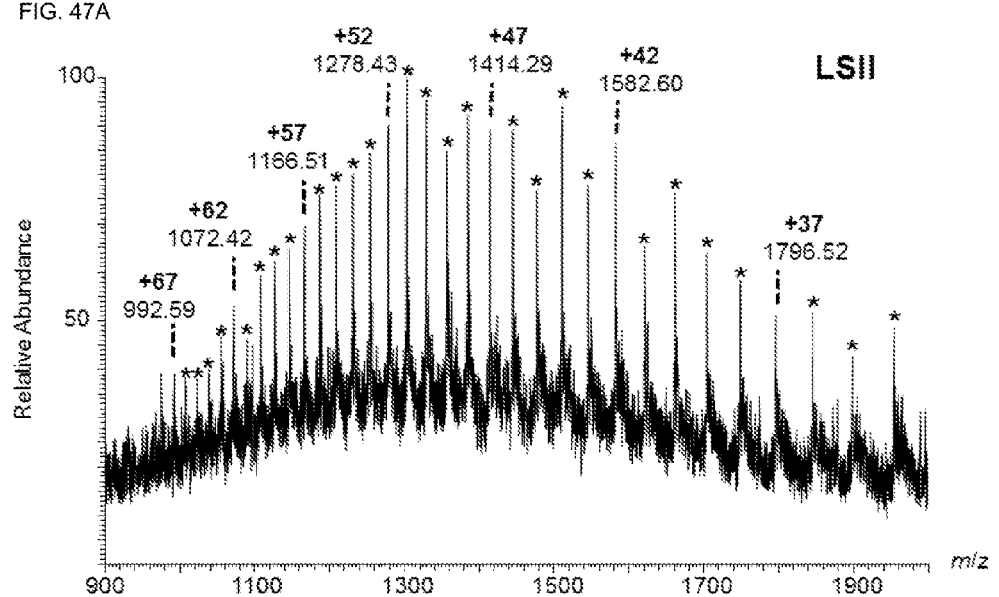
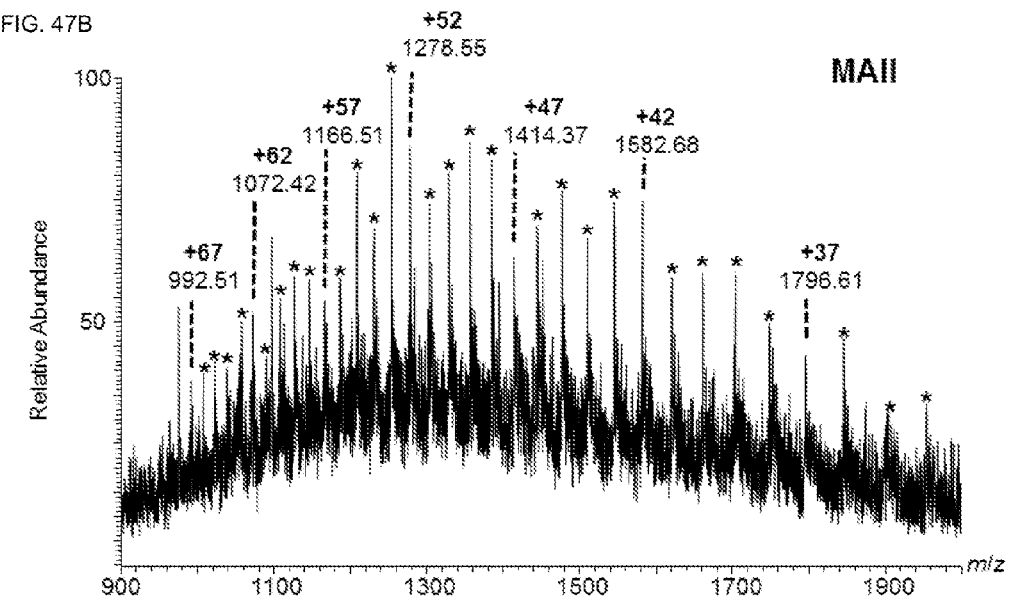

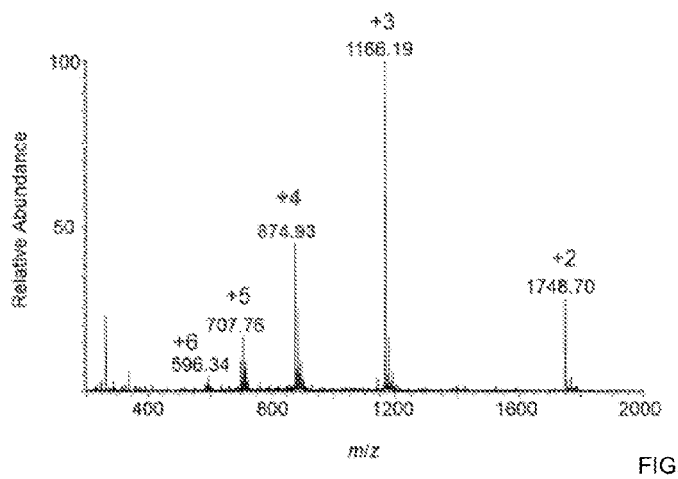
FIG. 51A
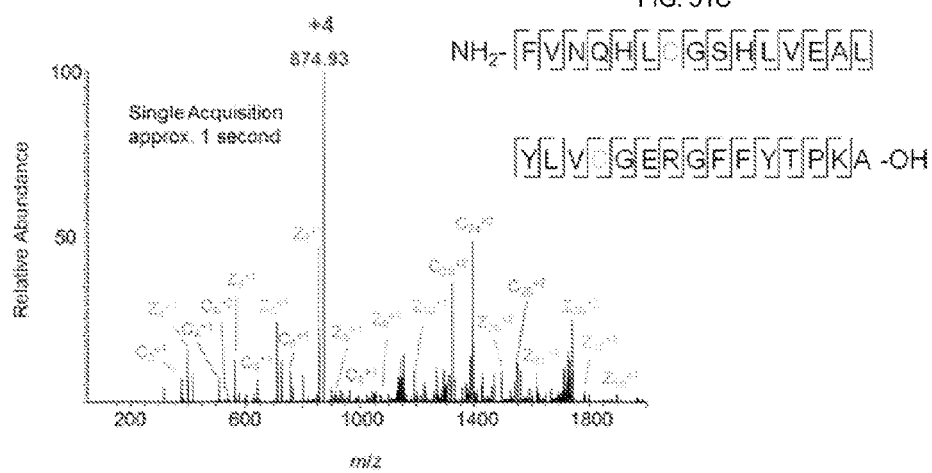
FIG. 51B
FIG. 51C

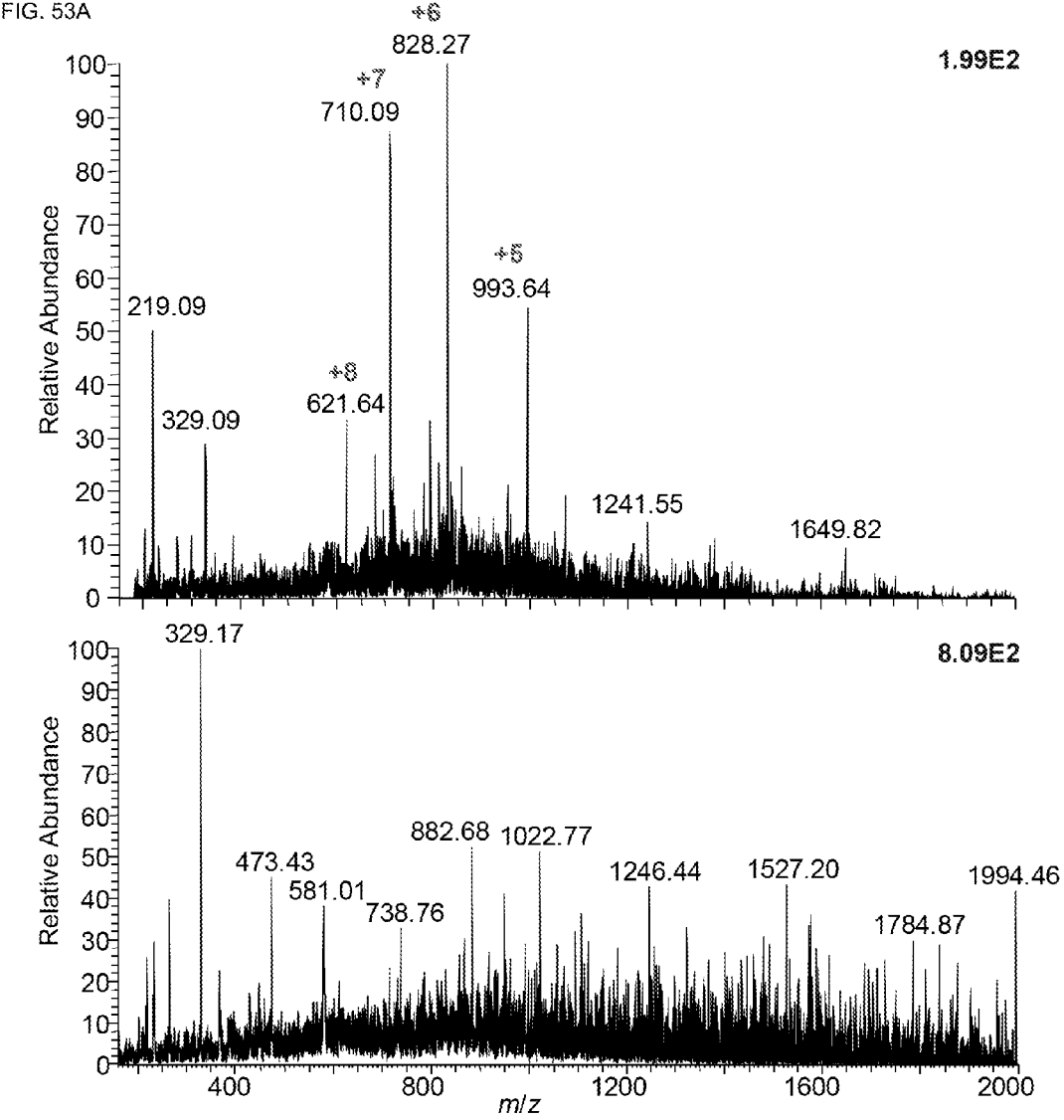

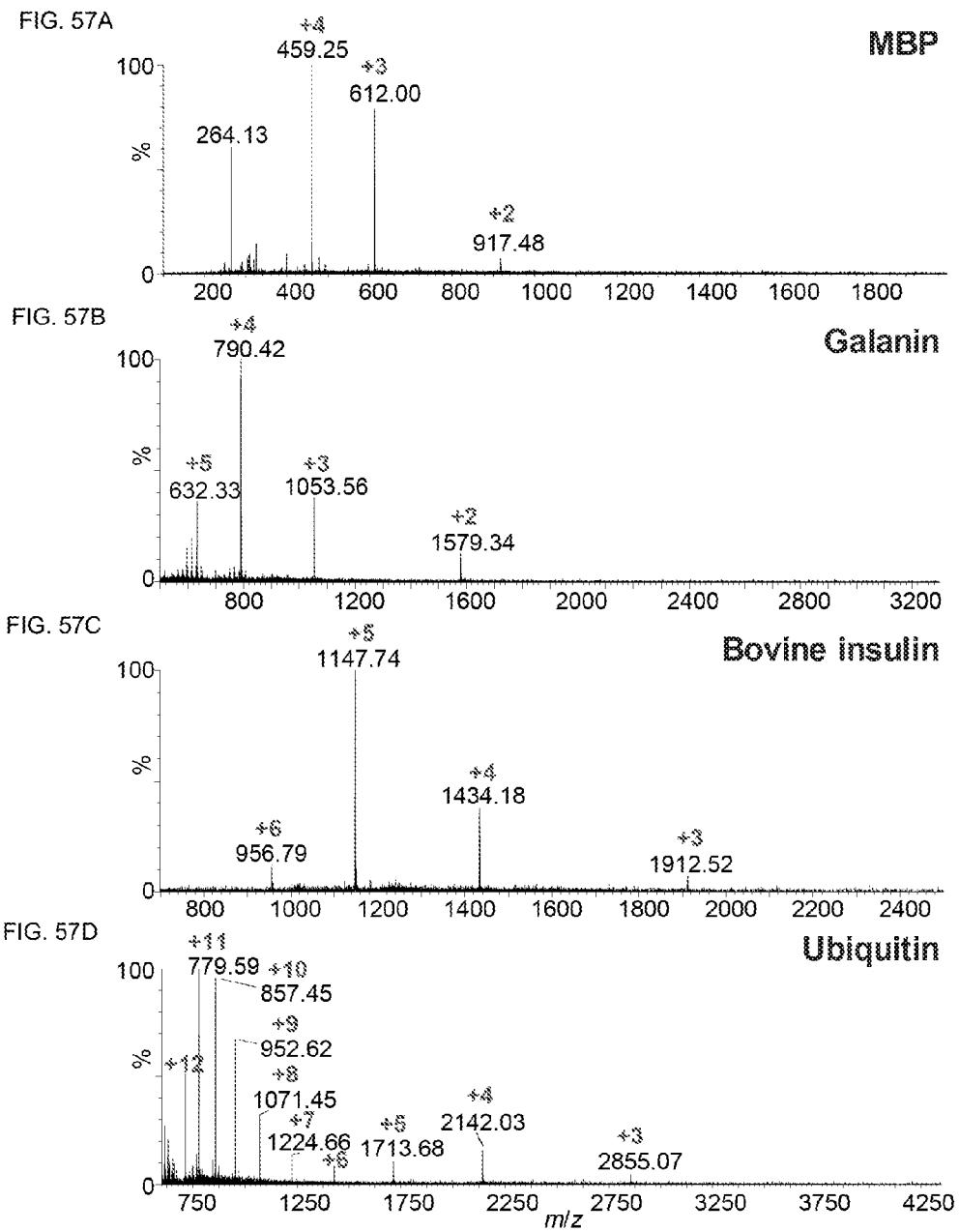

FIG. 58A    FIG. 58B
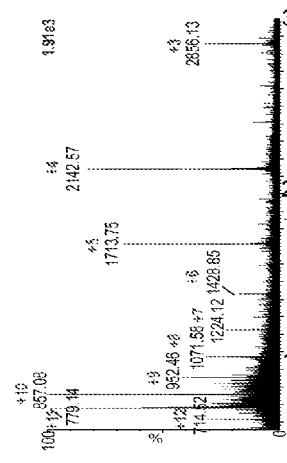
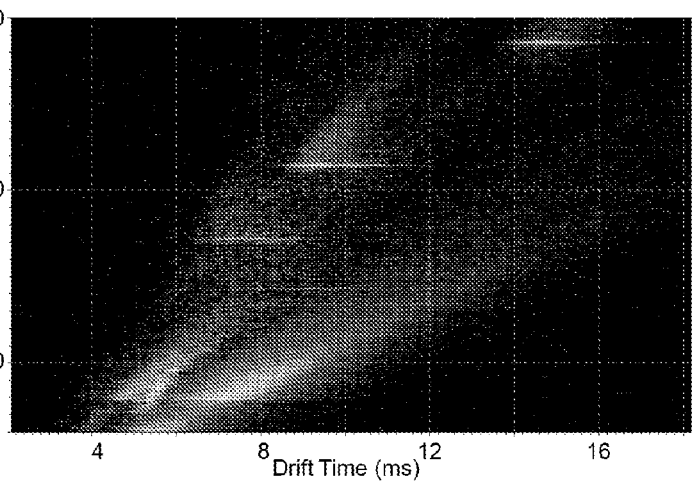
FIG. 58C    FIG. 58D

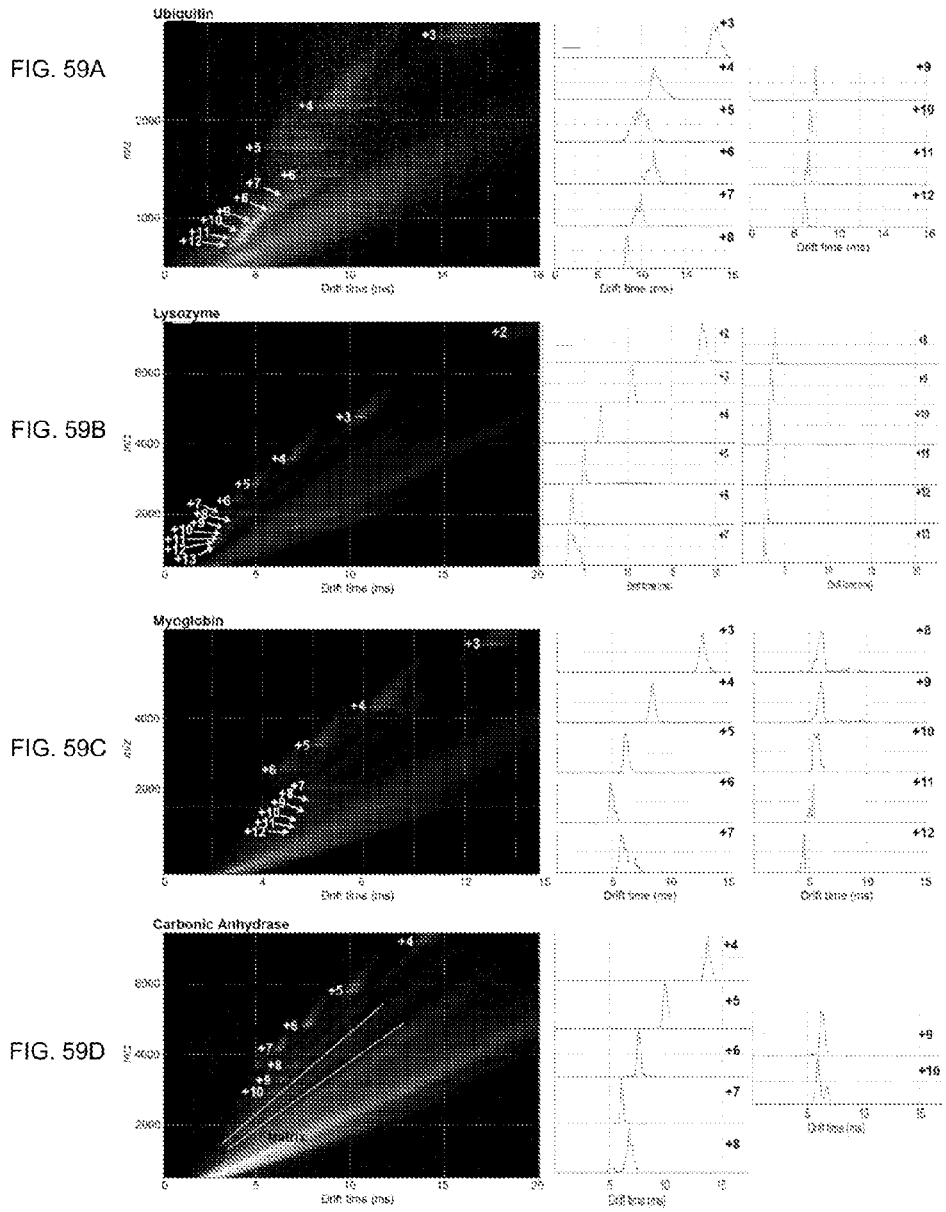

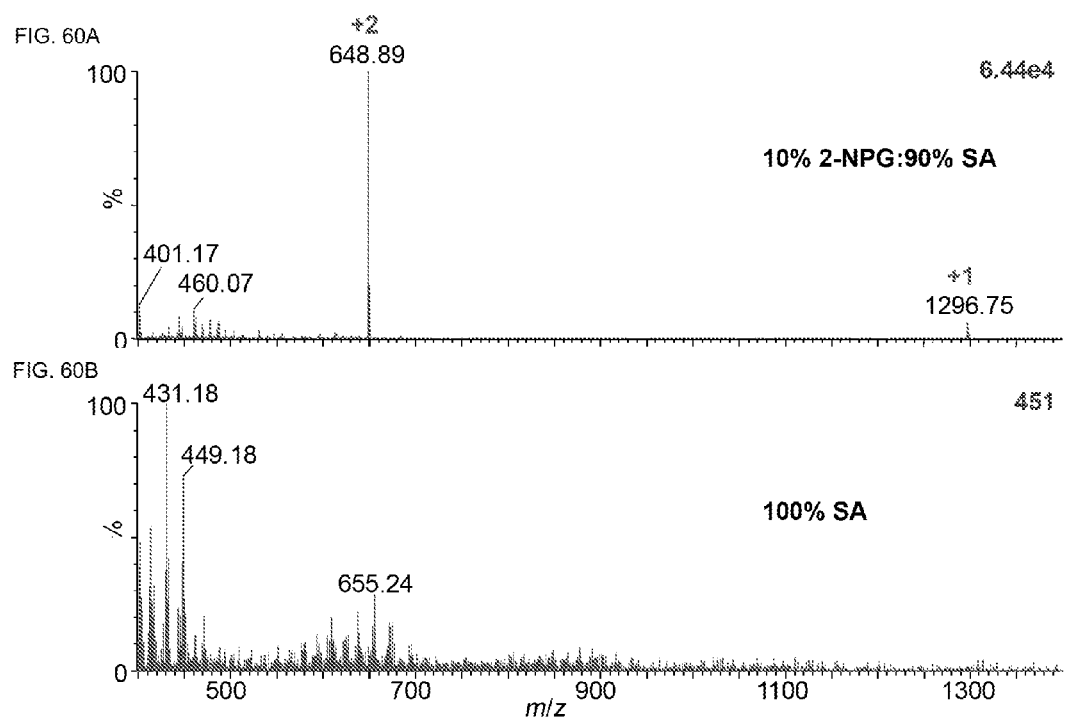

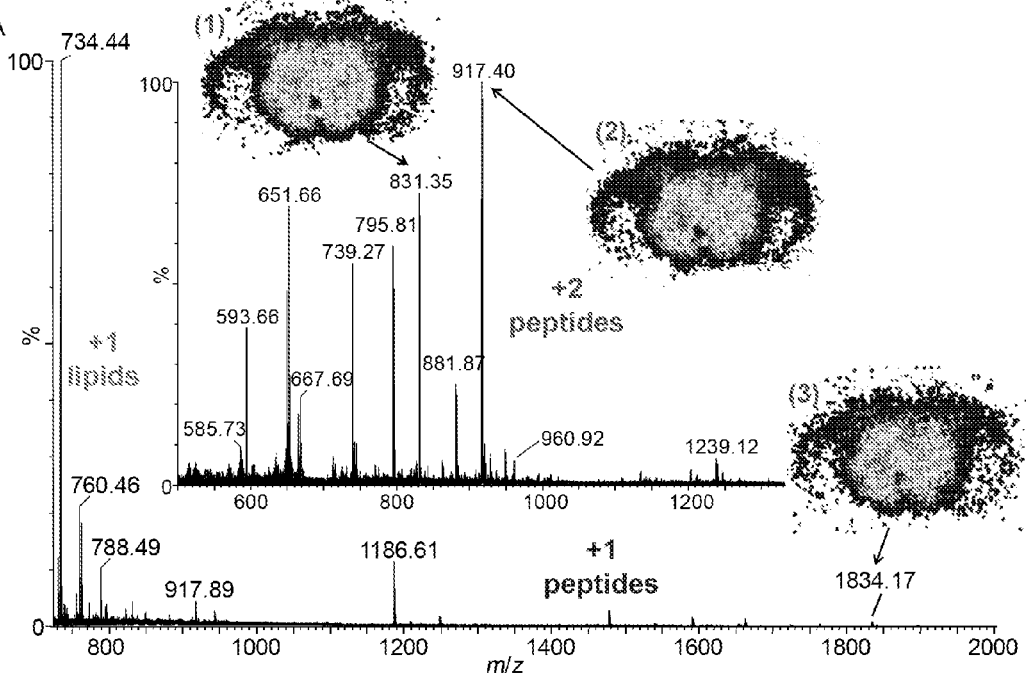

FIG. 66A
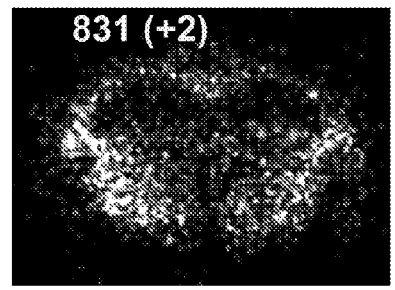
FIG. 66B
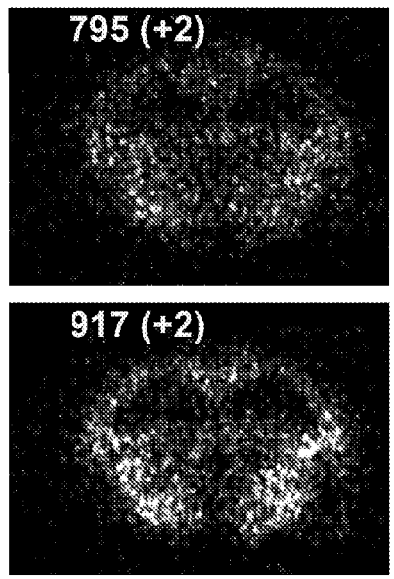
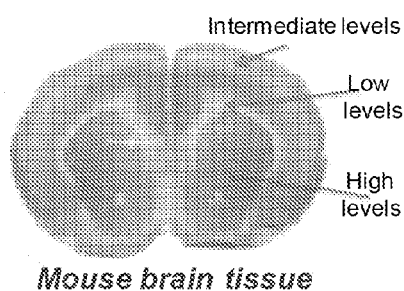
FIG. 66C
FIG. 66D

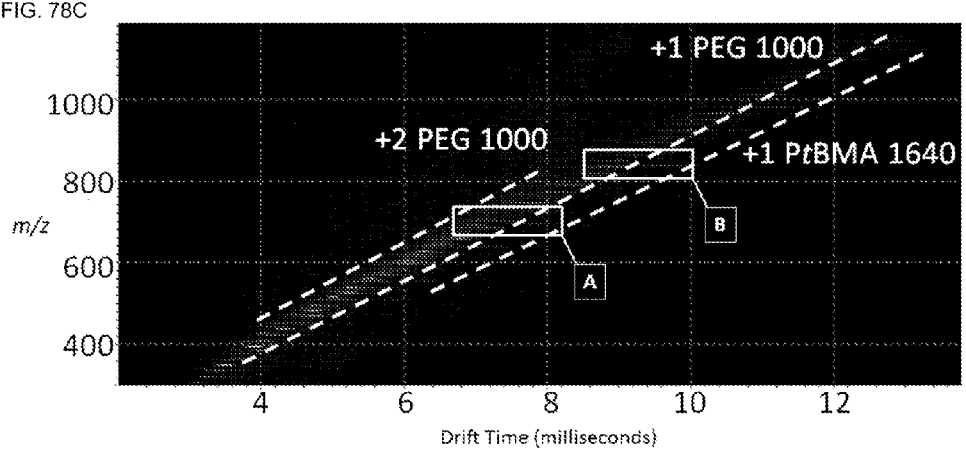
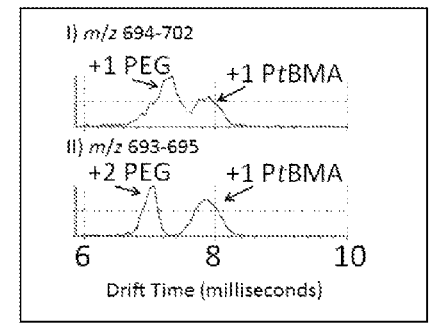
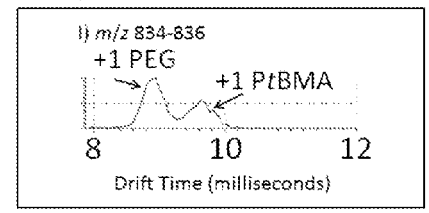
FIG. 78C
FIG. 78B
FIG. 78A

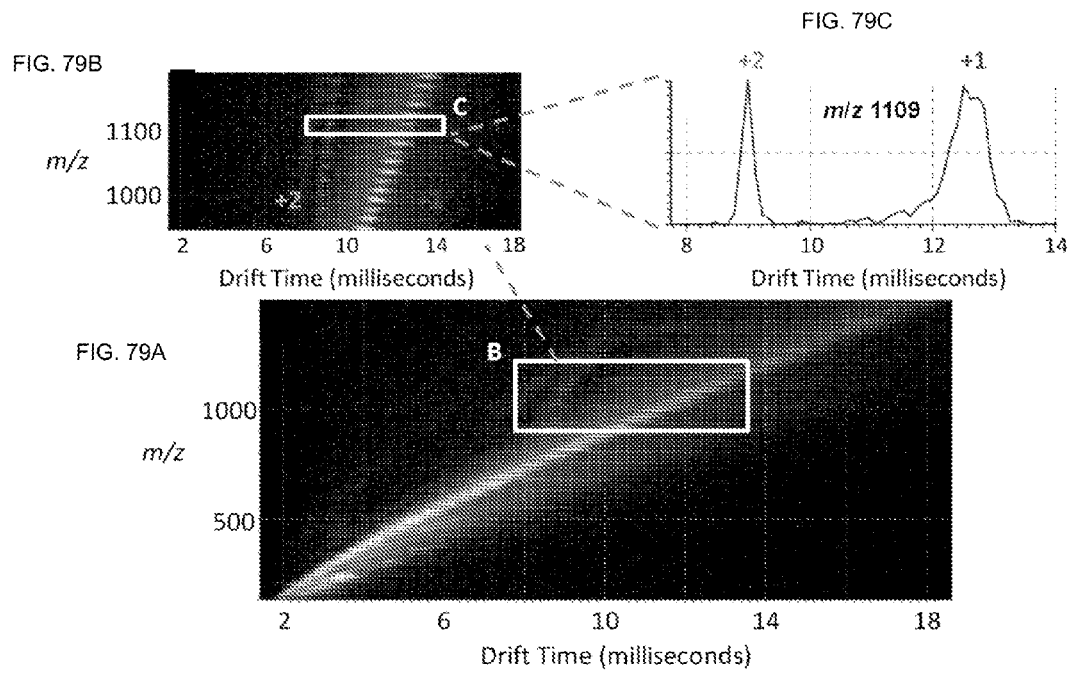

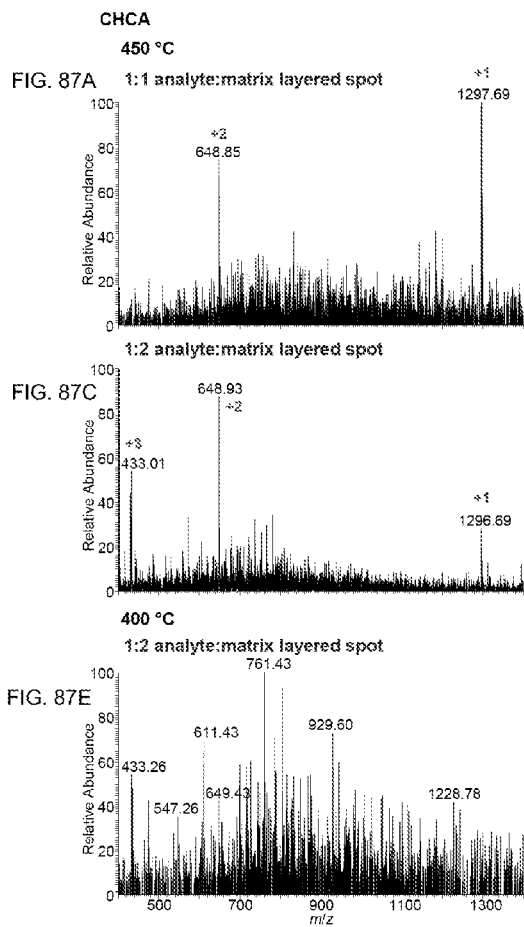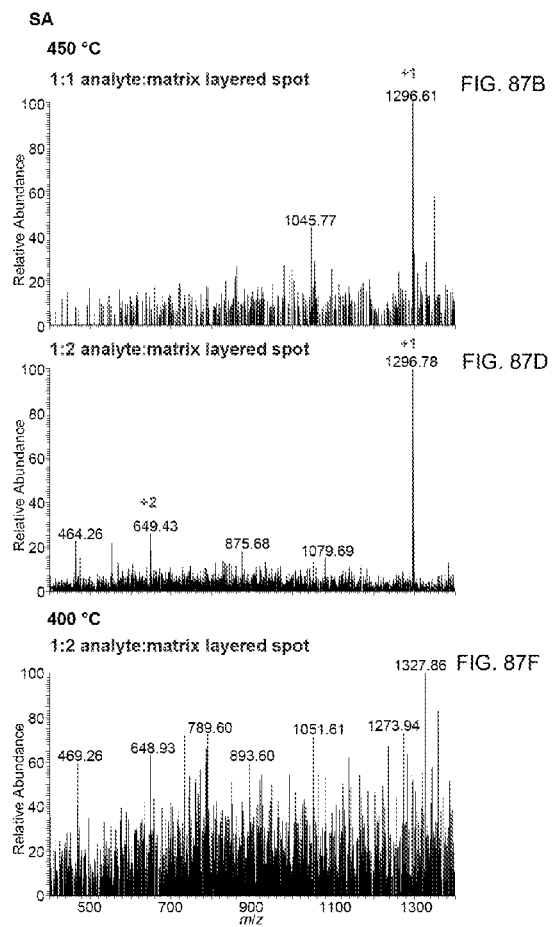

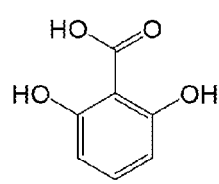
2,6-Dihydroxybenzoic acid
m.p. 165 °C
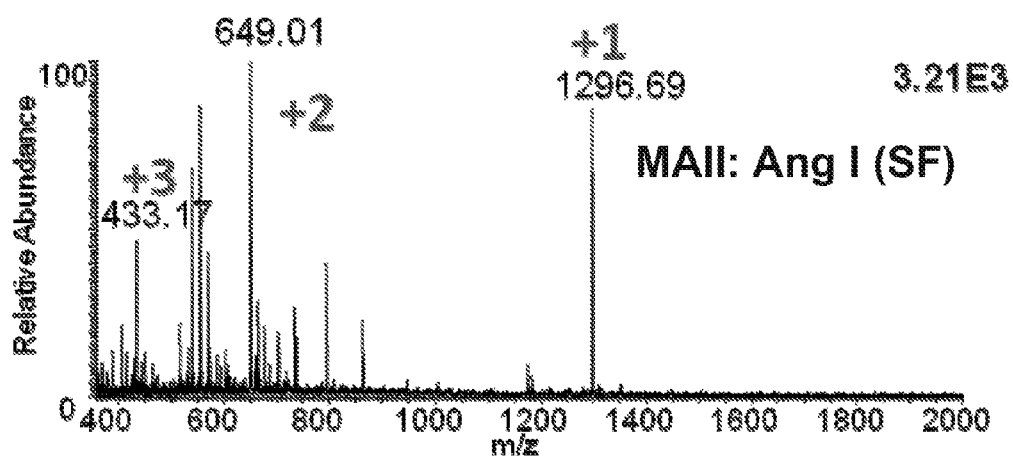
FIG. 90

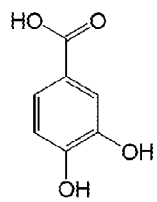
3,4-Dihydroxybenzoic acid
m.p. 197-200 °C
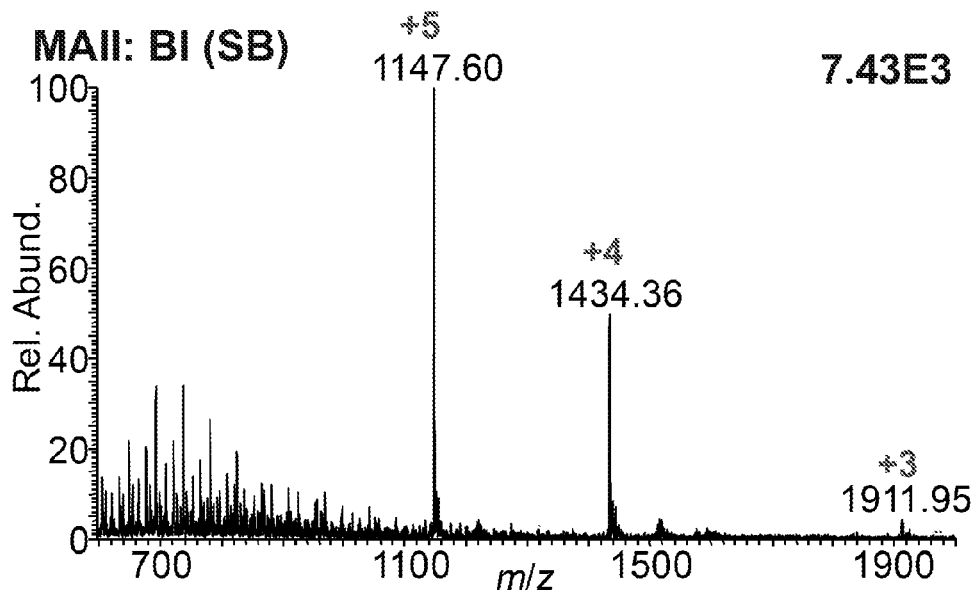
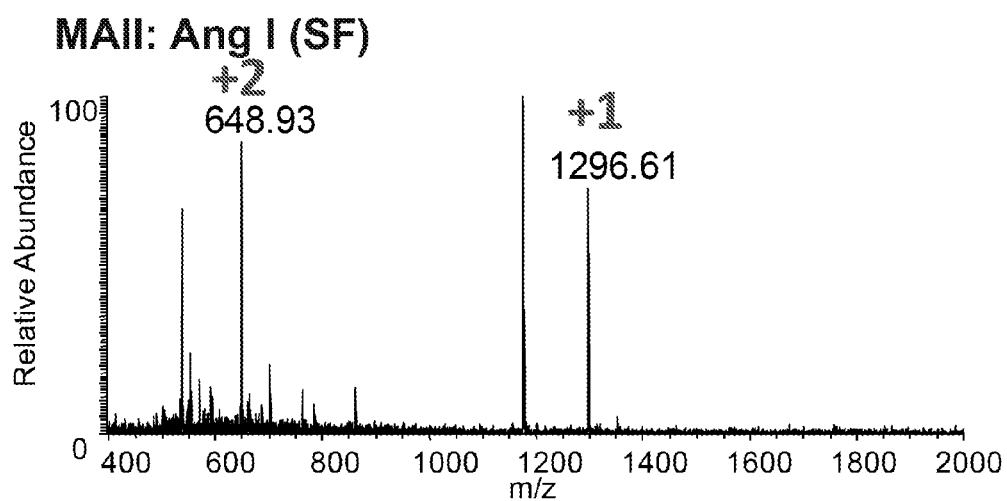
FIG. 91

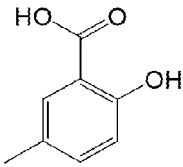
5-Methylsalicylic acid
m.p. 151-155 °C
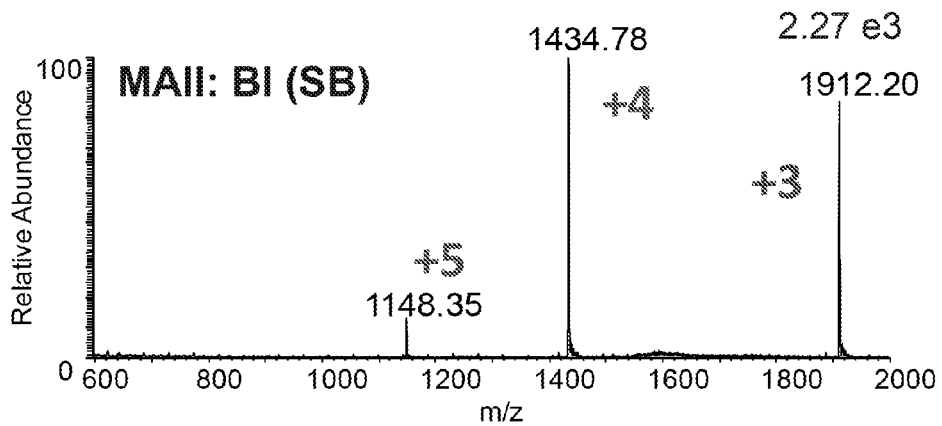
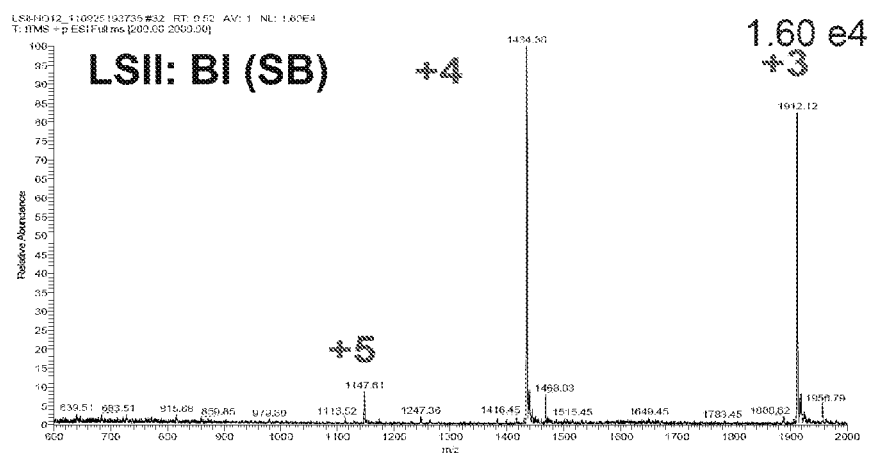
FIG. 92

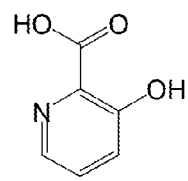
3-Hydroxypicolinic
acid m.p. 208-212 °C
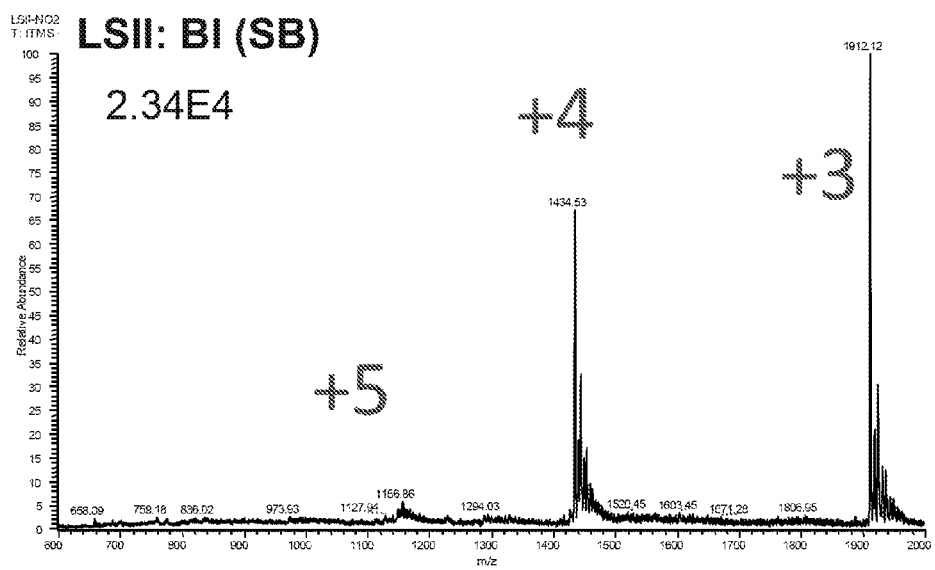
FIG. 93

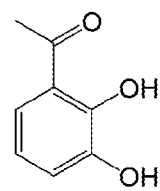
2,3-Dihydroxyacetophenone
m.p. 96-99 °C
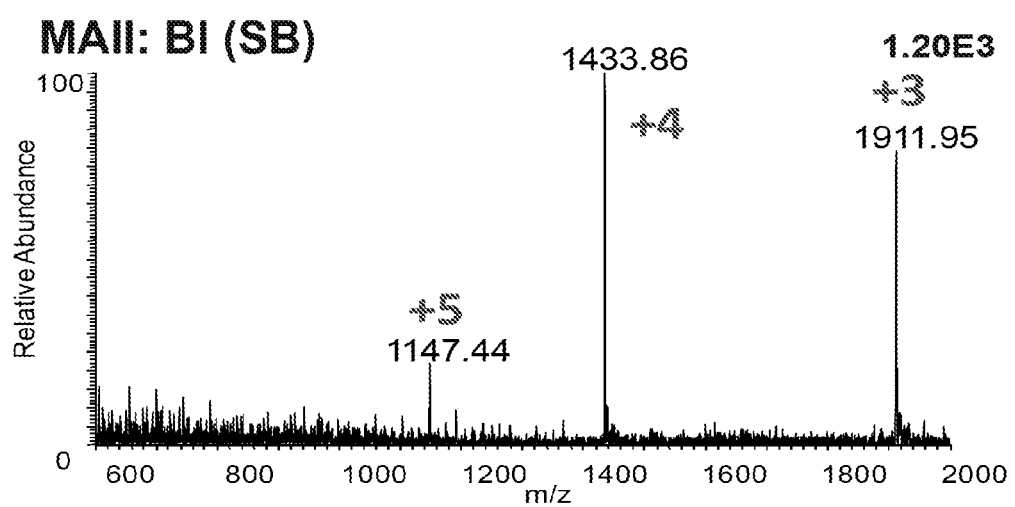
FIG. 94

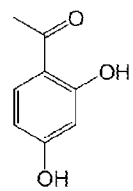
2,4-Dihydroxyacetophenone
m.p. 143-147°C
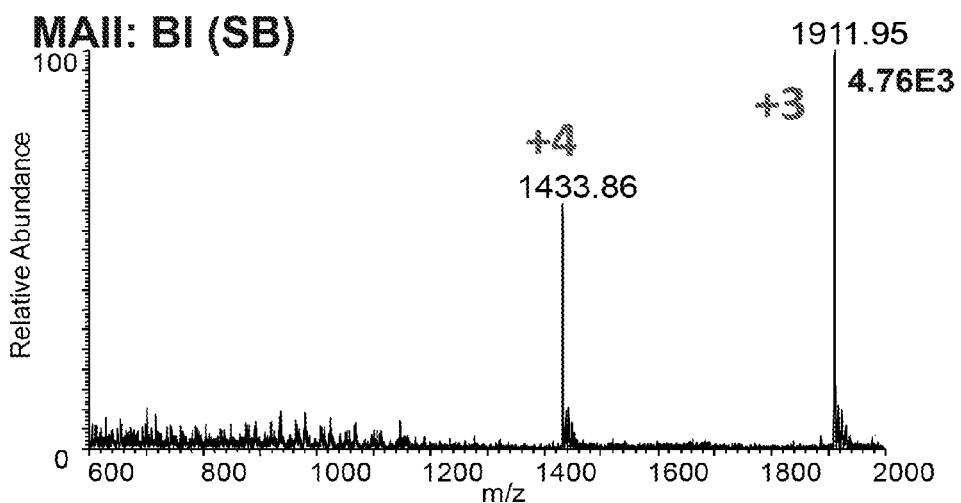
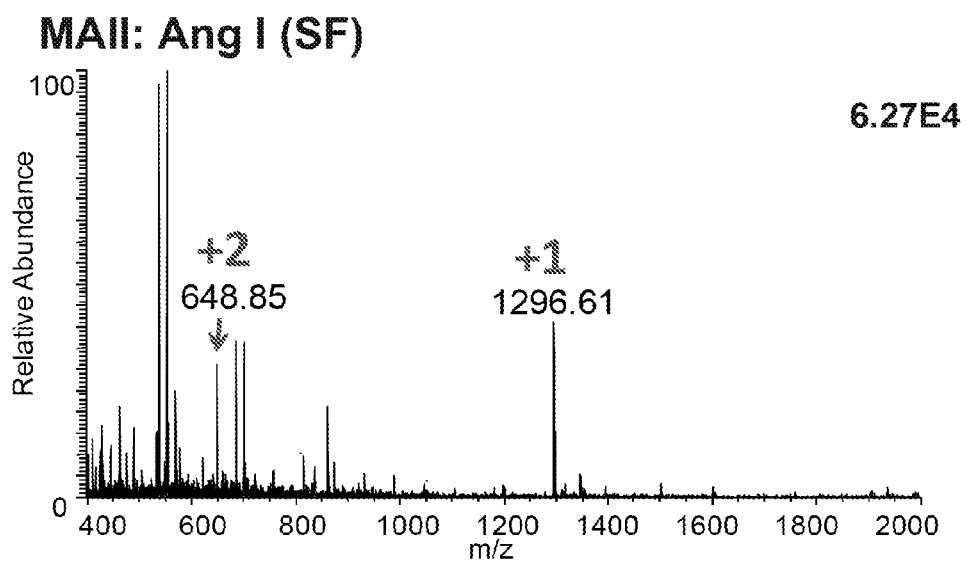
FIG. 95

2,4,6-Trihydroxyacetophenone
m.p. 218-222 °C
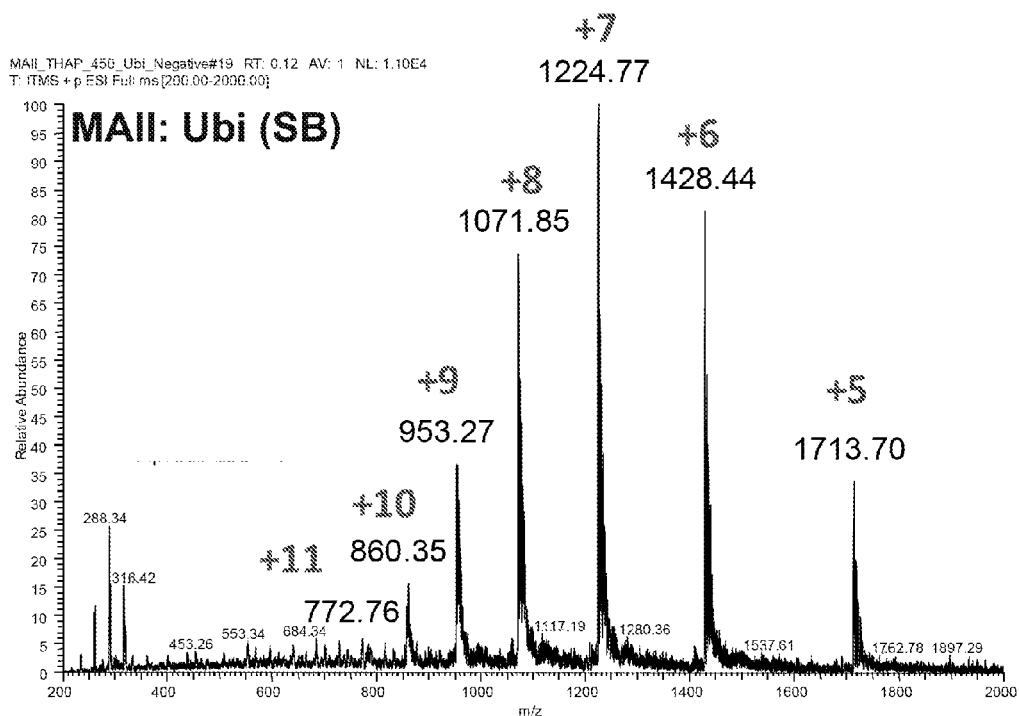
FIG. 96

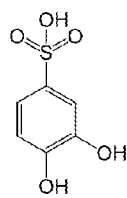
3,4-dihydroxybenzenesulfonic acid
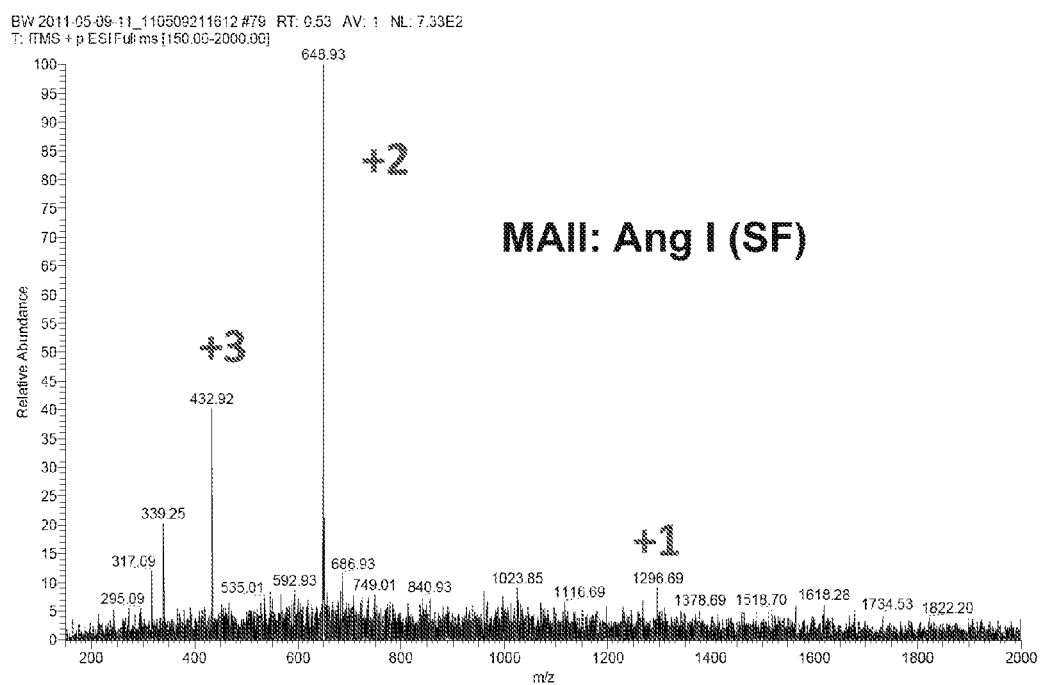
FIG. 97

4-Nitrocatechol
m.p. 173-177 °C
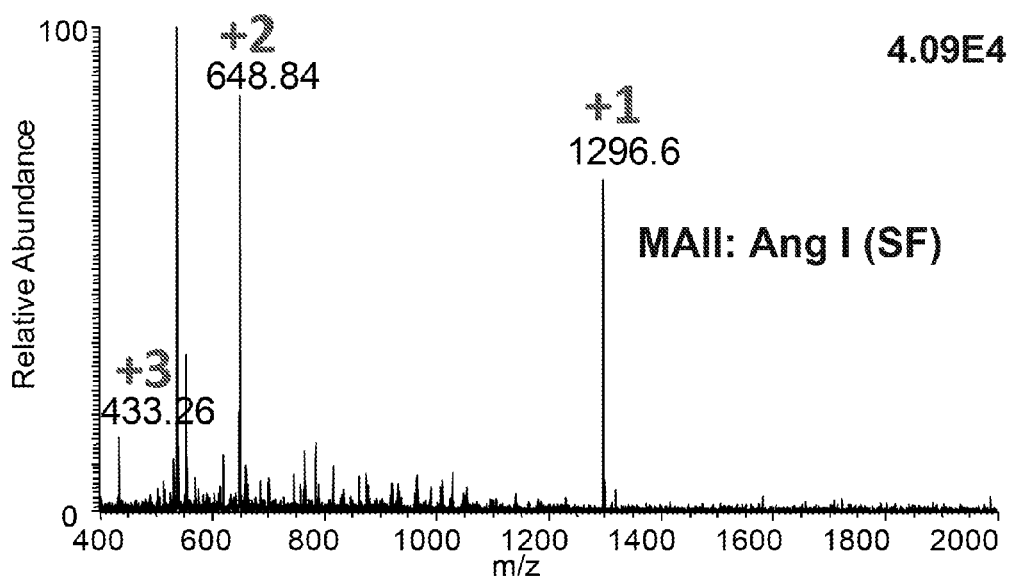
FIG. 98

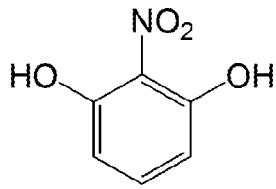
2-Nitroresorcinol
m.p. 81-83 °C
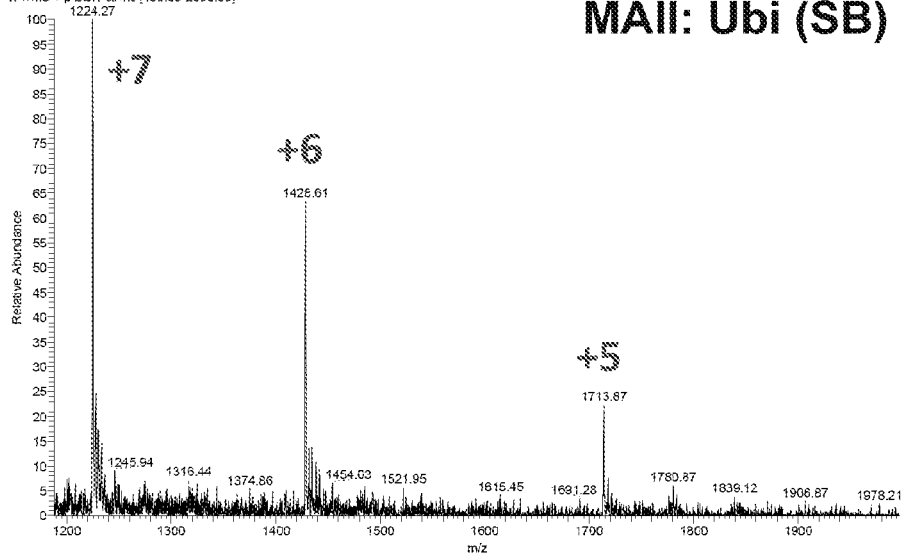
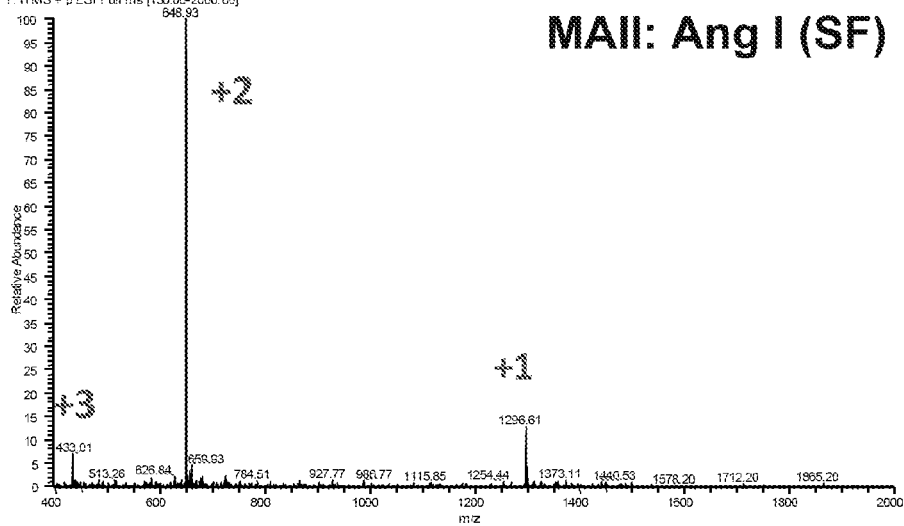
FIG. 99

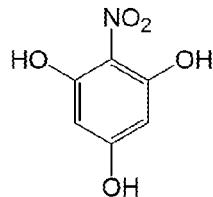
2-Nitrophloroglucinol
m.p. 189-193 °C
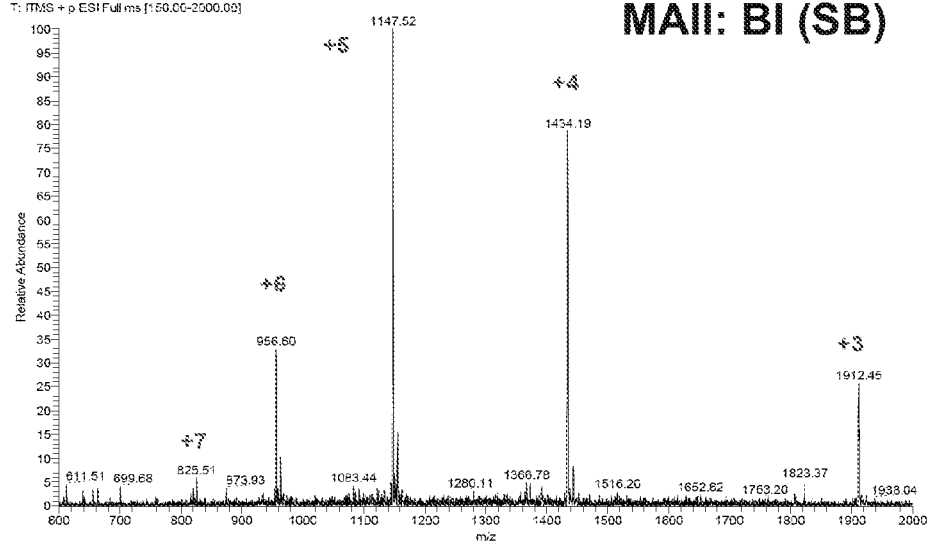
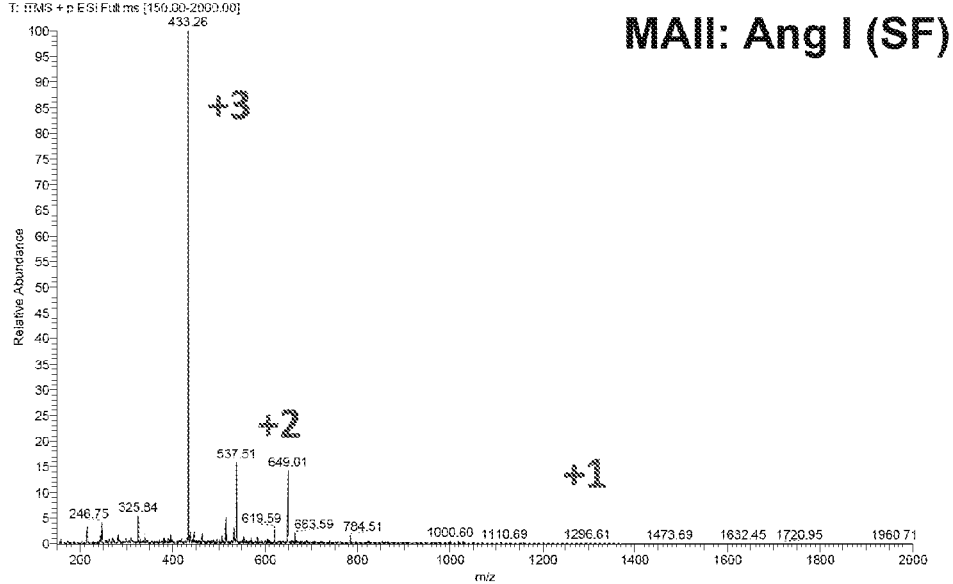
FIG. 100

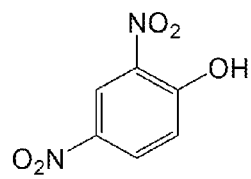
2,4-Dinitrophenol
m.p. 108-112 °C
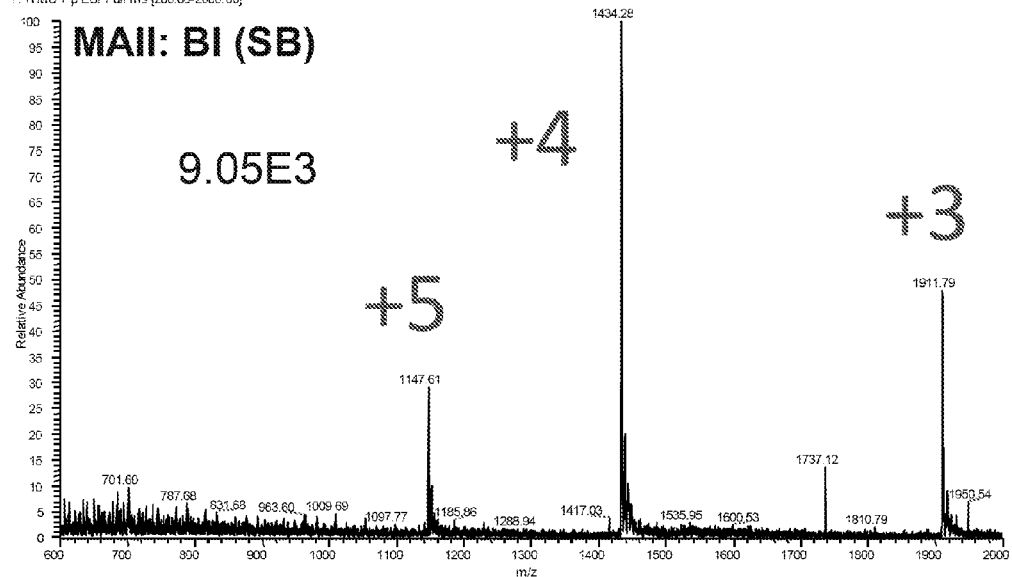
FIG. 102

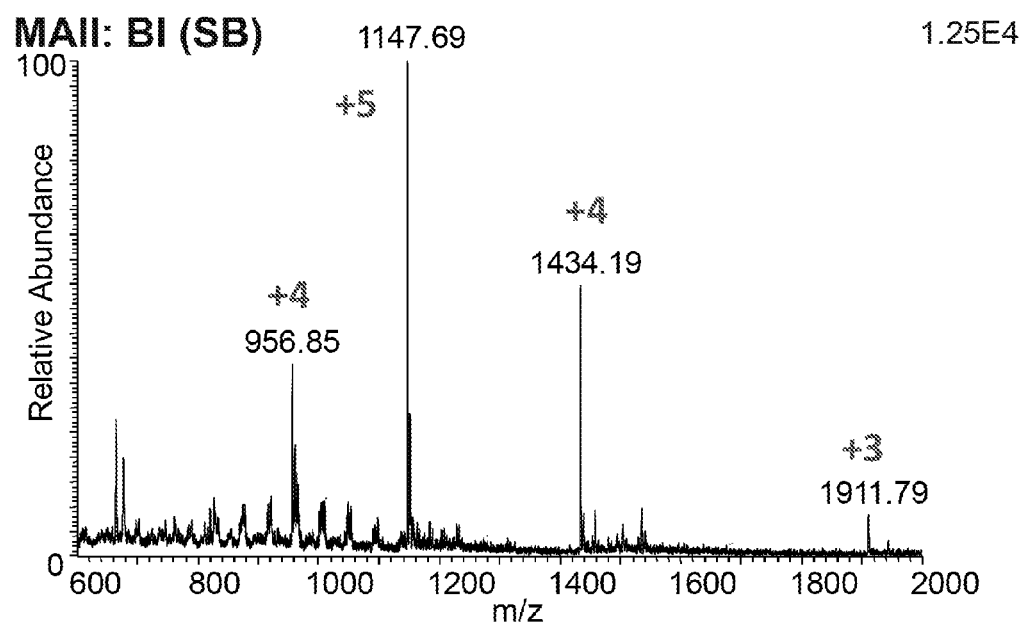
FIG. 103

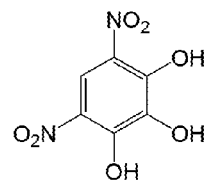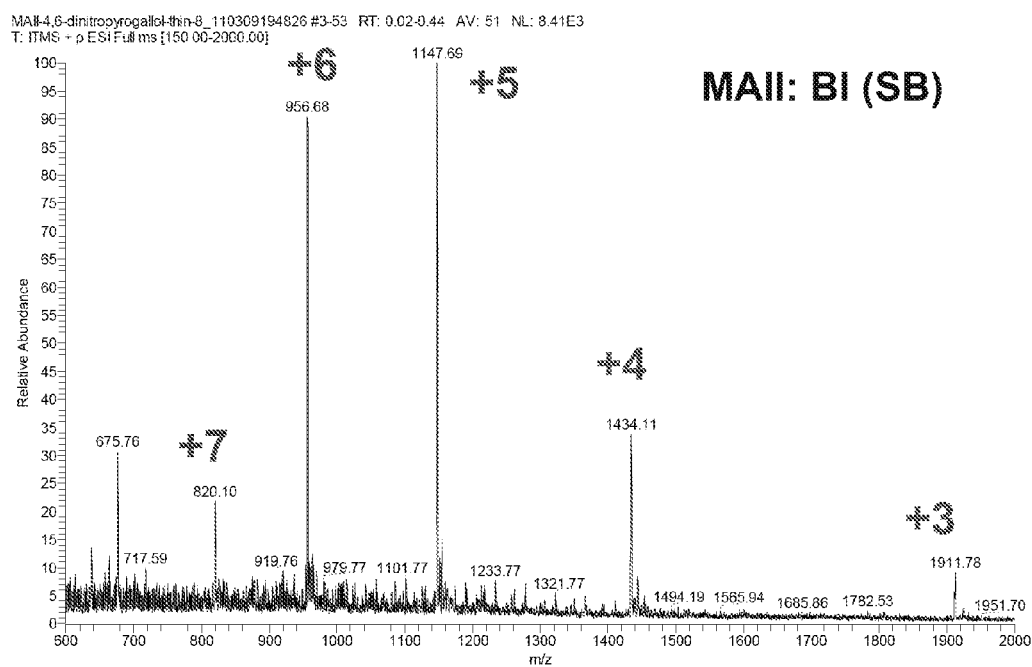
FIG. 104

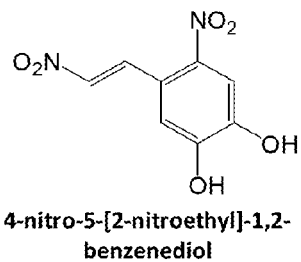
4-nitro-5-[2-nitroethyl]-1,2-benzenediol
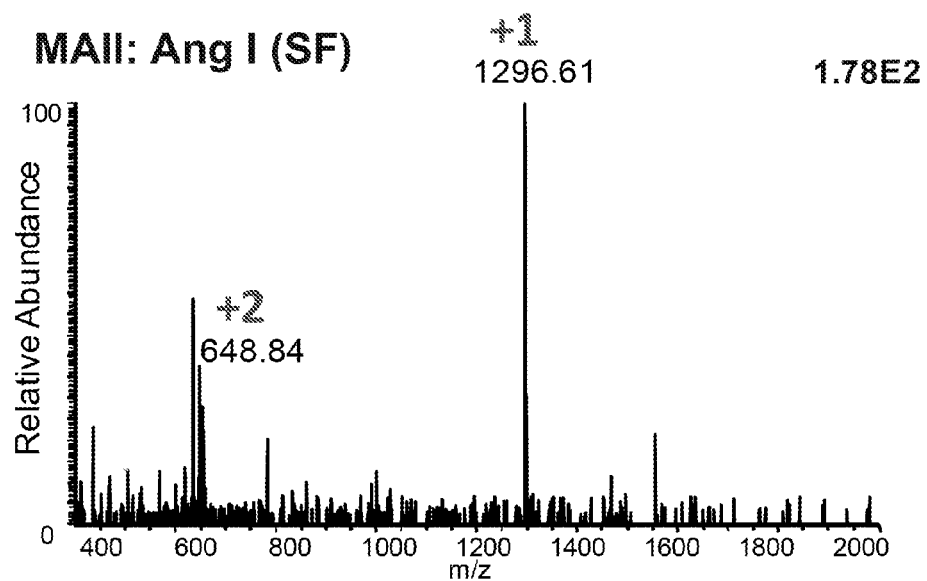
FIG. 105

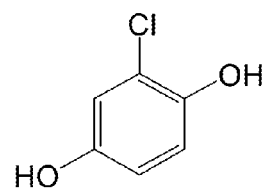
Chlorohydroquinone
m.p. 263 °C
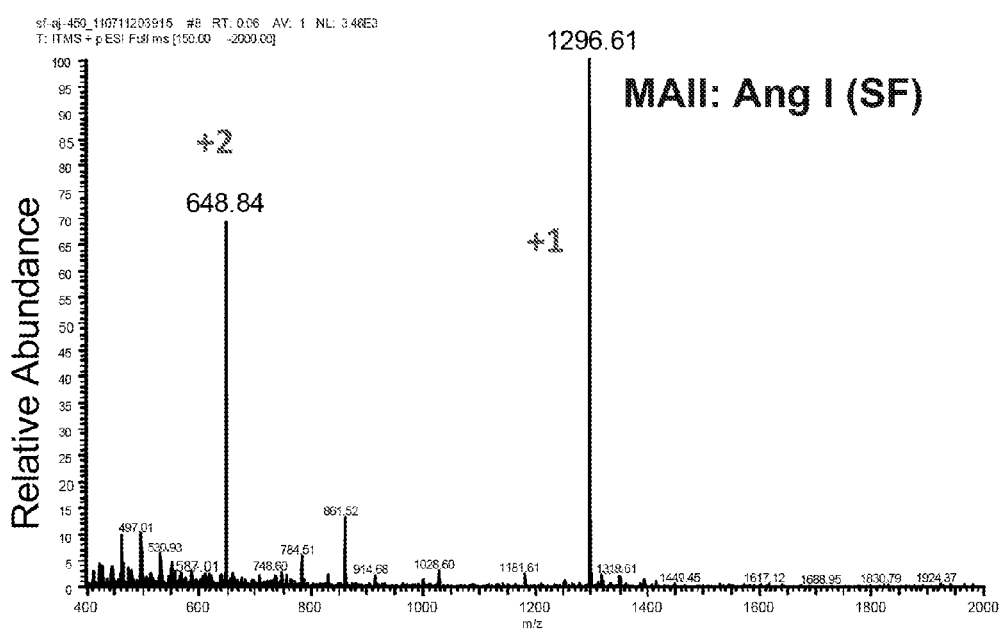
FIG. 106

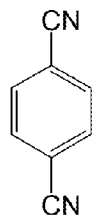
1,4-Dicyanobenzene
m.p. 223-226 °C
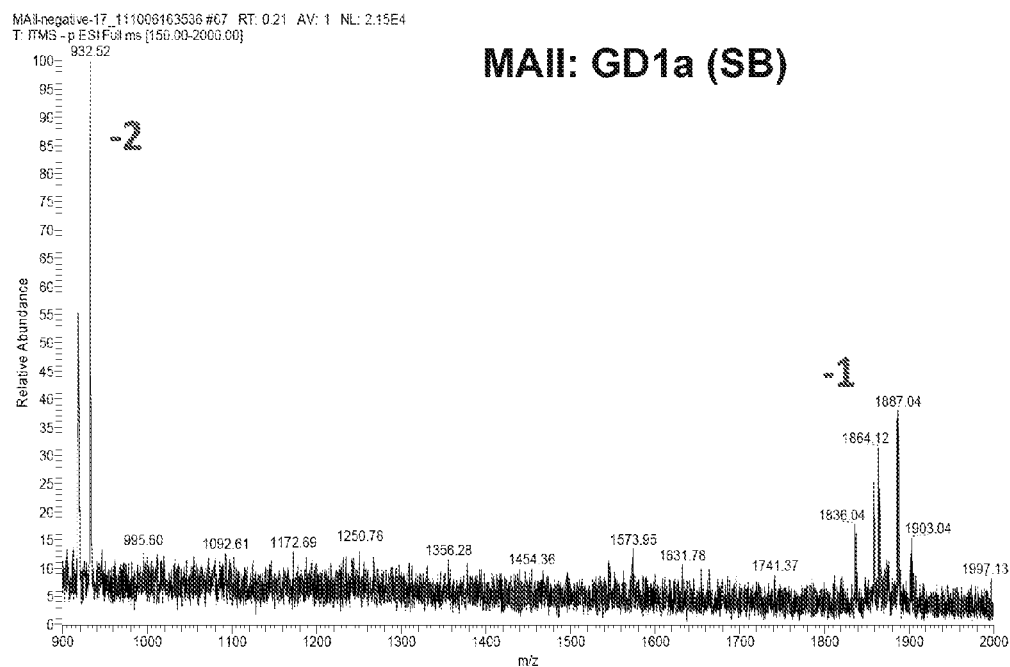
FIG. 107

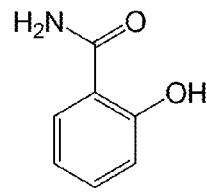
Salicylamide
m.p. 140-144 °C
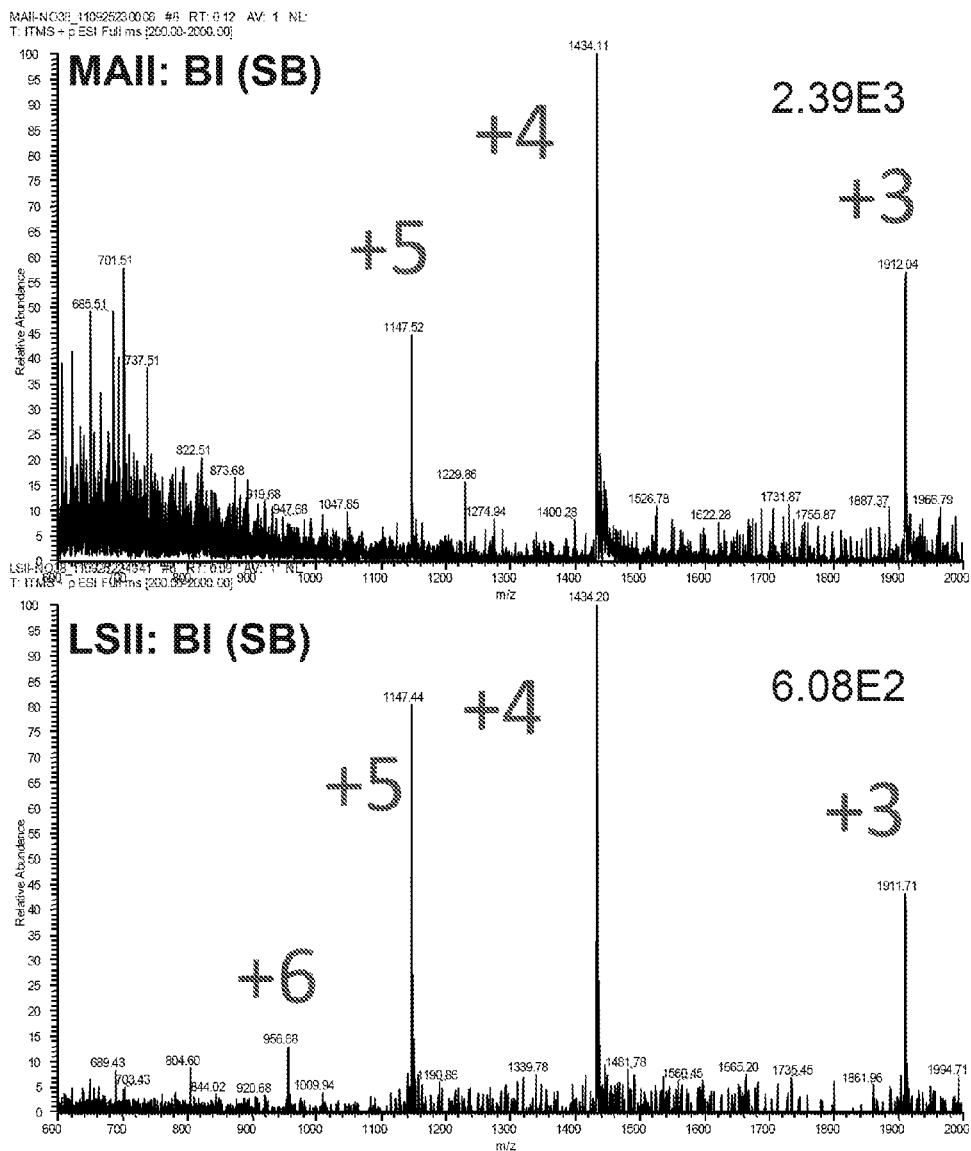
FIG. 108

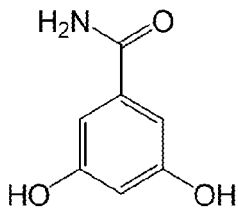
3,5-Dihydroxybenzamide
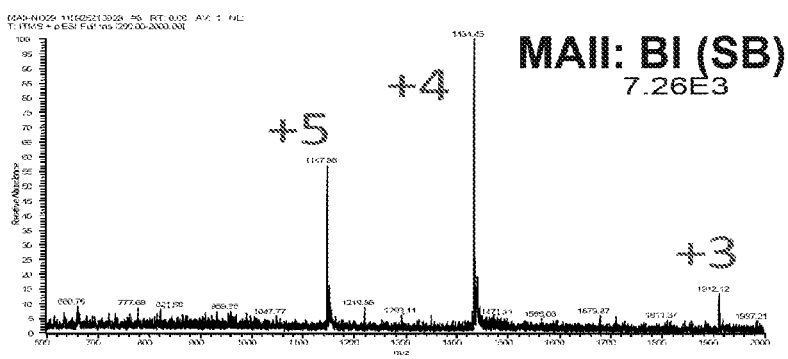
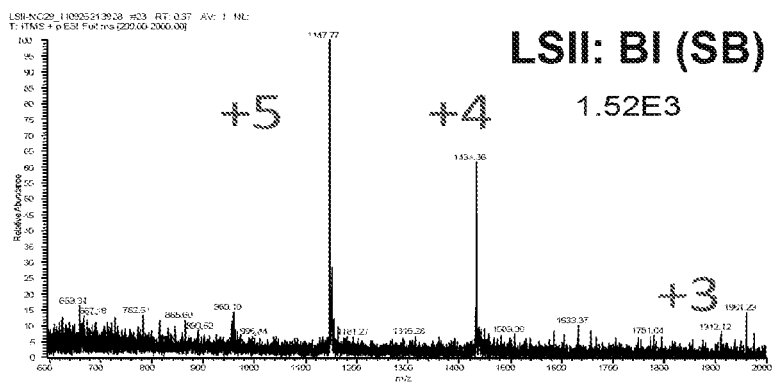
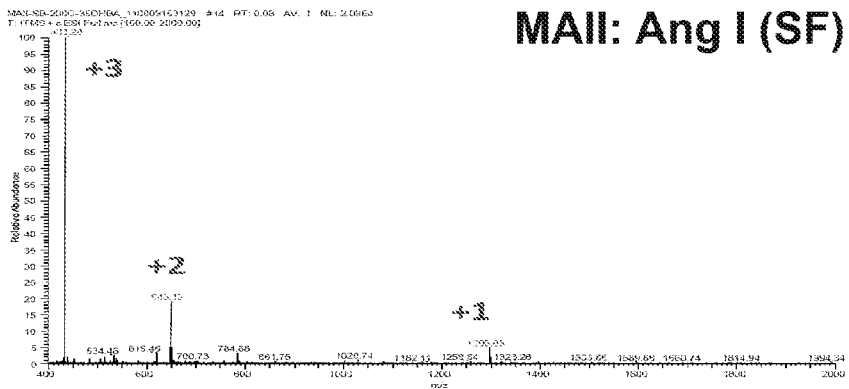
FIG. 110

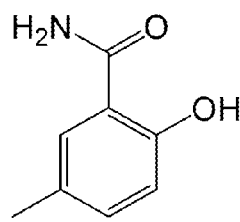
2-Hydroxy-5-methylbenzamide
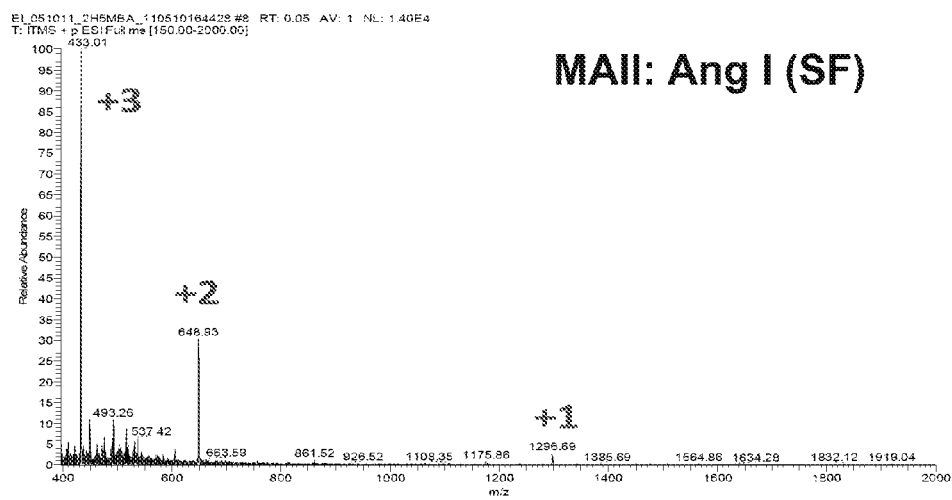
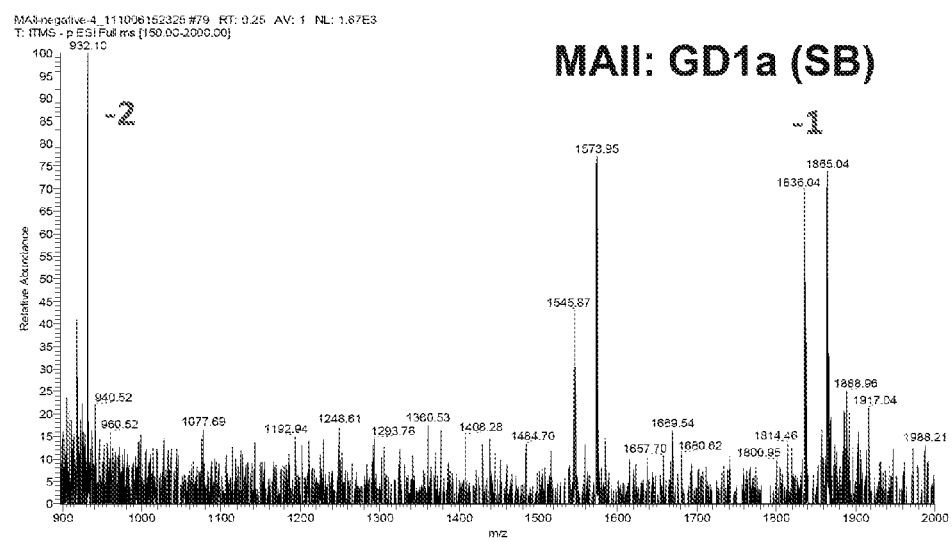
FIG. 111

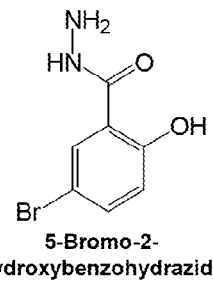
5-Bromo-2-hydroxybenzohydrazide
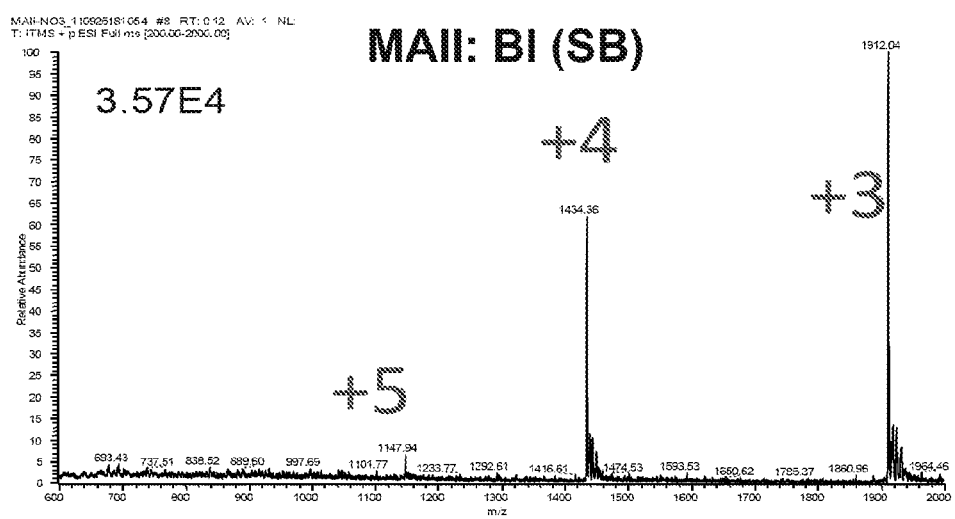
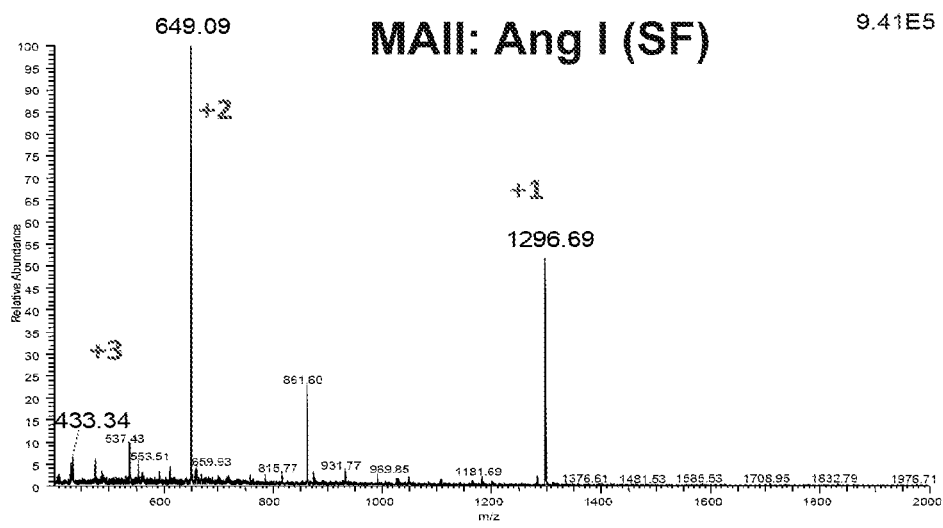
FIG. 112

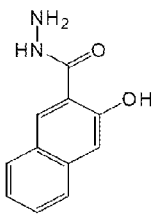
3-Hydroxy-2-naphthoic hydrazide
m.p. 205-208 °C
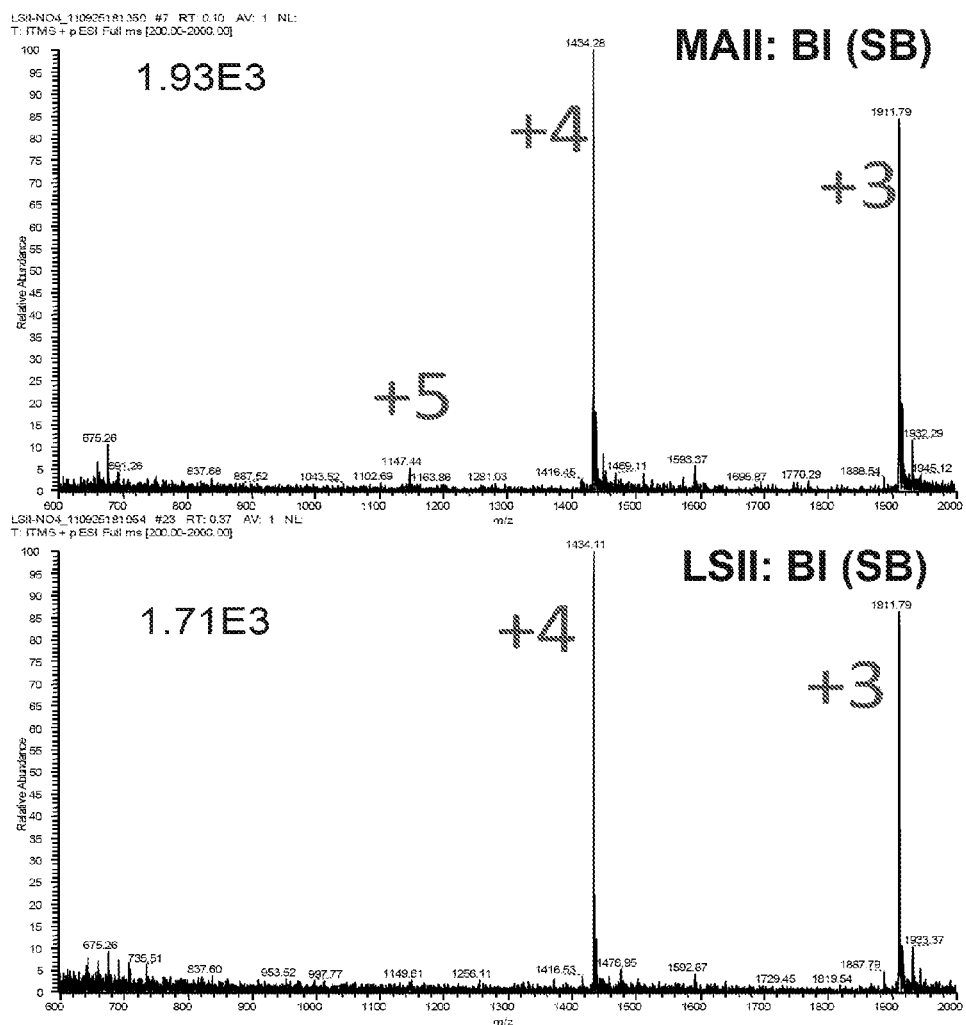
FIG. 113

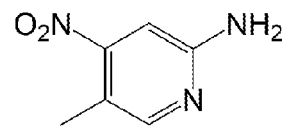
2-Amino-4-methyl-3-nitropyridine
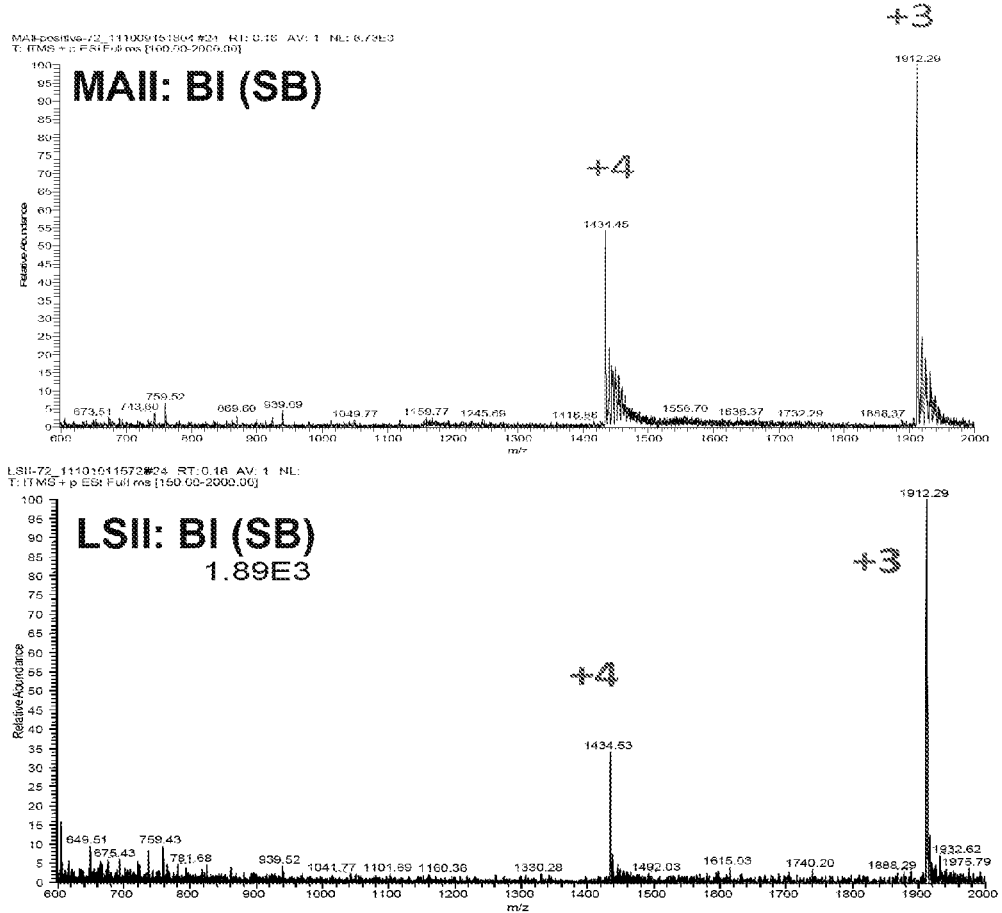
FIG. 115

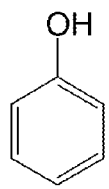
Phenol
m.p. 40-43 °C
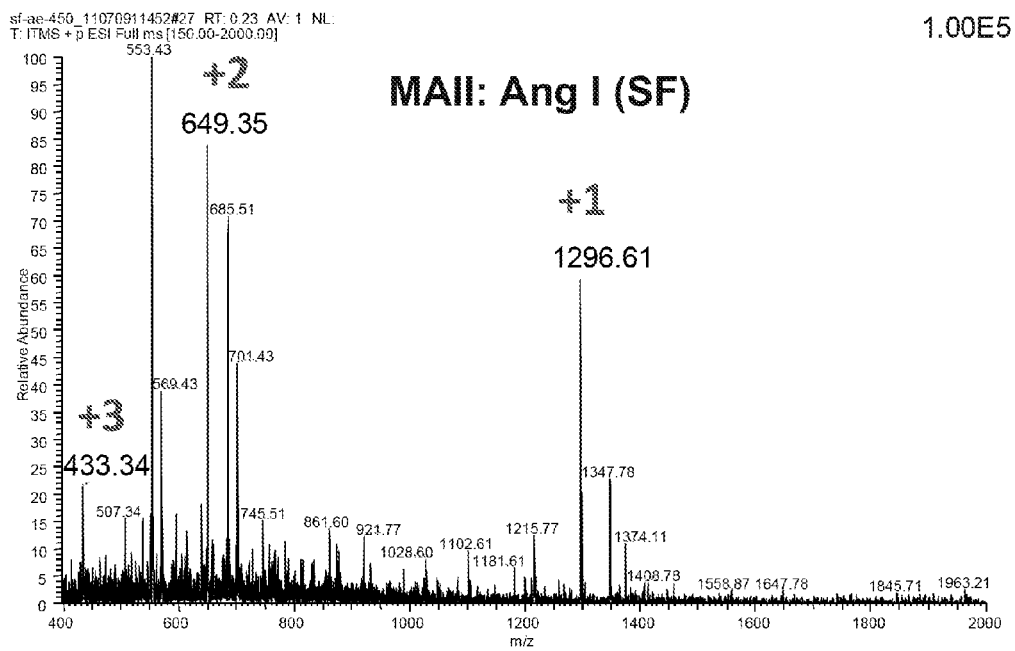
FIG. 116

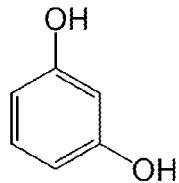
Resorcinol
m.p. 109-112 °C
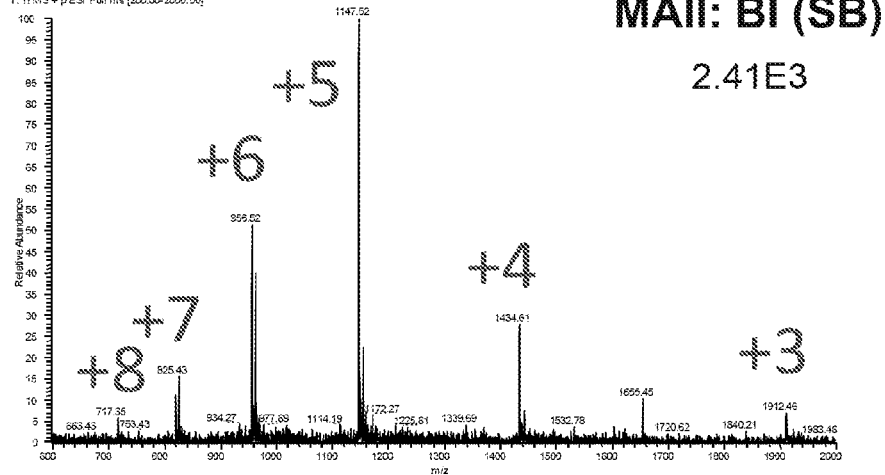
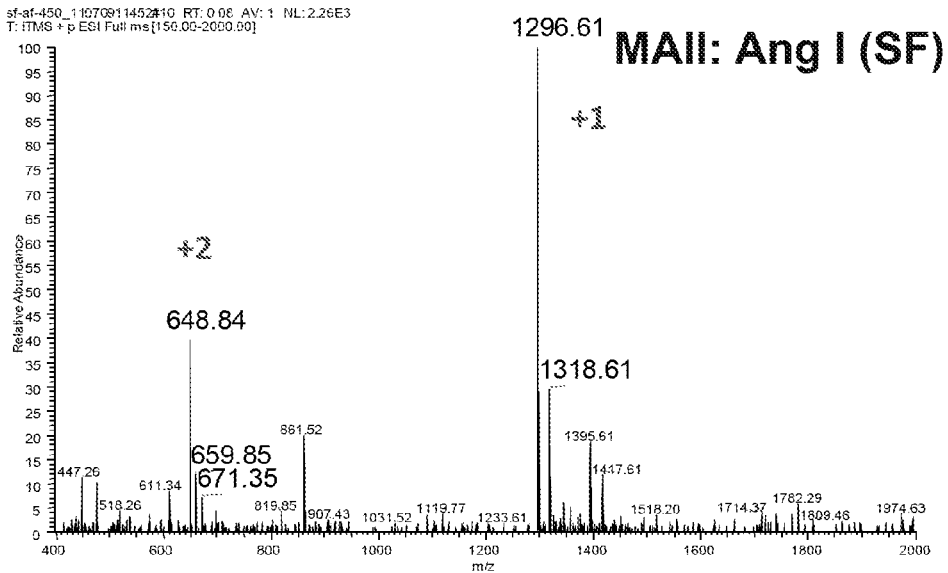
FIG. 117

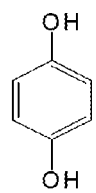
Hydroquinone
m.p. 171-173 °C
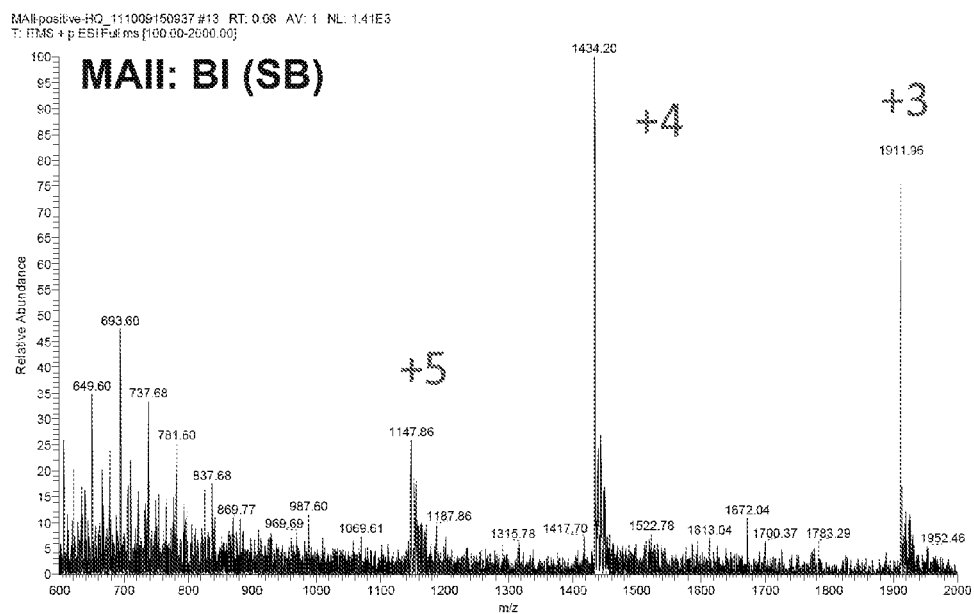
FIG. 118

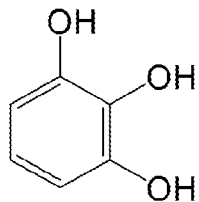
Pyrogallol
m.p. 131-135 °C
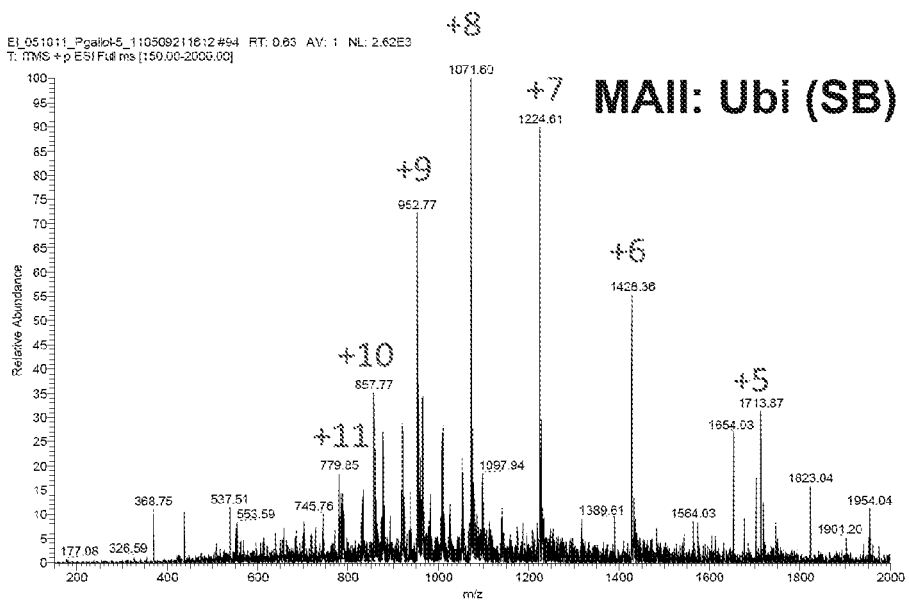
MAII: Ubi (SB)
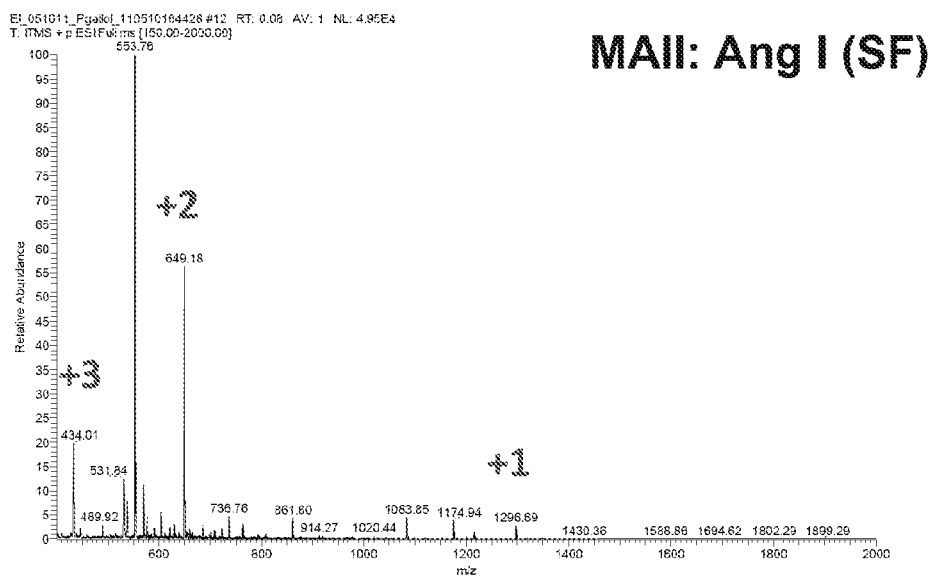
MAII: Ang I (SF)
FIG. 120

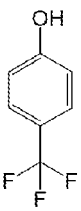
4-Trifluoromethyl phenol
m.p. 46-47 °C
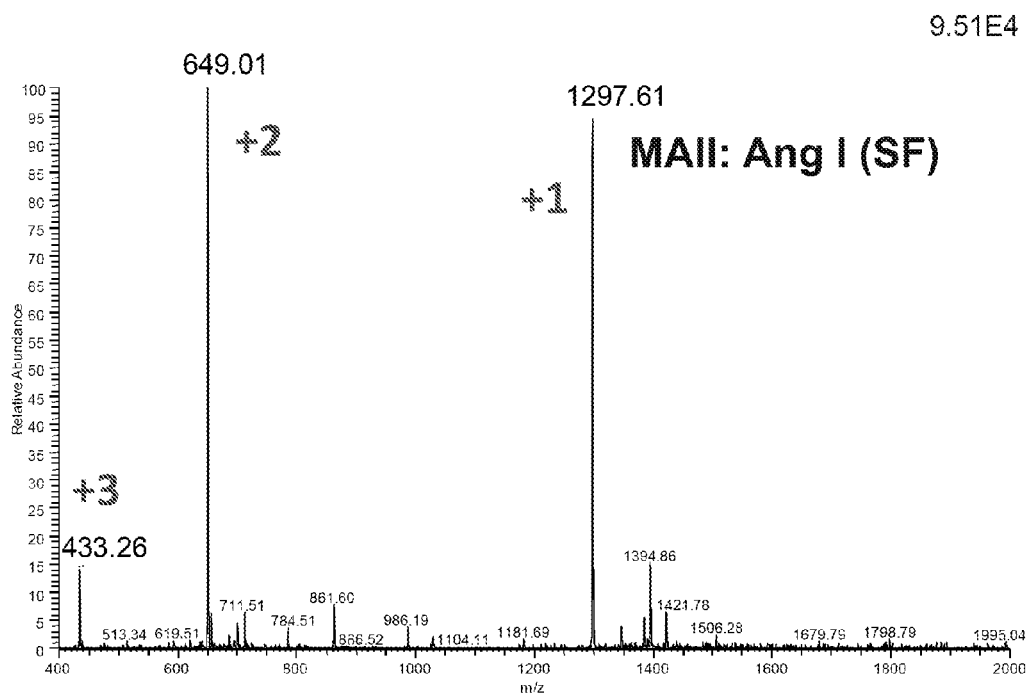
FIG. 121

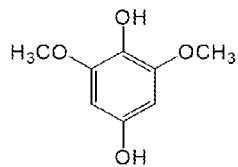
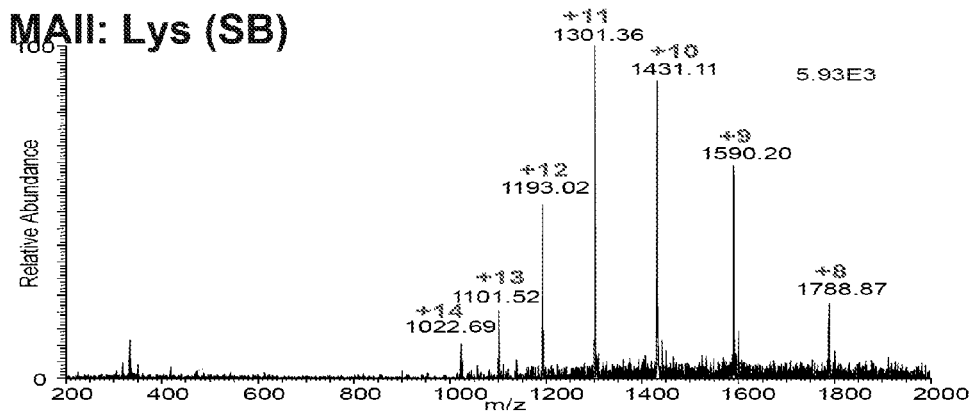
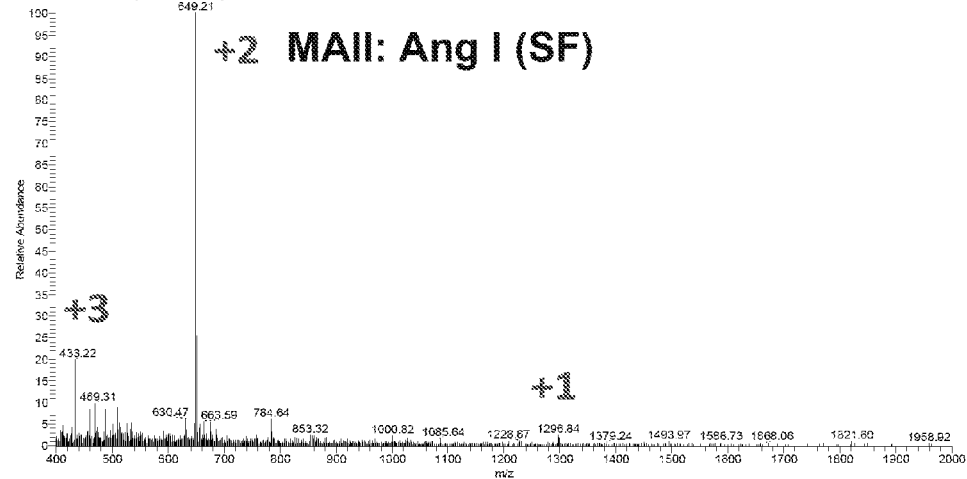
FIG. 122

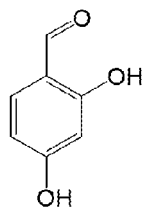
2,4-Dihydroxybenzaldehyde
m.p. 135-137 °C
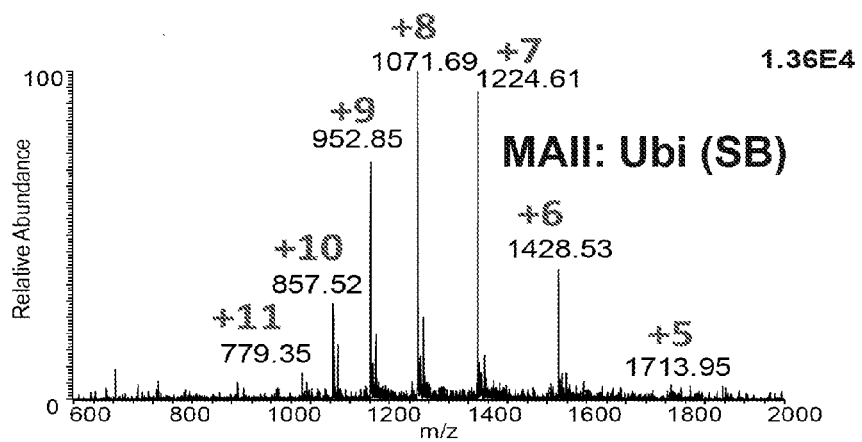
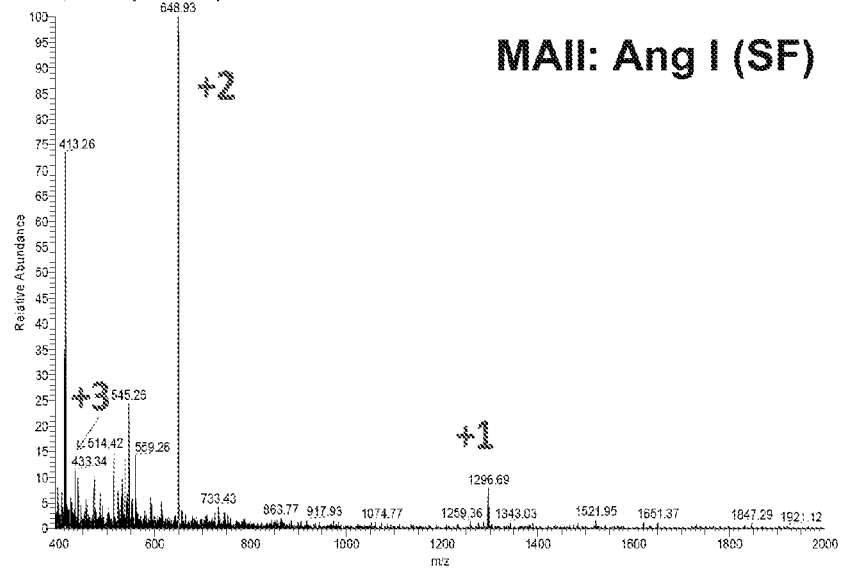
FIG. 123

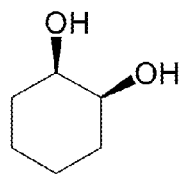
cis-1,2-Cyclohexandediol
m.p. 98-101 °C
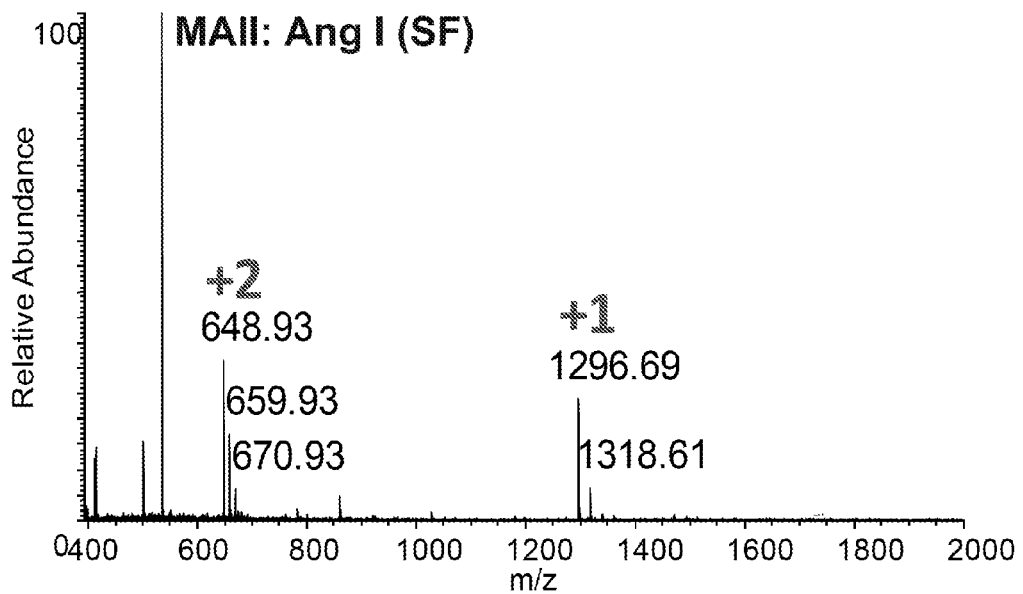
FIG. 124

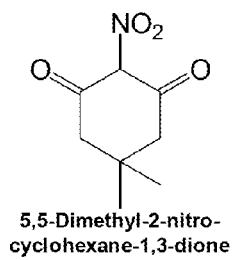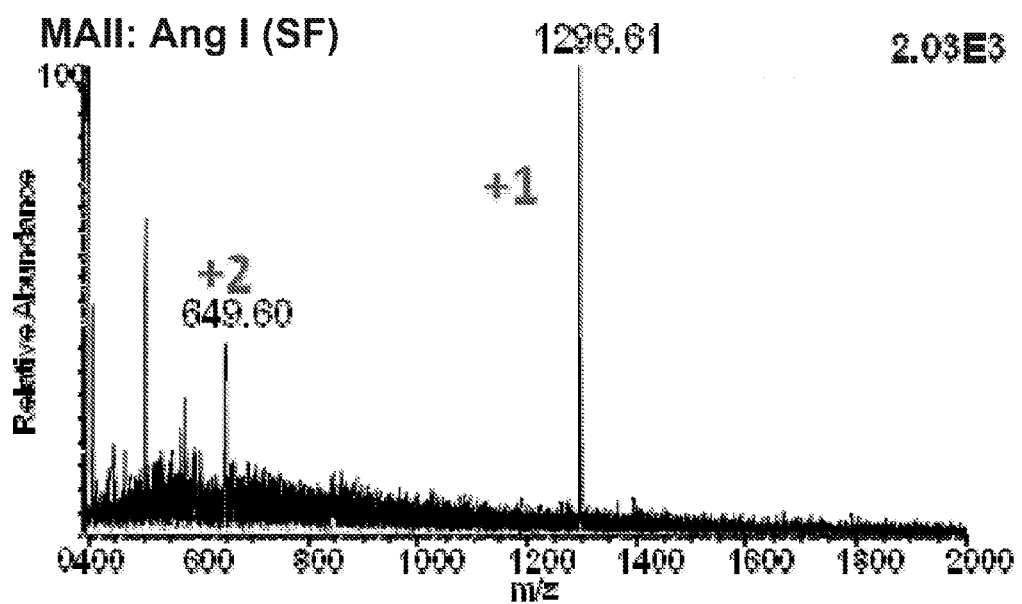
FIG. 125

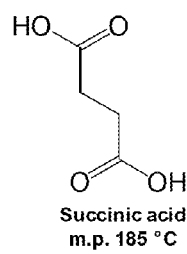
Succinic acid
m.p. 185 °C
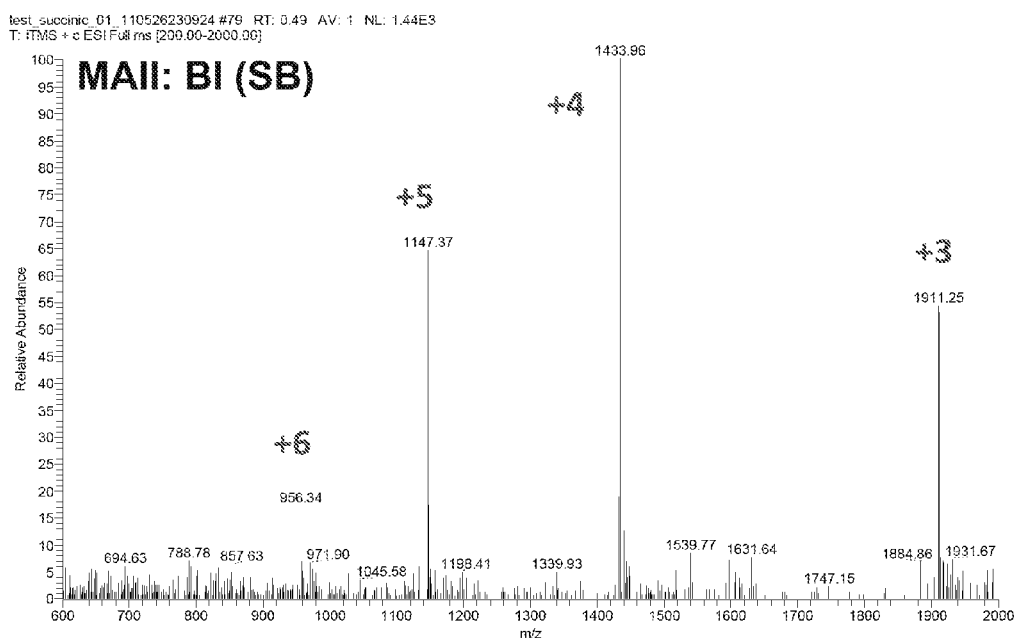
FIG. 126

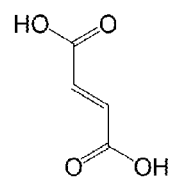
Fumaric acid
m.p. 287 °C
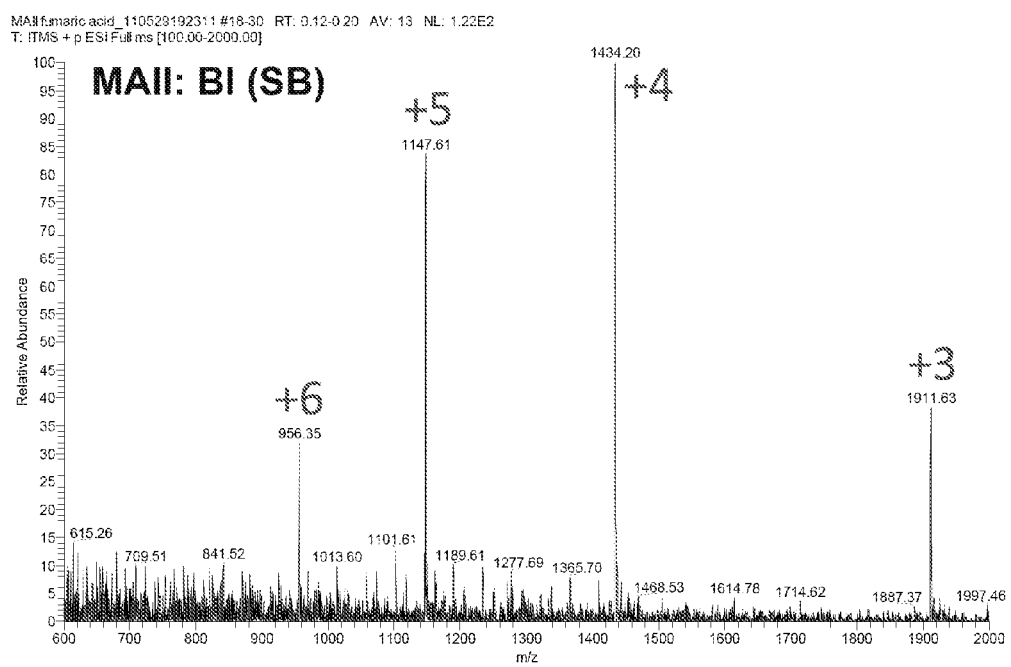
FIG. 127

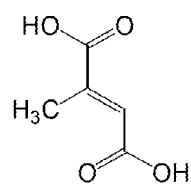
Mesaconic acid
m.p. 200-202 °C
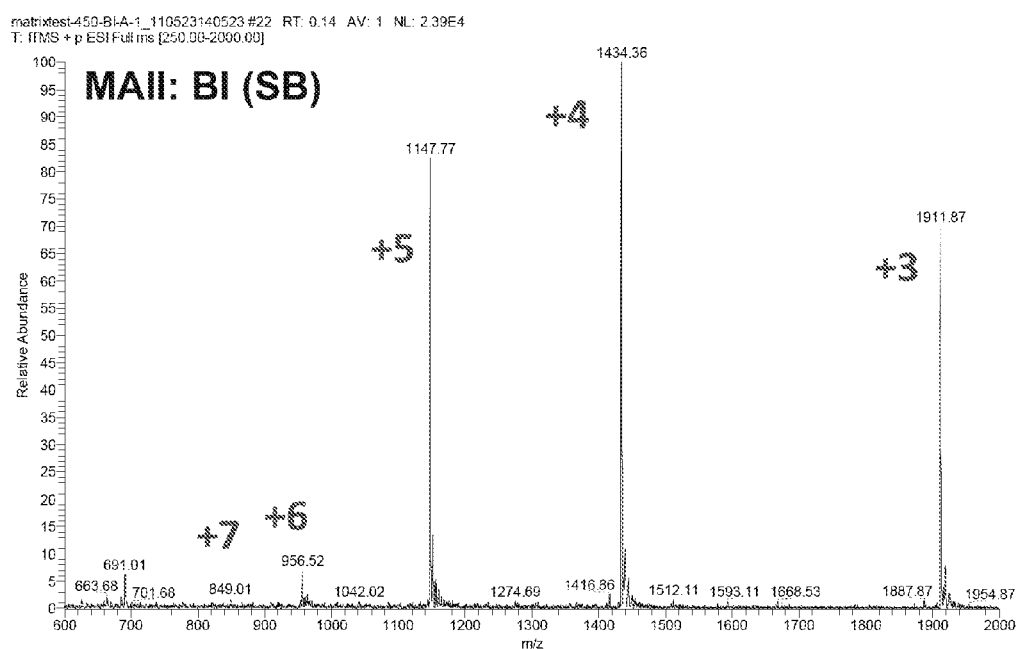
FIG. 128

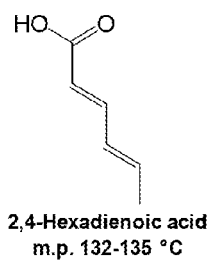
2,4-Hexadienoic acid
m.p. 132-135 °C
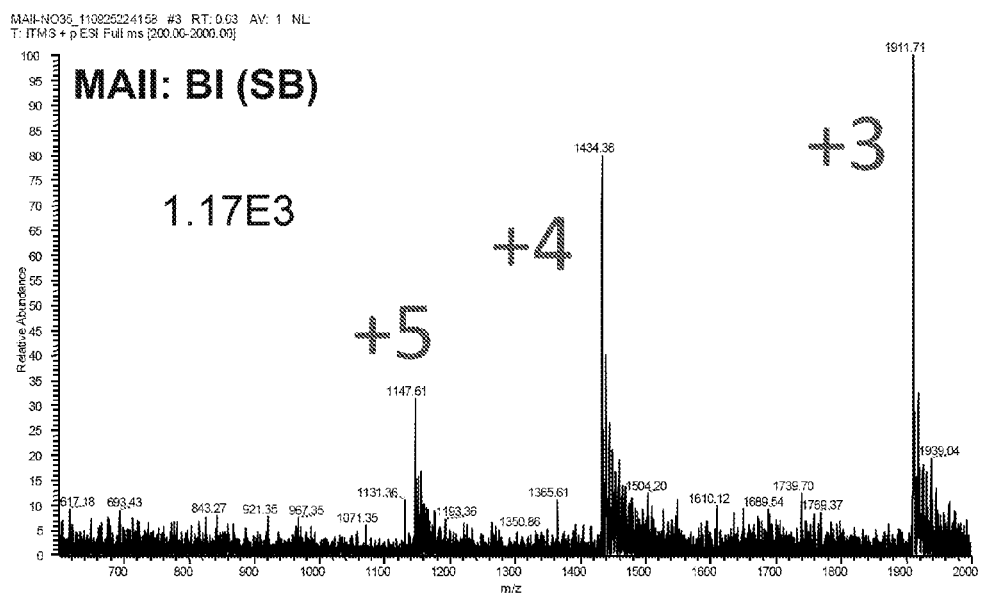
FIG. 129

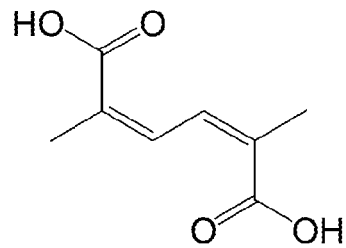
cis,cis-2,5-Dimethylmuconic acid
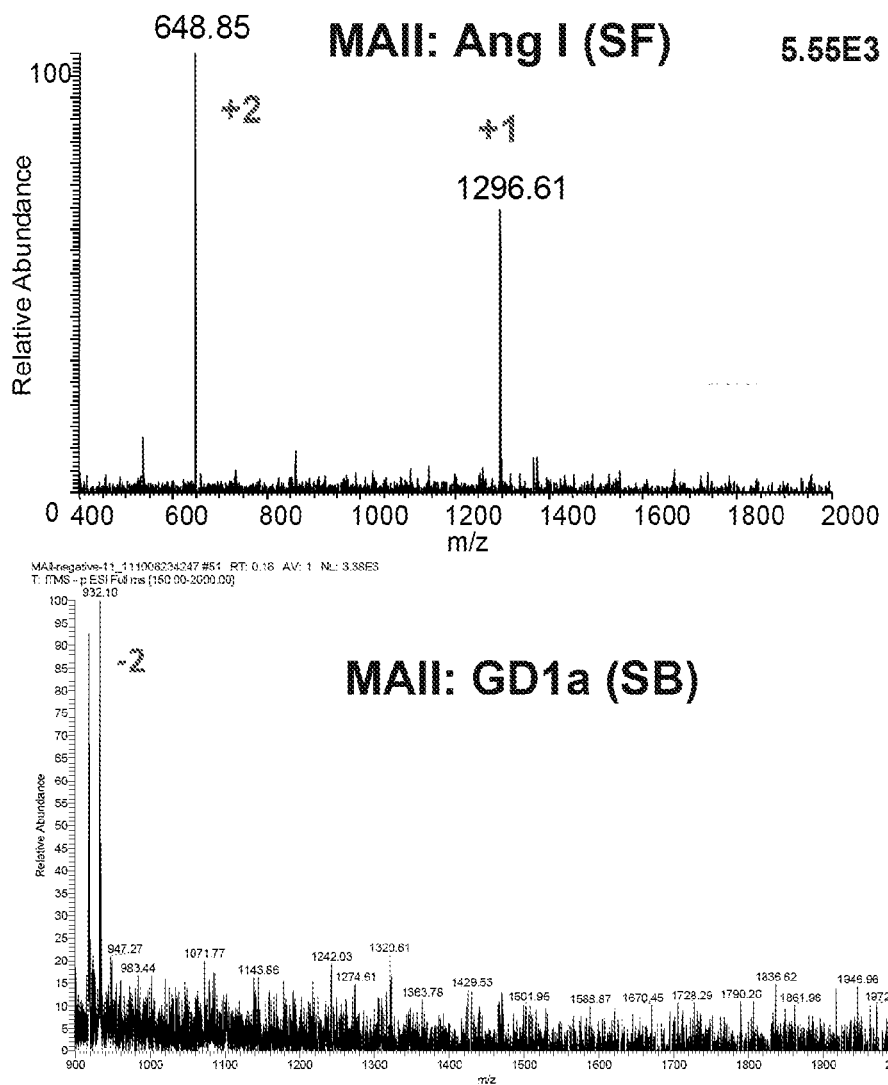
FIG. 130

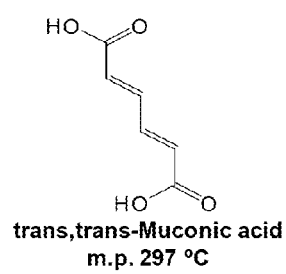
trans,trans-Muconic acid
m.p. 297 °C
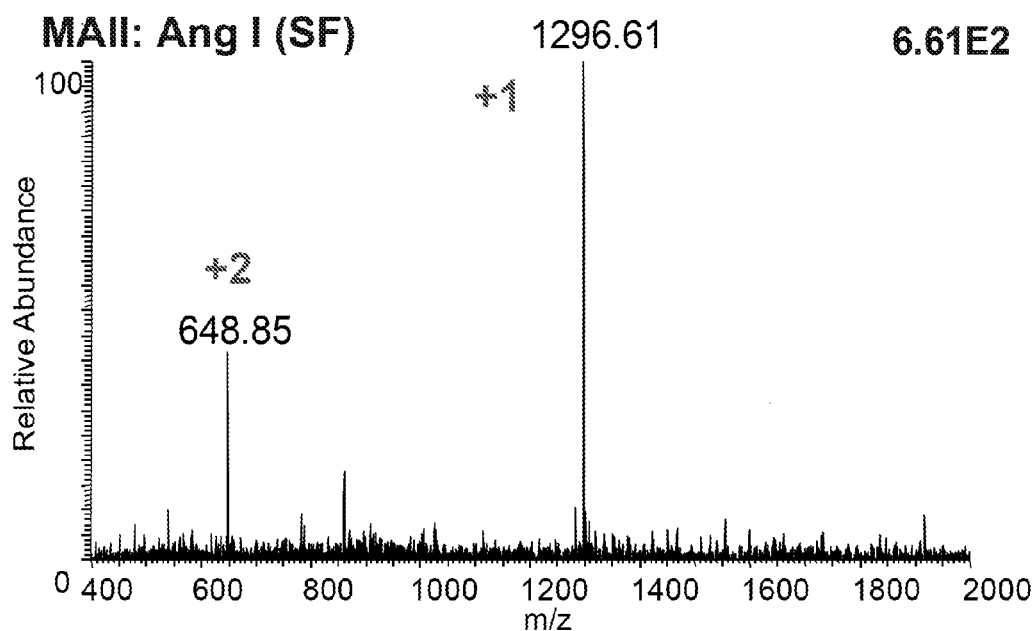
FIG. 131

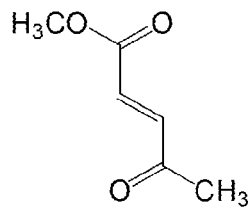
Methyl 4-oxo-2-pentenoate
m.p. 60 °C
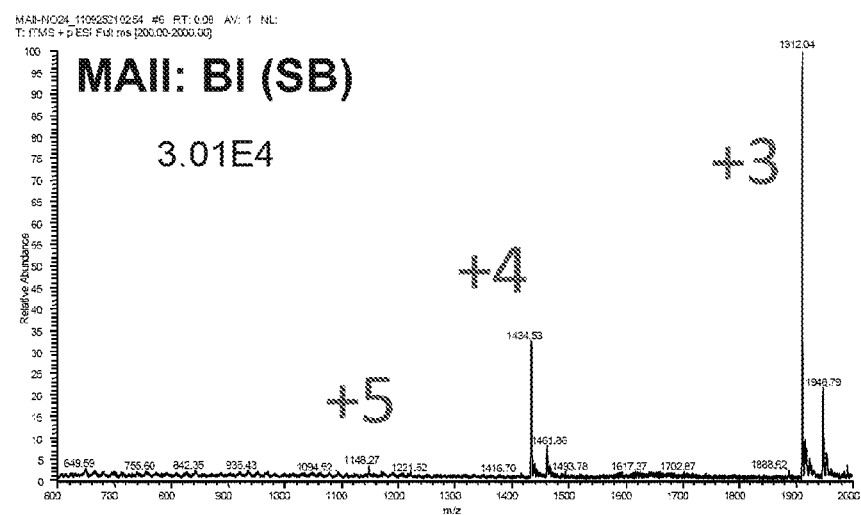
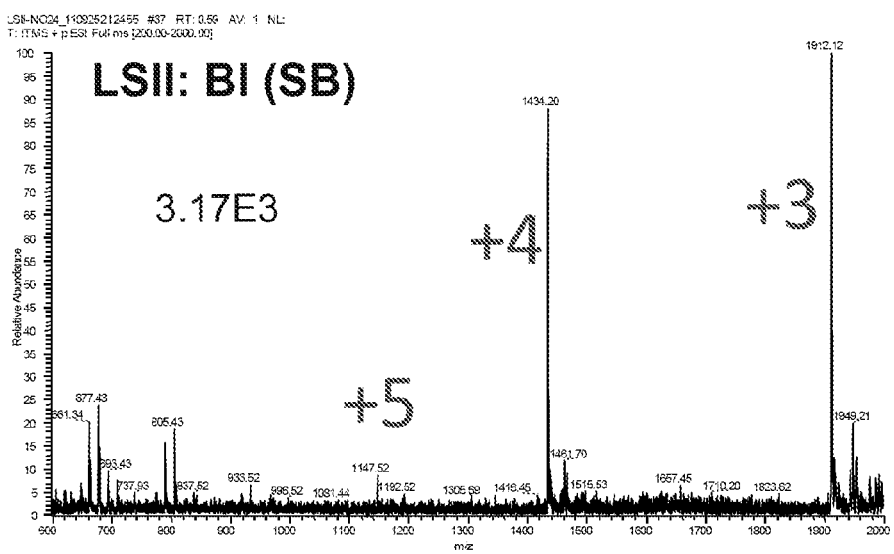
FIG. 132

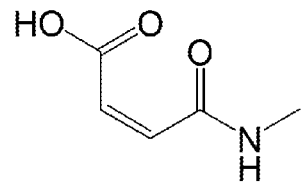
*N*-methylmaleamic acid
m.p. 147-150 °C
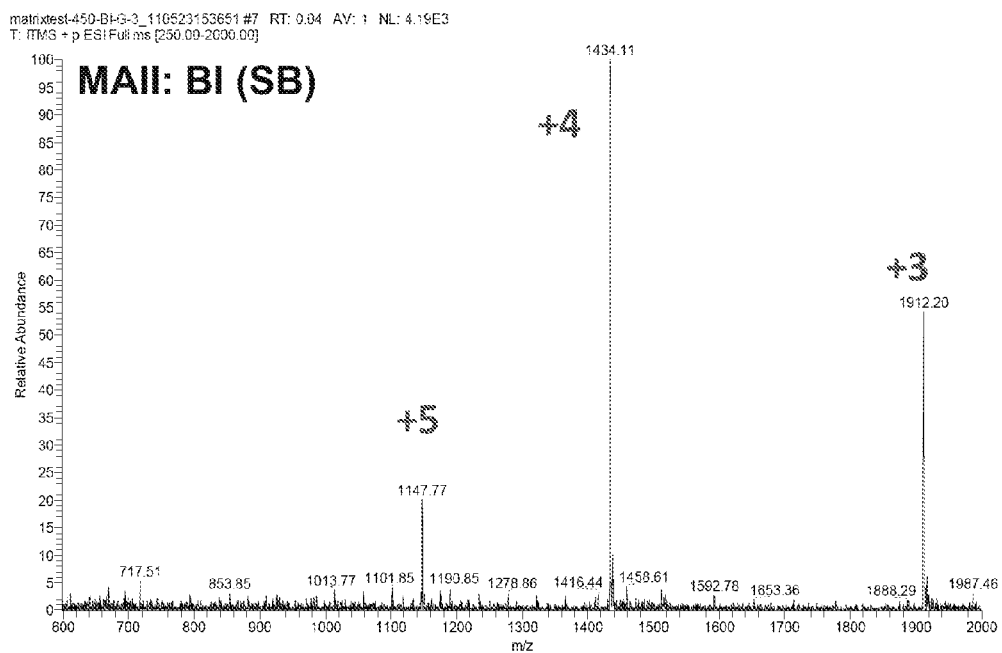
FIG. 133

FIG. 135A) Benzoic Acids
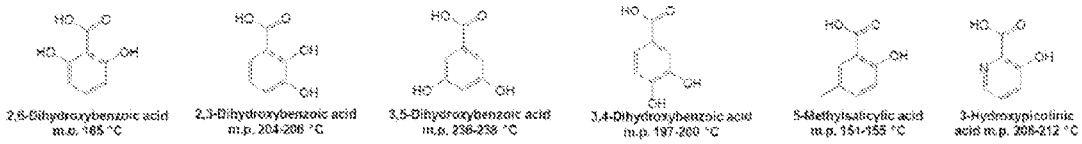
FIG. 135B) Acetophenones
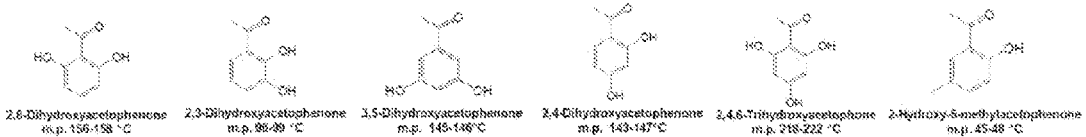
FIG. 135C) Sulfonated Compounds
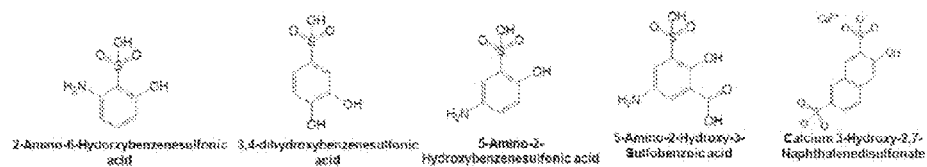
FIG. 135D) Nitro Compounds
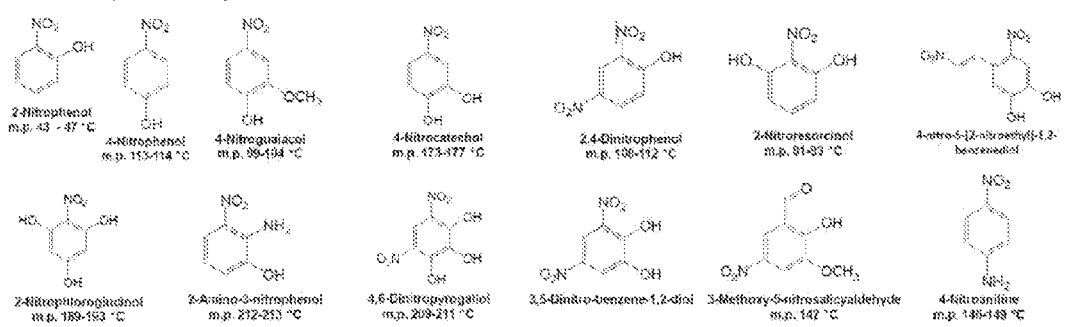
FIG. 135E) Halogenated Compounds    FIG. 135F) Cyano Compounds
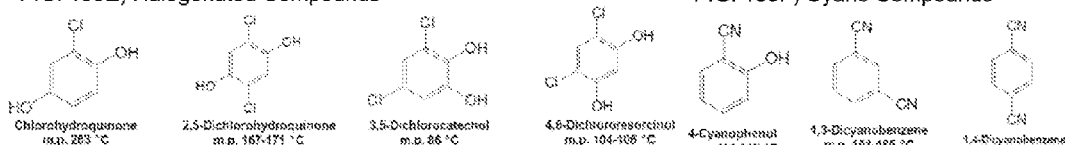
FIG. 135G) Benzamides
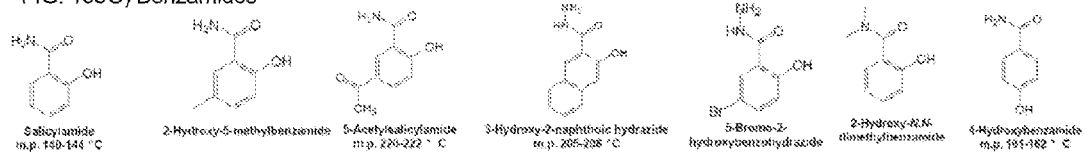
FIG. 135

FIG. 135H) Pyridine Compounds
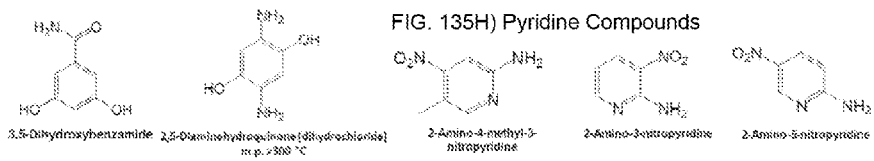
FIG. 135I) Phenols / Alcohols
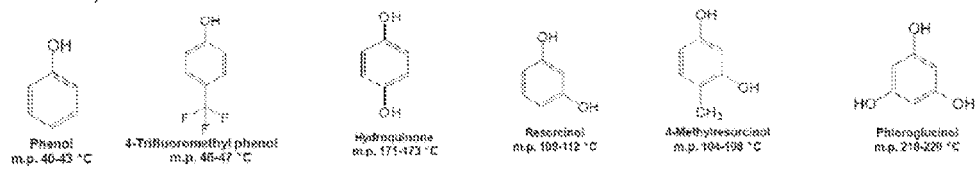
FIG. 135J) Benzaldehyde
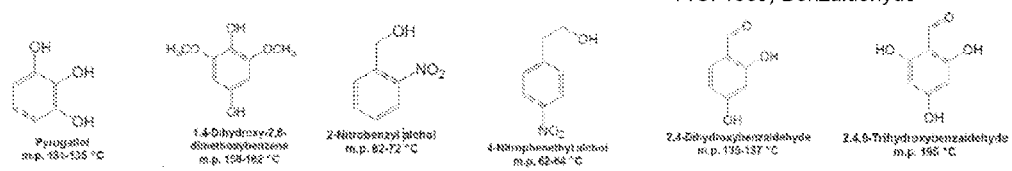
FIG. 135K) Non-Aromatic Ring
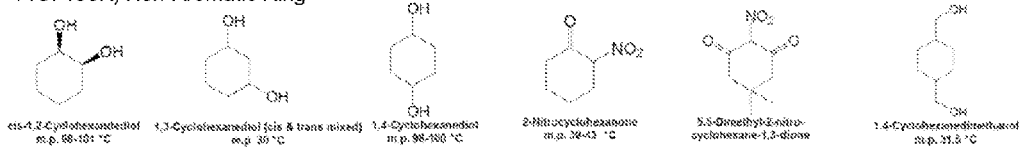
FIG. 135L) Linear Compounds
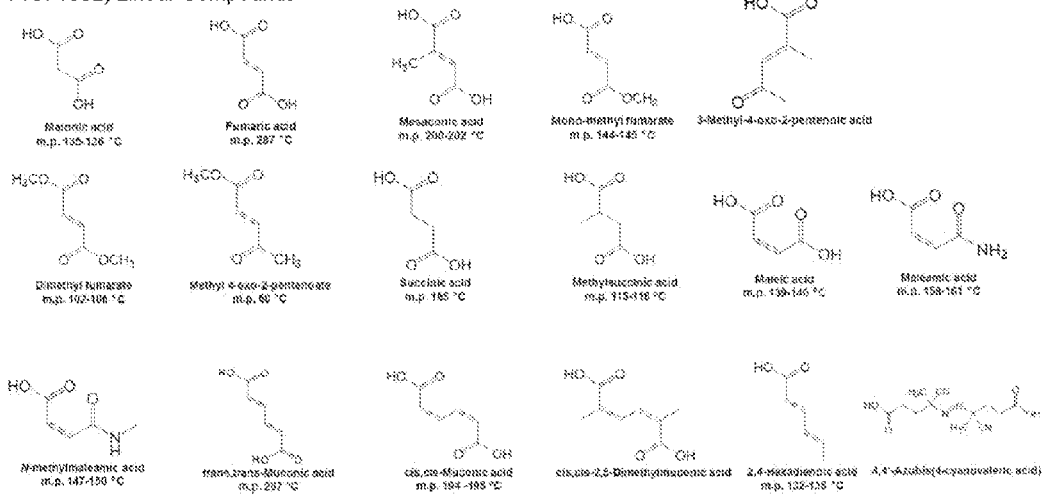
FIG. 135. con't.

SYSTEMS AND METHODS EXTENDING THE LASERSPRAY IONIZATION MASS SPECTROMETRY CONCEPT FROM ATMOSPHERIC PRESSURE TO VACUUM

CROSS REFERENCE TO RELATED APPLICATIONS

This application is a national phase application of International Patent Application No. PCT/US2011/057769 filed on Oct. 25, 2011, which claims priority to and the benefit of U.S. Provisional Patent Application No. 61/406,509, filed Oct. 25, 2010, U.S. Provisional Patent Application No. 61/422,016, filed Dec. 10, 2010, and U.S. Provisional Patent Application No. 61/493,400, filed Jun. 3, 2011, the entire contents of each of which are incorporated by reference herein.

FIELD OF THE DISCLOSURE

Systems and methods disclosed herein allow analysis of macromolecular structures using laserspray ionization on matrix-assisted laser desorption/ionization (MALDI) mass spectrometers and methods of use that are capable of producing abundant, multiply-charged ions from the solid state and directly from surfaces at intermediate pressure and high vacuum. The systems and methods are improved using matrixes that lower the thermal requirements for ion formation of the analyte or with the addition of supplemental energy supplied for ion formation.

BACKGROUND OF THE DISCLOSURE

Matrix-assisted laser desorption/ionization (MALDI) mass spectrometry (MS) has been an important analytical method for a variety of fields, especially related to analysis of synthetic and biopolymers. The method has been extended from a high vacuum (HV) technique in which time-of-flight (TOF) mass analyzers provided nearly unlimited mass range to intermediate pressure (IP) and atmospheric pressure (AP) techniques interfaced to mass analyzers having limited mass-to-charge (m/z) range. Production of singly charged ions on these m/z limited instruments, however, eliminated the ability to mass analyze high-mass compounds. Small molecule analysis is also limited by the chemical background associated with the ionization of the desired analyte e.g., drugs and metabolites, at any of the pressure regimes used. Inducing fragmentation using collision induced dissociation (CID) of singly charged ions produces little sequence information; newer and more potent fragmentation methods such as electron transfer dissociation (ETD) and electron capture dissociation (ECD) are not applicable to singly charged analyte ions. MALDI operates from the solid state and is a surface method enabling surface imaging approaches to determine the localization of certain analytes within a surface. Commercial MALDI ion source technology operates the laser in reflection geometry limiting the spatial resolution and speed of analysis. To increase the speed, expensive high repetition lasers can be employed more rapidly enabling the measurement of ~100 shots of sub-spectra to be combined as to what is referred to in MALDI as a mass spectrum and in case of imaging of surfaces used to determine analytes location within a surface employing respective computing programs. Advantages of singly charged ions are the simplicity of data interpretation, especially of complex mixtures.

Electrospray ionization (ESI) is an ionization method whereby a voltage, usually several thousand volts, is placed between a capillary through which a solution is passed and a counter electrode which contains the entrance to the vacuum of the mass spectrometer. Highly charged liquid droplets are formed in the ESI process and desolvation of these droplets leads to formation of bare ions that are sampled by the mass spectrometer. While the MALDI method produces primarily singly charged ions, the ESI liquid introduction method produces ions of high charge states if multiple ionization sites exist on the analyte molecule. Small molecules such as drugs and small peptides and lipids produce singly charged ions. Improved characterization is achieved utilizing multiply charged ions using activation methods including but not limited to CID, ETD, and ECD for powerful fragmentation of the analytes at will in the mass analyzer for sequence or structural information including but not limited to posttranslational modifications of analytes including but not limited to peptides and proteins intact and enzymatically digested. The disadvantage is the complexity and data interpretation associated with multiply charged ions especially with increasing complexity of the analyte and that sprayable conditions need to be achieved limiting applications to systems that can be solubilized and "sprayed".

Inlet ionization methods include laserspray ionization (LSI), matrix assisted inlet ionization (MAII), and solvent assisted inlet ionization (SAII) producing abundant highly charged ions without the use of a voltage from the solid state (MAII, LSI) or solution (SAII). Laserspray ionization (LSI) MS is a surface method that has the potential to characterize macromolecular structures directly from their native and complex environment with high spatial resolution important in surface imaging such as tissue. LSI was introduced on high performance mass spectrometers (Orbitrap, SYNAPT G2, LTQ Velos with ETD capabilities) operating at AP without the application of any electrical field demonstrating its usefulness for tissue analysis and surface imaging of e.g., lipids, peptides, proteins, and synthetic polymers on mass range limited mass spectrometers. The production of highly charged ions directly from surfaces in high abundance allows sequencing of for example peptides and proteins using ETD. Chemical background associated with LSII is minute. While LSI at AP offers many advantages, there is still room for improvement, especially relative to sensitivity limitations associated with the transfer of ions from AP-to-vacuum, and additional systems and methods for use in the analysis of macromolecular structures.

SUMMARY OF THE DISCLOSURE

Embodiments disclosed herein provide systems and methods for producing multiply-charged ions (MCIs) and analyzing macromolecular structures using LSI at vacuum (LSIV). In particular embodiments, there is a pressure drop and the application of heat in LSI at IP and HV. The systems and methods additionally provide matrix compounds that facilitate this production of MCIs. The disclosed systems and methods provide additional avenues for the analysis of macromolecular structures than previously available.

Besides the fundamental implications of these embodiments, an important potential analytical advantage, other than use of commercial instruments with and without modification, is the potential for high and/or better sensitivity compared to laserspray ionization inlet (LSII) and AP, IP and vacuum MALDI. The analysis of peptides and proteins directly from tissue using embodiments disclosed herein produces nearly identical mass spectra and drift time distribution appearance observed with LSI at AP and from solution using electrospray ionization (ESI). Peptides and proteins directly from their native and complex tissue environment produce nearly identical results as compared to the pure and synthesized standard indicating similar structures.

One embodiment disclosed herein provides a method of producing MCIs from a matrix/analyte association comprising contacting the matrix/analyte association with a laser; allowing entry of the matrix/analyte association into a mass spectrometer comprising an IP zone wherein the matrix/analyte or matrix/analyte association is exposed to a decrease in pressure following the entry thereby producing the MCIs.

One embodiment disclosed herein provides a method of producing MCIs from a matrix/analyte or a matrix/analyte association comprising contacting the matrix/analyte or matrix/analyte association with a laser; allowing entry of the matrix/analyte or matrix/analyte association into a mass spectrometer comprising an HV zone wherein the matrix/analyte or matrix/analyte association is exposed to a decrease in pressure following the entry thereby producing the MCIs.

One embodiment disclosed herein provides a method of producing MCIs from a matrix/analyte or a matrix/analyte association comprising contacting the matrix/analyte or matrix/analyte association with a laser; allowing entry of the matrix/analyte or matrix/analyte association into a mass spectrometer comprising an IP zone and an HV zone wherein the matrix/analyte or matrix/analyte association is exposed to a decrease in pressure following the entry thereby producing the MCIs.

In another embodiment, the IP zone is from 25 mTorr to 760 Torr. In another embodiment, the method does not utilize supplemental heat or a heated inlet ionization region utilizing proper matrix materials such as, for example, 2,5-dihydroxyacetophenone (2,5-DHAP).

In another embodiment, the method further comprises acquiring a mass spectrum of the analyte. In another embodiment, measurements are obtained in the positive or negative detection mode. Another embodiment comprises acquiring a fragmentation spectrum. Another embodiment comprises acquiring ion mobility spectrometry (IMS) data. In another embodiment, the method further comprises evaluating the mass spectrum to determine characteristics of the analyte.

In another embodiment, the method further comprises placing an amount of the matrix/analyte association on a target plate of the mass spectrometer. In another embodiment, the placing occurs using the dried droplet method or thin layer method.

In another embodiment, the matrix an organic compound with or without aromaticity and may include 2,5-DHAP, 2-nitrophloroglucinol (2-NPG) or 4,6-dinitropyrogallol (4,6-DNPG). I. In another embodiment, the analyte comprises a protein intact or enzymatically digested, peptide including posttranslational modified such as oxidation, acetylation, phosphorylation, lipid including fragile gangliosides, carbohydrate, oligonucleotide, synthetic polymer, animal, plant or human tissue. In another embodiment, the laser is a 355 nm Nd:YAG laser.

Another embodiment includes a method of preparing and analyzing a matrix/analyte association for MS analysis comprising mixing an analyte solution with a matrix solution to form a matrix/analyte solution; depositing the matrix/analyte solution onto a metal or glass plate using e.g., a dried droplet method thereby forming a matrix/analyte association; contacting the matrix/analyte association with a laser beam; producing a matrix/analyte association in the gas phase within a mass spectrometer comprising an IP zone wherein the matrix/analyte association is exposed to a decrease in pressure following the entry producing MCIs following the entry into the analyzer of the mass spectrometer; acquiring a mass spectrum of the analyte; and evaluating the mass spectrum to determine at least one characteristic of the analyte.

In another embodiment, the pressure within the IP zone is from 25 mTorr to 760 Torr. In another embodiment, the method does not utilize supplemental heat or a heated inlet ionization region although such heated regions may be beneficial.

In another embodiment, the analyte solution is prepared in a solvent of 50:50 ACN/water, 50:50 ACN/water with 0.1% TFA, 50:50 MeOH/water with 1% acetic acid, 50:50 ACN:water with 0.1% FA or 49:49:2 ACN:water:acetic acid. In another embodiment, the matrix solution is prepared as 20 mg 2,5-DHB in 100 µL of 50:50 ACN:water with 0.1% TFA; 10 mg CHCA in 2 mL MeOH:ACN; or 5 mg 2,5-DHAP in 300 µL 50:50 ACN:water. In another embodiment, the concentration of analyte in the matrix/analyte solution before deposition onto the metal or glass plate is 1 pmol $\mu L^{-1}$ but it is understood higher or lower concentration may be used. In another embodiment, the analyte comprises e.g., proteins, peptides, lipids, tissue (such as mouse brain drug treated and non treated), and synthetic polymers. In another embodiment, the mixing of the analyte solution and the matrix solution occurs at a 1:1 volume ratio. In another embodiment, the laser is a 337 nm nitrogen laser or a 355 nm Nd:YAG laser.

Another embodiment includes a method of preparing and analyzing a matrix/analyte association for MS analysis comprising mixing an analyte solution with a matrix solution to form a matrix/analyte solution at a 1:1 volume ratio; depositing the matrix/analyte solution onto a metal or glass plate using a dried droplet method thereby forming an matrix/analyte association; contacting the matrix/analyte association with a 337 nm nitrogen laser or a 355 nm Nd:YAG laser; allowing entry of the matrix/analyte association into a mass spectrometer comprising an IP zone with a pressure from 25 mTorr to 760 Torr wherein the matrix/analyte association is exposed to a decrease in pressure following the entry producing MCIs following the entry into the mass spectrometer; acquiring a mass spectrum of the analyte; and evaluating the mass spectrum to determine at least one characteristic of the analyte wherein the analyte comprises a protein, peptide or lipid and the matrix comprises an organic material with and without aromaticity, with high or poor solubility in organic and/or aqueous solution, with and without absorption at the laser wavelength, applied solvent-based or solvent-free as a pure matrix compound or as binary or tertiary matrix compound mixture.

Embodiments disclosed herein also include IP and high vacuum mass spectrometers as described herein and more particularly include mass spectrometers modified to function according to FIGS. 136-138 for positive and negative mode MS, IMS-MS, and MS/MS measurements.

BRIEF DESCRIPTION OF THE FIGURES

FIGS. 1A-1P. LSIV-MS mass spectra of [Glu1]-fibrinopeptide B (GFP); adrenocorticotropic hormone fragment (ACTH); bovine insulin (BI) and ubiquitin using 2,5-DHAP matrix with a laser energy of 200 or 500 on glass or metal plates. FIG. 1A: GFP using laser energy of 200 on glass plates; FIG. 1B: GFP using laser energy of 200 on metal plates; FIG. 1C: GFP using laser energy of 500 on glass plates; FIG. 1D: GFP using laser energy of 500 on metal plates; FIG. 1E: ACTH using laser energy of 200 on glass plates; FIG. 1F: ACTH using laser energy of 200 on metal plates; FIG. 1G: ACTH using laser energy of 500 on glass plates; FIG. 1H: ACTH using laser energy of 500 on metal plates; FIG. 1I: BI using laser energy of 200 on glass plates;

FIG. 1J: BI using laser energy of 200 on metal plates; FIG. 1K: BI using laser energy of 500 on glass plates; FIG. 1L: BI using laser energy of 500 on metal plates; FIG. 1M: ubiquitin using laser energy of 200 on glass plates; FIG. 1N: ubiquitin using laser energy of 200 on metal plates; FIG. 1O: ubiquitin using laser energy of 500 on glass plates; and FIG. 1P: ubiquitin using laser energy of 500 on metal plates.

FIG. 2A shows 2,5-DHAP in 50:50 ACN:water; FIG. 2B shows CHCA; and FIG. 2C shows 2,5-DHB both in 50:50 ACN:water with 0.1% TFA.

FIGS. 3A-3D. FIGS. 3A and 3B show photographs of the microscopy and FIGS. 3C and 3D show mass spectrum of the matrix/analyte mixture spot of angiotensin 1 (MW 1295) with saturated 2,5-DHAP matrix (prepared in 50:50 ACN:water) on a glass plate (FIG. 3C) before ablation and (FIG. 3D) after ablation using 200 laser energy. The center spot (FIG. 3A) provides preferentially the multiply charged ions shown in FIG. 3C.

FIGS. 4A and 4B. LSIV-MS mass spectra of N-acetylated myelin basic protein fragment (MBP, MW 1833) with 2,5-DHAP matrix acquired at intermediate pressure using the Waters SYNAPT G2 mass spectrometry instrument. FIG. 4A) LSI settings at 0 V and low laser power and FIG. 4B) MALDI settings at 20 V and high laser power. The charge state distribution observed in MALDI is compound and matrix dependent, but typically for any matrix the charge states, especially for larger molecules such as proteins and polymers, are low relative to ESI. On the other hand, using similar matrix preparation and laser ablation conditions as in MALDI, LSI produces abundant highly charged ions similar to ESI under AP and IP conditions. While the initial conditions in LSI and MALDI are similar, the results are drastically different. FIGS. 4A and 4B of myelin basic protein N-terminal fragment (MBP, MW 1833.2) obtained using the commercial IP-MALDI source on a SYNAPT G2 demonstrates the difference between LSIV and MALDI mass spectra using the same mass spectrometer and matrix (DHAP)/analyte (MBP) sample spot. FIG. 4A shows charge states +2 to +4 while Figure FIG. 4B shows only the singly charged ion of MBP. The principle instrumental differences are that Figure FIG.4A is obtained under conditions tuned for multiply charged ions in ESI but operated at IP, minimizes the use of voltages and uses lower laser fluence than used for obtaining singly charged ions with the instrument tuned using 'factory' conditions for MALDI operation. These results show, under vacuum MALDI conditions, that highly charged ions can be observed similar to those observed in ESI and LSII provided proper instrumentation, tune conditions, laser fluence and matrix are employed. These observations have implications for rapid switching between multiply and singly charged ions from the same matrix/analyte spot providing the ability for improved fragmentation utilizing the highly charged ions and simplified mass spectra and interpretation utilizing singly charged ions.

FIGS. 6A-6D. LSIV-IMS-MS of a model mixture using 2,5-DHAP matrix on glass (FIGS. 6A and 6B) and metal plates (FIGS. 6C and 6D) including total mass spectrum with an inset +4 charged state distribution of BI (FIGS. 6A and 6C) and a 2-D plot of drift time vs. m/z (FIGS. 6B and 6D).

FIGS. 7A-7H. LSIV-IMS-MS of individual components of the model mixture using 2,5-DHAP matrix and a laser energy of 500. FIG. 7A) SM on a glass plate; FIG. 7B) SM on a metal plate; FIG. 7C) Ang I on a glass plate; FIG. 7D) Ang I on a metal plate; FIG. 7E) GFP on a glass plate; FIG. 7F) GFP on a metal plate; FIG. 7G) BI on a glass plate; and FIG. 7H) BI on a metal plate.

(FIG. 11A) 2-D plot of drift time vs. m/z with inset extracted drift time of +4 of BI and +2, +1 of Ang I, and (FIG. 11B) total mass spectrum with an inset of +4 BI distribution.

FIG. 12B) a total mass spectrum and Inset spectrum of +3 ion and the ion (+2) with the largest MW 3216.

FIG. 13A) Extracted data from FIG. 12; Drift time distributions of charge states +1 to +3: FIG. 13B) N-acetylated fragment of myelin basic protein [(MBP, characterized previously by ETD], FIG. 13C) from the synthesized neuropeptide (+1, +2, and +3, MW 1833).

FIG. 15A) +1 charge state of peptide a; FIG. 15B) +2 charge state of peptide a; FIG. 15C) +1 charge state of peptide b; FIG. 15D) +2 charge state of peptide b; FIG. 15E) +2 charge state of peptide c; FIG. 15F) +2 charge state of peptide d; FIG. 15G) +2 charge state of peptide e; FIG. 15H) +2 charge state of peptide f; FIG. 15I) +3 charge state of peptide g; and FIG. 15J) +3 charge state of peptide h.

FIG. 17A) laser energy of 50; FIG. 17B) laser energy of 100; FIG. 17C) laser energy of 150; FIG. 17D) laser energy of 200; FIG. 17E) laser energy of 250; FIG. 17F) laser energy of 300; FIG. 17G) laser energy of 400; and FIG. 17H) laser energy of 500.

FIG. 18A) glass plate, and FIG. 18B) metal plate.

FIG. 19A) TOF (cooling gas 10 mL $min^{-1}$ and trap gas flow (2.5 mL $min^{-1}$); FIG. 19B) IMS-TOF modes with He cell and IMS gas flow at 24 mL min$^{-1}$; FIG. 19C) He cell (180 mL min$^{-1}$); FIG. 19D) IMS cell (90 mL min$^{-1}$); and FIG. 19E) both gas flows increased.

FIGS. 20A, 20B, and 20C. Extracted drift times of the neuropeptide with charge states +2, +3, and +4 (when present): (FIG. 20A) from mouse brain tissue section by AP-LSIV-IMS-MS, and from the synthesized N-acetylated fragment of myelin basic protein obtained by (FIG. 20B) AP-LSI-IMSMS and (FIG. 20C) ESI-IMS-MS.

FIGS. 21A-21E. LSIV-MS at mass spectra of bovine insulin (MW 5731) acquired with IMS separation: default (FIG. 21A), no API gas on (FIG. 21B), and trap off (FIG. 21C), and without IMS separation: default (FIG. 21D), and no trap on (FIG. 21E).

FIG. 22A) AP-LSI and FIG. 22B) AP-MAII using the LTQ Velos with a capillary temperature heated to 300° C., FIG. 22C) IP-LSI from the SYNAPT G2 using the IP-MALDI source, and FIG. 22D) from high vacuum MALDI-TOF-TOF Bruker UltrafleXtreme instruments in reflectron mode.

FIGS. 23A and 23B. High vacuum MALDI mass spectrum of Lysozyme (MW 14.3 kDa) with 2-NPG matrix solution acquired in FIG. 23A) reflectron mode and FIG. 23B) linear mode the MALDI-TOF-TOF Bruker UltrafleXtreme instrument.

FIGS. 24A and 24B. High vacuum MALDI mass spectrum of lysozyme (MW 14.3 kDa) acquired in linear mode with FIG. 24A) 2-NPG and FIG. 24B) Sinapinic acid matrix solution using a MALDI-TOF BrukerAutoflex Speed instrument.

FIG. 25A) 2,5-DHB, FIG. 25B) 2,5-DHAP, FIG. 25C) 2-NPG, and FIG. 25D) 4,6-DNPG acquired using the LTQ Velos with the capillary temperature heated to 300° C.

FIG. 27C) Extracted +2 charged state mass spectrum of polyethylene glycol-dimethyl ether (PEGDME) (MW 2000) with +1 charged state in the full mass spectrum. Inset shows +2 charged state isotopic distributions.

FIGS. 29A, 29B, and 29C. High vacuum MALDI mass spectra of ubiquitin (MW 8559 Da) with different matrixes: FIG. 29A) 2-NPG, FIG. 29B) 2,5-DHB, and FIG. 29C) CHCA acquired in reflectron mode using the MALDI-TOF Bruker Ultraflex instrument.

FIGS. 30A, 30B, and 30C. High vacuum MALDI mass spectra of lysozyme (MW 14.3 kDa) with different matrixes: FIG. 30A) 2-NPG, FIG. 30B) 2,5-DHB, and FIG. 30C) CHCA acquired in linear mode using a MALDI-TOF Bruker Ultraflex instrument.

FIGS. 31A-31D. High vacuum MALDI mass spectra of bovine insulin (MW 5731) with 2-NPG matrix acquired using the reflectron mode with different pulsed ion extraction (PIE) delay: FIG. 31A) 0, FIG. 31B) 200, FIG. 31C) 400, and FIG. 31D) 600 ns from a MALDI-TOF Bruker UltrafleXtreme instrument.

FIG. 32B) SA matrixes with the capillary temperature heated to 300° C.; FIG. 32C) CHCA matrixes with the capillary temperature heated to 450° C.; and FIG. 32D) SA matrixes with the capillary temperature heated to 450° C.

FIG. 33C) ubiquitin (MW 8559 Da) from the LTQ-Velos with the capillary temperature heated to 300° C. using 4,6-DNPG as matrix. Inset shows +2 charged state isotopic distribution of PEG-1000.

FIGS. 34A, 34B, and 34C. High vacuum MALDI mass spectra of ubiquitin (MW 8559 Da) with 2,4-DNPG matrix acquired using the reflectron mode with different laser power: FIG. 34A) 65%, FIG. 34B) 70%, and FIG. 34C) 75% from a MALDI-TOF Bruker UltrafleXtreme instrument.

FIG. 35A) "160", FIG. 35B) "150", and FIG. 35C) "140".

FIGS. 36A-36E. High vacuum MALDI mass spectra of ubiquitin (MW 8559 Da) with 2-NPG matrix acquired using the reflectron mode with different laser power: FIG. 36A) 45%, FIG. 36B) 50%, FIG. 36C) 55%, FIG. 36D) 60%, and FIG. 36E) 65% from a MALDI-TOF Bruker UltrafleXtreme instrument.

FIG. 37A) 50%, FIG. 37B) 60%, and FIG. 37C) 65% from a MALDI-TOF Bruker UltrafleXtreme instrument.

FIGS. 38A and 38B. High vacuum MALDI mass spectra of FIG. 38A) bovine insulin (MW 5731 Da), and FIG. 38B) ubiquitin (MW 8559 Da) with 4,6-DNPG matrix acquired in reflectron mode using a MALDI-TOF Bruker Ultraflex instrument.

Figure 2A:
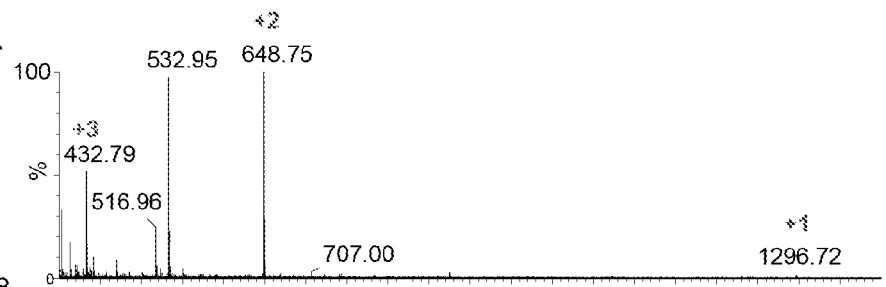
FIGS. 2A, 2B, and 2C. LSIV-MS mass spectra of Ang I with different matrixes with a laser energy of 500.

The following abbreviations are used in relation to FIGS. 39-89:

BI: 5 pmol μL$^{-1}$ bovine insulin (MW 5731) diluted in water unless specified;

Ubi: 5 pmol μL$^{-1}$ ubiquitin (MW 8561) diluted in water unless specified;

Lys: 5 pmol μL$^{-1}$ lysozyme (MW 14.3 kDa);

2-NPG: 2-nitrophloroglucinol (5 mg in 100 μL 50:50 acetonitrile (ACN):water);

2,5-DHAP: 2,5-dihydroxyacetophenone (5 mg in 150 μL ACN:water and warmed);

CHCA: α-cyanohydroxycinnamic acid (5 mg in 500 μL$^{-1}$ ACN:water with 0.1% trifluoroacetic acid (TFA);

SA: sinapinic acid acid (200 μL$^{-1}$ 50:50 ACN:water with 0.1% TFA);

CA: carbonic anhydrase (29.0 kDa);

BSA: bovine serum albumin (66.7 kDa);

Layer method: Analyte/matrix spot was prepared on glass plate using layer method in 1:1 or 1:2 analyte/matrix volume ratio and air dried;

Dried droplet method: Analyte/matrix mixture was prepared in 1:1 volume ratio and spotted 1 μL on glass plate using the dried droplet method;

Binary matrix: Prepared by volume percentage composition of each matrix;

FIGS. 39A-39E. MAII-MS of BI with 2-NPG prepared using layer method in 1:1 ratio and acquired at different acquisition temperature of the inlet capillary tube of the LTQ Velos mass spectrometer instrument: (FIG. 39A) 50° C., (FIG. 39B) 100° C., (FIG. 39C) 150° C., (FIG. 39D) 300° C., (FIG. 39E) 450° C.

Figure 40A:
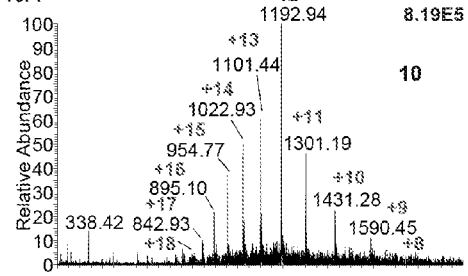
Figure 40E:
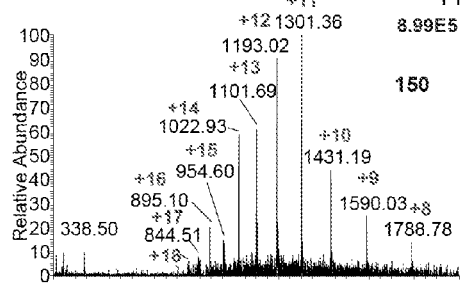
Figure 40B:
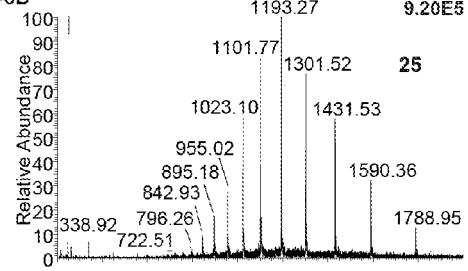
Figure 40F:
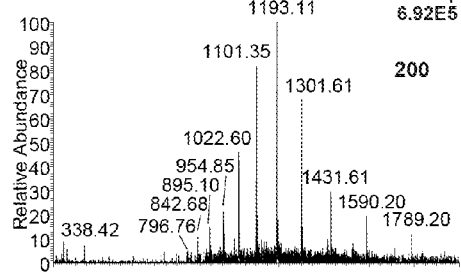
Figure 40C:
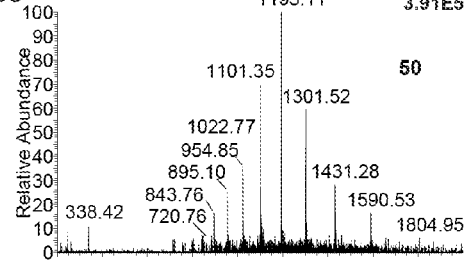
Figure 40G:
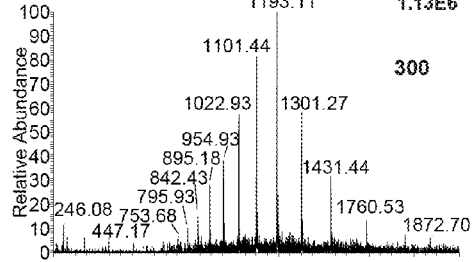
Figure 40D:
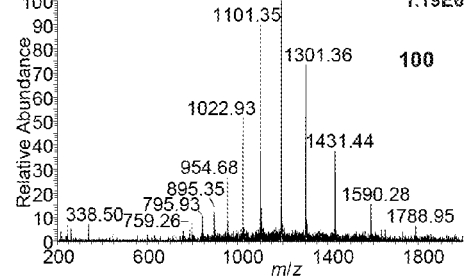
Figure 40H:
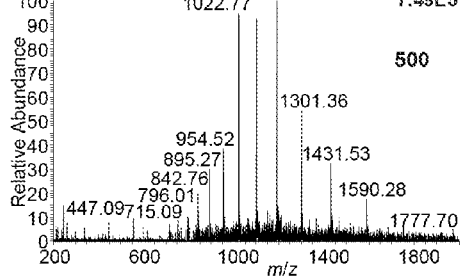

FIGS. 40A-40H. MAII-MS of Lys with 2-NPG matrix prepared in 1:1 layer method and acquired with different maximum injection times: FIG. 40A) 10, FIG. 40B) 25, FIG. 40C) 50, FIG. 40D) 100, FIG. 40E) 150, FIG. 40F) 200, FIG. 40G) 300, and FIG. 40H) 500 ms at 1 microscan and 450° C. inlet capillary temperature on LTQ-Velos mass spectrometer instrument.

FIGS. 41A-41F. MAII-MS of Lys with 2-NPG matrix prepared in layer method in 1: ratio and acquired with different microscans: FIG. 41A) 1, FIG. 41B) 2, FIG. 41C) 3, FIG. 41D) 5, FIG. 41E) 8, and FIG. 41F) 10 ms at 100 ms maximum injection time and 450° C. inlet capillary temperature on LTQ-Velos mass spectrometer instrument.

Figure 42A:
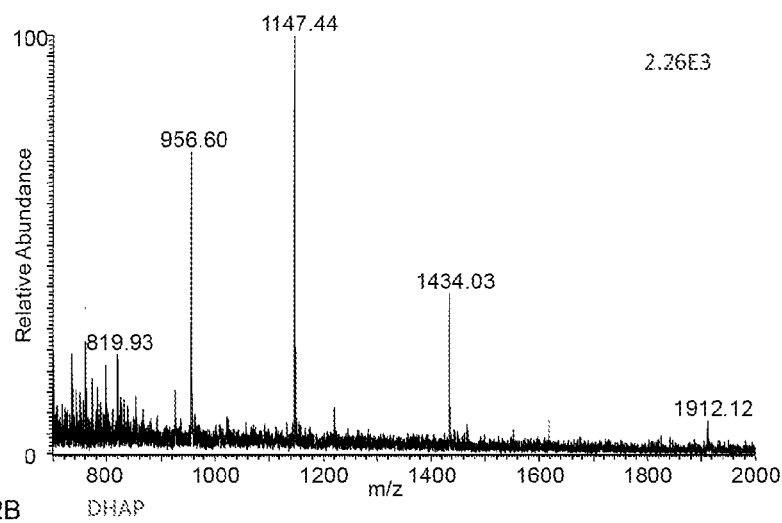
Figure 42B:
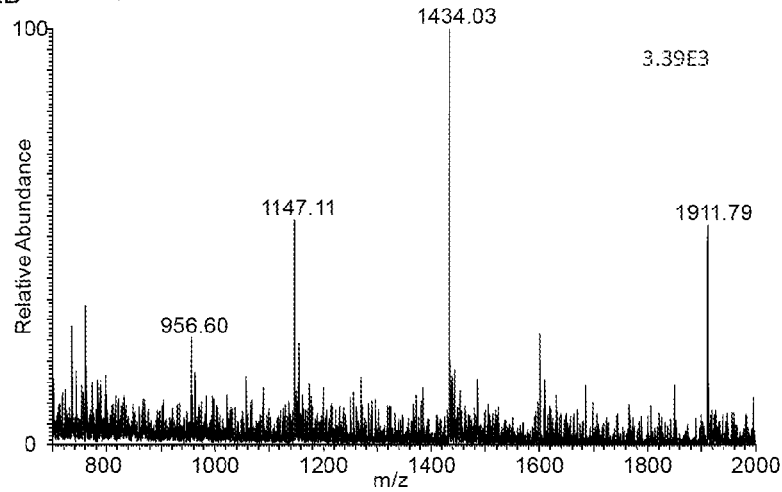
Figure 43A:
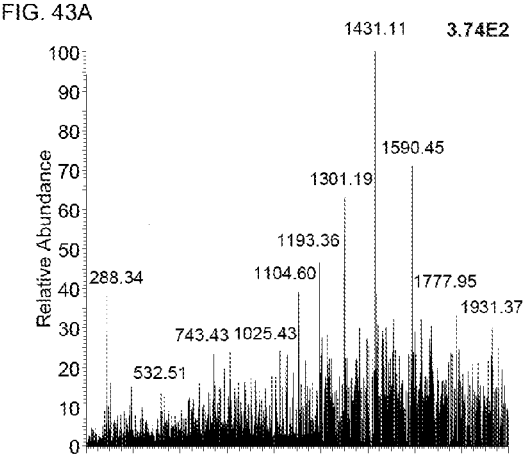
Figure 43B:
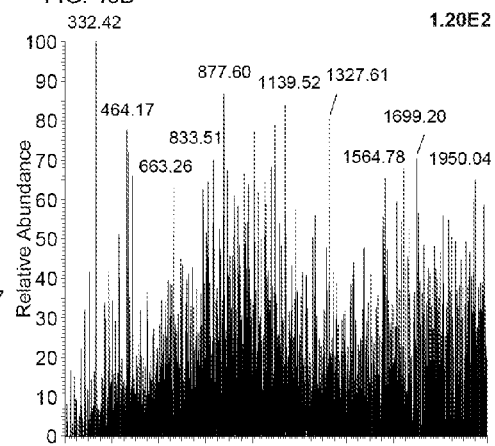
Figure 43C:
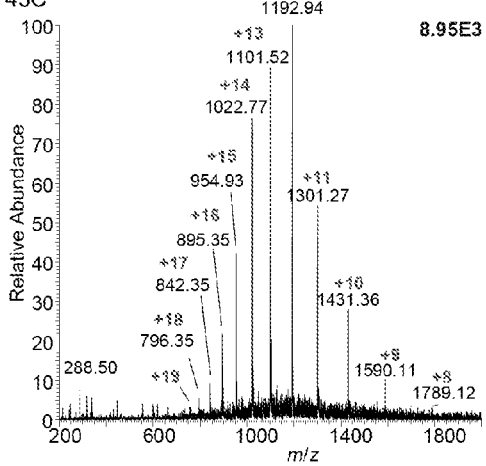
Figure 43D:
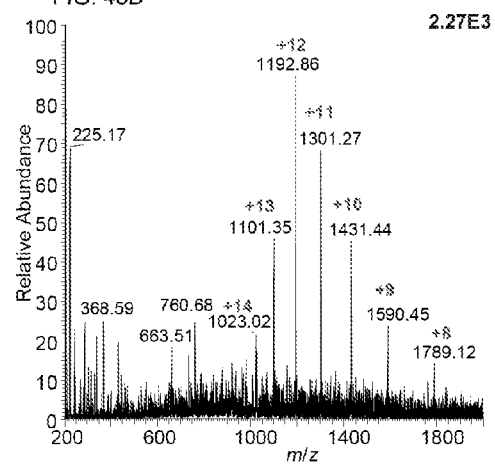

FIGS. 42A and 42B. MAII-MS sensitivity study of (FIG. 42A) 10 fmol pL$^{-1}$ with 2-NPG and (FIG. 42B) 50 fmol with 2,5-DHAP prepared using layer method in 1:1 ratio and blow dried using the Thermo LTQ-Velos mass spectrometer instrument with an inlet capillary temperature of 300° C.:

FIGS. 43A-43D. MAII of Lys with FIG. 43A) 100% CHCA, FIG. 43C) binary mixture of 5% 2-NPG and 95% CHCA, FIG. 43B) 100% SA, and FIG. 43D) binary mixture of 5% 2-NPG and 95% SA prepared using layer method in 1:2 ratio and acquired at 450° C. inlet capillary temperature on an LTQ-Velos mass spectrometer instrument using microscan of 2 and maximum injection time of 200 ms.

Figure 44A:
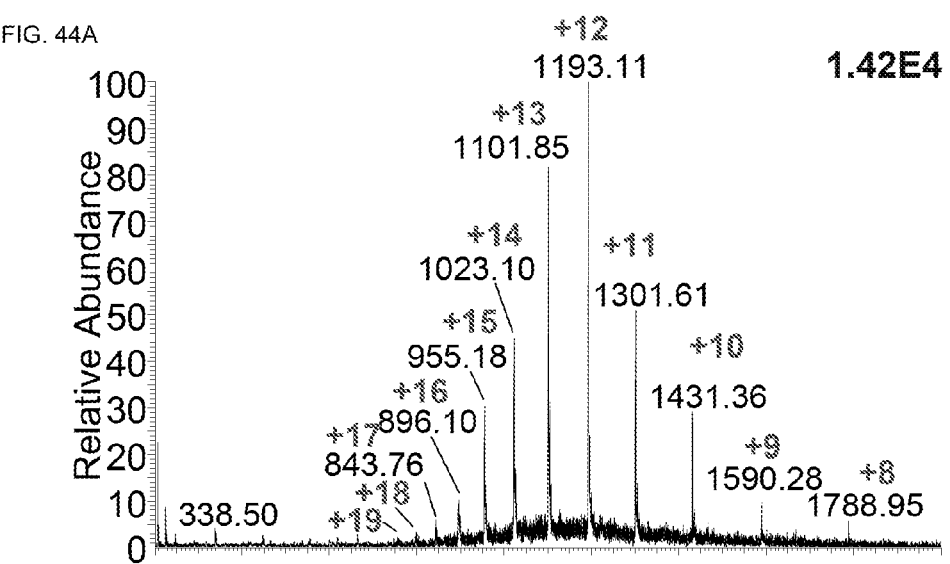
Figure 44B:
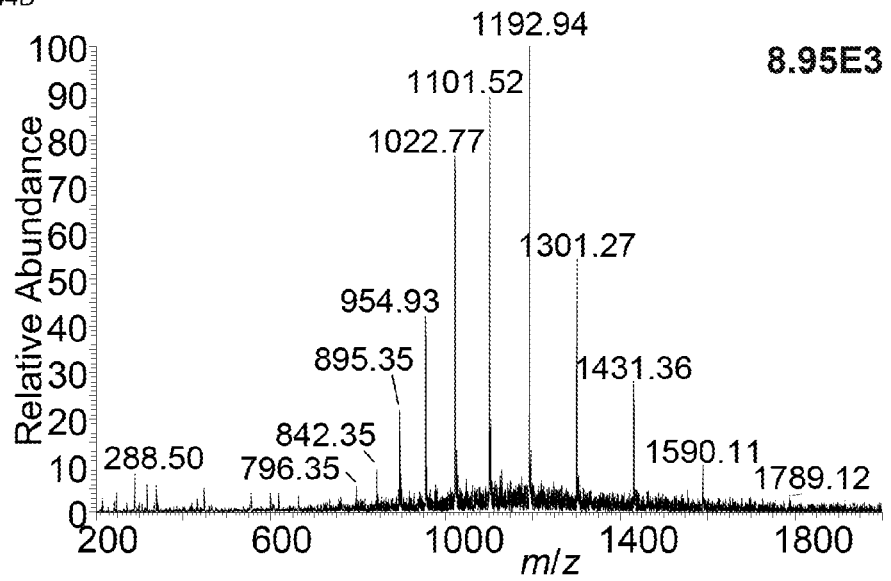

FIGS. 44A and 44B. LSII- (FIG. 44A) and MAII-MS (FIG. 44B) of Lys with binary matrix mixture of 5% 2-NPG and 95% CHCA prepared using layer method in 1:2 ration and acquired at 450° C. inlet capillary temperature on an LTQ-Velos mass spectrometer instrument using microscan of 2 and maximum injection time of 200 ms.

Figure 45A:
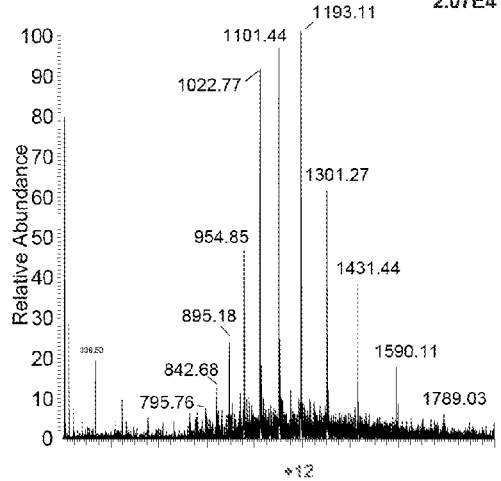
Figure 45B:
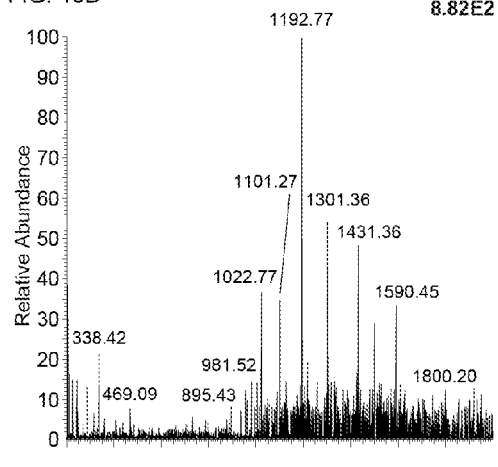
Figure 45C:
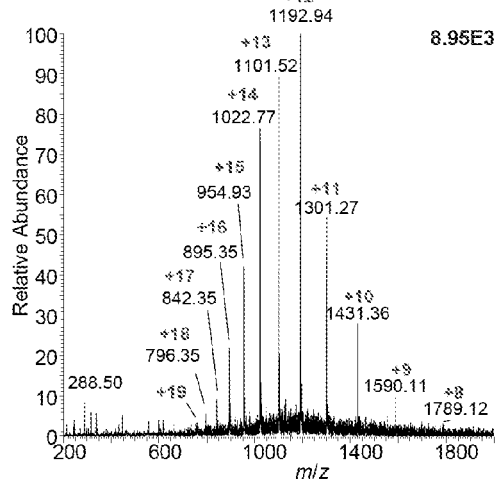
Figure 45D:
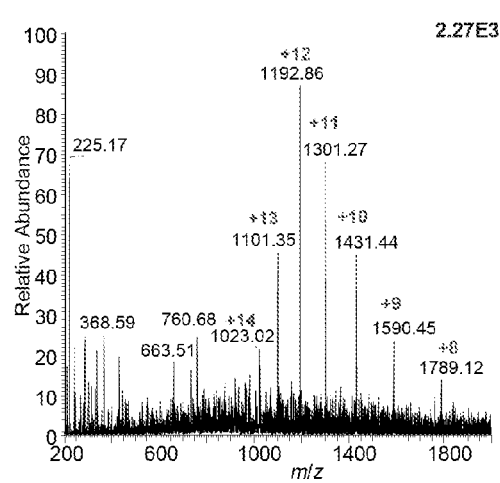

FIGS. 45A-45D. MAII-MS of Lys with binary matrix mixture of 5% 2-NPG and 95% CHCA and 5% 2-NPG and 95% SA prepared using layer method in 1:2 ratio and acquired at 300° C. and 450° C. inlet capillary temperature on an LTQ-Velos mass spectrometer instrument using microscan of 2 and maximum injection time of 200 ms. FIG. 45A) 5% 2-NPG and 95% CHCA, 300° C.; FIG. 45B) 5% 2-NPG and 95% SA, 300° C.; FIG. 45C) 5% 2-NPG and 95% CHCA, 450° C.; and FIG. 45D) 5% 2-NPG and 95% SA, 450° C.

Figure 46A:
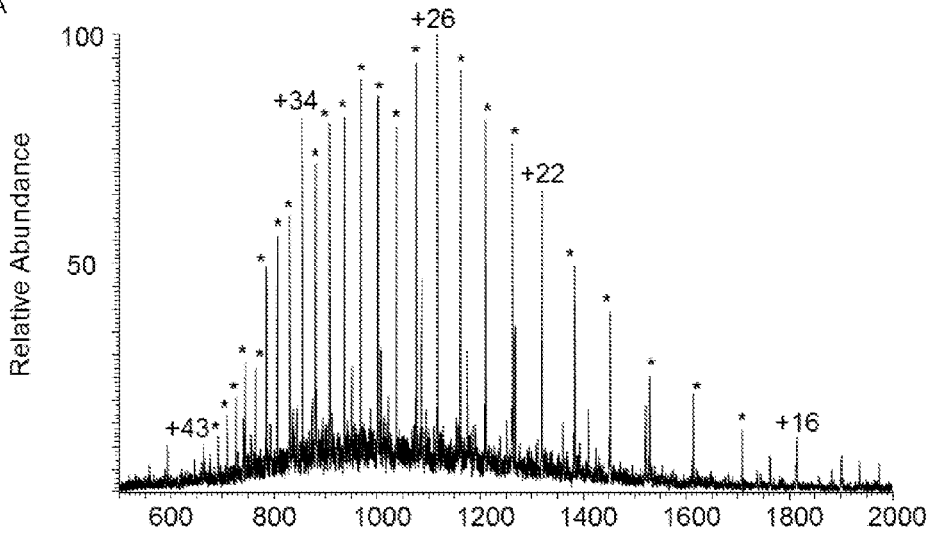
Figure 46B:
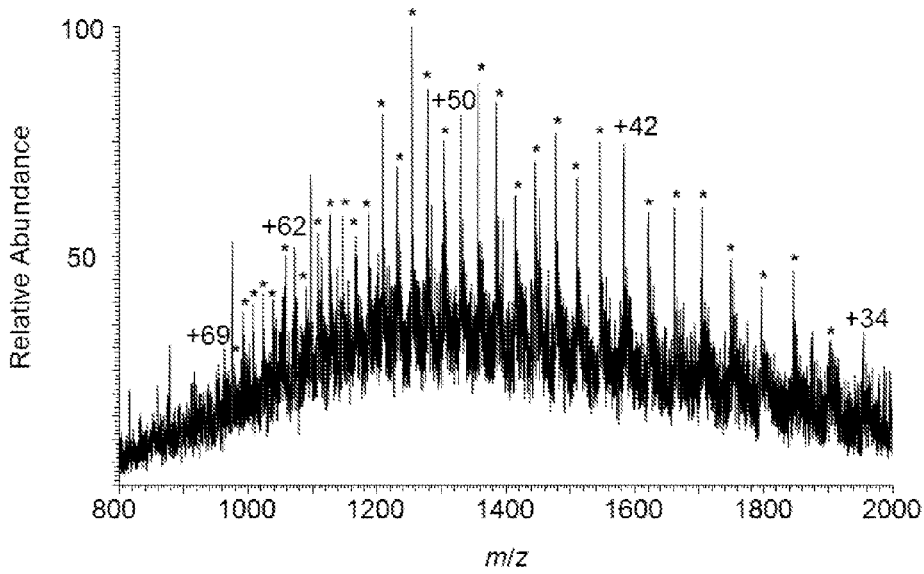

FIGS. 46A and 46B. LSII-MS of (FIG. 46A) 10 pmol pL$^{-1}$ CA and (FIG. 46B) a 10 second acquisition of 20 pmol pL$^{-1}$ BSA with 2-NPG matrix prepared using layer method. Data acquired on the LTQ-Velos mass spectrometer instrument at 300° C. inlet capillary temperature with (FIG. 46A) 2, 200 ms and (FIG. 46B) 10, 100 ms microscans and maximum injection time, respectively.

FIGS. 47A and 47B. (FIG. 47A) LSII-MS and (FIG. 47B) MAII-MS of 20 pmol of BSA with 2-NPG matrix prepared using layer method and acquired on the LTQ-Velos mass spectrometer instrument at 200° C. inlet capillary temperature at 10 microscans and 100 ms maximum injection time. The starred and labeled peaks are believed to be the protonated multiply charged molecules.

Figure 48:
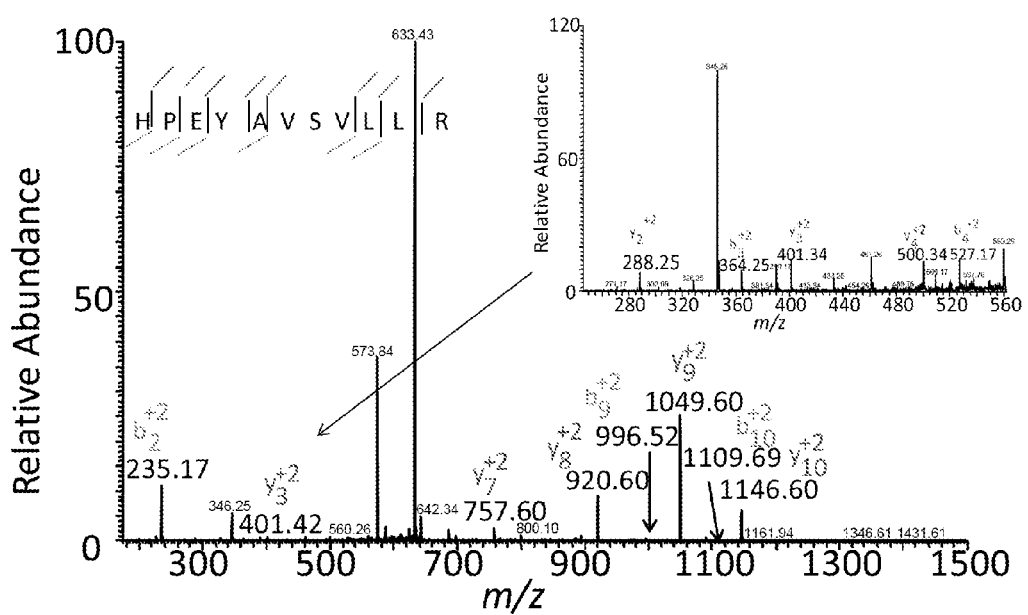

FIG. 48. MAII-CID MS/MS of 2 pmol μL$^{-1}$ of BSA tryptic digest mixed with 4 μL of 2-NPG using layer method on a metal spatula and acquired on the LTQ-Velos mass spectrometer instrument at 325° C. inlet capillary with microscans of 2 and 100 ms maximum injection time. Precursor ion selected was m/z of 642.60 [M+2H]$^{2+}$ and fragment ions produced at a collision energy of 30 and selection window of ±0.9.

Figure 49:
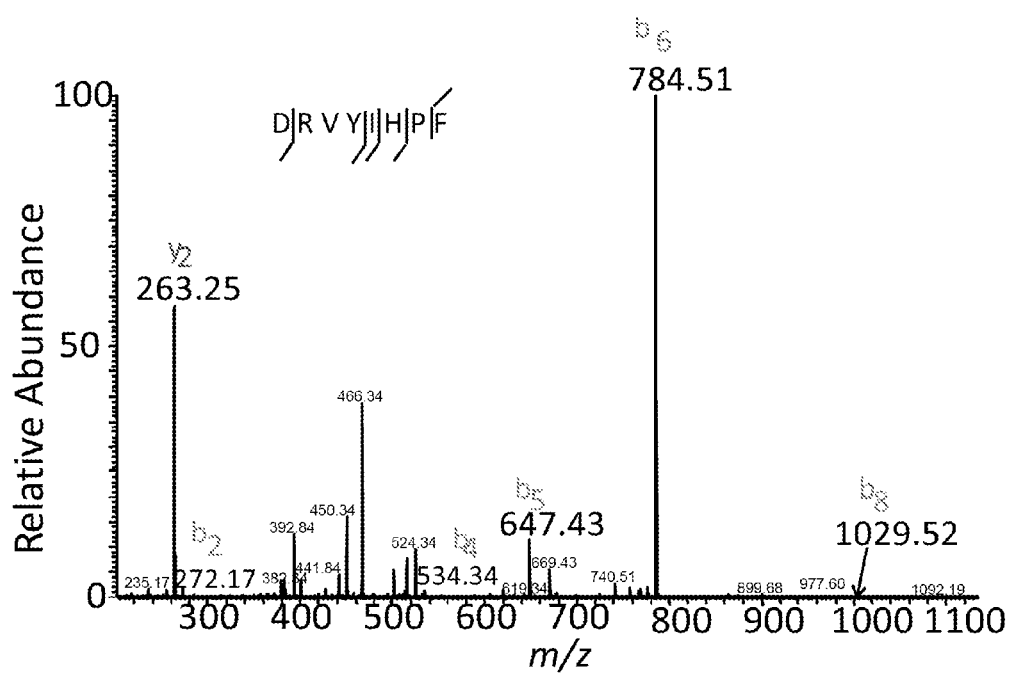

FIG. 49. MAII-CID-MS/MS mass spectrum of 1 pmol μL$^{-1}$ Ang II with 2 μL of 2-NPG using layer method on a metal spatula and acquired on the LTQ-Velos mass spectrometer instrument 325° C. inlet capillary temperature with 2 microscans and 100 ms maximum injection time. Precursor ion selected was m/z of 524.01 [M+2H]$^{2+}$ and fragmentation ions produced at a collision energy of 27 and selection window of ±0.9.

Figure 50:
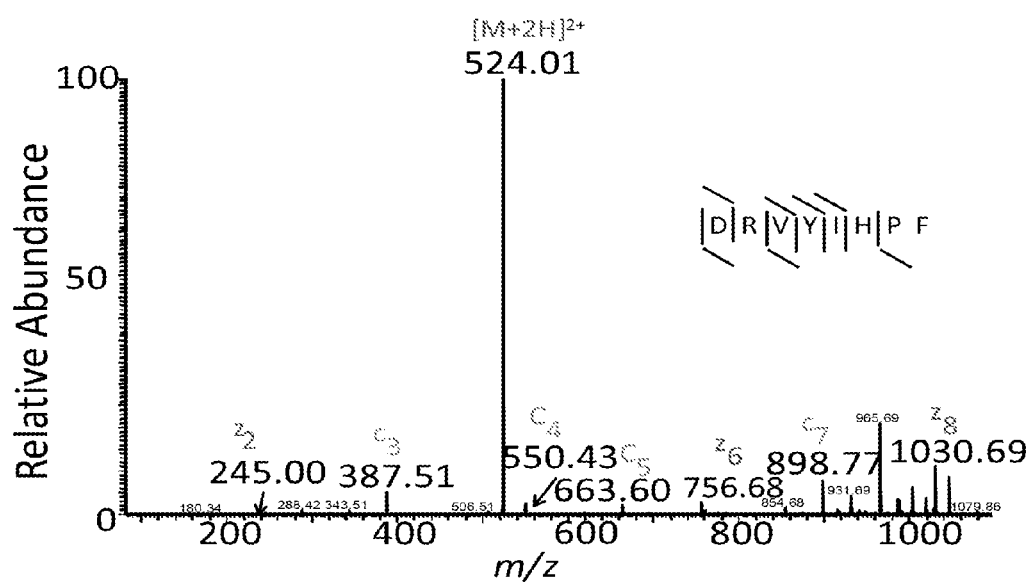

FIG. 50. MAII-ETD-MS/MS of 1 pmol μL$^{-1}$ Ang II with 2 μL of 2-NPG using layer method on a metal spatula and acquired on the LTQ-Velos mass spectrometer instrument at 325° C. inlet capillary temperature with 2 microscan and 100 ms maximum injection time. Precursor ion selected was m/z of 524.01 [M+2H]$^{2+}$ and fragment ions produced at an activation time of 500 ms and selection window of ±0.9.

FIGS. 51A, 51B, and 51C. MAII (FIG. 51A) full mass spectrum of 5 pmol pL$^{-1}$ BI B chain oxidized (MW 3495 Da) and (FIG. 51B) ETD-MS/MS of the +4 charge state with 2-NPG as matrix prepared using the layer method and acquired on the LTQ-Velos mass spectrometer instrument at 325° C. inlet capillary temperature with 1 microscan and 50 ms maximum injection time. The ETD activation time was set to 800 ms and 25 V of supplemental activation energy. (FIG. 51C) shows the nearly 100% sequence coverage that was obtained from a single MAII-ETD-MS/MS acquisition in (FIG. 51B).

Figure 52A:
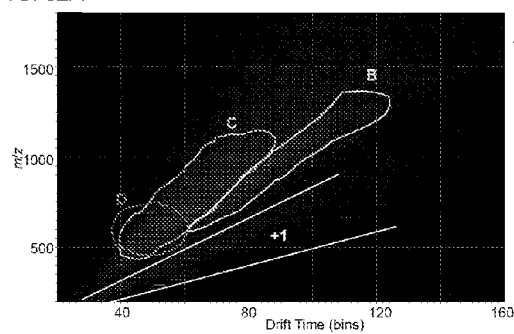
Figure 52B:
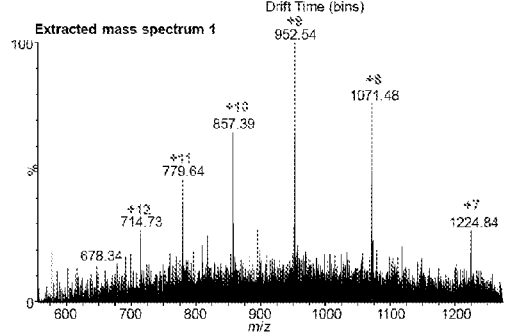
Figure 52C:
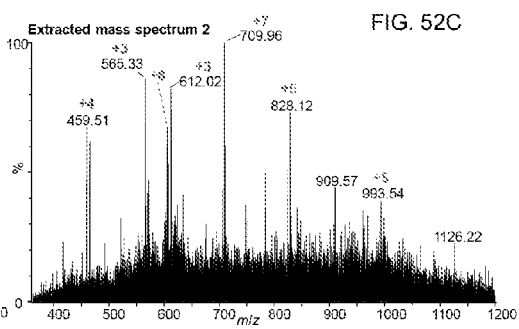
Figure 52D:
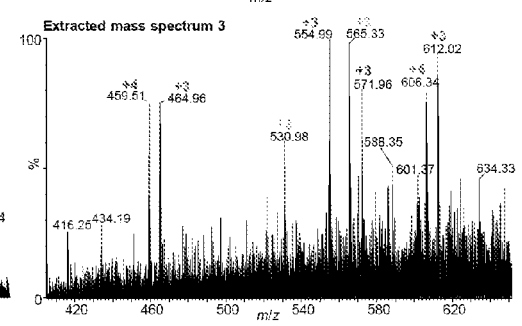

FIGS. 52A-52D. LSII-IMS-MS of delipified mouse brain tissue acquired using the SYNAPT G2 mass spectrometer instrument with a Nanolockspray source: FIG. 52A) 2-dimensional plot of drift time vs. m/z and extracted mass spectra from the 2-D plot, FIG. 52B) An 8.5 kDa protein contamination, FIG. 52C) endogenous 5 kDa protein and the identified neuropeptide, N-acetylated myelin basic protein (MBP MW 1833), and FIG. 52D) +2 to +4 charged states of peptides detected directly from delipified mouse brain tissue spray coated with a binary matrix of 10% 2-NPG (50 mg in 1 mL ACN:water) and 90% 2,5-DHAP (300 mg in 9 mL ACN:water) matrix solution and added with several 0.5 pL spots of 2,5-DHAP matrix solution on top. Source temperature was set at 150° C.

FIGS. 53A and 53B. LSII-MS obtained directly from delipified mouse brain tissue mounted on a FIG. 53A) CHCA precoated and FIG. 53B) plain glass plate, both spray coated with binary mixture of 10% 2-NPG and 90% 2,5-DHAP matrix solution, and acquired using the LTQ-Velos mass spectrometer with inlet capillary temperature of 350° C., microscan of 2, and maximum injection times of 600 ms.

Figure 54:
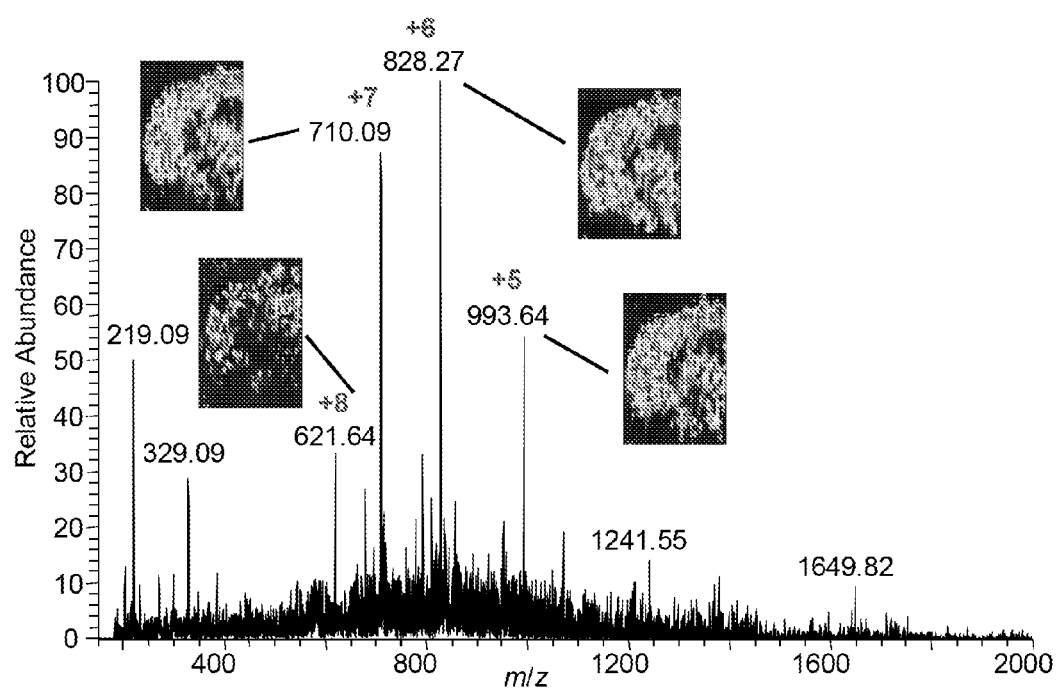

FIG. 54. LSII-MS images of the different charge states of a 5 kDa protein detected directly from delipified mouse brain tissue on a CHCA precoated glass plate (delipified and spray coated with binary mixture of 10% 2-NPG and 90% 2,5-DHAP matrix solution) acquired using the LTQ-Velos mass spectrometer instrument with an inlet capillary temperature of 350° C. The images showed almost half of the mouse brain tissue slice which acquisitions were done with the correct settings of 2 microscans and 600 ms maximum injection time.

Figure 55:
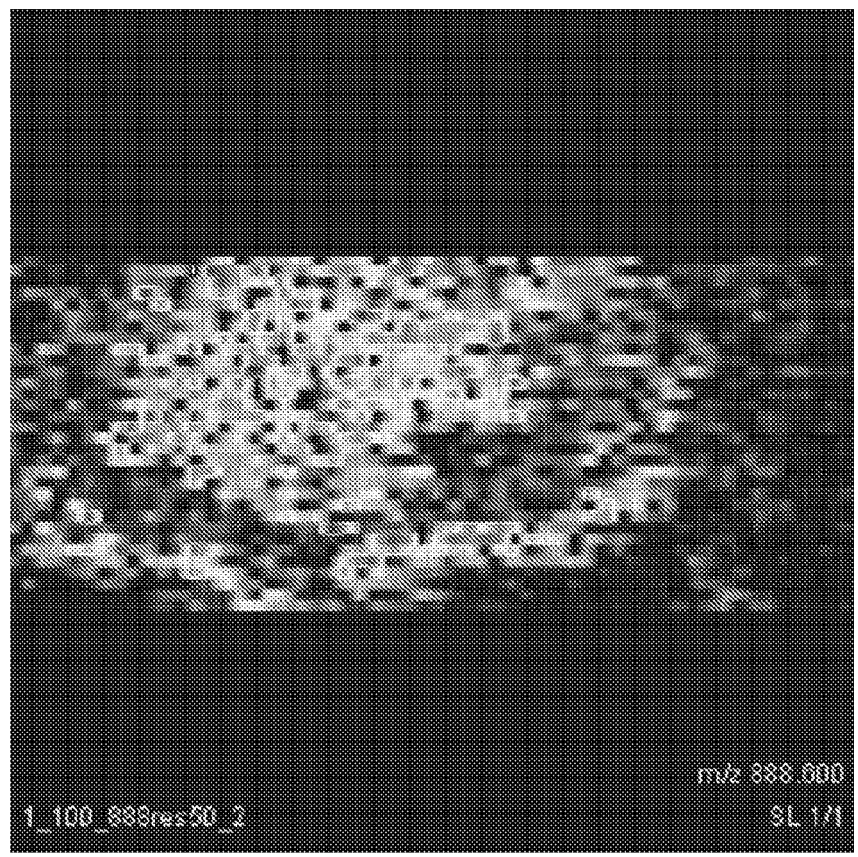

FIG. 55. LSII [M-H]$^{-1}$ ion image of 888.7 from mouse brain tissue using a glass slide pre- coated with matrix. The image was obtained on a Thermo LTQ-Velos mass spectrometer instrument with an inlet capillary temperature of 450° C., microscan of 1, and maximum inject time of 100 ms. Each row was acquired in 0.19 minutes.

Figure 56A:
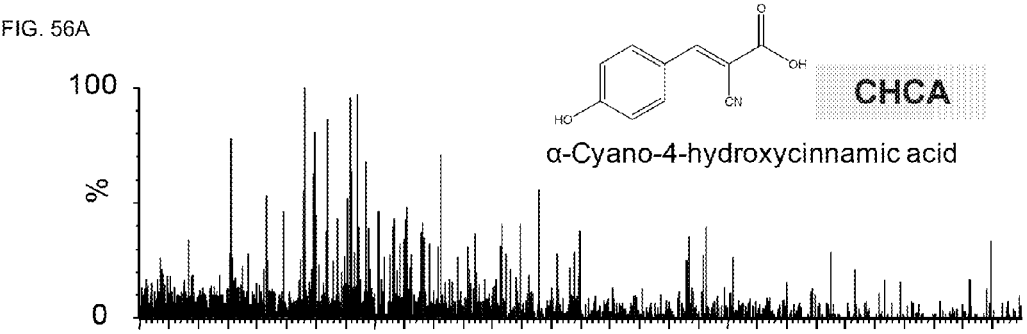
Figure 56B:
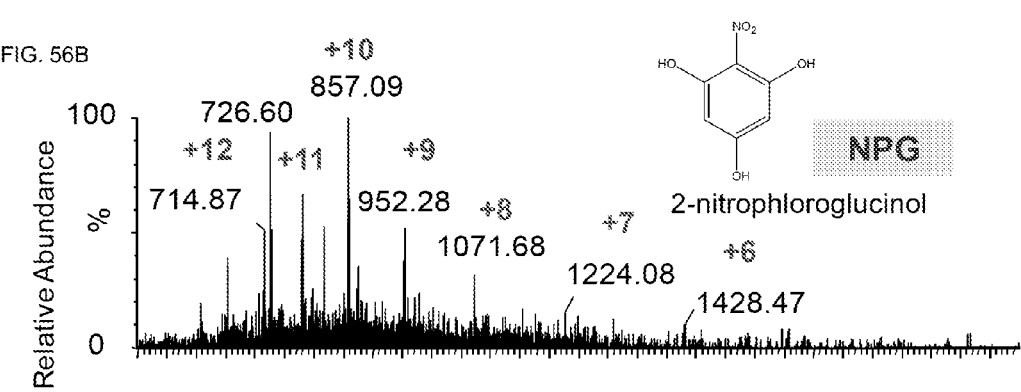
Figure 56C:
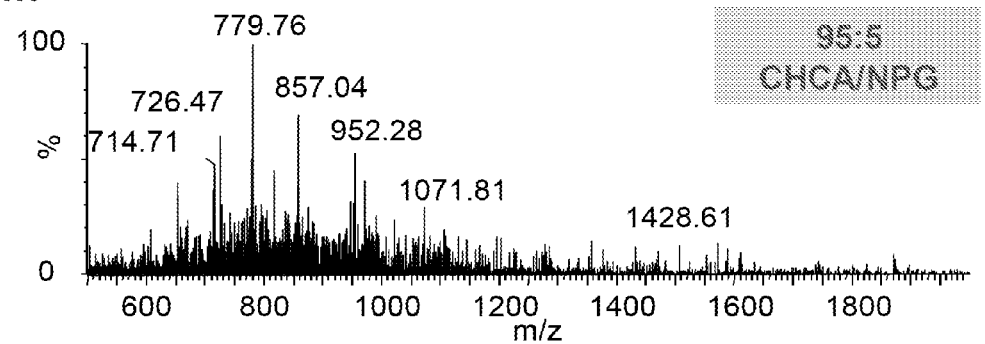

FIGS. 56A, 56B, and 56C. LSII-MS of Ubi with FIG. 56A) 100% CHCA, FIG. 56B) 100% NPG, and FIG. 56C) binary matrix mixture of 5% 2-NPG and 95% CHCA using an IR laser at 1064 nm wavelength acquired on the SYNAPT G2 mass spectrometer instrument with source temperature at 150° C.

FIGS. 57A-57D. LSIV-MS at IP of peptides and proteins in water with 2-NPG matrix prepared using the dried droplet method in 1:1 ratio: (FIG. 57A) 1 pmol $pL^{-1}$ N-acetylated myelin basic protein fragment (MBP, MW 1833 Da), (FIG. 57B) 1 pmol $pL^{-1}$ galanin (MW 3158 Da), (FIG. 57C) 1 pmol $pL^{-1}$ bovine insulin (MW 5731 Da), and (FIG. 57D) 2.5 pmol $pL^{-1}$ ubiquitin (MW 8561 Da). Low laser fluence ('140-175') was used for all the acquisitions.

FIGS. 58A-58D. LSIV-IMS-MS at IP of 2.5 pmol $pL^{-1}$ ubiquitin 2-NPG matrix prepared using droplet method in 1:1 ratio and obtained using the SYNAPT G2 mass spectrometer instrument with a MALDI source. Total mass spectra (FIG. 58A) and 2-D plot of drift time vs. m/z (FIG. 58B) tuned with different quad settings of 500, 1000, 1000 of masses 1, 2, 3 ramping, respectively at low laser power. Total mass spectra (FIG. 58C) and 2-D plot of drift time vs. m/z (FIG. 58D) tuned with different quad settings using the auto profile settings of the instrument at high laser power.

FIGS. 59A-59H. LSIV-IMS-MS at IP of 2.5 pmol $pL^{-1}$ proteins in water with 2-NPG matrix prepared using droplet method and acquired on a SYNAPT G2 mass spectrometer with a MALDI source. The 2-D plots for each charge state are displayed for (FIG. 59A) ubiquitin, (FIG. 59B) lysozyme, (FIG. 59C) myoglobin, and (FIG. 59D) carbonic anhydrase. The extracted drift times for each charge state are displayed for (FIG. 59E) ubiquitin, (FIG. 59F) lysozyme, (FIG. 59G) myoglobin, and (FIG. 59H) carbonic anhydrase. Low laser fluence was used for all the acquisitions.

FIGS. 60A and 60B. LSIV-MS at IP of 2.5 pmol $pL^{-1}$ angiotensin I (MW 1295) in water using FIG. 60A) binary matrix of 10% 2-NPG and 90% SA and FIG. 60B) 100% SA prepared using droplet method in 1:1 ratio and acquired using the MALDI source of SYNAPT G2 mass spectrometer instrument. Laser fluence used is '200'.

Figure 61A:
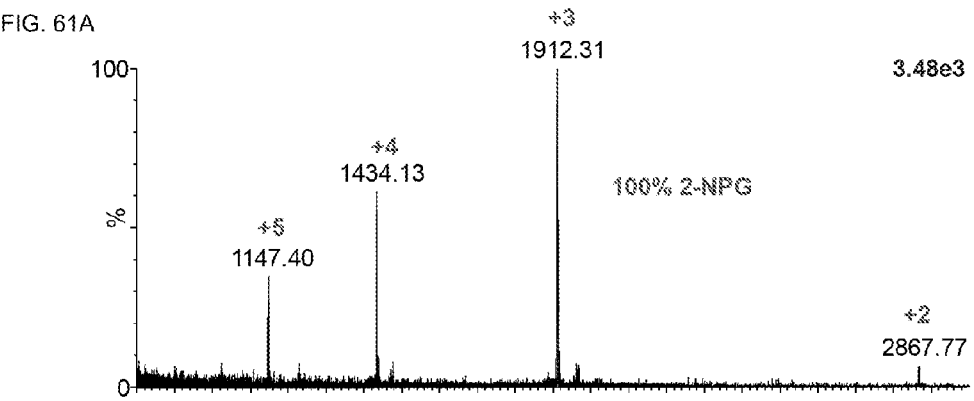
Figure 61B:
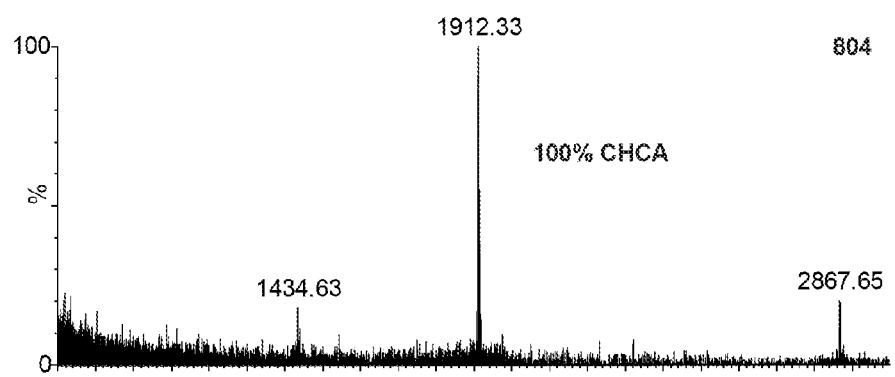
Figure 61C:
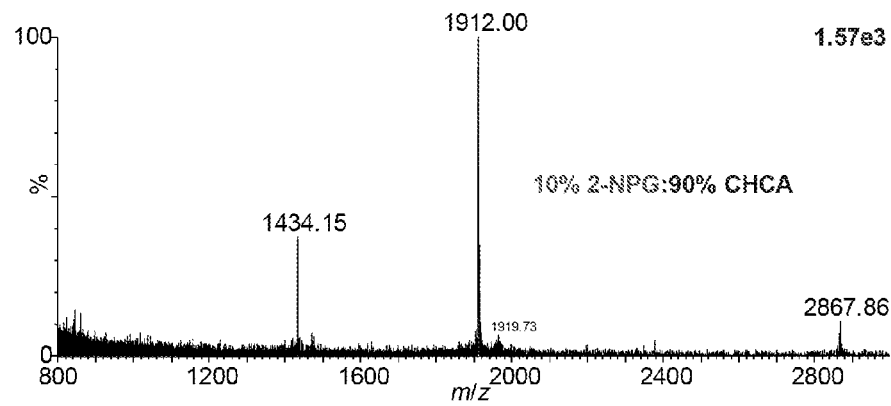
Figure 62A:
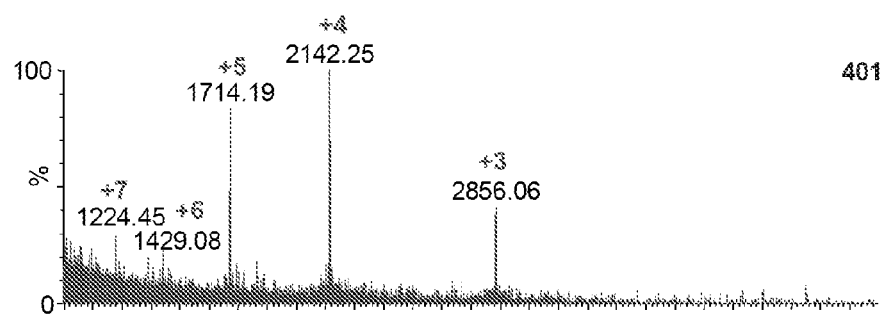
Figure 62B:
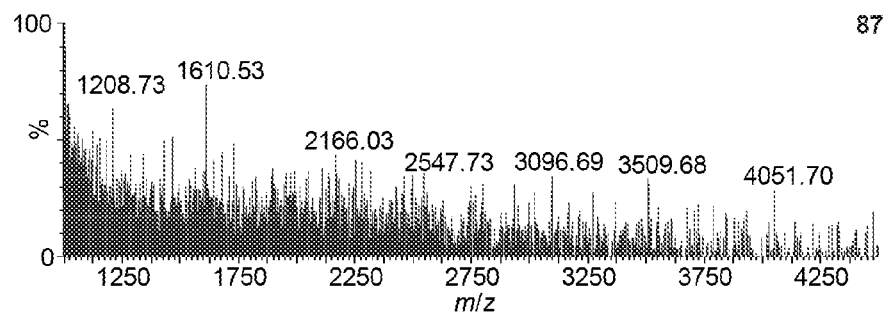
Figure 62C:
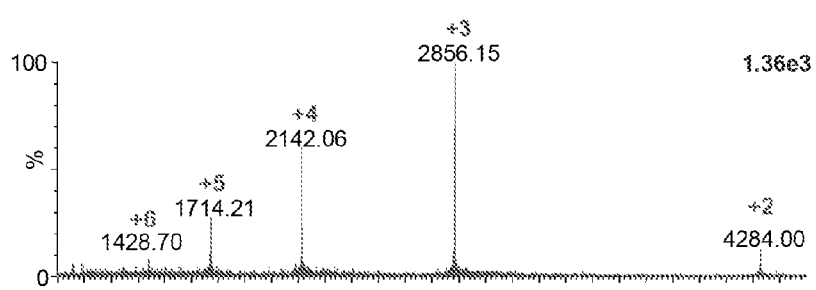
Figure 62D:
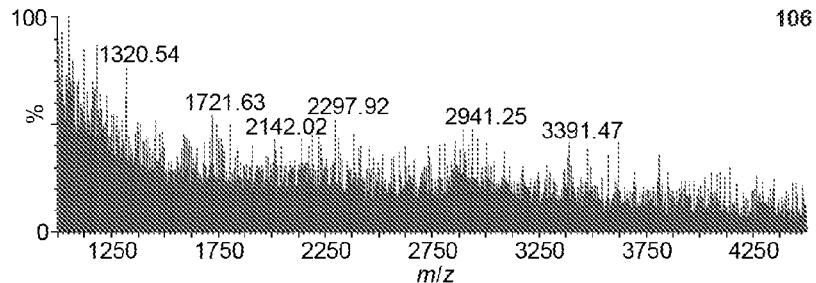

FIGS. 61A, 61B, and 61C. LSIV-MS at IP of 2.5 pmol $pL^{-1}$ BI with FIG. 61A) 100% 2-NPG, FIG. 61B) 100% CHCA, and FIG. 61C) a binary matrix of 10% 2-NPG and 90% CHCA prepared using droplet method in 1:1 ratio and acquired on the SYNAPT G2 mass spectrometer instrument with a MALDI source using an adjusted quad settings preferencing MCIs.

FIGS. 62A-62D. LSIV-MS at IP of 2.5 pmol pL-1 ubiquitin in water with (FIGS. 62A and 62C) binary mixture of 10% 2-NPG and 90% 4-nitroaniline and (FIGS. 62B and 62D) 100% 4-nitroaniline prepared using droplet method in 1:1 analyte/matrix volume ratio and spotted 1 pL on a glass plate. Data acquired using (FIGS. 62A and 62B) LSI and (FIGS. 62C and 62D) MALDI settings of the SYNAPT G2 mass spectrometer instrument with a MALDI source.

Figure 63A:
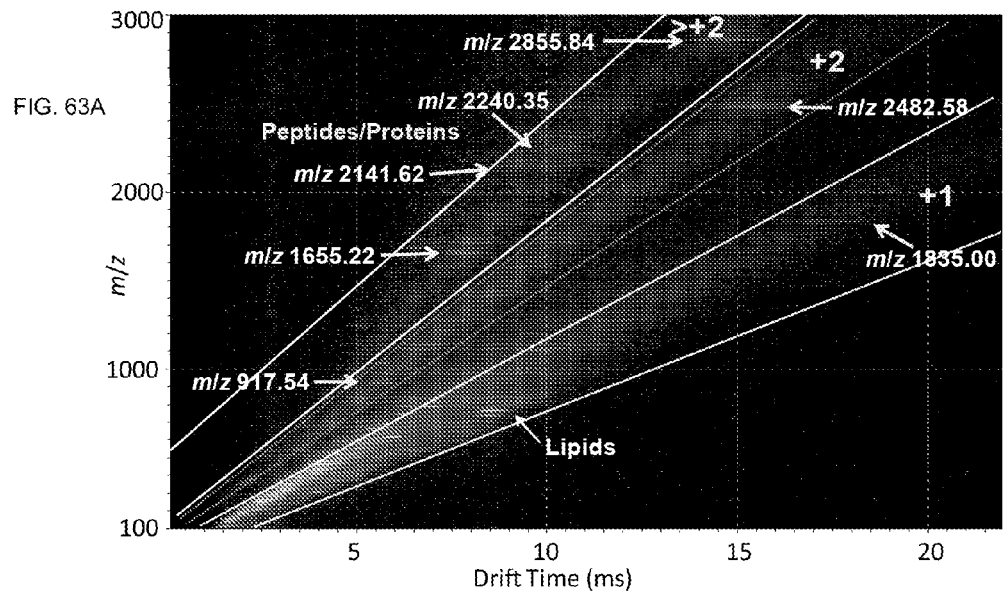
Figure 63B:
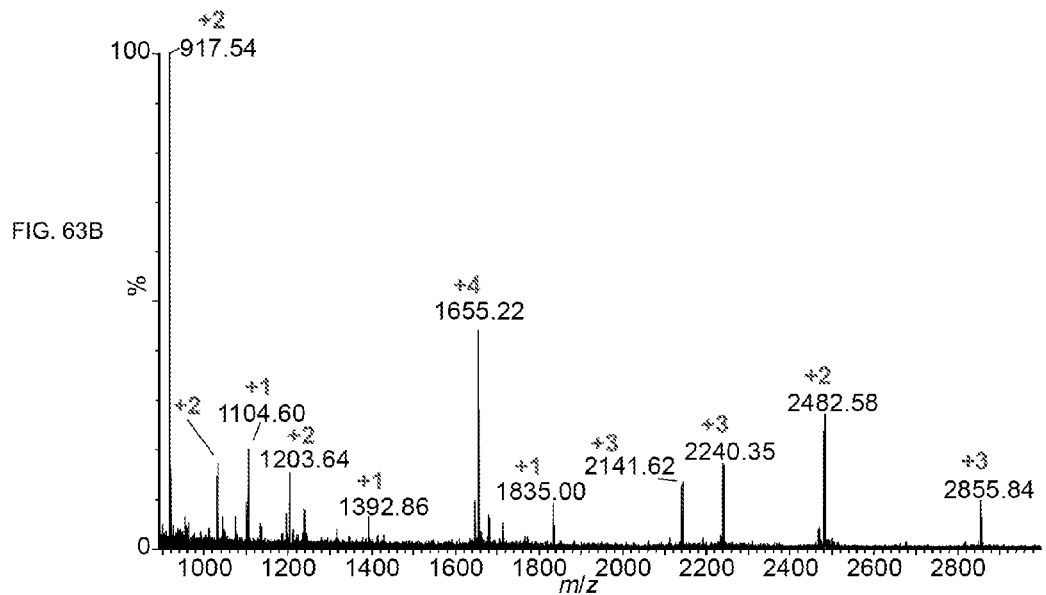

FIGS. 63A and 63B. LSIV-IMS-MS at IP FIG. 63A) 2-dimensional plot of drift time vs. m/z and FIG. 63B) total mass spectrum of lipids, peptides, and proteins detected directly from delipified mouse brain tissue spotted with 100% 2-NPG matrix. The production of MCIs and with gas phase separation, lipids, peptides, and proteins are well separated into charged state families.

Figure 64A:
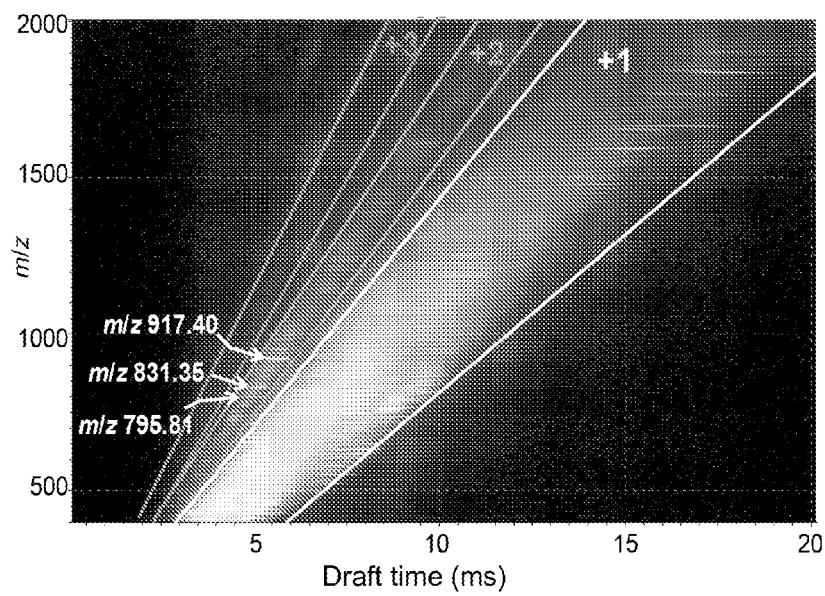
Figure 64B:
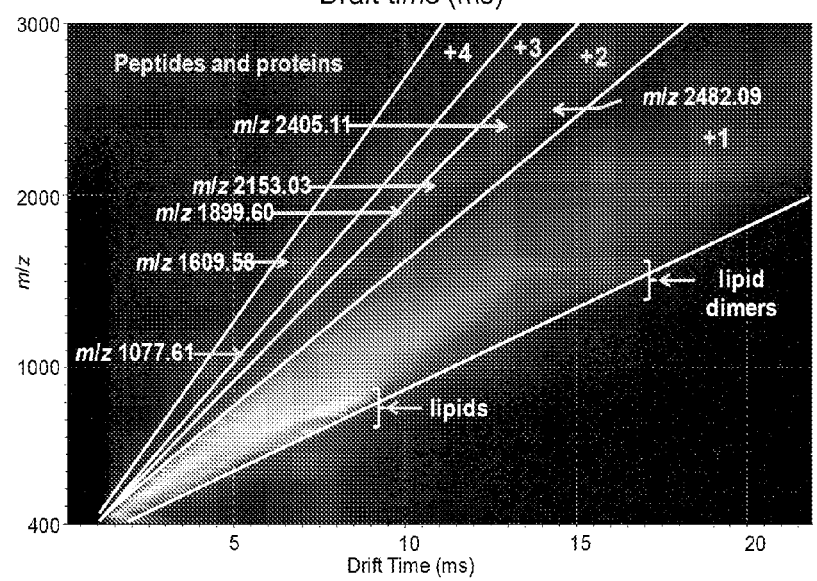

FIGS. 64A and 64B. LSIV-IMS-MS at IP 2-D plots of drift time vs. m/z from delipified mouse brain tissue mounted on FIG. 64A) plain glass plate and spray coated with 100% 2-NPG and FIG. 64B) CHCA precoated glass plate and spray coated with 90% 2,5-DHAP and 10% 2-NPG.

FIGS. 65A and 65B. LSIV imaging at IP from an aged delipified mouse brain tissue spray with 100% 2-NPG matrix solution showing images of endogenous neuropeptides peptides. (FIG. 65A) Total mass spectrum, (FIG. 65B) Inset mass spectrum of the +2 peptides with the images of the most abundant signals: (1) m/z 831 and (2) the identified neuropeptide, N-acetylated myelin basic protein fragment m/z 917 and (3) its +1 charged state m/z 1834.

FIGS. 66A-66D. LSIV imaging at IP of endogenous neuropeptides from delipified mouse brain tissue spray coated with 100% 2-NPG matrix solution: (FIG. 66A) m/z 795 (+2), (FIG. 66B) m/z 831 (+2), and (FIG. 66C) m/z 917 (+2), the identified neuropeptide MBP. (FIG. 66D) shows the location of this protein and its abundance in the mouse brain tissue (from Allen mouse brain atlas).

Figure 67:
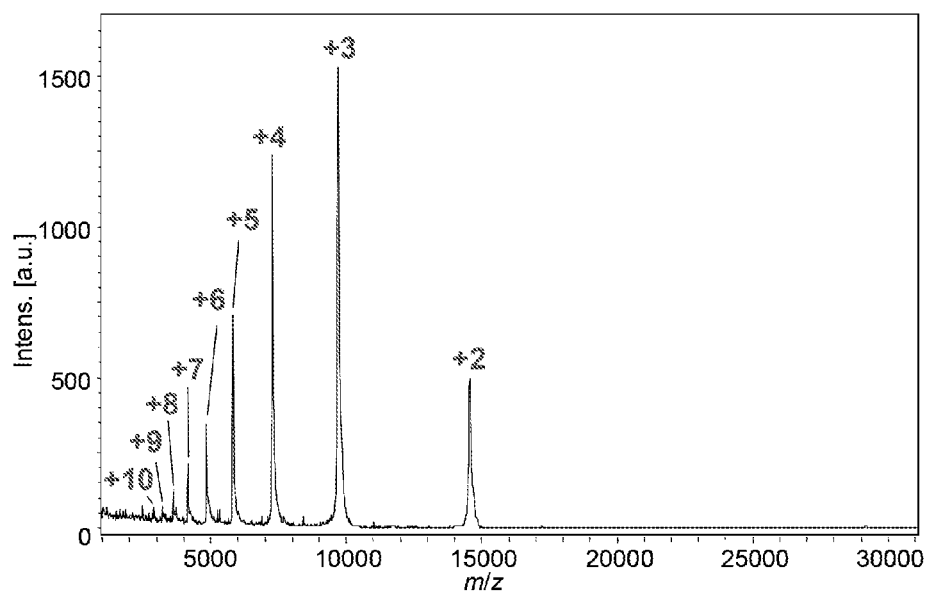

FIG. 67. LSIV-MS at HV of CA with 2-NPG matrix prepared using droplet method in 1:1 ratio and acquired in reflectron mode using a Bruker MALDI-TOF-TOF UltrafleXtreme mass spectrometer at 50% laser power.

Figure 68A:
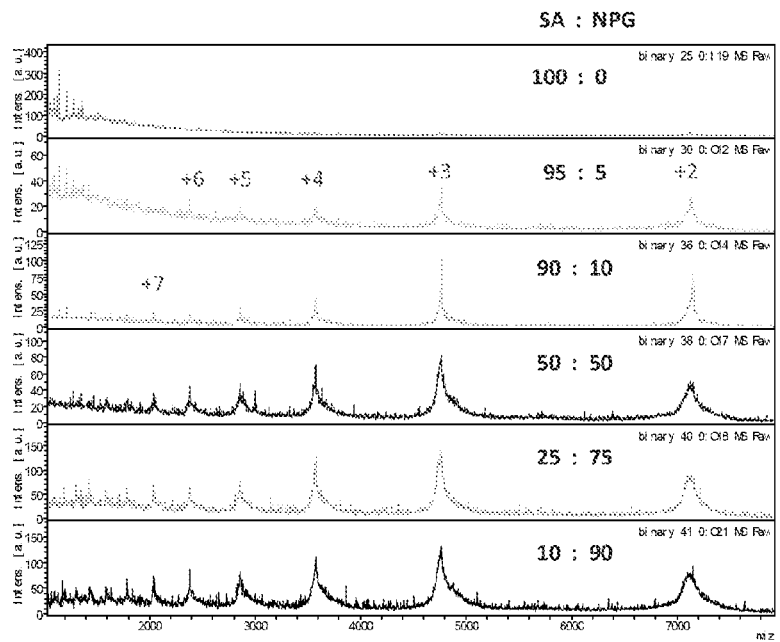
Figure 68B:
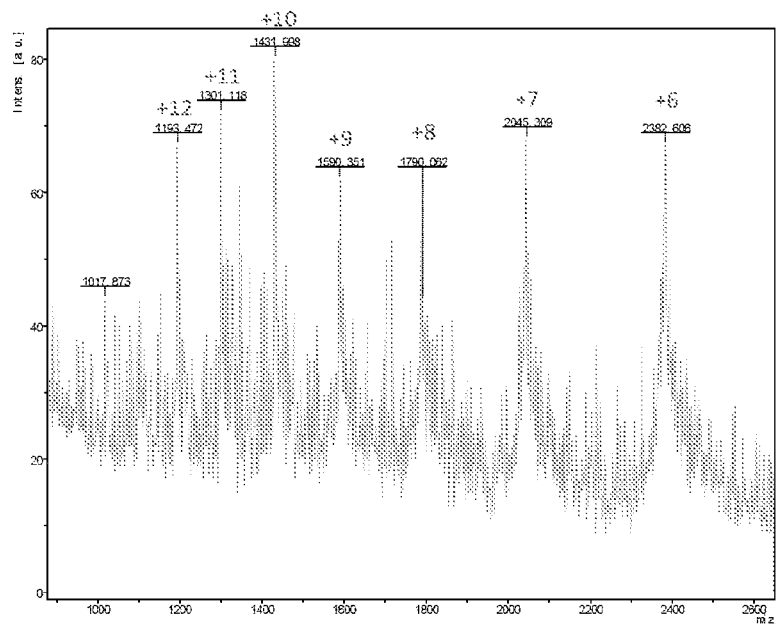

FIGS. 68A and 68B. LSIV-MS at HV of Lys with binary mixture of SA and 2-NPG using different composition by volume labeled in FIG. 68A. Data were acquired in positive reflectron mode using the Bruker UltrafleXtreme MALDI-TOF-TOF mass spectrometer instrument. The mass spectrum shown in FIG. 68B is the zoomed-in spectrum using 25% SA and 75% 2-NPG. Charge state observed is up to +12.

Figure 69A:
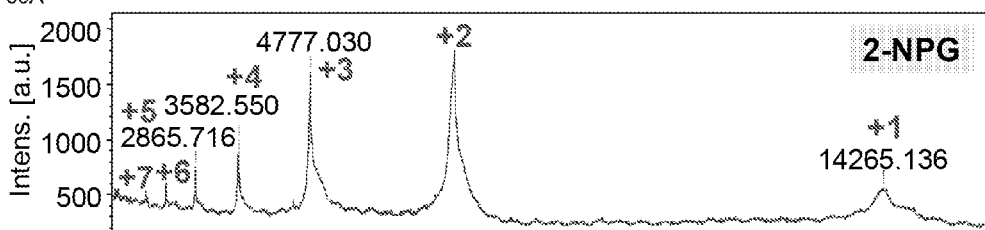
Figure 69B:
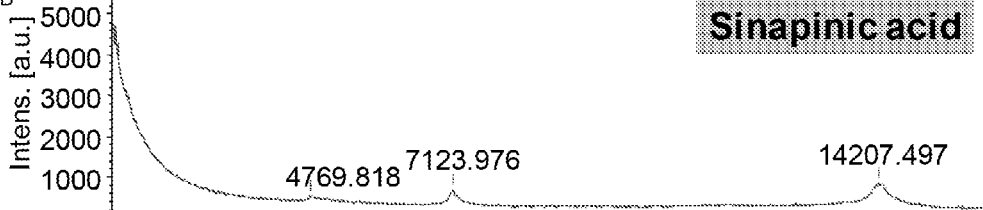
Figure 69C:
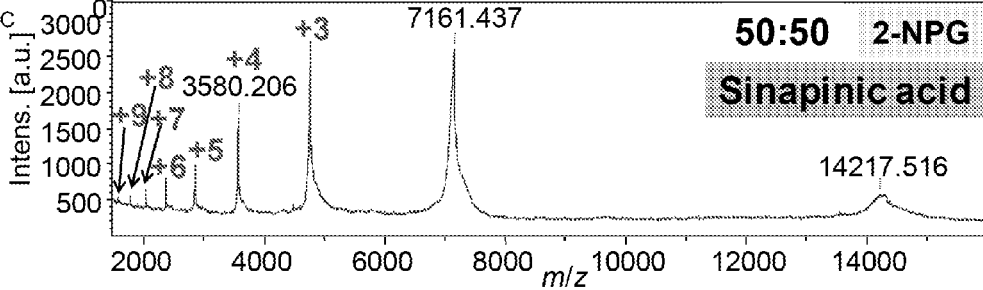

FIGS. 69A, 69B, and 69C. LSIV at HV of Lys with FIG. 69A) 100% 2-NPG, FIG. 69B) 100% SA, and FIG. 69C) binary mixture of 50% 2-NPG and 50% SA. Data were acquired in positive reflectron mode using the Bruker UltrafleX Speed MALDI-TOF mass spectrometer instrument.

Figure 70A:
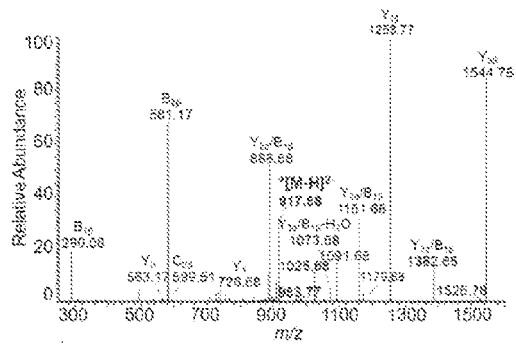
Figure 70C:
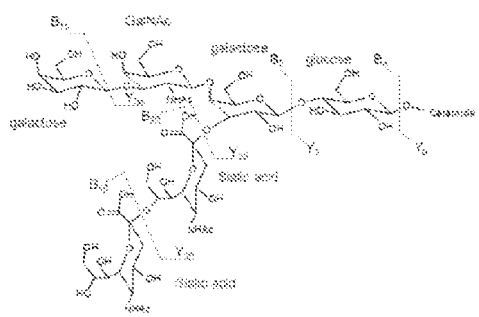
Figure 70B:
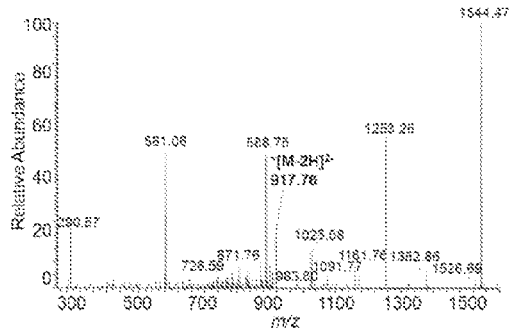

FIGS. 70A, 70B, and 70C. Collision induced dissociation (CID) of $GD_{1b}$ ganglioside from (FIG. 70A) purchased sample (Sigma Aldrich, St. Louis, Mo.) and (FIG. 70B) directly from mouse brain tissue. The $[M-2H]^{2-}$ peak at 917.5 was selected as the parent ion. In (FIG. 70A), 5 pmol GD1b with 2,5-DHAP matrix, an isotopic width of 0.7, collision energy 25 eV, and activation time of 10 msec were used. The most abundant fragment at m/z 1544 corresponds to the loss of a sialic acid (FIG. 70C). Several characteristic fragments identifying the ganglioside species as $GD_{1b}$ are also present, including m/z 581, corresponding to two attached sialic acids; m/z 1382, the loss of the end group sugars (one sialic acid and one galactose); and m/z 1161, the loss of the end group sugars and the GalNAc attached to the galactose. Similar fragments occur in a mouse brain tissue section spotted with 0.5 pL of 2,5-DHAP (FIG. 70B) (isotopic width 1.0, collision energy 40 eV, activation time 10 msec).

Figure 71A:
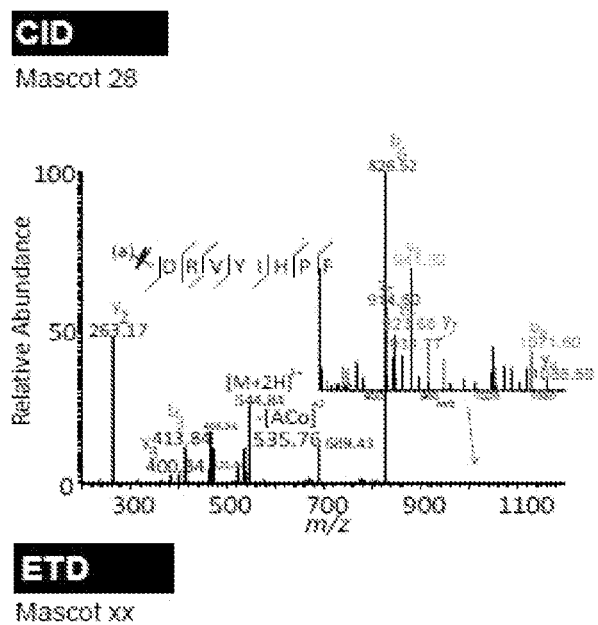
Figure 71B:
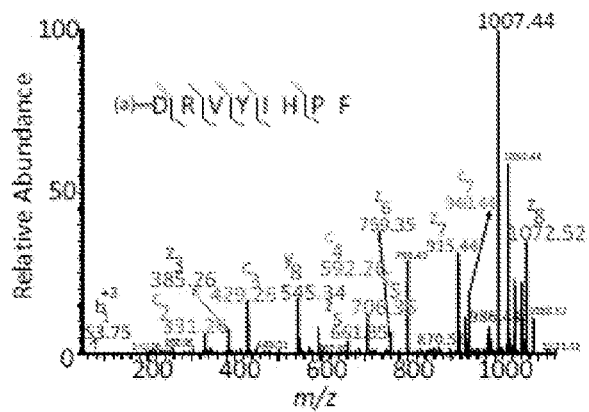

FIGS. 71A and 71B. AP-MAII MS/MS mass spectra of 2 pmol $pL^{-1}$ acetylated angiotensin II (MW 1088) with 2,5-DHAP as matrix using (FIG. 71A) CID and (FIG. 71B) ETD on Thermo LTQ-Velos mass spectrometer instrument at an inlet capillary temperature of 350° C.

Figures 72A, 72B:
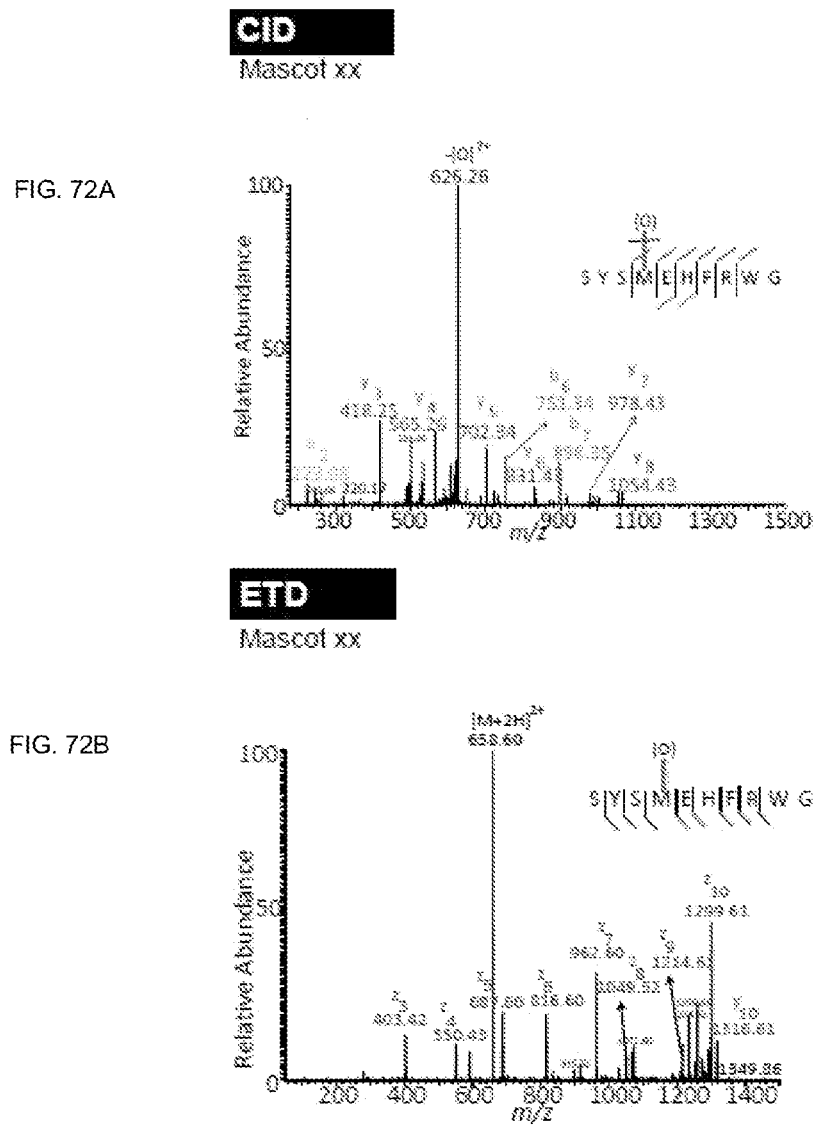

FIGS. 72A and 72B. AP-MAII MS/MS mass spectra of 2 pmol $pL^{-1}$ oxidized ACTH fragment (1-10) (MW 1315) with 2,5-DHAP as matrix using (FIG. 72A) CID and (FIG. 72B) ETD on Thermo LTQ-Velos mass spectrometer instrument at an inlet capillary temperature of 350° C.

Figure 73A:
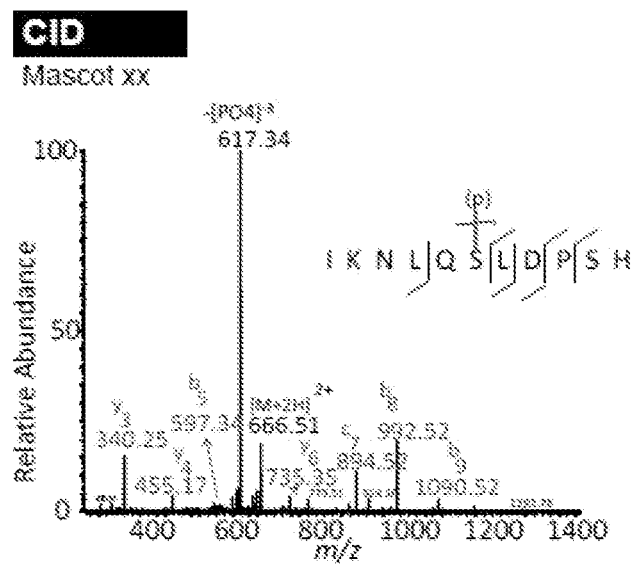
Figure 73B:
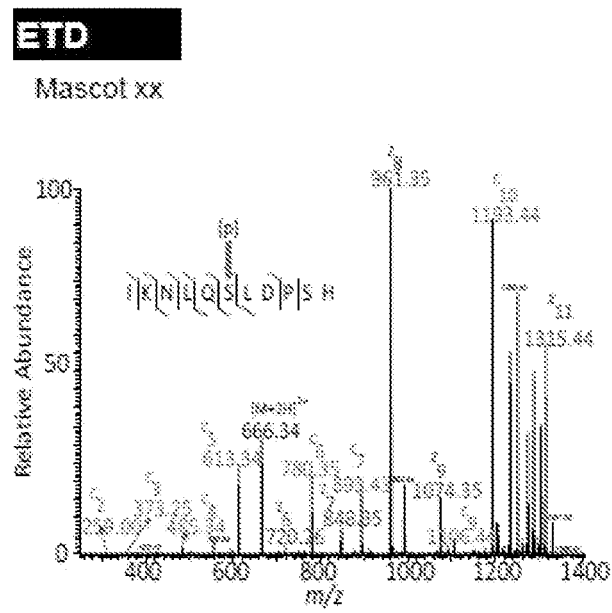

FIGS. 73A and 73B. AP-MAII MS/MS mass spectra in negative mode of 2 pmol $pL^{-1}$ phosphorylated cholecystokinin (MW 1334) with 2,5-DHAP as matrix using (FIG. 73A) CID and (FIG. 73B) ETD on Thermo LTQ-Velos mass spectrometer instrument at an inlet capillary temperature of 350° C.

Figure 74A:
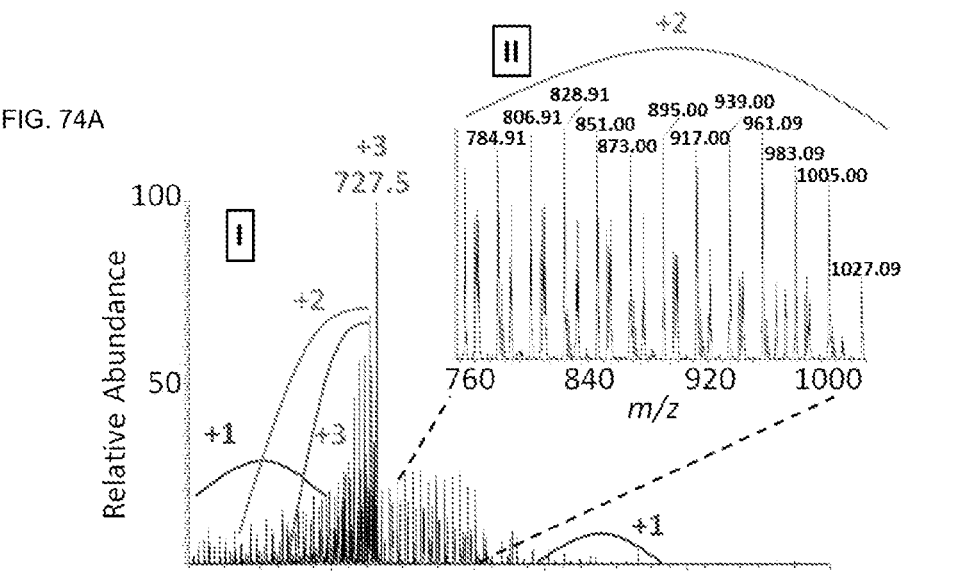
Figure 74B:
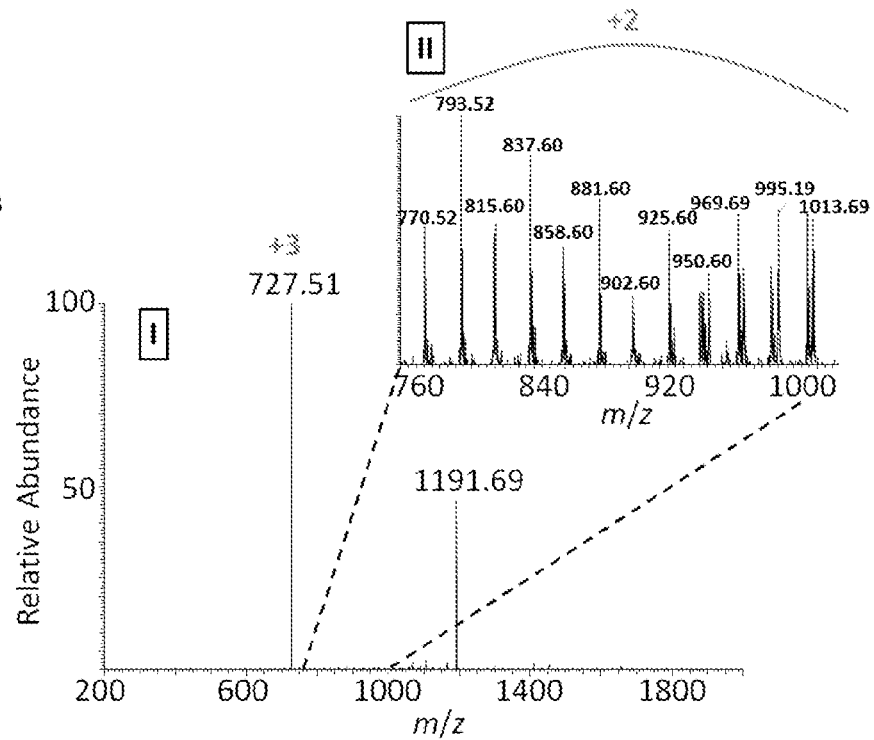

FIGS. 74A and 74B. A single (FIG. 74A) CID-LSI-MS/MS and (FIG. 74B) ETD-LSII-MS/MS scan of PEGDME-2000 with (I) Full and (II) Inset fragment ion mass spectra using a 2,5-DHAP and LiCl matrix (400:1 salt:polymer molar ratio) on an LTQ-Velos mass spectrometer. The triply charged m/z 727.5 was selected with a ±0.7 mass unit window. (FIG. 74A) CID fragmentation was induced with collision energy of "50". (FIG. 74B) ETD fragmentation was obtained by permitting the reagent gas fluoranthene to react for 500 milliseconds.

Figure 75A:
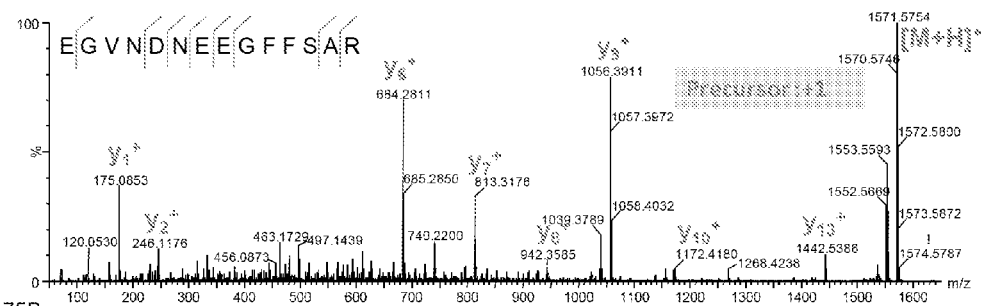
Figure 75B:
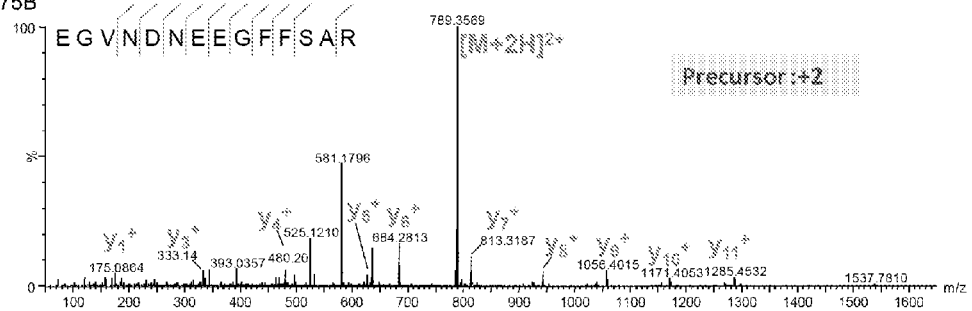

FIGS. 75A and 75B. LSIV-CID-MS/MS at IP mass spectra of 2.5 pmol pL$^{-1}$ GFP with 2,5-DHAP prepared using droplet method in 1:1 ratio and acquired on a SYNAPT G2 mass spectrometer with a MALDI source. (FIG. 75A) +1 and (FIG. 75B) +2 fragment ions produced from precursor ions +1 and +2 charge states respectively.

Figure 76A:
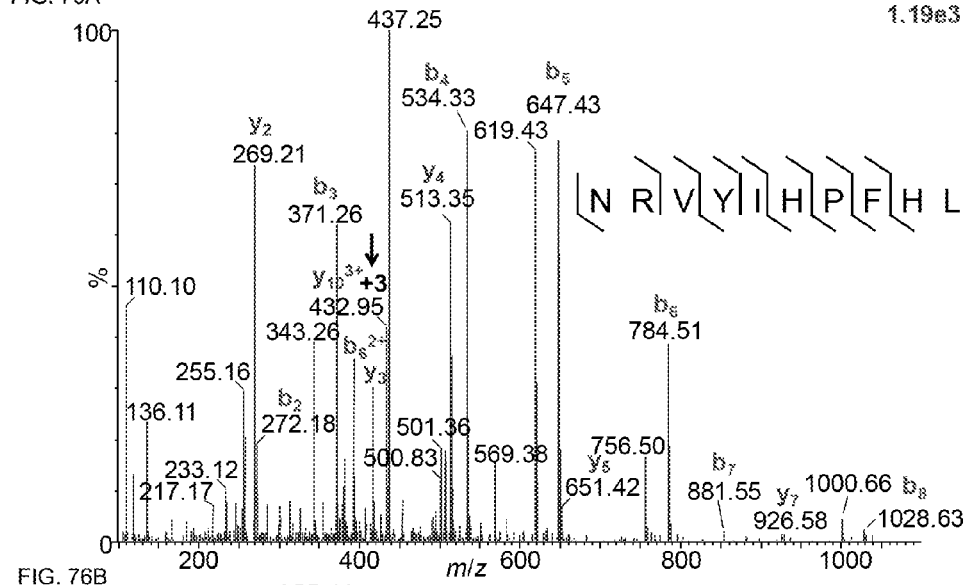
Figure 76B:
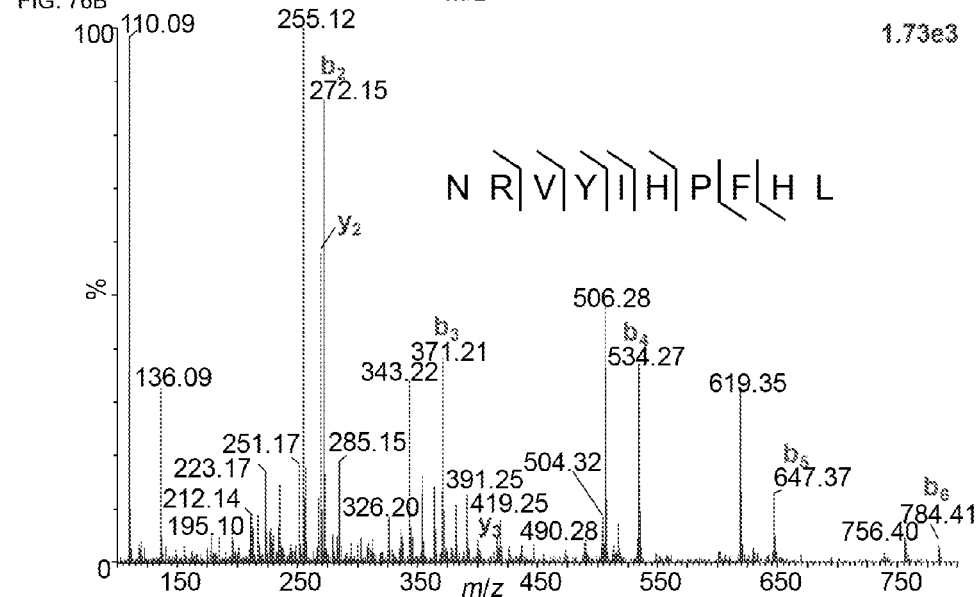

FIGS. 76A and 76B. LSIV-CID-MS/MS at IP mass spectrum of 2.5 pmol pL$^{-1}$ angiotensin I with 2,5-DHAP prepared using droplet method in 1:1 ratio and acquired using the MALDI source of SYNAPT G2 mass spectrometer instrument at "200" laser fluence. Precursor ion selected is +3 charged state (m/z 432.95). CID fragment ions produced by FIG. 76A) triwave trap DC bias at '75' and FIG. 76B) trap voltage on at 32 V.

Figure 77A:
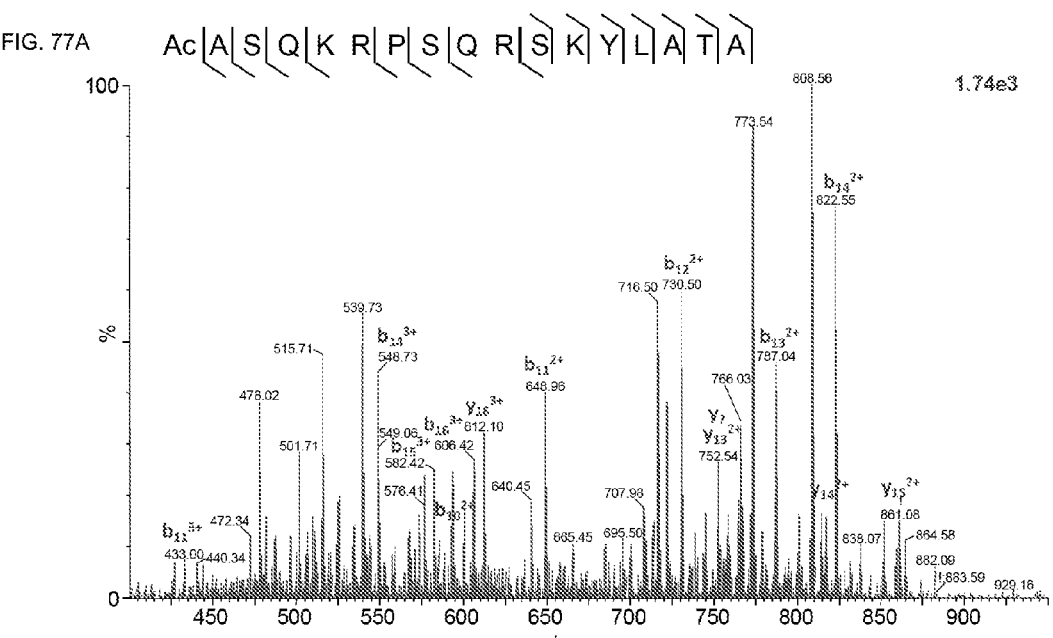
Figure 77B:
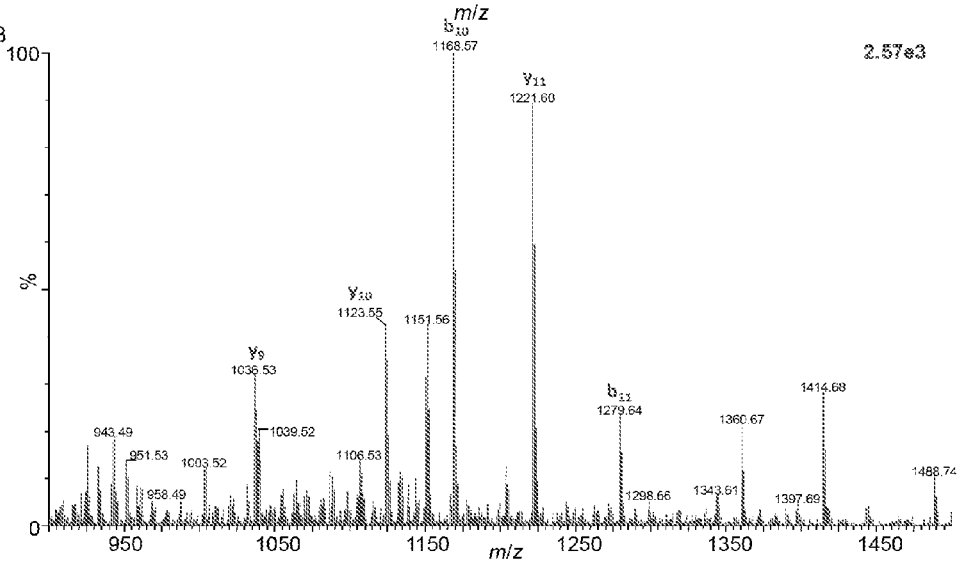
Figure 80A:
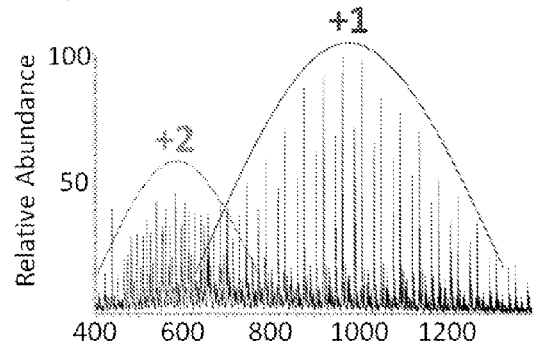
Figure 80B:
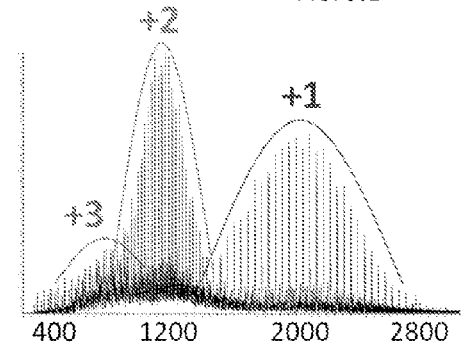
Figure 80C:
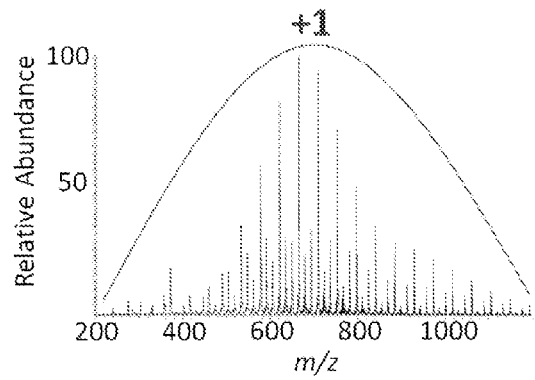
Figure 80D:
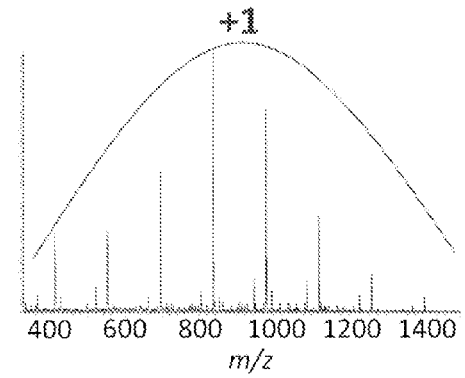

FIGS. 77A and 77B. LSIV-CID-MS/MS at IP of 2.5 pmol pL$^{-1}$ N-acetylated myelin basic protein fragment (MBP) with 2,5-DHAP prepared using droplet method in 1:1 ratio and acquired using the MALDI source of SYNAPT G2 mass spectrometer instrument at "200" laser fluence. Precursor ion selected are +3 (m/z 611.92) and +2 (m/z 917.49) charge states. FIG. 77A) +2, +3 and FIG. 77B) 30 1 fragment ions from +3 and +2 precursor ions respectively. Trap voltage used are 32 V and 58 V for +3 and +2 charge states respectively.

FIGS. 78A, 78B, and 78C. (FIG. 78C) LSII-IMS-MS 2-D plot of drift time vs. m/z of a mixture of 30 pmol of poly ethylene glycol (PEG) 1000 and 30 pmol of poly(t-butyl methacrylate) (PtBMA) 1640 with 4,6-dinitropyrogallol (4,6-DNPG) and LiCl (400:1 salt:analyte molar ratio) as matrix and acquired on a Waters SYNAPT G2 mass spectrometer instrument using the Nanolockspray source. The drift time distributions were created from the drift time integrations of m/z regions (FIG. 78A) 694-702 and (FIG. 78B) 834-836. The source temperature was held at 150° C. with additional 10 V of resistance heating through a wire-coiled home-built desolvation tube device Similar to teachings from Inutan Ellen & Trimpin J. Proteome Res. 9 (11) 6077-6081, 2010.

FIGS. 79A, 79B, and 79C. (FIG. 79A) A full LSIV-IMS-MS at IP 2-D plot of PEG DME 2000 with 4,6-dinitropyrogallol (4,6-DNPG) and LiCl (400:1 salt:analyte molar ratio) as matrix acquired on a Waters SYNAPT G2 mass spectrometer instrument with a MALDI source. The inset area (FIG. 79B) shows separation of +1 and +2 ions and their integrated drift times at m/z 1109 can be seen in (FIG. 79C).

FIGS. 80A-80D. LSII-MS analysis of polymers on the LTQ-Velos mass spectrometer with 500:1 salt:analyte molar ratios and a 400° C. ion transfer capillary: (FIG. 80A) PEG-1000 using a 2,5-DHAP and NaCl matrix, (FIG. 80B) 4-arm PEG-2000 using LiCl and 2-NPG, (FIG. 80C) Pentaethyritol ethoxylate (PEEO) 800 using a 2,5-DHAP and LiCl matrix, and (FIG. 80D) PtBMA using a 2,5-DHB and NaCl matrix.

Figure 81:
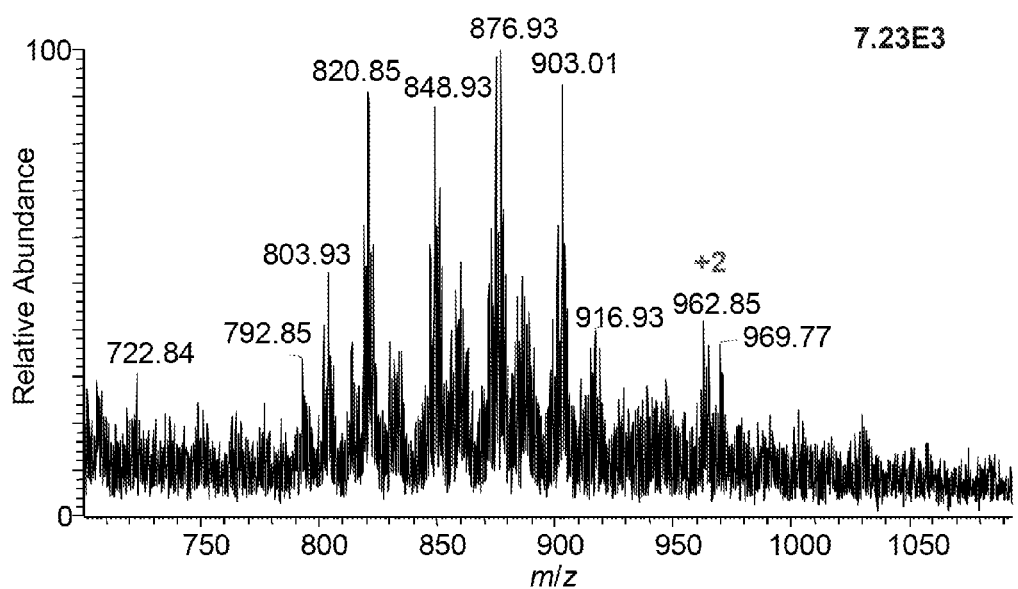
Figure 82A:
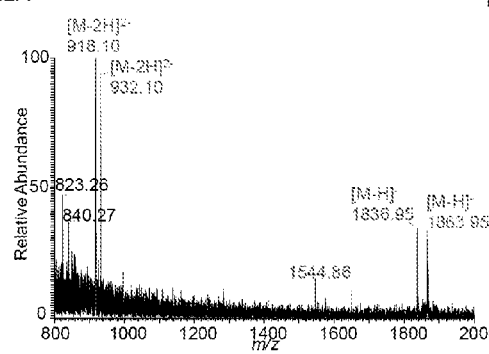
Figure 82C:
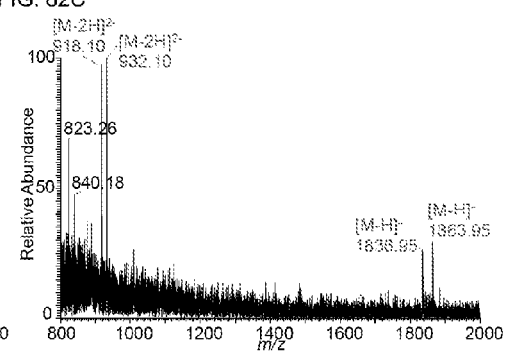
Figure 82B:
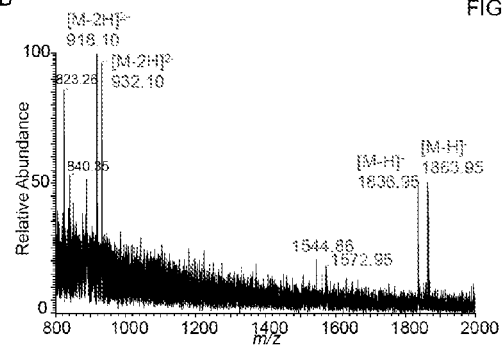
Figure 82D:
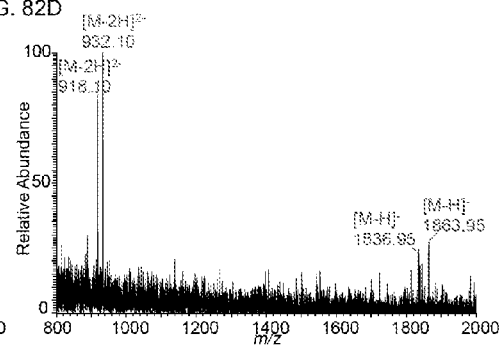

FIG. 81. LSII-MS mass spectrum of crude algae extract with 4,6-DNPG matrix acquired using the LTQ-Velos mass spectrometer with an inlet capillary temperature of 450° C.

FIGS. 82A-82D. LSII-MS negative mode analysis of 5 pmol pL$^{-1}$ GD1b ganglioside (MW 1838, 1866 Da) with 2-amino-3-nitrophenol matrix, prepared using the layer method, and acquired on the LTQ-Velos mass spectrometer instrument at (FIG. 82A) 450° C., (FIG. 82B) 400° C., (FIG. 82C) 350° C. and (FIG. 82D) 250° C. inlet capillary temperature.

Figure 83:
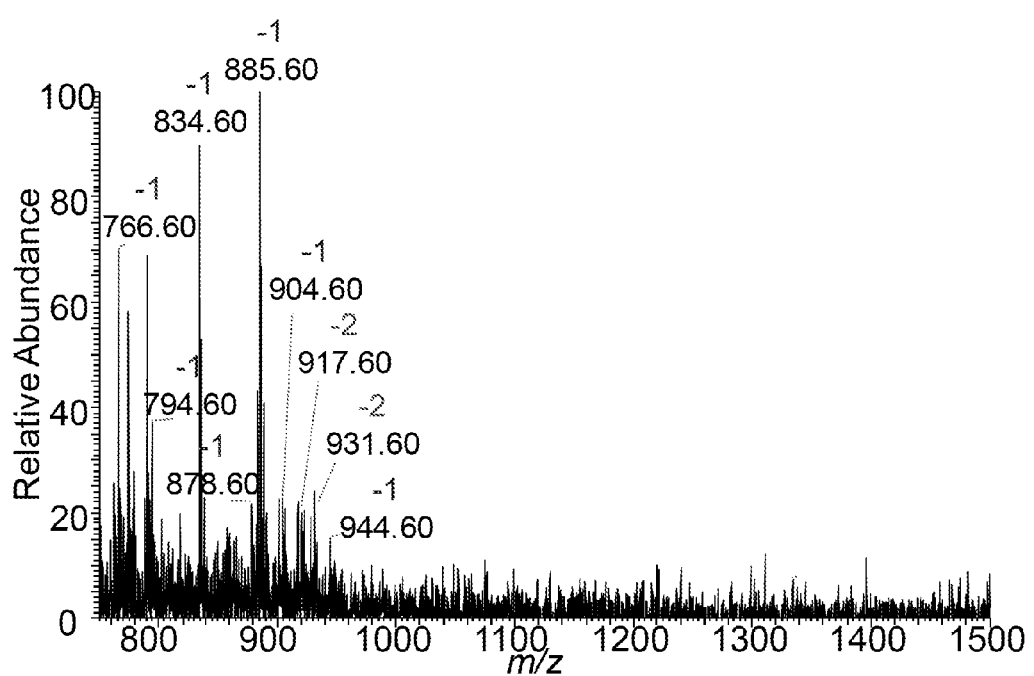
Figure 84A:
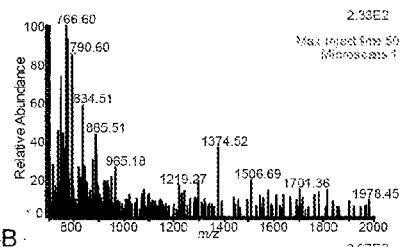
Figure 84B:
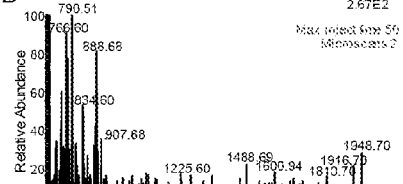
Figure 84C:
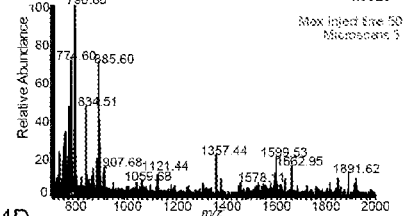
Figure 84D:
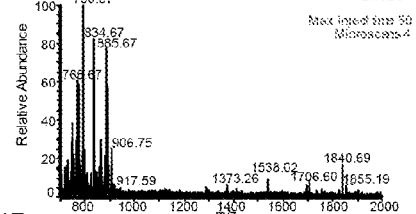
Figure 84E:
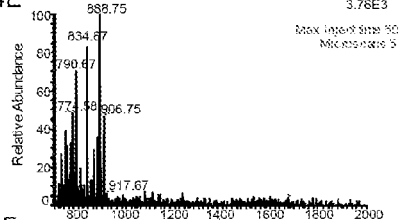
Figure 84F:
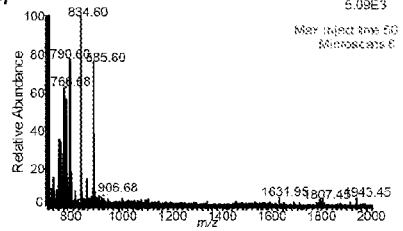
Figure 84G:
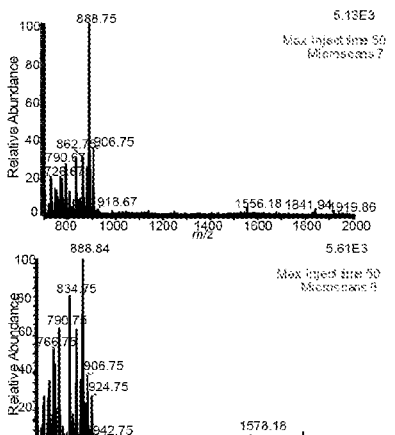
Figure 84H:
Figure 84I:
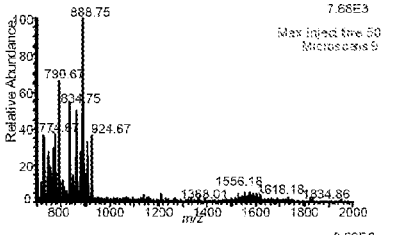
Figure 84J:
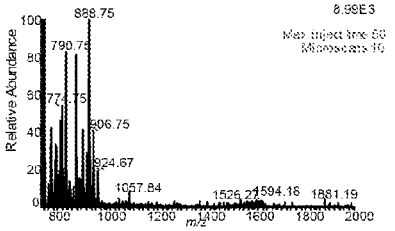
Figure 84K:
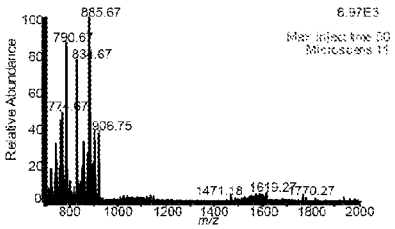
Figure 84L:
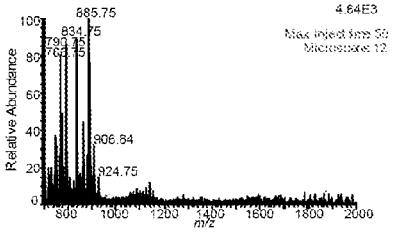
Figure 85A:
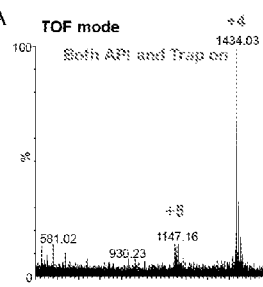
Figure 85B:
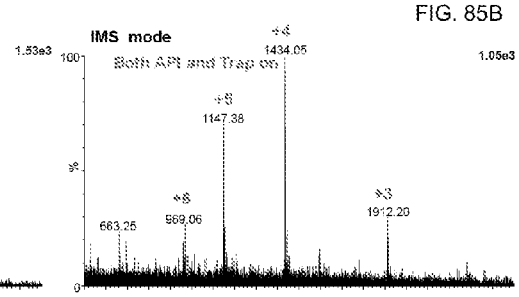
Figure 85C:
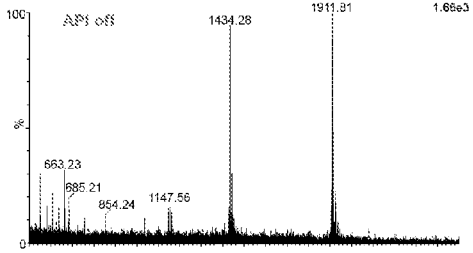
Figure 85D:
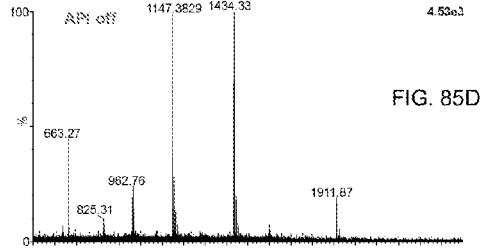
Figure 85E:
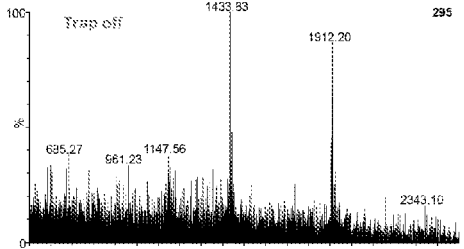
Figure 85F:
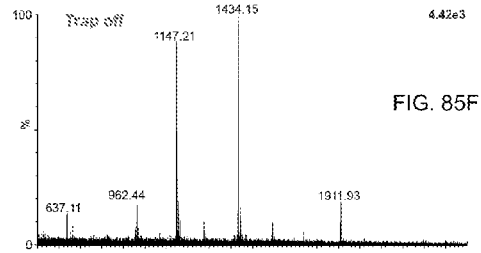
Figure 85G:
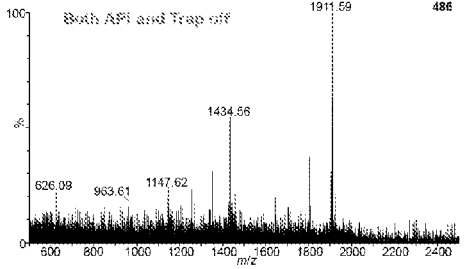
Figure 85H:
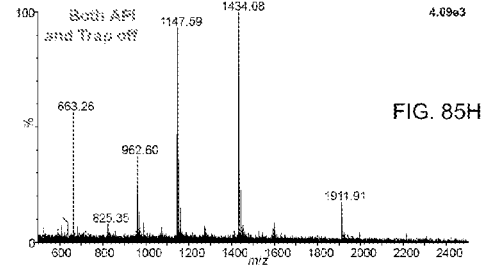

FIG. 83. LSII-MS of mouse brain tissue spotted with 0.5 pL of 2-amino-3-nitrophenol matrix and analyzed in negative ion mode on the LTQ-Velos mass spectrometer instrument at 250° C. inlet capillary temperature. Several lipid species are detected, including phosphatidylserine (m/z 834), phosphatidylinisitol (m/z 885.60) and sulfatides (m/z 878.60). Labile GD1 gangliosides, are detected without fragmentation at m/z 917.60 and 931.60.

FIGS. 84A-84L. Single shot LSII acquisitions of mouse brain tissue in negative ion mode spotted with 2,5-DHAP matrix at 50 max inject time and 1-12 microscans (FIGS. 84A-84L, respectively) acquired on a Thermo LTQ-Velos mass spectrometer instrument with an inlet capillary temperature of 450° C.

FIGS. 85A-85H. LSII-MS of BI with 2,5-DHAP matrix prepared using layer method in 1:4 ratio and acquired using the SYNAPT G2 mass spectrometer with a Nanolockspray source acquired at 150° C. source temperature: FIGS. 85A, 85C, 85E, and 85G) TOF mode only with gas flows from API and Trap and FIGS. 85B, 85D, 85F, and 85H) with IMS (additional He and IMS gas flows): (FIGS. 85A and 85B) both API gas and Trap gas on, (FIGS. 85C and 85D) API gas off, (FIGS. 85E and 85F) Trap gas off, and (FIGS. 85G and 85H) both API and Trap gas off.

Figure 86A:
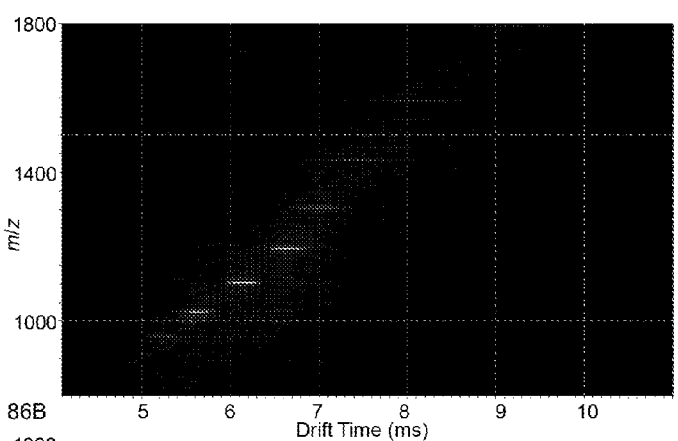
Figure 86B:
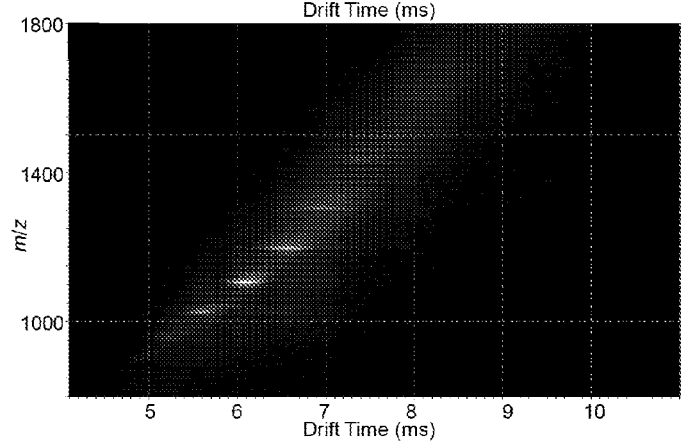
Figure 86C:
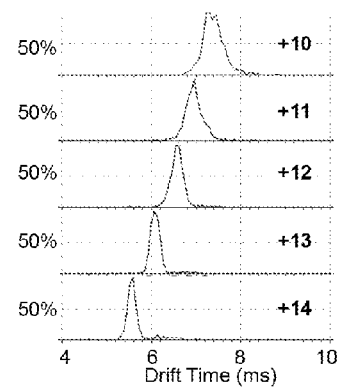
Figure 86D:
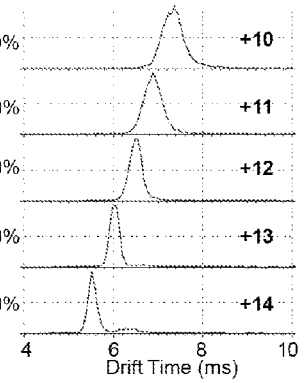

FIGS. 86A-86D. AP-LSII-IMS-MS 2-D plots of drift time vs. m/z of 5 pmol pL$^{-1}$ lysozyme acquired with FIG. 86A) 2-NPG matrix using 90° bent tube and FIG. 86B) 2,5-DHAP matrix in straight tube on SYNAPT G2 mass spectrometer using the Nanolockspray source. Extracted drift times of +10 to +14 charge states; FIG. 86C) 2-NPG matrix using 90° bent tube and FIG. 86D) 2,5-DHAP matrix in straight tubessss on SYNAPT G2 mass spectrometer using the Nanolockspray source. Analyte/matrix spot was prepared in 1:3 layer method on a glass plate and blow dried.

FIGS. 87A-87F. MAII-MS mass spectra of 2 pmol Ang. I prepared in 1:1 (FIGS. 87A and 87B) and 1:2 (FIGS. 87C-87F) analyte:matrix ratio with CHCA (FIGS. 87A, 87C, and 87E) and SA (FIGS. 87B, 87D, and 87F) acquired at 450° C. (FIGS. 87A-87D) and 400° C. (FIGS. 87E and 87F) inlet capillary temperature using an LTQ-Velos mass spectrometer instrument.

Figure 88A:
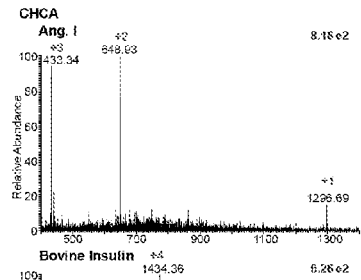
Figure 88B:
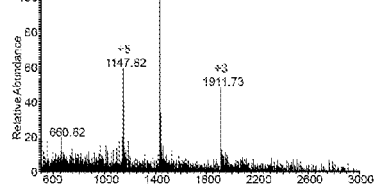
Figure 88C:
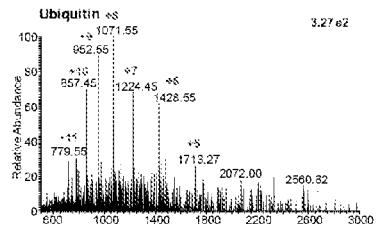
Figure 88D:
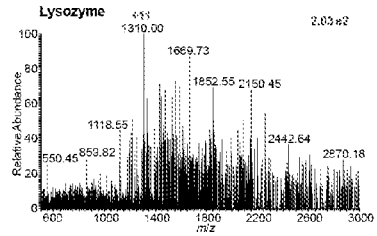
Figure 88E:
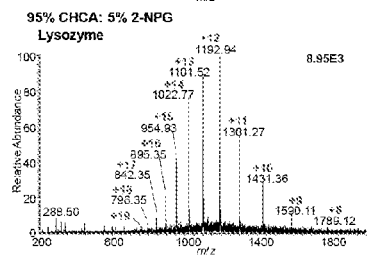
Figure 88F:
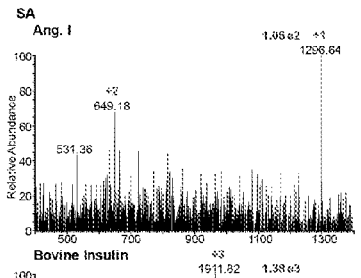
Figure 88G:
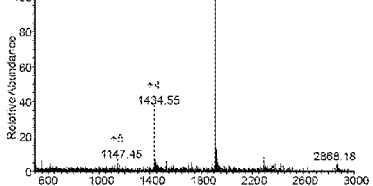
Figure 88H:
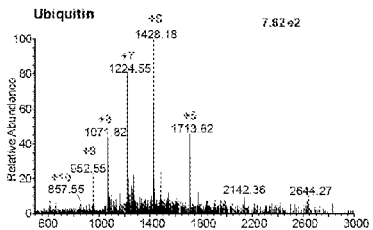
Figure 88I:
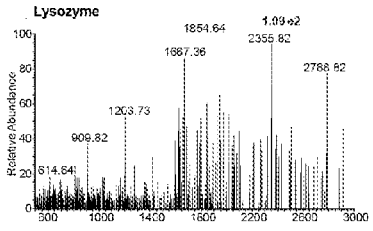
Figure 88J:
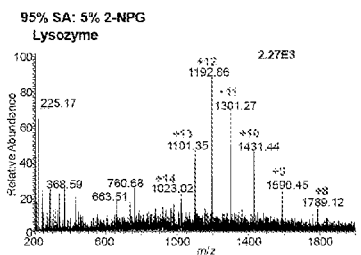

FIGS. 88A-88J. MAII-MS mass spectra of 5 pmol of FIGS. 88A and 88F) Ang. I, FIGS. 88B and 88G) bovine insulin, FIGS. 88C and 88H) ubiquitin, and FIGS. 88D and 88I) lysozyme with CHCA (FIGS. 88A-88D) and SA (FIGS. 88F-88I) acquired at 450° C. inlet capillary temperature using an LTQ-Velos mass spectrometer instrument. Mass spectra of lyzozyme using binary matrix mixture of 95% CHCA: 5% 2-NPG (FIG. 88E) and 95% SA: 5% 2-NPG (FIG. 88J). Analyte/matrix spot was prepared in 1:2 ratio using layer method on a glass plate and air dried.

Figure 89A:
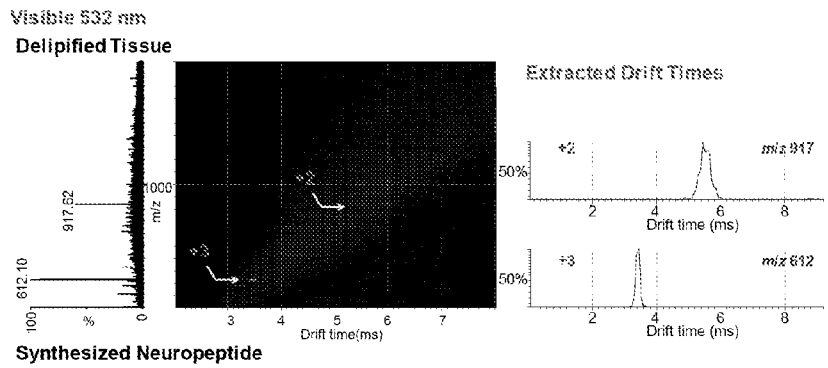
Figure 89B:
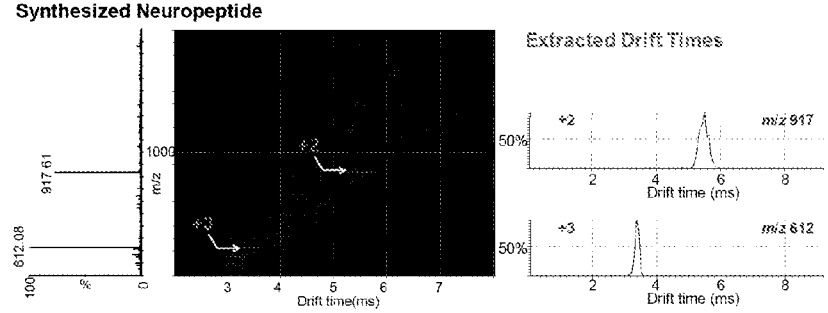
Figure 89C:
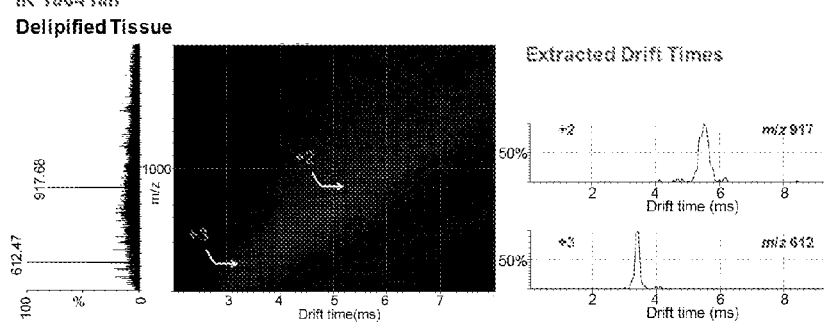
Figure 89D:
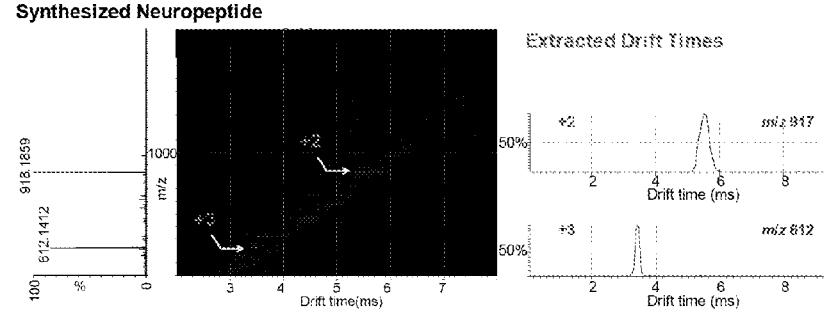

FIGS. 89A-89D. LSII-IMS-MS of the neuropeptide, MBP, from FIGS. 89A and 89C) delipified mouse brain tissue and FIGS. 89B and 89D) syntheiszed MBP peptide using 2,5-DHAP matrix at 532 nm (FIGS. 89A and 89B) and 1064 nm wavelengths (FIGS. 89C and 89D). Mass spectra (left panel), 2-D plots of drift time vs. m/z (middle panel) and extracted drift times for +2 and +3 ions (right panel) are displayed.

The following abbreviations are used accordance with FIGS. 90-134 which show mass spectra obtained with matrix compositions described in FIGS. 135A-135L:
BI: 5 pmol μL$^{-1}$ bovine insulin (MW 5731) diluted in water;
Ubi: 5 pmol μL$^{-1}$ ubiquitin (MW 8561) in water;
Lys: 5 pmol μL$^{-1}$ lysozyme (MW 14.3 kDa) in water;
Ang I: angiotensin I (MW 1295) in water;
GD1a: 5 pmol μL$^{-1}$ (MW 1837, 1865) diluted in 50:50 methanol:water and analyzed in negative mode;

SB: solvent based analysis using 1 μL of the analyte and add matrix on top (5 mg in 50 μL 50:50 ACN:H₂O and warmed if not dissolved completely) in 1:1 analyte:matrix volume ratio using layer method on glass plate and air dried;

SF: solvent-free analysis using 10 μL of 1 mg mL$^{-1}$ ang. I evaporated to complete dryness, added with powder matrix, homogenized, and spotted on a glass plate using a ball-mill device at 25 Hz frequency for 10 min.

The data presented in FIGS. 90-134 was acquired using the Thermo LTQ-Velos mass spectrometer instrument with an inlet capillary temperature of 450° C., microscan of 5, and maximum injection time of 20 ms.

FIG. 90. MAII-MS of Ang I (SF) with 2,6-dihydroxybenzoic acid matrix.

FIG. 91. MAII-MS of BI (SB) and Ang I (SF) with 3,4-dihydroxybenzoic acid matrix.

FIG. 92. MAII-MS and LSII-MS of BI (SB) with 5-methylsalisylic acid matrix.

FIG. 93. LSII-MS of BI (SB) with 3-hydroxypicolinic acid matrix.

FIG. 94. MAII-MS of BI (SB) with 2,3-dihydroxyacetophenone matrix.

FIG. 95. MAII-MS of BI (SB) and Ang I (SF) with 2,4-dihydroxyacetophenone matrix.

FIG. 96. MAII-MS of Ubi (SB) with 2,4,6-trihydroxyacetophenone matrix.

FIG. 97. MAII-MS of Ang I (SF) with 3,4-dihydroxybenzenesulfonic acid matrix.

FIG. 98. MAII-MS of Ang I (SF) with 4-nitrocatechol matrix.

FIG. 99. MAII-MS of Ubi (SB) and Ang I (SF) with 2-nitroresorcinol matrix.

FIG. 100. MAII-MS of BI (SB) and Ang I (SF) with 2-nitrophloroglucinol matrix.

Figure 101:
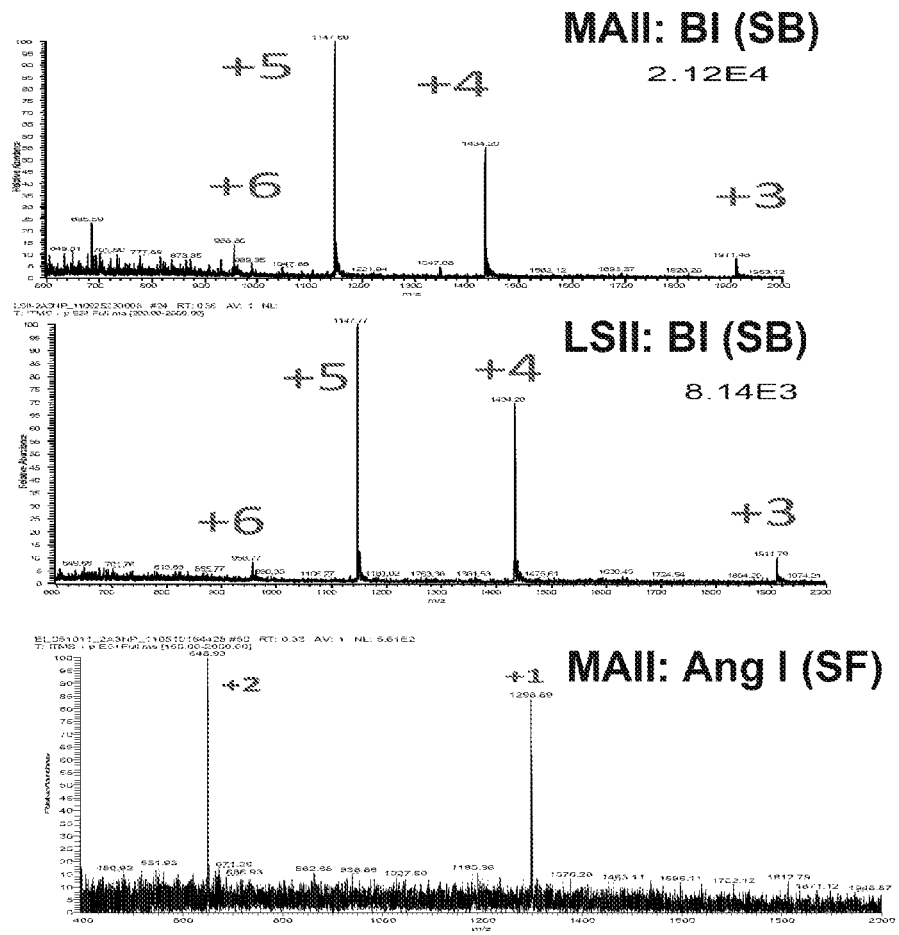

FIG. 101. MAII-MS of BI (SB) and Ang I (SF), and LSII-MS of BI (SB) with 2-amino-3-nitrophenol matrix.

FIG. 102. MAII-MS of BI (SB) with 2,4-dinitrophenol matrix.

FIG. 103. MAII-MS of BI (SB) with 3,5-dinitro-benzene-1,2-diol matrix.

FIG. 104. MAII-MS of BI (SB) with 4,6-dinitropyrogallol matrix.

FIG. 105. MAII-MS of Ang I (SF) with 4-nitro-5-[2-nitroethyl]-1,2-benzenediol matrix.

FIG. 106. MAII-MS of Ang I (SF) with chlorohydroquinone matrix.

FIG. 107. MAII-MS of GD1a (SB) with 1,4-dicyanobenzene matrix.

FIG. 108. MAII-MS and LSII-MS of BI (SB) with salicylamide matrix.

Figure 109:
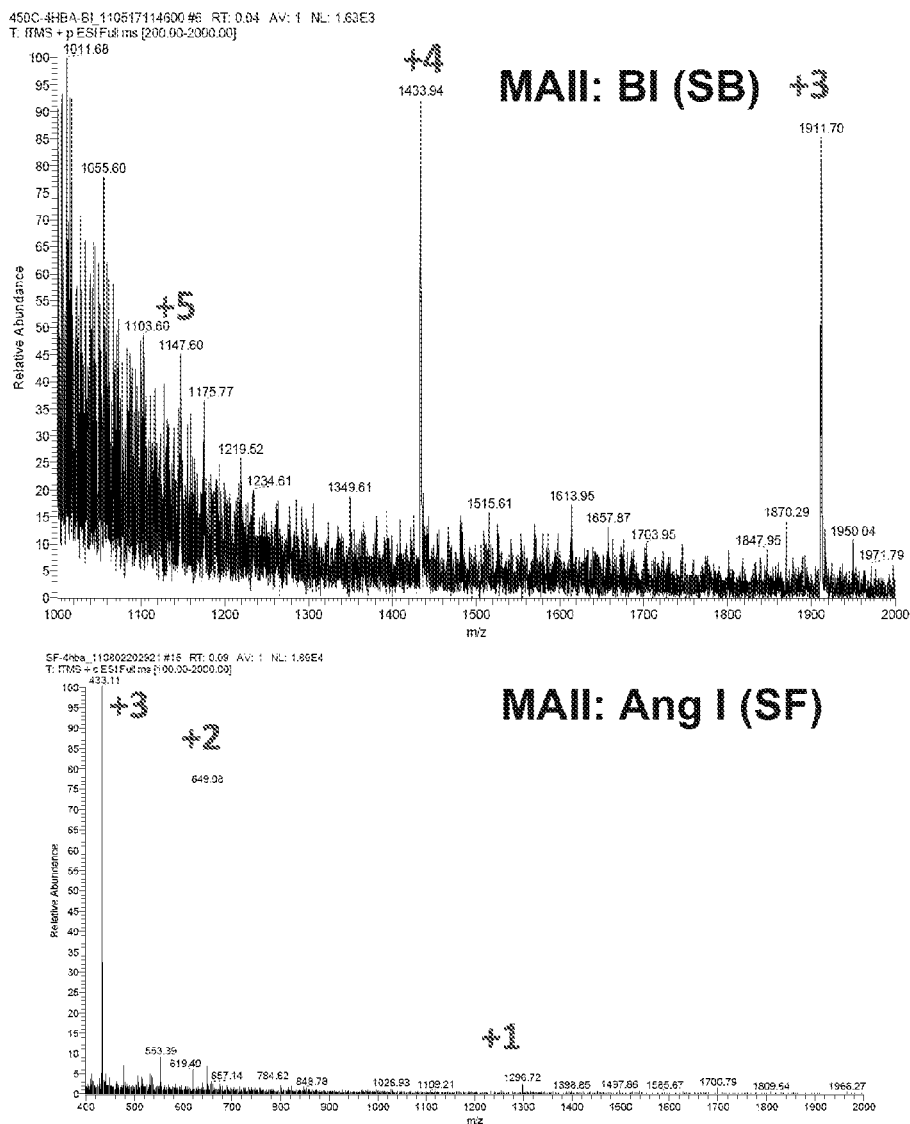

FIG. 109. MAII-MS of BI (SB) and Ang I (SF) with 4-hydroxybenzamide matrix.

FIG. 110. MAII-MS of BI (SB) and Ang I (SF), and LSII of BI (SB) with 3,5-dihydroxybenzamide matrix.

FIG. 111. MAII-MS of Ang I (SF) and GD1a (SB) with 2-hydroxy-5-methylbenzamide matrix.

FIG. 112. MAII-MS of BI (SB) and Ang I (SF) with 5-bromo-2-hydroxybenzohydrazide matrix.

FIG. 113. MAII-MS and LSII-MS of BI (SB) with 3-hydroxy-2-naphthoic hydrazide matrix.

Figure 114:
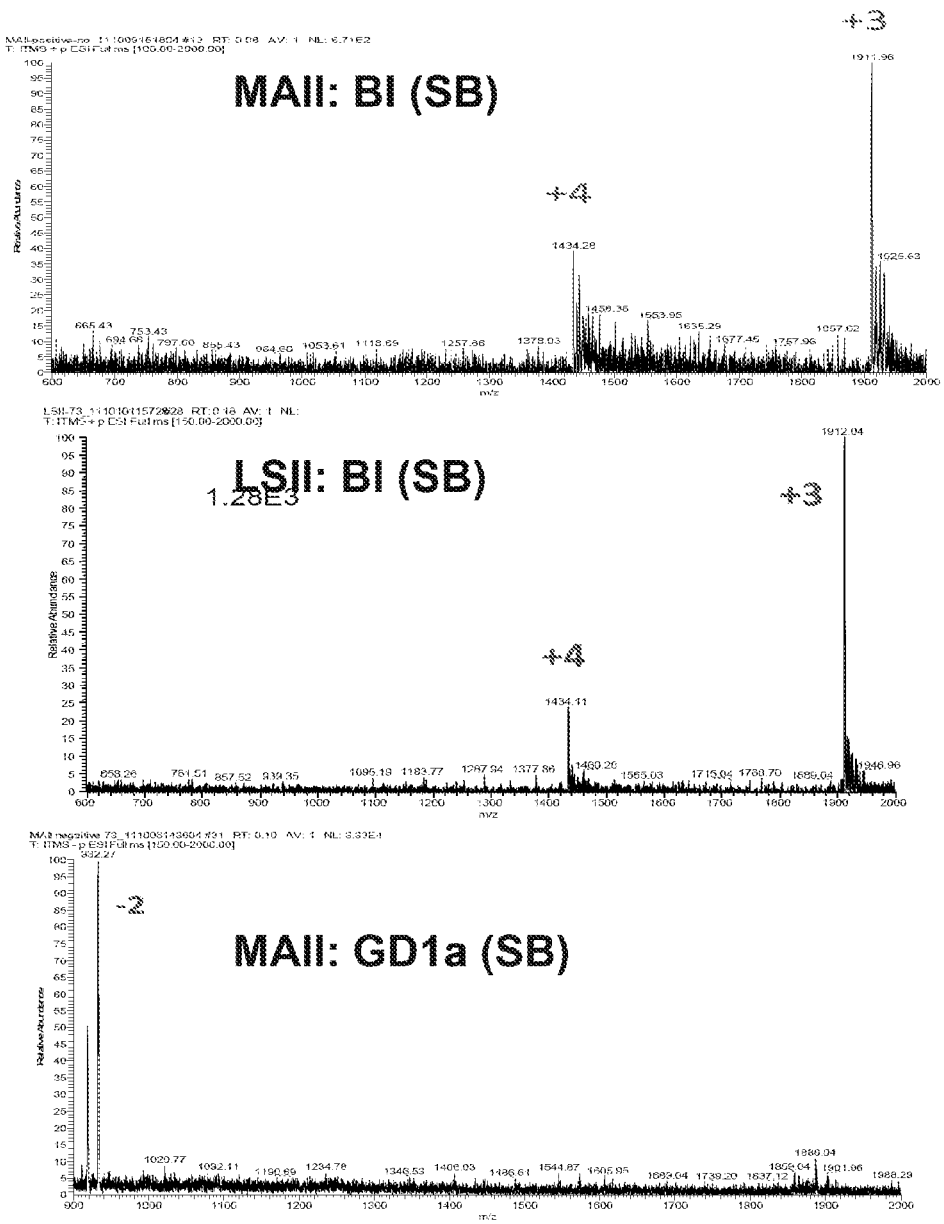

FIG. 114. MAII-MS and LSII-MS of BI (SB), and MAII of GD1a (SB) with 2-amino-3-nitropyridine matrix.

FIG. 115. MAII-MS and LSII-MS of BI (SB) with 2-amino-4-methyl-3-nitropyridine matrix.

FIG. 116. MAII-MS of Ang I (SF) with phenol matrix.

FIG. 117. MAII-MS of BI (SB) and Ang I (SF) with resorcinol matrix.

FIG. 118. MAII-MS of BI (SB) with hydroquinone matrix.

Figure 119:
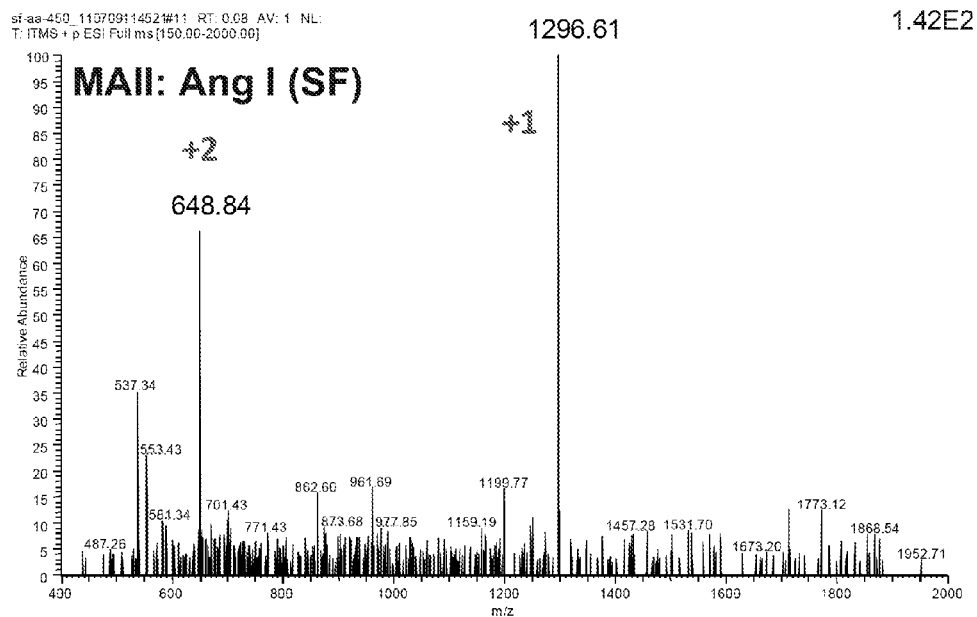

FIG. 119. MAII-MS of Ang I (SF) with phloroglucinol matrix.

FIG. 120. MAII-MS of Ubi (SB) and Ang I (SF) with pyrogallol matrix.

FIG. 121. MAII-MS of Ang I (SF) with 4-trifluoromethyl phenol matrix.

FIG. 122. MAII-MS of Lys (SB) and Ang I (SF) with 1,4-dihydroxy-2,6-dimethoxybenzene matrix.

FIG. 123. MAII-MS of Ubi (SB) and Ang I (SF) with 2,4-dihydroxybenzaldehyde matrix.

FIG. 124. MAII-MS of Ang I (SF) with cis-1,2-cyclohexandediol matrix.

FIG. 125. MAII-MS of Ang I (SF) with 5,5-dimethyl-2-nitrocyclohexane-1,3-dione matrix.

FIG. 126. MAII-MS of BI (SB) with succinic acid matrix.

FIG. 127. MAII-MS of BI (SB) with fumaric acid matrix.

FIG. 128. MAII-MS of BI (SB) with mesaconic acid matrix.

FIG. 129. MAII-MS of BI (SB) with 2,4-hexadienoic acid matrix.

FIG. 130. MAII-MS of Ang I (SF) and GD1a (SB) with cis,cis-2,5-dimethylmuconic acid matrix.

FIG. 131. MAII-MS of Ang I (SF) with trans,trans-muconic acid matrix.

FIG. 132. MAII-MS and LSII-MS of BI (SB) with methyl-4-oxo-2-pentenoate matrix.

FIG. 133. MAII-MS of BI (SB) with N-methylmaleamic acid matrix.

Figure 134:
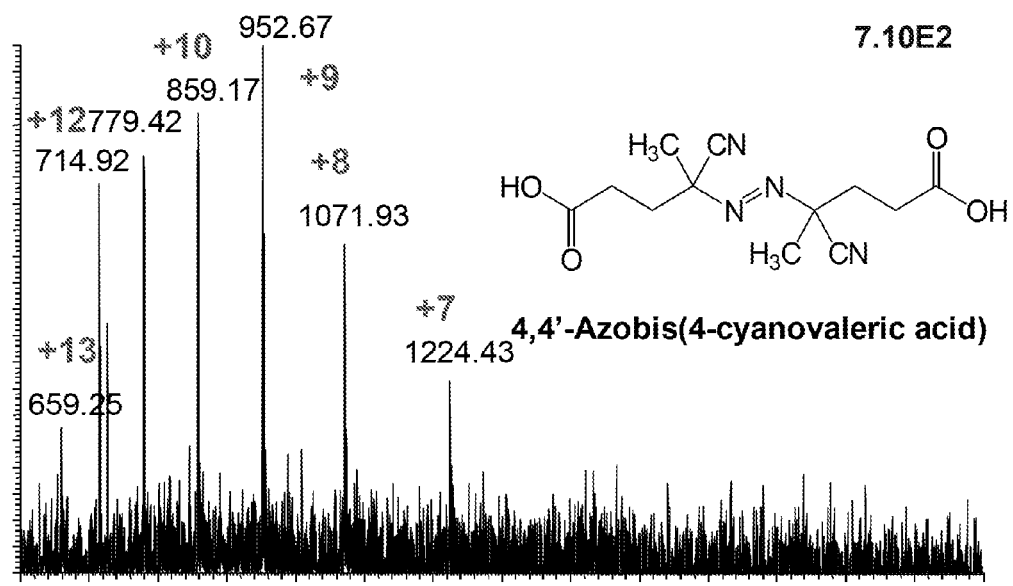

FIG. 134. MAII-MS of Ubi (SB) with 4,4'-azobis(4-cyanovaleric acid) matrix.

FIGS. 135-138 provide matrix compositions and equipment configurations that can be used with the systems and methods disclosed herein.

FIGS. 135A-135L show matrix compounds that have been shown to produce multiply charged ions upon impact of a force such as a laser beam when sufficient energy is provided in combination with a pressure drop region to initiate ion formation of the matrix/analyte association and also remove neutral matrix from the charged matrix/analyte association by a desolvation process. FIG. 135A shows benzoic acids; FIG. 135B shows acetophenones; FIG. 135C shows sulfonated compounds; FIG. 135D shows nitro compounds; FIG. 135E halogenated compounds; FIG. 135F shows cyano compounds; FIG. 135G shows benzamides; FIG. 135H shows pyridine compounds; FIG. 135I shows phenols/alcohols; FIG. 135J shows benzaldehydes; FIG. 135K shows non-aromatic rings; and FIG. 135L shows linear compounds.

Figure 136:
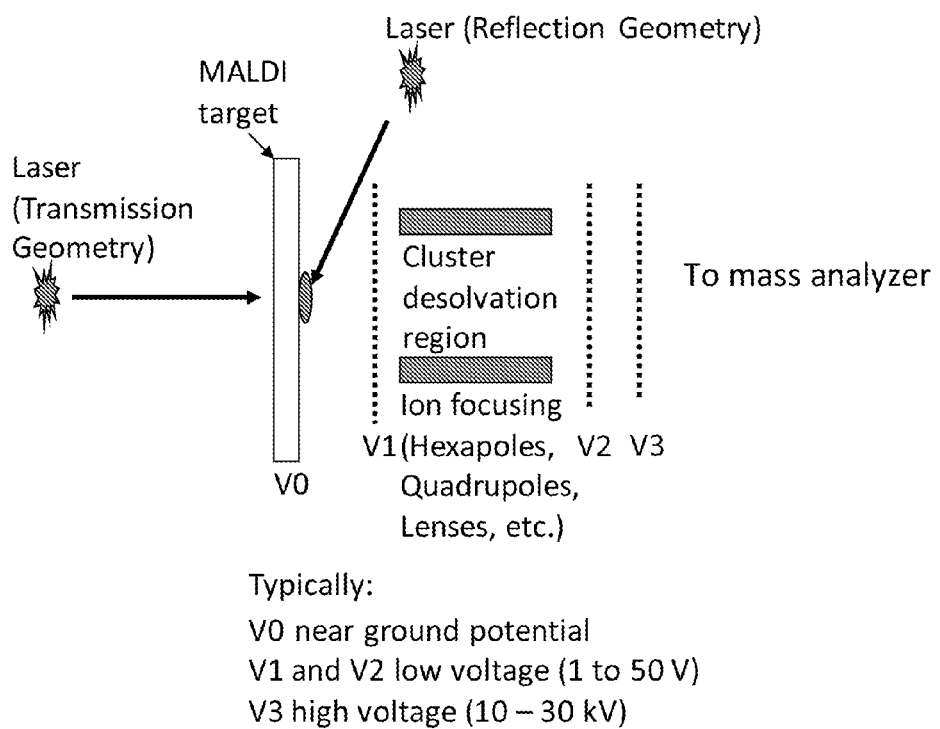

FIG. 136 particularly shows a schematic of an intermediate pressure source for producing multiply charged LSI ions showing laser ablation of a matrix/analyte association in either transmission or reflective geometry.

Figure 137:
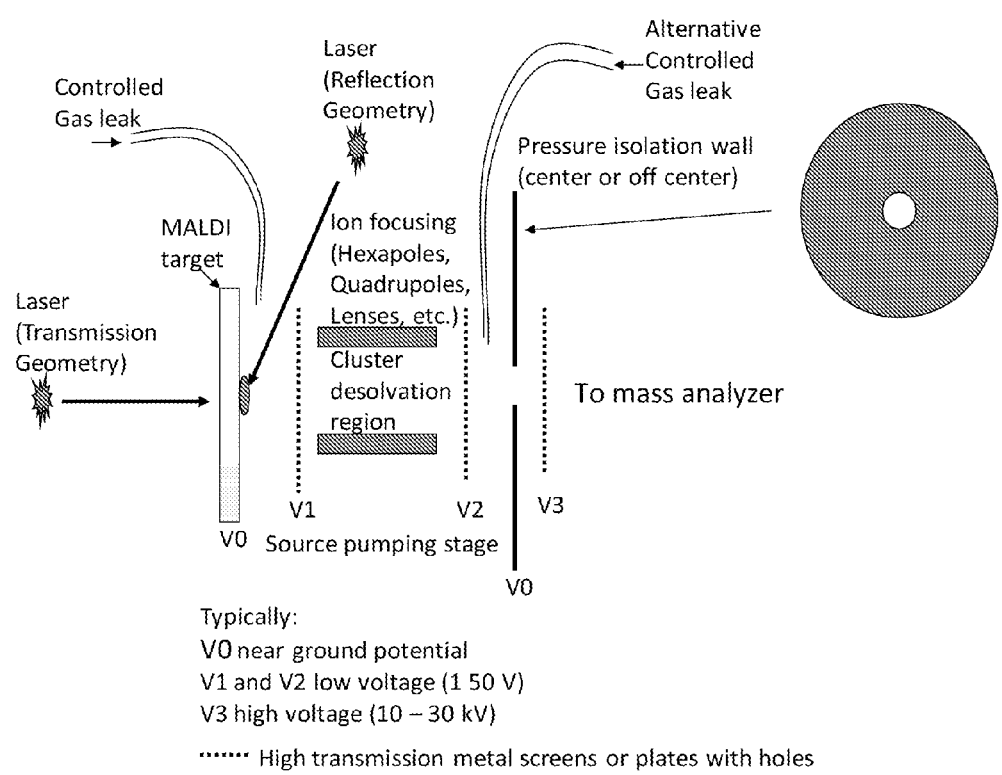

FIG. 137 shows a high vacuum source for production of LSI ions.

Figure 138:
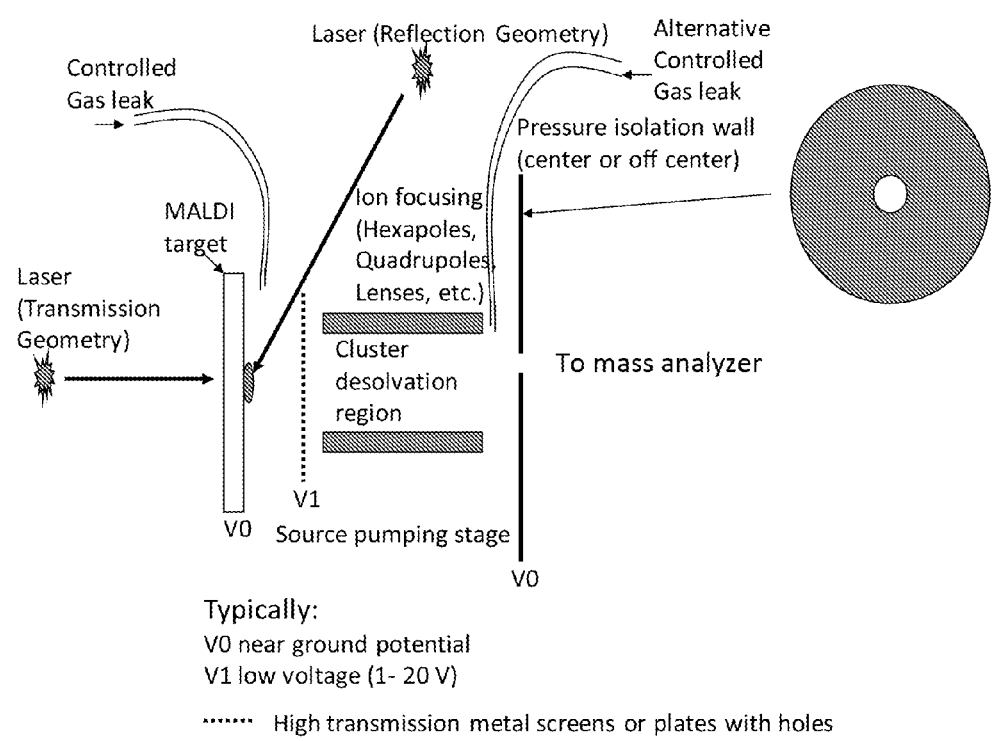

FIG. 138 shows another representation of a vacuum ion source useful for producing multiply charged ions by laser-spray ionization.

DETAILED DESCRIPTION

LSI is similar to MALDI in that laser ablation of a solid state matrix (e.g. 2,5-DHAP) initiates the ionization process. However, unlike MALDI, LSI produces ions from certain matrixes without the necessity for laser wavelength absorption. Moreover, in LSI higher laser energy can be employed than is common with MALDI, often allowing acquisition of peptide and protein mass spectra from a single laser shot with charge state ion abundances similar to ESI. These characteristics of LSI make it compatible with rapid analyses and powerful fragmentation techniques such as ETD.

Differences between LSI and ESI are that ESI produces MCIs from a solution state employing high voltage whereas LSI produces MCIs from a solid state in the presence of a matrix by laser ablation without applied voltage. Embodiments disclosed herein provide systems and methods of utilizing commercial MALDI mass spectrometer ion sources at IP or HV. Ionization to produce these MCIs under the lower pressure conditions of IP or HV does not require specific heating or a special inlet ion transfer region. Instead, similar charge states of peptides and small proteins are produced compared to LSI at AP and/or MAII by providing a pressure drop region with a suitable matrix and laser energy.

In LSII, a higher temperature in the ion transfer region is required for ionization of proteins and for formation of multiply charged negative ions relative to the heat required for peptides in the positive ion mode. Accordingly, LSII is LSI where a inlet tube is used to transfer ions from AP to vacuum. Ionization occurs in the AP to vacuum region by the assistance of both thermal energy and vacuum (pressure drop).

LSIV is LSI where no inlet tube is used to transfer ions from AP to vacuum. LSIV includes use of IP and HV mass spectrometers. With IP mass spectrometers it is believed that ionization occurs in the IP to vacuum region by the assistance of both thermal energy (provided by the laser impact) and vacuum (pressure drop from IP to HV. HV LSIV does not produce the ultimate high charge states observed at AP and IP; however, SCIs are also not observed so the process is not MALDI.

MAII is LSI without the use of a laser. Pressure drop is thought to cause the ionization observed with this method.

SAII uses a solution state employing common solvents and mixtures thereof. It is a liquid introductory method of MAII. Because it is from solution it can be combined with liquid chromatography separation methods. There is also nanoSAII which uses nano flow rates to introduce solution in to which the analyte is dissolved.

MAII, LSII and LSIV operate from the solid state using organic matrixes. Matrixes are generally powders, although can also be liquids. The matrix materials are dissolved and combined with the analyte in solution or directly on the sample holder. More than one matrix composition can be used with an analyte to enhance the performance of each pure compound in one or more aspects.

The organic matrix can have high to poor solubility in solution and can, but does not need to absorb energy at the particular wavelength of a laser used to ablate the material (when a laser is utilized as the force to trigger exchange of charge between the matrix and analyte). The matrix/analyte can be loaded onto a sample plate as a solvent-based solution or as a solvent-free pure matrix/analyte association, binary matrix/analyte association, tertiary matrix/analyte association, etc. So long as the matrix/analyte association includes properties so that when a force is applied to it and it experiences a drop in pressure, multiply charged ions are produced. Heat can facilitate the production of multiply charged ions.

In case of MAII, SAII, and LSII (all forms of inlet ionization) the ion abundance of the multiply charged ions is increased when heat to, for example, 450° C. is applied. This provides the opportunity to make use of many more matrixes. In other words if one supplies sufficient thermal energy one can convert many organic compounds to useful matrixes. Thus, it is speculated that if an inlet could be heated to >450° C., there would likely be an increase in ion abundance of analytes even further.

As used herein AP is around 760 Torr. IP is from around 0.01 mTorr up to about AP. HV is any pressure below 0.01 mTorr. In particular embodiments, the IP zone is from $10^{-3}$ Torr to 200 Torr. In other particular embodiments, the gas phase comprises a high vacuum zone with a pressure from $10^{-9}$ Torr to $10^{-3}$ Torr.

Producing multiply charged peptide and protein ions brings important advantages to surface analysis. Besides extending the mass range of mass spectrometers with limited m/z range typically found with AP ionization instruments, ETD fragment ion studies can be used for improved characterization. Embodiments disclosed herein demonstrate significant and unexpected gas-phase separation of mixture compositions in the IMS dimension of a commercial IMS-MS instrument without the use of any solvents made possible by the efficient production of MCIs.

The equipment used in embodiments disclosed herein comprises three parts: the source, the analyzer and the detector. Embodiments disclosed herein can utilize any mass spectrometer that operates or can be modified to operate at IP or HV in the source or in the analyzer.

Without being bound by theory, it is believed that the passageway between the point of laser ablation and the HV of the mass analyzer with LSIV is where the production of charged matrix/analyte clusters and droplets occurs. Accordingly, the passageway becomes by definition a source. This is in contrast to the passageway of AP-MALDI where it is believed that the ions are formed very near (within 25 microns) of the matrix/analyte surface by the photon energy from a laser and transported to the mass analyzer. In LSIV the laser is a convenient way to ablate the matrix/analyte sample and transfer the ablated material into the passageway to charge the matrix/analyte clusters/droplets. The matrix/analyte is ablated by the laser and receives energy therefrom. This energy residing in the matrix/analyte association along with a drop in pressure from the high pressure ablation plume to the vacuum of the mass analyzer provides the necessary conditions for producing charged matrix/analyte associations. For formation of the "bare" MCIs the matrix must be removed from the charged matrix/analyte association. This can be enhanced in a number of ways. Use of a volatile matrix material such as 2,5-DHAP that absorbs at the laser wavelength can evaporate matrix from only the receipt of energy from the laser beam after the formation of small charged matrix/analyte associations. Collisions of the charged matrix/analyte associations with a surface or with gas molecules can enhance loss of matrix and formation of bare MCIs. Supplying energy, in the form of heat or other means such as a quadrupole field in the presence of a background gas can enhance loss of neutral matrix and formation of MCIs. The "bare" MCIs. Thus, the motion of the charged cluster droplets in such a field in the presence of a gas can also remove matrix molecules.

Vacuum pumps bring the analyzer eventually to HV. In this instance there is a significant pressure drop that the matrix/analyte clusters pass through. In this scenario, ions can be formed as late as in the analyzer which is less desirable for commercial use. Incorporation of chambers (with gas type and pressure changes) and obstacles for collisions with surfaces in the source region desolvates matrix/analyte clusters and produces MCIs. Commercial MALDI sources mounted to the analyzer are available for, without limitation, e.g., Waters (SYNAPT G2) and Thermo (LTQ, Orbitrap).

Using 2-NPG matrix at AP, bovine serum albumin (BSA), ~66 kDa, is the highest molecular weight observed with (LSII) and without the use of a laser (MAII) providing 67 charges at as little as 200° C. supplied to the inlet of the mass spectrometer. Using 2-NPG matrix, carbonic anhydrase (CA), ~29 kDa, is the highest molecular weight protein observed with the systems and methods disclosed herein to date. For example the SYNAPT G2 has a mass range limitation of 8000 while CA has a molecular weight of 29 kDa. Accordingly, embodiments disclosed herein make higher molecular weight compounds observable by high performance instruments such as the SYNAPT G2, Orbitrap (Thermo Fisher Scientific, Waltham, Mass.) and Fourier Transform-Ion Cyclotron Resonance (FT-ICR) mass spectrometers. High performance mass spectrometers commonly operate in a mass range up to 2000 or 4000.

While not always required at IP or HV improving desolvation of the matrix and analyte to extend the mass range (>ubiquitin 8.5 kDa) can be achieved by thermal energy and/or gas (helium gas transfers heat particularly well). Radiative heat can also aid desolvation. Radiative heat would be beneficial because it can be easily used with existing technology in place such as the hexapole. Accordingly, while thermal energy is not required in the LSIV systems using the matrix compounds disclosed herein (including 2,5-DHAP) its use can improve sensitivity and extend the types of compounds that produce MCIs. For example, in LSII, introducing thermal energy in the pressure drop region allowed proteins with molecular weights as high as 66 kDa (bovine serum albumin) to be detected as MCIs (charge states to +67) and without the use of a laser (MAII).

Heat applied to the commercial ion transfer capillary is available with the IonMax sources of Orbitrap and LTQ Thermo Fisher Scientific instruments. Instrumentation lacking the heated capillary AP to vacuum zone can be retrofitted to perform LSII by mounting a homebuilt device on the sample cone of the ion entrance orifice of the mass spectrometer that can be independently heated. For example, tubing, such as copper tubing (⅛ in. o.d., 1/16 in. i.d., X 1 in. L) can be coated with a layer of cement (e.g. Sauereisen cement; Insolute Adhesive Cement Powder no. P1) wrapped with 24 gauge nichrome wire (Science Kit and Boreal Labs, Tonawanda, N.Y.) and finally coated with another layer of cement. One end of the tubing can be sanded to fit the device in use. Both ends of the coiled nichrome wire can be connected with, for example, alligator clips, to the insulated copper wire from a variac (Powerstat Variable Transformer Type 116).

The passageway from the AP-MALDI source to the ion optics and mass analyzer/detector can be an ion sampling orifice, capillary or the like. The term "passageway" as used herein, means any form whatsoever that operates successfully within the context of the disclosed embodiments. It is possible that the passageway can be of such short length relative to the opening diameter that it may be called an orifice. Other transport guides including tube(s), multiple ion guide(s), skimmer(s), lense(s) or combinations thereof which are or may come to be used can operate successfully within the scope of the embodiments disclosed herein.

As is understood by one of ordinary skill in the art, MALDI can produce a small number of doubly charged ions of small proteins/large peptides. If the molecule becomes larger, there can even be triply charged ions in low abundance. The singly charged parent ion, however, is usually the most abundant ion in MALDI, with the exception of some very large molecules (>30,000 MW) where the doubly or even triply charged ions become abundant with certain matrix compounds absorbing at the laser wavelength of the matrix.

Low abundance MCIs have been observed at AP using an IR laser and a matrix absorbing at the laser wavelength. This type of "MCIs" does not reflect the multiple or highly charged ions of embodiments disclosed herein achieved with LSIV. Instead, embodiments disclosed herein, and as demonstrated in the Examples and FIGs, provide high abundance ions with charge states resembling the charge states of ESI. That is, when those of ordinary skill in the art refer to ESI and MCIs, they associate this terminology with high abundance of MCIs. In contrast, when one of ordinary skill in the art refers to MALDI and MCIs, they associate the wording with low abundance of moderately charged ions. While both terminologies can be used within the context of ESI, LSI (at AP and vacuum) and/or MALDI, embodiments disclosed herein are best described by reference to highly abundant MCIs. In fact one might argue that peptides (small systems) cannot be highly charged because these peptides can only support two or so charges. Accordingly, within the context of the present disclosure, embodiments disclosed herein referred to as "multiply charged" are also highly charged for the respective system (i.e. particular lipid, protein or peptide) and in high abundance. Thus, for example, a peptide of molecular weight of 1200 might be expected to be singly charged in MALDI and predominately doubly or even triply charged in LSIV, whereas a peptide of molecular weight 5000 in MALDI is still predominately singly charged with low abundant doubly charged ions, but in LSIV this peptide would be expected to have +4 and +5 charge state ions as the most abundant ions and little or no singly charged ions (SCIs).

As used herein, "matrix" refers to any molecule having the ability to transfer or receive charges from the analyte. Absorption at the wavelength of the laser is not a requirement. Matrix compositions disclosed herein may include a compound represented by a formula:

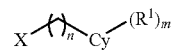

and salts thereof;

wherein Cy is a carbocyclic or heterocyclic ring or ring system;

n is 0 to 5;

m is 0 to 5;

X is OH, $NH_2$, $NO_2$ or CN;

each $R^1$ is independently H, or an atom or moiety having a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol, or when two $R^1$ are taken together they can form a 3, 4, 5, 6, 7 or 8-membered ring optionally substituted with 1 to 4 $R^1$; and each $R^2$ and each $R^3$ is independently selected from H, OH, $NH_2$, $NO_2$, lower alkyl, phenyl, alkenyl, alkynyl, alkoxy, or heteroalkyl.

For convenience, the term "molecular weight" is used with respect to a moiety, atom, or part of a molecule to indicate the mass of the atom, or sum of the atomic masses of the atoms in the moiety or part of a molecule, even though it may not be a complete molecule.

In another embodiments, matrix compositions disclosed herein include optionally substituted phenyl, such as those depicted in FIGS. 135A-135L as well as those having the formula

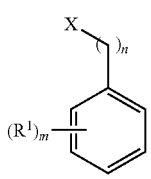

and salts thereof;
each $R^1$ is independently selected from H, lower alkyl, aryl, alkenyl, alkynyl, alkylaryl, arylalkyl, alkoxy, aryloxy, arylalkoxy, alkoxyalkylaryl, alkylamino, aminoalkyl, dialkylamino, arylamino, aminoaryl, heteroalkyl, nitroalkenyl, $NH_2$, $NR^2R^3$, OH, $OR^2$, CN, $NO_2$, $OCF_3$, $CF_3$, Br, Cl, F, 1-amidino, 2-amidino, alkylcarbonyl, $SR^2$, $SOR^2$, $SO_2R^2$, $CO_2R^2$, $COR^2$, $CONR^2R^3$, or $CSNR^2R^3$, or when two $R^1$ are taken together they can form a phenyl or phenyl substituted with 1 to 4 $R^1$; and
each $R^2$ and each $R^3$ is independently selected from H, OH, $NH_2$, $NO_2$, lower alkyl, phenyl, alkenyl, alkynyl, alkoxy, or heteroalkyl.

In another embodiment, matrix compositions disclosed herein have the formula

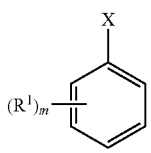

and salts thereof;
wherein each $R^1$ is independently selected from H, lower alkyl, $NH_2$, $NR^2R^3$, OH, $OR^2$, $NO_2$, F, Cl, Br, CN, $SOR^2$, $SO_2R^2$, $CO_2R^2$, $COR^2$ or $CONR^2R^3$, or when two $R^1$ are taken together they can form a phenyl or phenyl substituted with 1 to 4 $R^1$; and
each $R^2$ and each $R^3$ is independently selected from H, OH, or lower alkyl.

In another embodiment, matrix compositions disclosed herein have a structure selected from

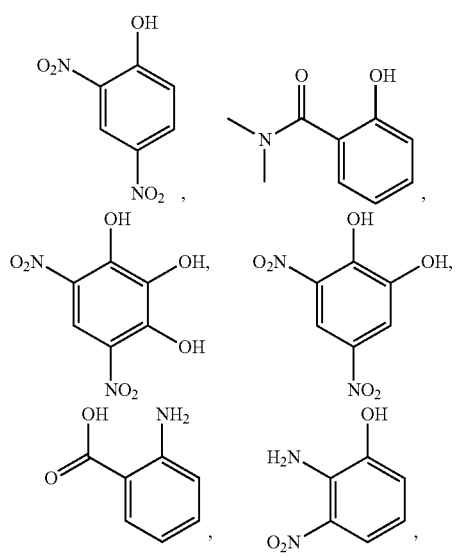

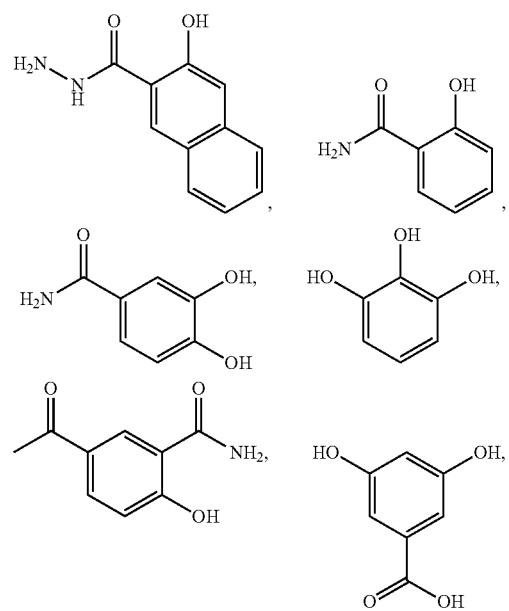

-continued
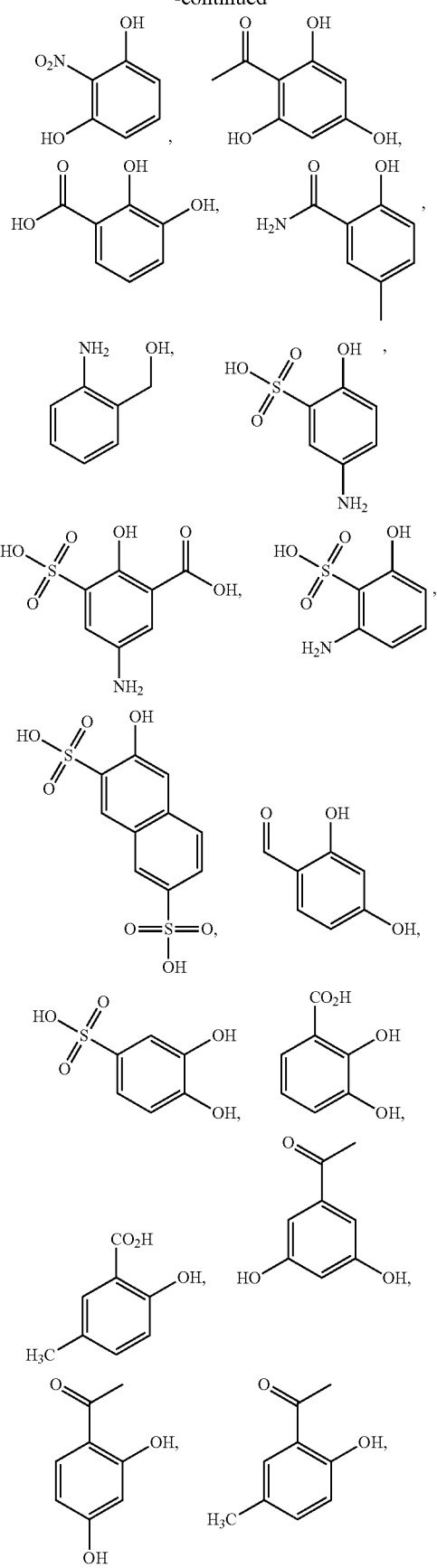
-continued
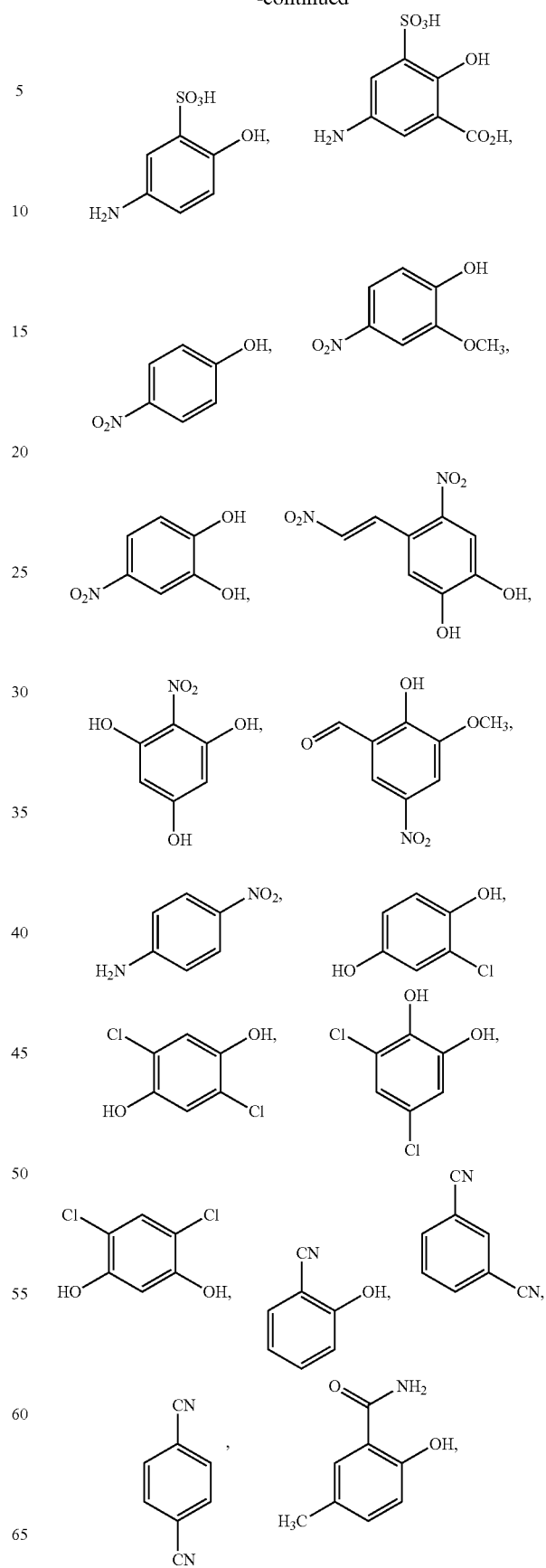

-continued

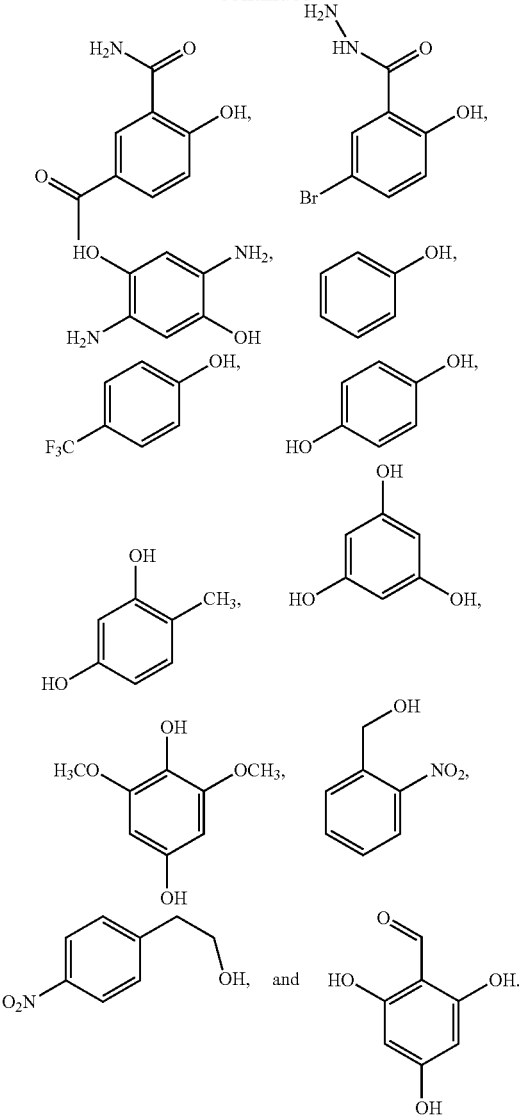

In another embodiment, matrix compositions disclosed herein are optionally substituted heteroaromatic compounds, such as optionally substituted pyrindine represented by a formula:

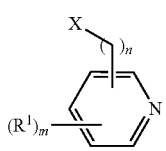

and salts thereof;
m is 0 to 4;
each $R^1$ is independently selected from H, lower alkyl, aryl, alkenyl, alkynyl, alkylaryl, arylalkyl, alkoxy, aryloxy, arylalkoxy, alkoxyalkylaryl, alkylamino, aminoalkyl, dialkylamino, arylamino, aminoaryl, heteroalkyl, nitroalkenyl, $NH_2$, $NR^2R^3$, OH, $OR^2$, CN, $NO_2$, $OCF_3$, $CF_3$, Br, Cl, F, 1-amidino, 2-amidino, alkylcarbonyl, $SR^2$, $SOR^2$, $SO_2R^2$, $CO_2R^2$, $COR^2$, $CONR^2R^3$, or $CSNR^2R^3$, or when two $R^1$ are taken together they can form a phenyl or phenyl substituted with 1 to 4 $R^1$; and
each $R^2$ and each $R^3$ is independently selected from H, OH, $NH_2$, $NO_2$, lower alkyl, phenyl, alkenyl, alkynyl, alkoxy, or heteroalkyl.

In another embodiment, matrix compositions disclosed herein have the formula

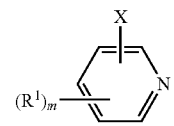

and salts thereof;
wherein each $R^1$ is independently selected from H, lower alkyl, $NH_2$, $NR^2R^3$, OH, $OR^2$, $NO_2$, $SOR^2$, $SO_2R^2$, $CO_2R^2$, $COR^2$ or $CONR^2R^3$, or when two $R^1$ are taken together they can form a phenyl or phenyl substituted with 1 to 4 $R^1$; and
each $R^2$ and each $R^3$ is independently selected from H, OH, or lower alkyl.

In another embodiment, matrix compositions disclosed herein have a structure selected from

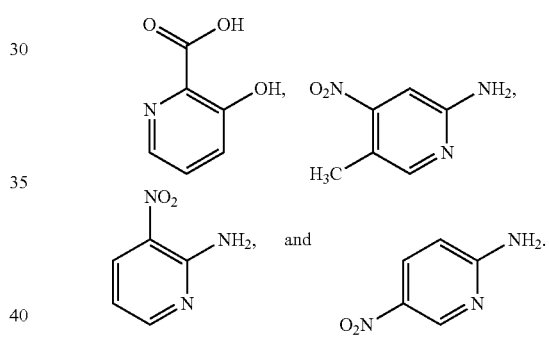

In another embodiment, matrix compositions disclosed herein are optionally substituted cycloalkyl compounds, such as optionally substituted cyclohexyl represented by a formula:

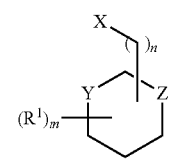

and salts thereof;
Y and Z are independently $CR^aR^b$ or C=O;
each $R^1$ is independently selected from H, lower alkyl, aryl, alkenyl, alkynyl, alkylaryl, arylalkyl, alkoxy, aryloxy, arylalkoxy, alkoxyalkylaryl, alkylamino, aminoalkyl, dialkylamino, arylamino, aminoaryl, heteroalkyl, nitroalkenyl, $NH_2$, $NR^2R^3$, OH, $OR^2$, CN, $NO_2$, $OCF_3$, $CF_3$, Br, Cl, F, 1-amidino, 2-amidino, alkylcarbonyl, $SR^2$, $SOR^2$, $SO_2R^2$, $CO_2R^2$, $COR^2$, $CONR^2R^3$, or $CSNR^2R^3$, or when two $R^1$ are taken together they can form a phenyl or phenyl substituted with 1 to 4 $R^1$; each $R^a$ and each $R^b$ is independently selected from H, lower alkyl, aryl, alkenyl, alkynyl, alkylaryl, arylalkyl, alkoxy, aryloxy, arylalkoxy, alkoxyalkylaryl, alkylamino, aminoalkyl, dialkylamino, arylamino, aminoaryl, heteroalkyl, nitroalkenyl, $NH_2$, $NR^2R^3$, OH, $OR^2$, CN, $NO_2$, $OCF_3$, $CF_3$, Br, Cl, F, 1-amidino, 2-amidino, alkylcarbonyl, $SR^2$, $SOR^2$, $SO_2R^2$, $CO_2R^2$, $COR^2$, $CONR^2R^3$, or $CSNR^2R^3$; and each $R^2$ and each $R^3$ is independently selected from H, OH, $NH_2$, $NO_2$, lower alkyl, phenyl, alkenyl, alkynyl, alkoxy, or heteroalkyl.

In another embodiment, matrix compositions disclosed herein have the formula

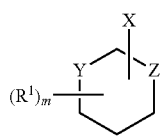

and salts thereof;
wherein each $R^1$ is independently selected from H, lower alkyl, $NH_2$, $NR^2R^3$, OH, $OR^2$, $NO_2$, $SOR^2$, $SO_2R^2$, $CO_2R^2$, $COR^2$ or $CONR^2R^3$, or when two $R^1$ are taken together they can form a phenyl or phenyl substituted with 1 to 4 $R^1$; and each $R^2$ and each $R^3$ is independently selected from H, OH, or lower alkyl.

In another embodiment, matrix compositions disclosed herein have a structure selected from

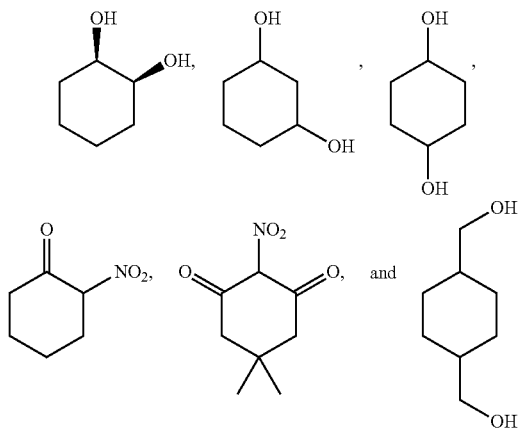

In another embodiment, matrix compositions disclosed herein have the formula

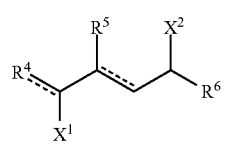

and cis-trans isomers and salts thereof;
wherein $X^1$ and $X^2$ are each independently selected from H, =O, =S, OH, $NH_2$, $NO_2$ or lower alkyl;
a dashed line represents the presence or absence of a double bond;
$R^4$, $R^5$, and $R^6$ are independently selected from H, lower alkyl, alkenyl, alkynyl, alkoxy, alkylamino, aminoalkyl, dialkylamino, heteroalkyl, $NH_2$, $NR^7R^8$, OH, $OR^7$, CN, $NO_2$, $OCF_3$, $CF_3$, Br, Cl, F, 1-amidino, 2-amidino, alkylcarbonyl, $SR^7$, $SOR^7$, $SO_2R^7$, $CO_2R^7$, $COR^7$, $CONR^7R^8$ or $CSNR^7R^8$; and each $R^7$ and each $R^8$ are each independently selected from H, OH, $NH_2$, $NO_2$, lower alkyl, alkenyl, alkynyl, alkoxy, or heteroalkyl.

In another embodiment, matrix compositions disclosed herein have the formula

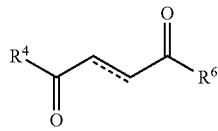

and salts thereof;
wherein $R^4$ and $R^6$ are each independently selected from $OR^7$, OH, or lower alkyl.

In another embodiment, matrix compositions disclosed herein have a structure selected from

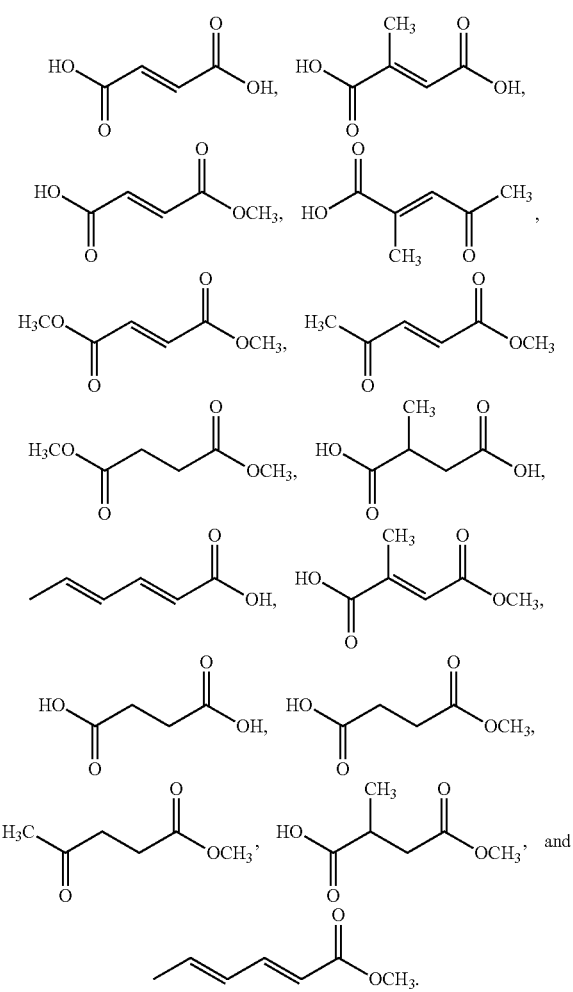

In another embodiment, matrix compositions disclosed herein have the formula

[Structure: R⁹—(ring with X³, X⁴)—R¹⁰]

and salts thereof;
wherein X³ and X⁴ are each independently selected from H, =O, =S, OH, NH₂, NO₂ or lower alkyl;
a dashed line represents the presence or absence of a double bond;
$R^9$ and $R^{10}$ are each independently selected from H, lower alkyl, alkenyl, alkynyl, alkoxy, alkylamino, aminoalkyl, dialkylamino, heteroalkyl, $NH_2$, $NR^{11}R^{12}$, OH, $OR^{11}$, CN, $NO_2$, $OCF_3$, $CF_3$, Br, Cl, F, 1-amidino, 2-amidino, alkylcarbonyl, $SR^{11}$, $SOR^{11}$, $SO_2R^{11}$, $CO_2R^{11}$, $COR^{11}$, $CONR^{11}R^{12}$, or $CSNR^{11}R^{12}$; and
$R^{11}$ and $R^{12}$ are each independently selected from H, OH, $NH_2$, $NO_2$, lower alkyl, alkenyl, alkynyl, alkoxy, or heteroalkyl.

In another embodiment, matrix compositions disclosed herein have the formula

[Structure: R⁹—C(=O)—CH=CH—C(=O)—R¹⁰]

and salts thereof;
wherein $R^9$ and $R^{10}$ are each independently selected from $OR^{11}$, OH, $NH_2$, $NH_2CH_3$ or lower alkyl.

In another embodiment, matrix compositions disclosed herein have a structure selected from

[Structures: HO-C(=O)-CH=CH-C(=O)-OH, H₂N-C(=O)-CH=CH-C(=O)-OH, and HN(CH₃)-C(=O)-CH=CH-C(=O)-OH]

In another embodiment, matrix compositions disclosed herein have the formula

[Structure with R⁴, R⁵, R¹⁴, X², R⁶, X¹, R¹³, R¹⁵]

and cis-trans isomers and salts thereof;
wherein $X^1$ and $X^2$ are each independently selected from H, =O, =S, OH, $NH_2$, $NO_2$ or lower alkyl;
a dashed line represents the presence or absence of a double bond;
$R^4$, $R^5$, $R^6$, $R^{13}$, $R^{14}$, and $R^{15}$ is independently selected from H, lower alkyl, alkenyl, alkynyl, alkoxy, alkylamino, aminoalkyl, dialkylamino, heteroalkyl, $NH_2$, $NR^7R^8$, OH, $OR^7$, CN, $NO_2$, $OCF_3$, $CF_3$, Br, Cl, F, 1-amidino, 2-amidino, alkylcarbonyl, $SR^7$, $SOR^7$, $SO_2R^7$, $CO_2R^7$, $COR^7$, $CONR^7R^8$ or $CSNR^7R^8$; and each $R^7$ and each $R^8$ are each independently selected from H, OH, $NH_2$, $NO_2$, lower alkyl, alkenyl, alkynyl, alkoxy, or heteroalkyl.

In another embodiment, matrix compositions disclosed herein have a structure selected from

[Structures: HO-C(=O)-CH=CH-CH=CH-C(=O)-OH; HO-C(=O)-CH=CH-CH=CH-C(=O)-OH, and HO-C(=O)-C(CH₃)=CH-CH=C(CH₃)-C(=O)-OH]

In another embodiment, matrix compositions disclosed herein have the formula

[Structure: R⁴—C(X¹)(H)—C(R⁵)(H)—C(X²)(H)—R⁶]

and salts thereof;
wherein $X^1$ and $X^2$ are each independently selected from H, =O, =S, OH, $NH_2$, $NO_2$ or lower alkyl;
$R^4$, $R^5$, and $R^6$ are independently selected from H, lower alkyl, alkenyl, alkynyl, alkoxy, alkylamino, aminoalkyl, dialkylamino, heteroalkyl, $NH_2$, $NR^7R^8$, OH, $OR^7$, CN, $NO_2$, $OCF_3$, $CF_3$, Br, Cl, F, 1-amidino, 2-amidino, alkylcarbonyl, $SR^7$, $SOR^7$, $SO_2R^7$, $CO_2R^7$, $COR^7$, $CONR^7R^8$ or $CSNR^7R^8$; and
each $R^7$ and each $R^8$ are each independently selected from H, OH, $NH_2$, $NO_2$, lower alkyl, alkenyl, alkynyl, alkoxy, or heteroalkyl.

In another embodiment, matrix compositions disclosed herein have a structure

[Structure: HO-C(=O)-CH₂-C(=O)-OH]

With respect to any relevant formula above, in some embodiments, any of $R^a$, $R^b$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, or $R^{15}$ may Rc, $C_{1-6}$ alkenyl, $C_{1-6}$ alkynyl, $NH_2$, $NR^cR^d$, OH, $OR^c$, CN, $NO_2$, $OCF_3$, $CF_3$, Br, Cl, F, $SR^c$, $SOR^c$, $SO_2R^c$, $CO_2R^c$, $COR^c$, $CONR^cR^d$ or $CSNR^cR^d$, wherein $R^c$ and $R^d$ may independently be H; lower alkyl, including: linear or branched alkyl having a formula $C_aH_{a+1}$, or cycloalkyl having a formula $C_aH_{a-1}$, wherein a is 1, 2, 3, 4, 5, or 6, such as linear or branched alkyl of a formula: $CH_3$, $C_2H_5$, $C_3H_7$, $C_4H_9$, $C_5H_{11}$, $C_6H_{13}$, etc., or cycloalkyl of a formula: $C_3H_5$, $C_4H_7$, $C_5H_9$, $C_6H_{11}$, etc.

One matrix composition disclosed herein, 2-NPG, produces highly-charged ions under AP and IP LSI conditions, and also produces highly-charged ions in MS at HV conditions commonly used in MALDI MS.

A second matrix composition, disclosed herein, 4,6-DNPG, produces abundant multiply-charged ions at elevated inlet temperature and AP.

As non-limiting examples, ultraviolet (UV), (electronic), visible (VIS), infrared (IR) (vibrational and/or rotational), or center punch (shockwave) or combinations thereof can be used to generate transfer or receipt of charges.

FIGS. 135A-135L show matrix compounds that have been shown to produce multiply charged ions upon impact of a force such as a laser beam when sufficient energy is provided in combination with a pressure drop region to initiate ion formation of the matrix/analyte association and also remove neutral matrix from the charged matrix/analyte association by a desolvation process.

FIGS. 136-138 demonstrate equipment configurations that can be used with the systems and methods disclosed herein. In FIGS. 136-138, an ionization method comprising a laser with a laser beam that intersects a matrix/analyte association deposited on a plate which may be opaque or transparent to the laser beam, the plate being under vacuum so that ablation of the matrix/analyte association produces particles or droplets that are heated by absorption of the laser energy and traverse from the higher pressure region near the matrix surface to the lower pressure region of the mass analyzer producing ions with multiple charges that are mass analyzed in a mass spectrometer are shown. The matrix is capable of both producing the initial ionization in the pressure drop region and loss of matrix by evaporation before mass analysis by the mass spectrometer. Heat or other energy may be supplied in the pressure drop region to facilitate evaporation of the matrix and production of multiply charged ions for mass analysis.

FIG. 136 particularly shows a schematic of an intermediate pressure source for producing multiply charged LSI ions showing laser ablation of a matrix/analyte association in either transmission or reflective geometry. Matrix/analyte is ablated from the surface in a plume of vaporized matrix that produces an initial high pressure region, but dispersion of the matrix and matrix/analyte association from the surface rapidly reduces the pressure. The matrix/analyte heated by the energy from the absorbed laser beam traveling through the pressure drop region produces charged matrix/analyte droplets, possibly by a statistical fracturing process. An LSI matrix not only allows formation of the charged droplets but desolvation of the matrix to produce the "bare" analyte ions. As shown in the figure, desolvation can occur far downstream from the ablation process. Radiofrequency fields or heat in the downfield region can aid desolvation of matrix and production of "bare" ions.

FIG. 137 shows a high vacuum source for production of LSI ions. In this figure the laser ablates in transmission or reflective geometry. A gas is added to facilitate desolvation of neutral matrix molecules from the charged matrix/analyte association ablated from the surface. The added gas facilitates evaporation/sublimation of neutral matrix in a radiofrequency field or the convective transfer of heat to release the "bare" analyte ions. Alternatively, but not shown, the charge matrix/analyte clusters can be made to collide with a surface to facilitate removal of the neutral matrix producing the "bare" analyte ions.

FIG. 138 shows another representation of a vacuum ion source useful for producing multiply charged ions by laser-spray ionization. This source is similar to that in FIG. 137 except that it is suitable for intermediate pressure laserspray ionization. In LSI-MS, the laser beam preferentially penetrates the tissue in transmission geometry (TG) relative to the ion entrance orifice of the mass spectrometer. Operating the laser in TG is not a requirement but is favorable over reflective geometry for simplicity of alignment, reproducibility, speed of acquisition, and high spatial resolution. FIG. 138 provides an especially beneficial equipment configuration for use with LSIV. FIGS. 136 and 137 depict vacuum MALDI sources for LSI. FIG. 138 depicts an IP MALDI source for LSI.

The effect of laser energy on the formation of MCIs is notable for many of the matrixes. It is believed that suitable lasers include UV, VIS, and IR lasers such as nitrogen lasers, $CO_2$ lasers, Er-YAG lasers, Nd-YAG, Er-YILF, Er-YSGG and the like. Typical laser energies which are useful in LSIV analysis of biopolymers include 0.1-1.0 Joules $cm^{-2}$. Typical laser wavelengths are 200-800 nm (UV-VIS wavelengths) and 1.0-12 μm (IR wavelengths), and in particular embodiments, 1.44 μm. IR laser application to tissue may prove especially beneficial in the embodiments disclosed herein because IR lasers may better tolerate the presence of salts.

In summary, LSIV produces a high number of MCIs using a laser ablation process and offers the potential of high sensitivity. The production of MCIs provides astonishing gas-phase separation of mixture compositions in the IMS dimension without the use of any solvents when ablated from the solid state directly form a surface. Producing multiply charged peptide and protein ions from a laser ablation process also provides important advantages for surface analysis. In addition to extending the mass range of mass spectrometers with limited m/z range, typically found with AP ionization instruments, advanced fragmentation methods such as ETD can be implemented providing improved characterization.

Whereas particular embodiments disclosed herein utilize a laser to produce heat for the matrix/analyte droplets to undergo a fracturing process to produce highly charged clusters and improve sensitivity, other heat sources can also be used. For example, this heat can come from, without limitation, convective heating or irradiative heating. Additionally or alternatively, gas in a radiofrequency region could be used to cause the clusters to undergo collisions leading to desolvation and production of naked multiply charged analyte ions. While any appropriate gas can be used, helium is preferred. Fracturing processes assist in the production of multiply charged analyte ions. This can be for example achieved by having the matrix/analyte droplet guided in a z-spray (Waters), off center/axis (Waters, Thermo), s-lense (Thermo) or against a pole (Thermo), means similar to what has been used in the past for removing undesired clusters.

The practical utility of LSIV in combination with IMS-MS is demonstrated by the analysis of model mixtures composed of a lipid, peptides, and a protein. Further, endogenous multiply charged peptides are observed directly from delipified mouse brain tissue with drift time distributions that are nearly identical in appearance to those obtained from a synthesized neuropeptide standard analyzed by either LSI or ESI IMS-MS at AP. Efficient solvent-free gas-phase separation enabled by the IMS dimension separates the multiply charged peptides from lipids that remained on the tissue. Lipid and peptide families are exceptionally well separated because of the ability of LSIV to produce multiply charging.

The following examples provide non-limiting examples of embodiments described herein.

EXAMPLES

A number of parameters were explored for their influence to provide multiply charged peptide and protein ions with high abundance and good reproducibility. These parameters included the sample support (glass or metal), matrix compounds, solvent (methanol (MeOH), water, acetonitrile (ACN), acidified conditions and combinations therein), laser energy (relative values with settings of low 50 to high 500 on instrument settings), and pressure (IP and HV MALDI instruments). The following general materials and methods were used unless noted elsewhere herein.

Materials 2,5-DHAP (97% purity) and the solvents, ACN, MeOH, trifluroacetic acid (TFA), and acetic acid were obtained from Fisher Scientific Inc. (Pittsburgh, Pa.). 2,5-DHB (98% purity), ACTH (MW 2465), BI (from bovine pancreas (MW 5731)), SM (from chicken egg yolk (MW 703)), lysozyme, cytochrome C, angiotensin II, ubiquitin (from bovine erythrocytes), carbonic anhydrase (CA) and bovine serum albumin (BSA), PEG and PEGDME, all matrixes were obtained from Sigma Aldrich Inc. (St. Louis, Mo.). Ang I (MW 1295) was obtained from American Peptide Co. (Sunnyvale, Calif.). GFP (MW 1569) and CHCA (97% purity) were provided by Waters Co. (Manchester, England). Synthesized N-acetylated terminal fragment of MBP (N-acyl fragment (MW 1833)) was obtained from Anaspec (Fremont, Calif.). Other assessed compounds were obtained from Avantis.

Analyte solutions were prepared individually in 50:50 ACN/water, 50:50 ACN/water with 0.1% TFA (Ang I, ACTH), 50:50 MeOH/water with 1% acetic acid (Ang I, GFP, BI), 50:50: ACN:water with 0.1% FA (N-acyl MBP fragment) and 49:49:2 ACN:water:acetic acid (ubiquitin).

The matrix solutions were prepared saturated as 20 mg 2,5-DHB in 100 µL of 50:50 ACN:water with 0.1% TFA; 10 mg CHCA in 2 mL MeOH:ACN; or 5 mg 2,5-DHAP in 300 µL 50:50 ACN:water.

The matrix/analyte mixtures were prepared in 1:1 volume ratios to make the final concentration of the analyte 1 pmol $\mu L^{-1}$ before deposition on target plates. One µL of the matrix/analyte mixture was used and deposited on metal and glass plates using the dried droplet method. In the dried droplet method includes placing a drop of matrix/analyte solution onto a sample plate and blowing it dry with warm air. The model mixture described herein included 1 pmol Ang I, 2 pmol GFP, 2 pmol BI and 2 pmol SM. The model mixture was prepared in 50:50 MeOH:water with 1% acetic acid.

For the tissue sample analyses, an aged delipified tissue slice was spotted with 0.2 µL of the 2,5-DHAP matrix solution and allowed to air dry prior to analysis.

LSIV-IMS-MS Methods & Settings

An IMS-MS SYNAPT G2 (Waters Corporation) mass spectrometer instrument with a MALDI source operating with a Nd:YAG laser (355 nm; FIGS. 21-29) was used. The instrument was operated using sensitivity and positive and negative ion modes. Sensitivity mode settings were 0 V for the sample plate, 10 V extraction, 10 V hexapole bias and 5 V aperture 0. Decreasing the laser power and minimizing voltage favors LSIV ions. Providing the least energy to the matrix/analyte during ionization increase the ion abundance of highly charged LSIV ions. ESI like settings increases the ion formation and transmission through the mass spectrometer including the IMS and TOF as well as ion detection. The laser energy ranged from 50 (low) to 500 (high; according to the manufacturer's settings) at a firing rate set at 200 Hz. Acquisitions were obtained from 1 to 2 minutes with a scan time set at 1 second. Once loaded the sample plate was under vacuum conditions of 0.211 mbar. The pressure in the drift cell was 3.23 mbar. The wave velocity used ranges from 550-650 m $s^{-1}$ and the wave height was at 40 V. The data was processed using DriftScope version 2.1 (Waters Corp., Manchester, UK) to extract and display two-dimensional (2-D) plot of drift time versus m/z ratios.

MALDI-TOF-MS Methods & Settings

A MALDI-TOF Ultraflex, Ultraflextreme, and Autoflex Speed mass spectrometer (Bruker, Bremen, Germany) equipped with a nitrogen laser (337 nm) was used to acquire mass spectrum of the same analyte/mixtures described above. The mass spectra were acquired using the reflectron positive-ion mode with a reflectron voltage of 20.30 kV and an ion source lens voltage of 8.85 kV. The laser repetition rate was set at 20 Hz and increments of 20 laser shots were used to acquire the mass spectrum with a total of 100 shots. The laser attenuation was set at 45%, 55% and 70% (highest; according to the manufacturer's settings) for MALDI and LSIV matrix compounds, e.g., CHCA and 2,5-DHB as well as 2,5-DHAP, 2-NPG, and 4,6-DNPG, respectively. Flex Analysis software was used to process the data and obtain the mass spectrum.

MALDI- and Nano-ESI-IMS-MS For Comparison with LSI at IP (LSIV) and AP (LSII)

ESI was set in mobility-TOF mode using positive ion sensitivity mode. A 1 pmol $\mu L^{-1}$ solution of MBP in 50:50 ACN/water with 0.1% TFA was infused at a flow rate of 1 µL $min^{-1}$. The capillary voltage was set at 3 kV, sampling cone at 50 V, and extraction cone at 4.4 V. Desolvation gas flow was at 500 L $h^{-1}$ and at a temperature of 150° C. For LSII, the lockspray motor was removed from the nanolockspray ion source housing and a copper tube desolvation device was mounted on the ion-inlet skimmer of the Waters Z-spray source which was heated to 150° C. as described in Inutan & Trimpin, J. Am. Soc. Mass. Spectrom. 2010, 21, 1260-1264 and Inutan & Trimpin, J. Proteome Res. 9:6077-6081, 2010 both of which are incorporated by reference herein for their teachings regarding the same. Particularly, the sanded end of a homemade heating device such as that described above can be fit through the cover desolvation device (cone gas nozzle) and over the end of the ion entrance skimmer (sample cone). The copper tube can be held to the cone gas nozzle with cement, such as Sauereisen cement and can be heated by application of up to 12 V from the variac.

A nitrogen laser (Spectra Physics VSL-337ND-S, Mountain View, Calif.) or Nd:YAG laser (at 1064, 532, 355 nm) was aligned directly with the orifice of the skimmer of a SYNAPT G2 (Waters) or LTQ Velos (Thermo). The LSI sample holder with 1 µL of matrix/analyte applied per sample was attached to the x,y,z-stage of the ion source and placed ~2 mm in front of the copper tube opening. The LSI sample holder was slowly moved through the focused laser beam using the manual xy-direction or automated xzy-direction of the stage. The IMS-MS data was processed using DriftScope version 2.1 (Waters Corp., Manchester, U.K) to extract and display 2-D plot of drift time (td) versus m/z ratios.

Results & Analysis

The mass spectra obtained from LSI at IP on a commercial MALDI-IMS-MS instrument (SYNAPT G2) were nearly identical to mass spectra obtained using ESI or LSI on the same instrument at AP.

As is the case in LSI at AP (LSII) using reflective geometry laser alignment, both glass and metal plates can be used with LSIV. Particularly, FIGS. 1A-1P shows LSIV-MS mass spectra of peptides and proteins: GFP (FIGS. 1A-1D), ACTH (FIGS. 1E-1H), BI (FIGS. 1I-1L), and ubiquitin (FIGS. 1M-1P) acquired using 2,5-DHAP matrix prepared in 50:50 ACN:water using laser energy of 200 (FIGS. 1A, 1B, 1E, 1F, 1I, 1J, 1M, and 1N) and 500 (FIGS. 1C, 1D, 1G, 1H, 1K, 1L, 1O, and 1P) on: glass plates (FIGS. 1A, 1C, 1E, 1G, 1I, 1K, 1M, and 1O) and metal plates (FIGS. 1B, 1D, 1F, 1H, 1J, 1L,

1N, and 1P). The glass plates provided typically higher abundance of MCIs than the metal plates.

Figure 2B:
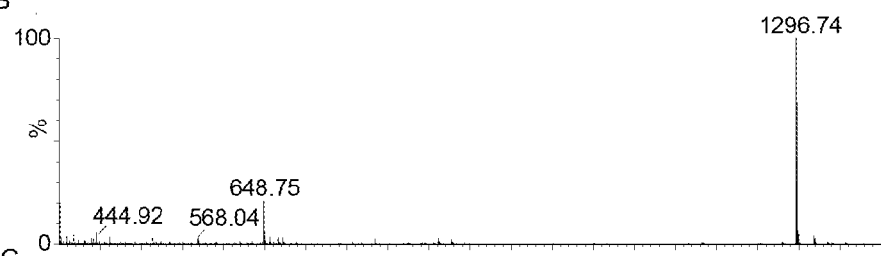
Figure 2C:
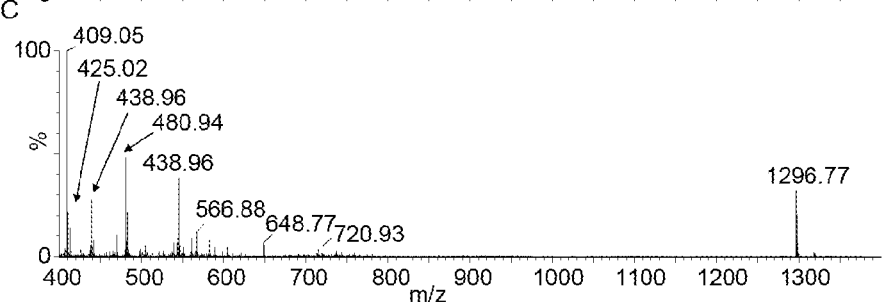
Figure 5A:
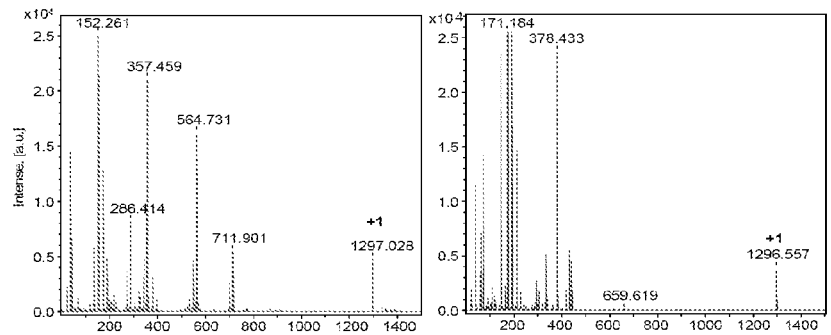
FIGS. 5A-5D. MALDI-TOF-MS mass spectra of Ang I (FIG. 5A), GFP (FIG. 5B), ACTH (FIG. 5C), and BI (FIG. 5D) under HV conditions using 2,5-DHAP matrix.
Figure 5B:
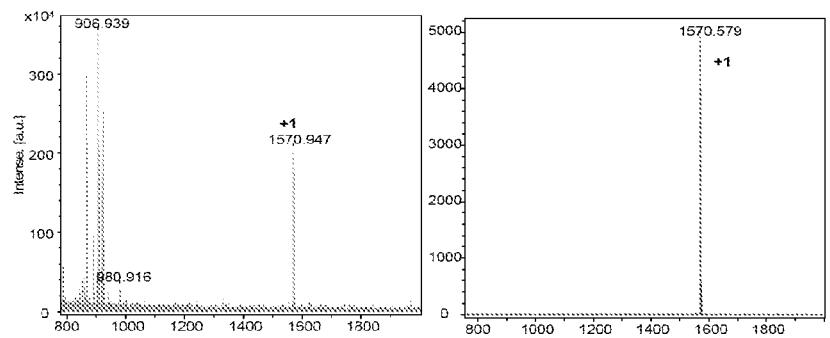
Figure 5C:
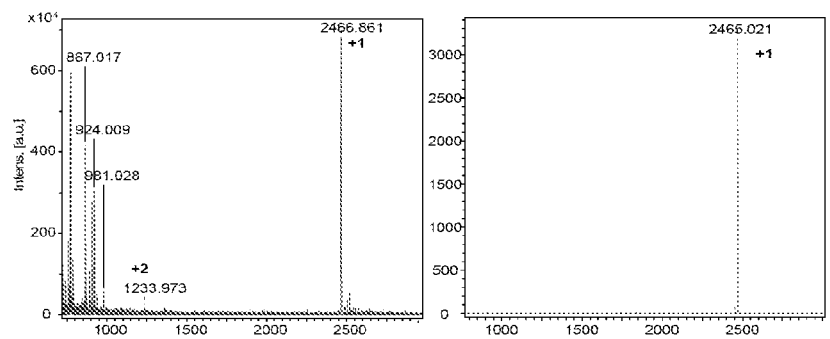
Figure 5D:
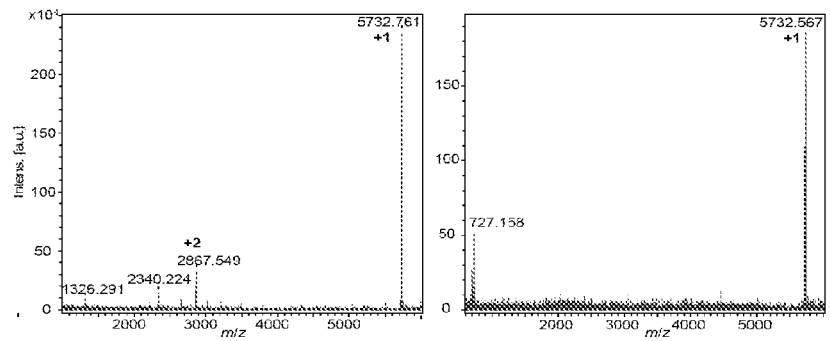

FIGS. 2A, 2B, and 2C show LSIV-MS mass spectra of Ang I acquired from different matrixes: (FIG. 2A) 2,5-DHAP in 50:50 ACN:water; (FIG. 2B) CHCA, and (FIG. 2C) 2,5-DHB both in 50:50 ACN:water with 0.1% TFA using a laser energy of 500. The best results were obtained with 2,5-DHAP.

In LSI, the sample preparation and morphology, determined by microscopy of the crystallized matrix/analyte also are important parameters affecting the relative abundances of SCIs and MCIs. FIGS. 3A-3D. FIGS. 3A and 3B show photographs of the microscopy and FIGS. 3C and 3D show mass spectrum of the matrix/analyte mixture spot of angiotensin 1 (MW 1295) with saturated 2,5-DHAP matrix (prepared in 50:50 ACN:water) on a glass plate (FIG. 3C) before ablation and (FIG. 3D) after ablation using 200 laser energy. The center spot (FIG. 3A) provides preferentially the multiply charged ions shown in FIG. 3O.

FIGS. 4A and 4B. LSIV-MS mass spectra of N-acetylated myelin basic protein fragment (MBP, MW 1833) with 2,5-DHAP matrix acquired at intermediate pressure using the Waters SYNAPT G2 mass spectrometry instrument. FIG. 4A) LSI settings at 0 V and low laser power and FIG. 4B) MALDI settings at 20 V and high laser power.

FIGS. 5A-5D shows MALDI-TOF-MS mass spectra of (FIG. 5A) Ang I, (FIG. 5B) GFP, (FIG. 5C) ACTH and (FIG. 5D) BI acquired under HV conditions using the same matrix/analyte mixture used to obtain the mass of spectra of LSIV-IMS-MS using 2,5-DHAP matrix prepared in 50:50 ACN:water. This FIG. demonstrates that in the absence of a pressure drop region, only SCIs are observed.

The practical utility of the ionization methods disclosed herein are shown through analysis of a mixture composed of a lipid (SM), peptides (Ang I, GFP) and a small protein (BI) using LSI matrix 2,5-DHAP, a glass plate sample holder, and a laser energy of 500. For example, FIGS. 6A and 6B shows LSIV-IMS-MS of the model mixture using a glass plate, 2,5-DHAP matrix (50:50 ACN:water), and 500 laser energy. FIG. 6 includes: FIGS. 6B and 6D) a 2-D plot of drift time versus m/z and extracted drift time for +4 BI ion; and FIGS. 6A and 6C) a total mass spectrum and Inset spectrum of +4 BI ion. FIGS. 6C and 6D show LSIV-IMS-MS of the model mixture using a glass plate, 2,5-DHAP matrix (50:50 ACN:water), and 500 laser energy.

FIGS. 7A-7H shows LSIV-IMS-MS of the pure components of the model mixture using 2,5-DHAP matrix prepared in 50:50 ACN:water using a laser energy of 500 from glass (FIGS. 7A, 7C, 7E, and 7G) or metal plates (FIGS. 7B, 7D, 7F, and 7H) and FIGS. 7A and 7B) SM; FIGS. 7C and 7D) Ang I; FIGS. 7E and 7F) GFP and FIGS. 7G and 7H) BI. FIGS. 6 and 7 demonstrate the 2-D dataset of drift time versus m/z separations of the LSIV-IMS-MS measurement of the model mixture and its pure components. In the total mass spectrum, the most abundant signal is Ang I observed with charge state +1 and +2. The other components of the model mixture, especially the higher charge states of the protein, are not very noticeable because of the low signal-to-noise ratio as compared to the higher abundant Ang I. Because of the exquisite sensitivity for the entire sample composition, the IMS-MS 2-D display allows these ions to be readily visualized.

SCIs of lipids and peptides fall nearly on the same diagonal indicating little separation in the IMS dimension. However, the charge states +1, +2, and +3 are well separated from each other. The highly charged protein ions +4, +5, and +6 fall on a diagonal line that is well separated from the lower charge states +3, +2, +1. The drift times of the different components in the sample are highly charged protein ions +6, +5, +4<multiply charged peptide and protein ions +3, +2<singly charged matrix ions<singly charged peptide and lipid ions. The separation trend and the insignificant separation between the SCIs is in accord with results seen using vacuum MALDI-IMS-MS. The extent of separation between the MCIs and the SCIs is of notable analytical utility.

Figure 8A:
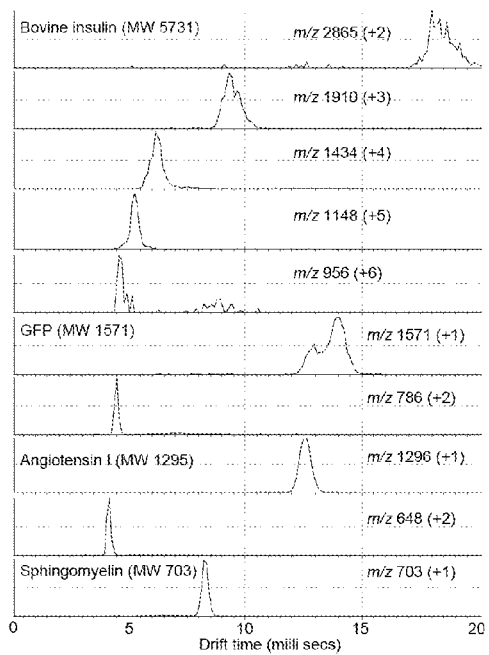
FIGS. 8A and 8B. Extracted drift times of individual components of the model mixture using 2,5-DHAP matrix with a laser energy of 500 and metal (FIG. 8A) and glass plates (FIG. 8B).
Figure 8B:
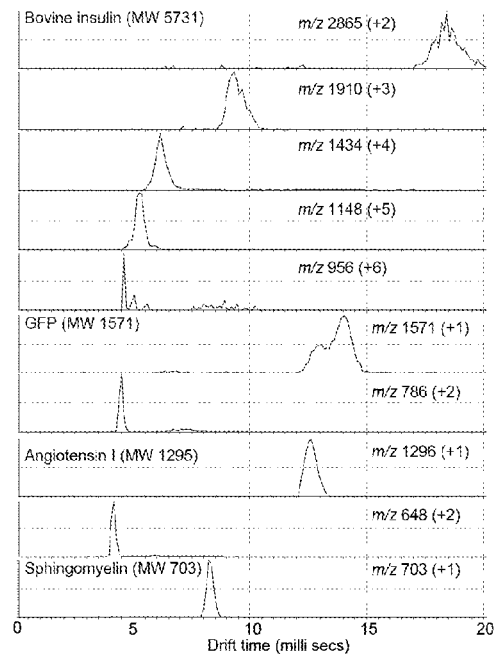

Extracted slices from 2-D datasets permit examining in detail different charge-state distributions even of low-abundant ions that would otherwise be difficult to extract, e.g., charge state +2 versus charge states +1 or +3. For example, FIGS. 8A and 8B show extracted drift times of the individual components of the model mixture using 2,5-DHAP matrix with a laser energy of 500 and metal (FIG. 8A) and glass plates (FIG. 8B).

Figure 9A:
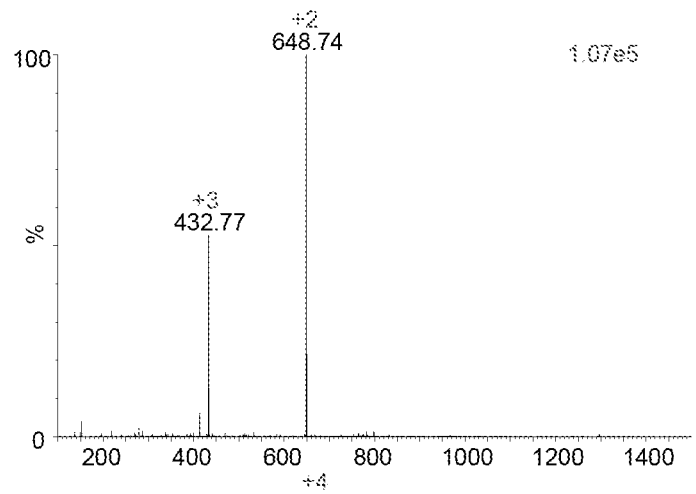
FIGS. 9A, 9B, and 9C. LSIV-MS mass spectra of Ang I (FIG. 9A), BI (FIG. 9B), and ubiquitin (FIG. 9C) using 2,5-DHAP matrix with a laser energy of 200 on a glass plate.
Figure 9B:
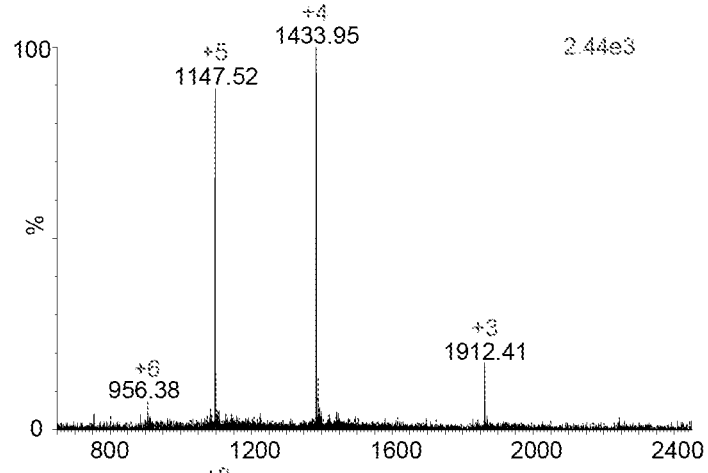
Figure 9C:
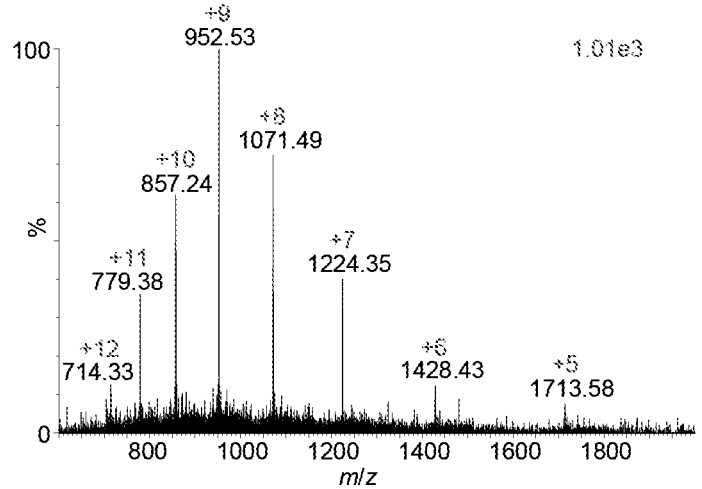

FIGS. 9A, 9B, and 9C. LSIV-MS mass spectra of Ang I (FIG. 9A), BI (FIG. 9B), and ubiquitin (FIG. 9C) using 2,5-DHAP matrix with a laser energy of 200 on a glass plate.

Figure 10:
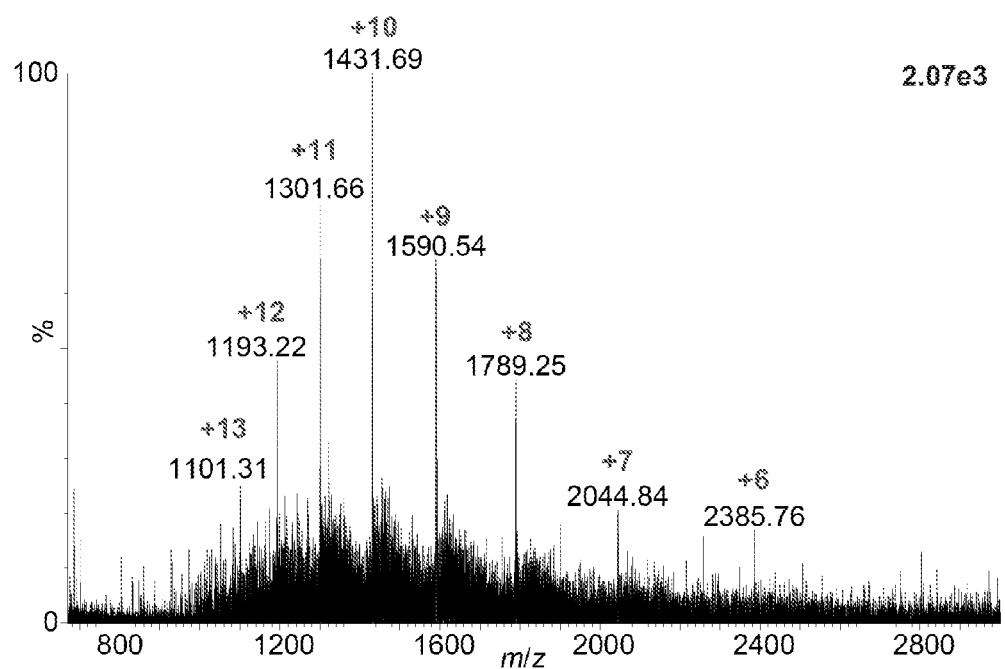
FIG. 10. LSIV-MS-MS of 2.5 pmol lysozyme (MW 14.3 kDa) with saturated 2,5-DHAP in ACN:water prepared using the droplet method with a laser fluence of 225. The matrix/analyte mixture was prepared in 1:1 volume ratio, spotted with 1 pl on a glass plate and air dried. This FIG. demonstrates that controllable parameters on the SYNAPT G2 (Waters Corp., Milford, Mass.) allow extension of the mass range at IP to proteins as large as lysozyme with charge states to +13.

FIG. 10 shows LSIV-MS-MS of 2.5 pmol lysozyme (MW 14.3 kDa) with saturated 2,5-DHAP in ACN:water prepared using the droplet method with a laser fluence of 225. The matrix/analyte mixture was prepared in 1:1 volume ratio, spotted with 1 pL on a glass plate and air dried. This FIG. demonstrates that controllable parameters on the SYNAPT G2 (Waters Corp., Milford, Mass.) allow extension of the mass range at IP to proteins as large as lysozyme with charge states to +13.

Figures 11A, 11B:
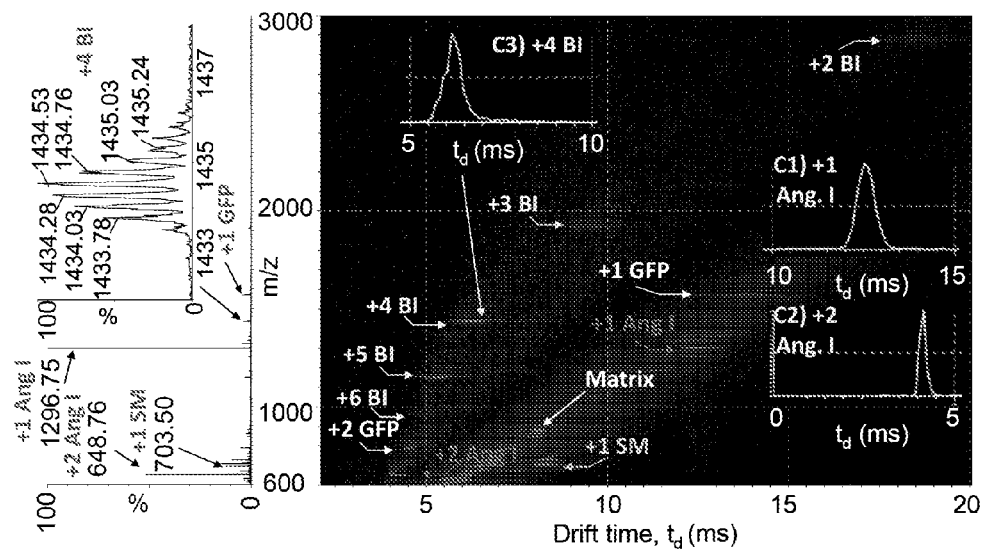
FIGS. 11A and 11B. LSIV-IMS-MS of a model mixture using 2,5-DHAP matrix on glass plate using 200 laser power.

FIGS. 11A and 11B. LSIV-IMS-MS of a model mixture using 2,5-DHAP matrix on glass plate using 200 laser power: (FIG. 11A) 2-D plot of drift time vs. m/z with inset extracted drift time of +4 of BI and +2, +1 of Ang I, and (FIG. 11B) total mass spectrum with an inset of +4 BI distribution.

Figure 12B:
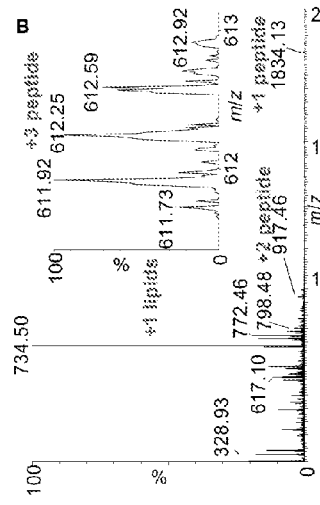
FIGS. 12A and 12B. LSIV-IMS-MS of delipified mouse brain tissue using a glass plate, 2,5-DHAP matrix and a laser energy of 500 with a FIG. 12A) 2-D plot of drift time versus m/z and extracted drift time for +3 ion.
Figure 12A:
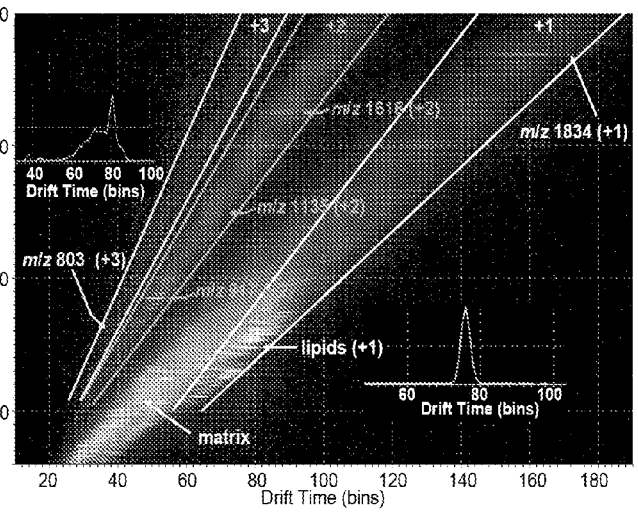

Analyses directly from mouse brain tissue using LSIV-IMS-MS were also conducted. FIG. 12 shows LSIV-IMS-MS of a delipified mouse brain tissue (previously analyzed using LSII-MS in combination with ultra-high mass resolution and ETD enabling identification of an endogenous neuropeptide directly from its native and complex environment; these analysis methods are described in Inutan et al., Mol. Cell. Proteomics, Vol. 10, Issue 2, 2011 (DOI: 10.1074/mcp.M110.000760) which is incorporated by reference herein for its teachings regarding the same) using a glass plate, 2,5-DHAP matrix (50:50 ACN:water), and a laser energy of 500. FIG. 12 includes: FIG. 12A) a 2-D plot of drift time versus m/z and extracted drift time for +3 ion; and FIG. 12B) a total mass spectrum and inset spectrum of +3 ion and the ion (+2) with the largest MW 3216. This FIG. 12 demonstrates that the disclosed systems and methods can be used obtain data directly from mouse brain tissue.

Figures 13A, 13B, 13C:
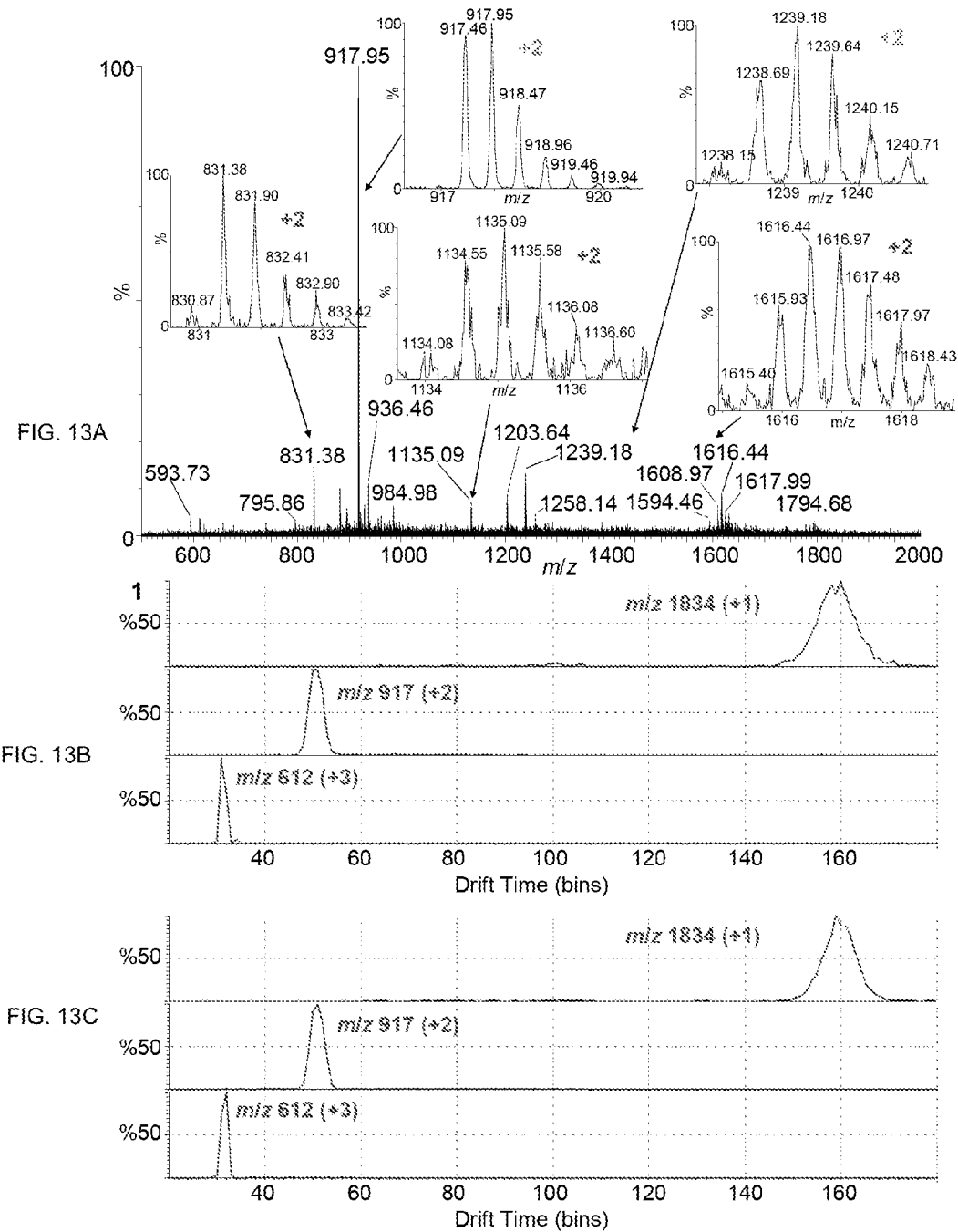
FIGS. 13A, 13B, and 13C.

FIG. 13 shows extracted data from FIG. 12 including: FIG. 13A) a mass spectrum of charge state family +2 and respective inset mass spectra; Drift time distributions of charge states +1 to +3: FIG. 13B) N-acetylated fragment of myelin basic protein [(MBP, characterized previously by ETD], FIG. 13C) from the synthesized neuropeptide (+1, +2, and +3, MW 1833). These show the drift time distributions obtained for +1, +2, and +3 for the N-acetylated fragment of MBP. This neuropeptide was recently characterized from this same tissue sample using an LSII-MS approach. Narrower drift time distributions are observed with increasing charge state, +1 to +3. Indeed, the drift time distributions of the SCIS are unexpectedly wide, as is the case for SCIS obtained from the defined mixture analysis for any of the peptides that showed singly and doubly charged ions, and may indicate more than one ionization mechanism for singly charged ion production. Trap technology devices could enhance the abundance of MCIs.

Figure 14:
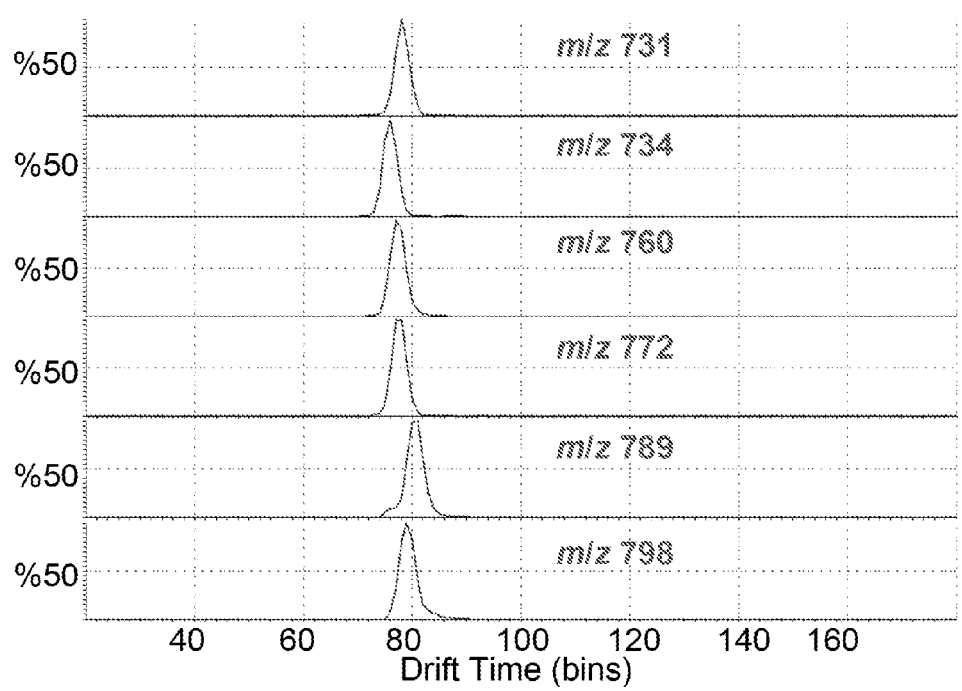
FIG. 14. Extracted drift times of lipids detected from an aged delipified mouse brain using 2,5-DHAP matrix and LSIV-IMS-MS with a laser energy of 500.
Figure 15:
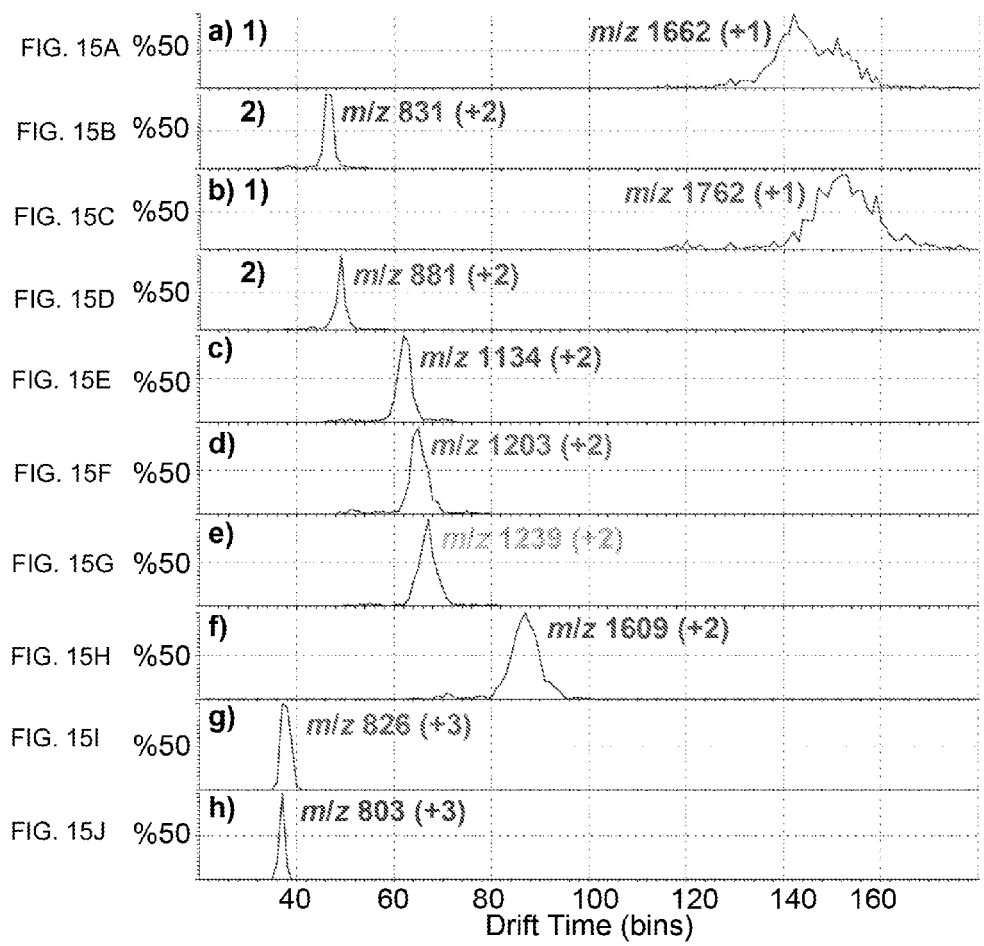
FIGS. 15A-15J. Extracted drift times of +1 +2 and +3 charged states of peptides detected from an aged delipified mouse brain using 2,5-DHAP matrix and LSIV-IMS-MS with a laser energy of 500.

As stated, extracted slices from 2-D datasets permit examining in detail different charge-state distributions even of low-abundant ions that would otherwise be difficult to extract. Here, FIG. 14 shows extracted drift times of lipids detected from the aged delipified mouse brain using 2,5-DHAP matrix and LSIV-IMS-MS with a laser energy of 500. FIGS. 15A-15J show extracted drift times of +1, +2, and +3 charged states of peptides detected from the aged delipified mouse brain using 2,5-DHAP matrix and LSIV-IMS-MS with a laser energy of 500. FIG. 15A) +1 charge state of peptide a; FIG. 15B) +2 charge state of peptide a; FIG. 15C) +1 charge state of peptide b; FIG. 15D) +2 charge state of peptide b; FIG. 15E) +2 charge state of peptide c; FIG. 15F) +2 charge state of peptide d; FIG. 15G) +2 charge state of peptide e; FIG. 15H) +2 charge state of peptide f; FIG. 15I) +3 charge state of peptide g; and FIG. 15J) +3 charge state of peptide h.

Figure 16:
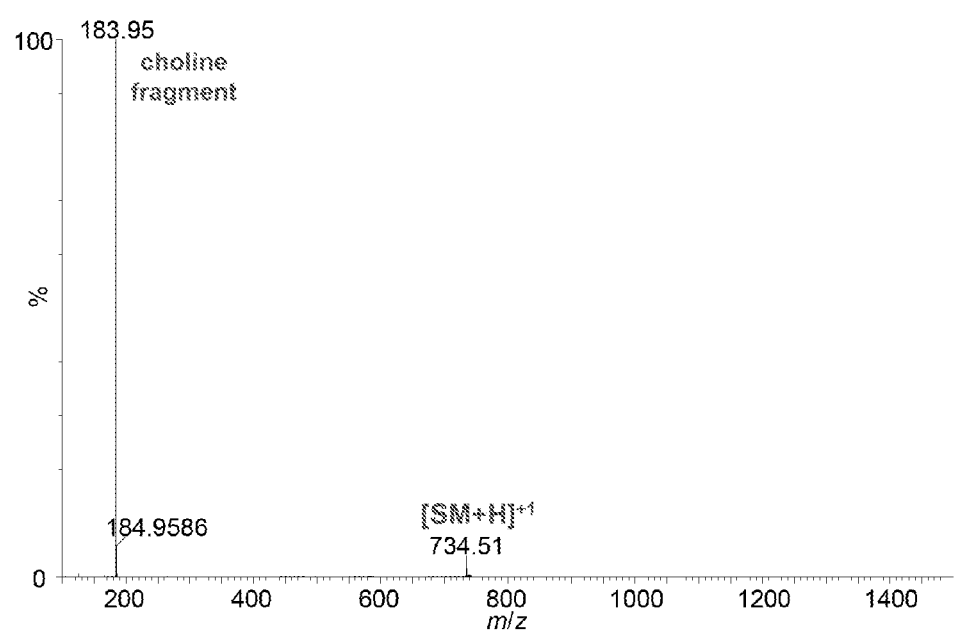
FIG. 16. LSIV-MS-MS of lipid sphingomyelin (SM) using collision induced dissociation (CID).

FIG. 16 shows IP LSI-MS-MS of lipid SM using CID acquired directly from the aged mouse brain tissue spotted with 2,5-DHAP matrix prepared in 50;50 ACN:water. A collision energy of 32 V was applied in the trapping cell to produce the choline fragment peak m/z 183. This FIG. demonstrates that tandem MS/MS can be used to characterize the structural composition directly from tissue material as is shown for a lipid with the loss of the choline head group using CID as the activation method. Other methods of fragmentation such as ETD, electron capture dissociation (ECD) and infrared multiphoton dissociation (RMPD) can be used as well. Accordingly, CID can be used to characterize lipid compositions directly from tissue.

Figure 17A:
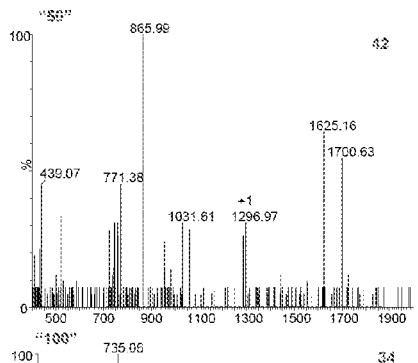
FIGS. 17A-17H. Summarized results for myelin basic protein (MBP) neuropeptide, using 2,5-DHAP matrix with laser energies from 50 to 500.
Figure 17B:
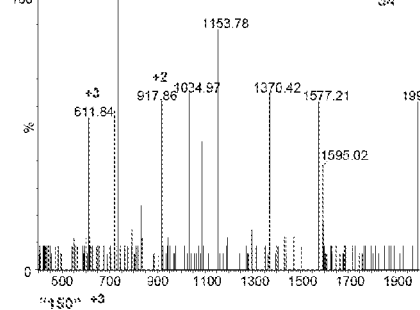
Figure 17C:
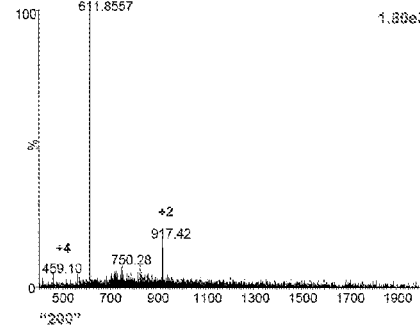
Figure 17D:
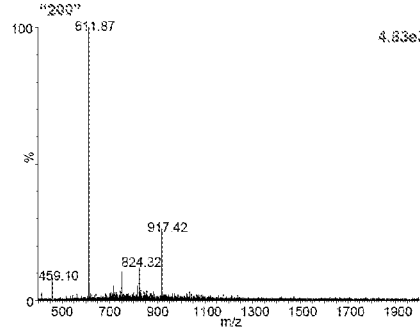
Figure 17E:
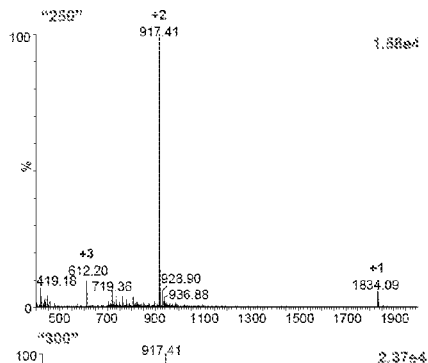
Figure 17F:
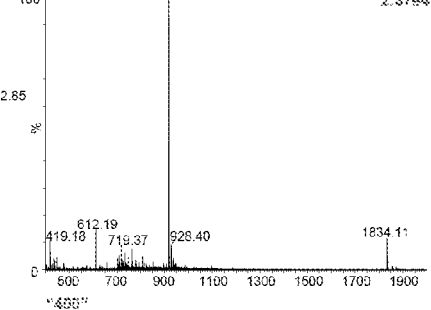
Figure 17G:
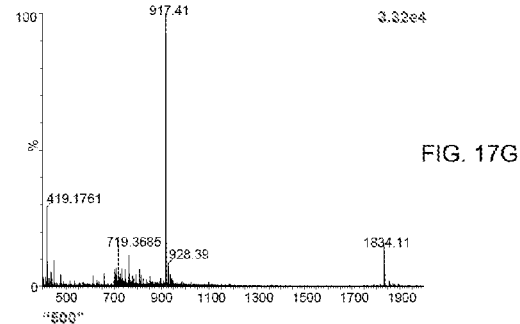
Figure 17H:
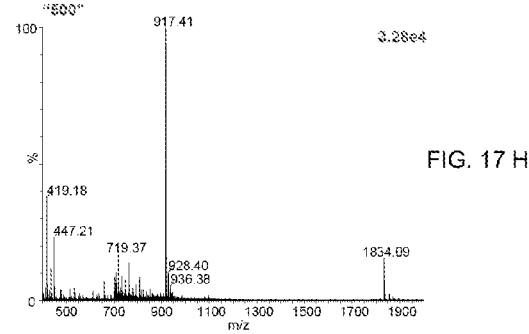

FIGS. 17A-17H show shows results for the MBP neuropeptide, using 2,5-DHAP matrix with laser energies from 50 to 500. FIG. 17A) laser energy of 50; FIG. 17B) laser energy of 100; FIG. 17C) laser energy of 150; FIG. 17D) laser energy of 200; FIG. 17E) laser energy of 250; FIG. 17F) laser energy of 300; FIG. 17G) laser energy of 400; and FIG. 17H) laser energy of 500.

Figure 18A:
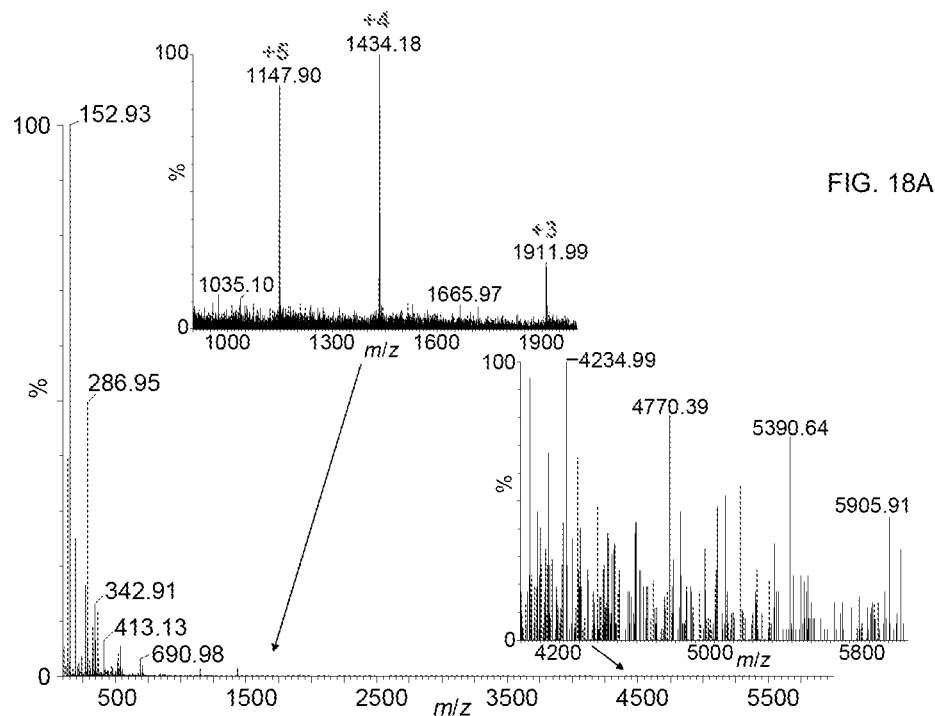
FIGS. 18A and 18B. Increasing the laser energy to 500 still provides only highly charged ions of BI with no singly-charged ions.
Figure 18B:
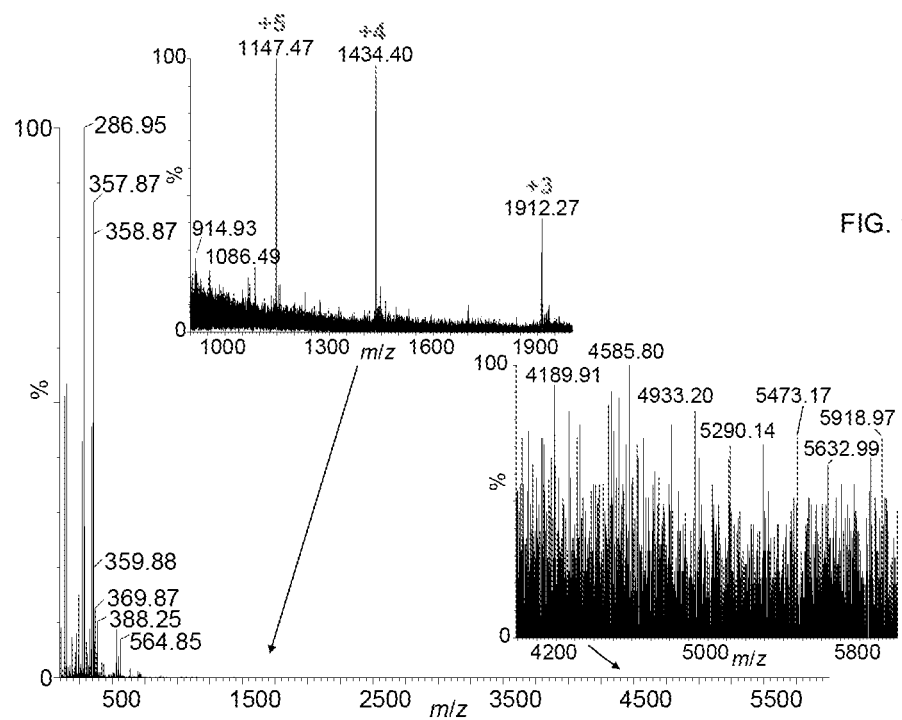
Figure 19A:
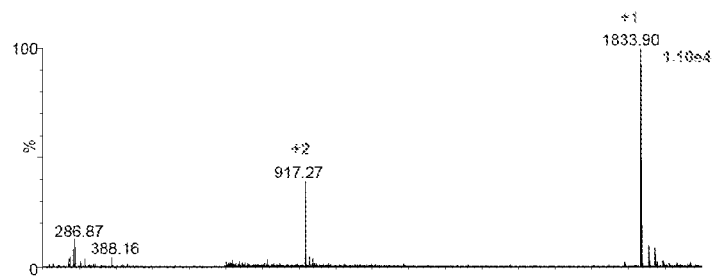
FIGS. 19A-19E. Addition of helium and/or nitrogen ($N_2$) gas results in observation of multiply charged ions.
Figure 19B:
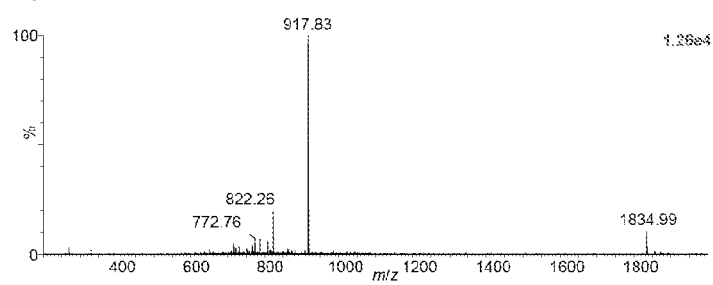
Figure 19C:
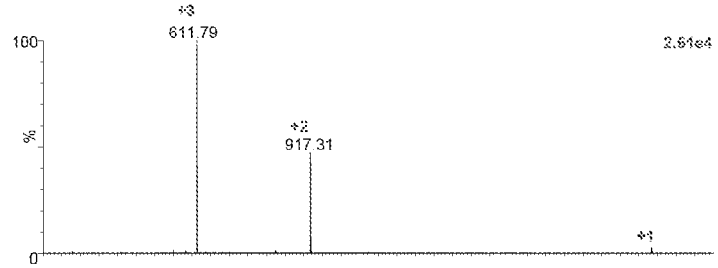
Figure 19D:
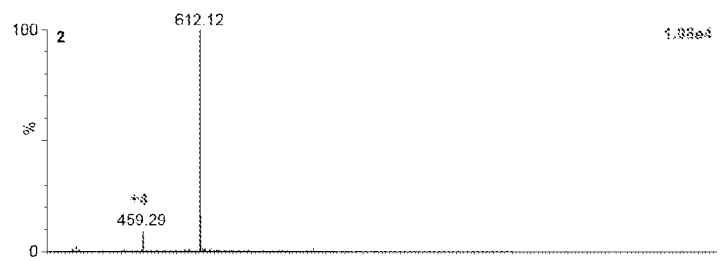
Figure 19E:
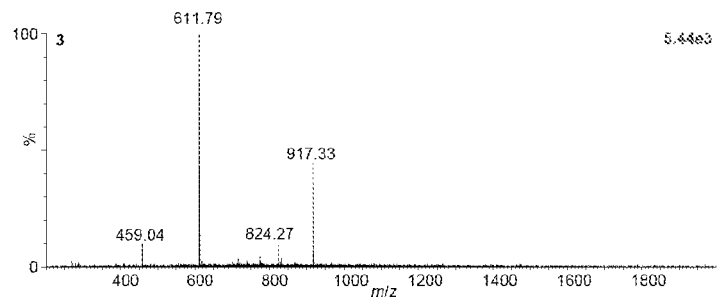

FIG. 18 shows that increasing laser energy to 500 still provides only MCIs of BI with no SCIs (FIG. 18A) glass plate, and FIG. 18B) metal plate). Further, the ion abundance of the background increases to the point of overwhelming the ion intensity of both the multiply and the SCIs present in the mass spectra. Accordingly, increasing the laser energy to 500 still provides only MCIs but no SCIs.

FIG. 19 shows that the addition of helium and/or nitrogen (N2) gas results in observation of multiply charged ions. FIG. 19A) TOF (cooling gas 10 mL min$^{-1}$ and trap gas flow (2.5 mL min$^{-1}$); FIG. 19B) IMS-TOF modes with He cell and IMS gas flow at 24 mL min$^{-1}$; FIG. 19C) He cell (180 mL min$^{-1}$); FIG. 19D) IMS cell (90 mL min$^{-1}$); and FIG. 19E) both gas flows increased.

Comparison of the results obtained with LSIV to those obtained with LSII are shown in FIGS. 20A, 20B, and 20C. This comparison shows that at IP using low laser energy of 200, the results closely resemble those obtained with unattenuated laser energy at AP. Increasing the laser energy at IP to 300 increases the abundance of the singly charged lipid and peptide ions at the expense of a notable increase in matrix background and decrease of the abundance of MCIs.

For further insight, the custom synthesized neuropeptide that was previously identified directly from tissue by a MASCOT search of LSI data from a LTQ-ETD and Orbitrap Exactive was obtained. The extraction of the drift times of the LSIV-IMS-MS measurements of SCIs again showed the unusual broad drift time distributions as compared to the MCIs.

FIGS. 20A, 20B, and 20C show extracted drift times of the neuropeptide with charge states +2, +3, and +4 (when present): (FIG. 20A) from mouse brain tissue section by AP-LSIV-IMS-MS, and from the synthesized N-acetylated fragment of myelin basic protein obtained by (FIG. 20B) AP-LSI-IMS-MS and (FIG. 20C) ESI-IMS-MS.

FIGS. 20A, 20B, and 20C show that while the charge state and drift time distribution appearance is nearly identical for the synthetic neuropeptide sample to that observed in LSII or ESI IMS-MS, singly charged ions are not present under AP conditions even though LSII uses significantly higher laser energy than those used with LSIV.

FIGS. 21A-21E. LSIV-MS at mass spectra of bovine insulin (MW 5731) acquired with IMS separation: default (FIG. 21A), no API gas on (FIG. 21B), and trap off (FIG. 21C), and without IMS separation: default (FIG. 21D), and no trap on (FIG. 21E).

Figure 22A:
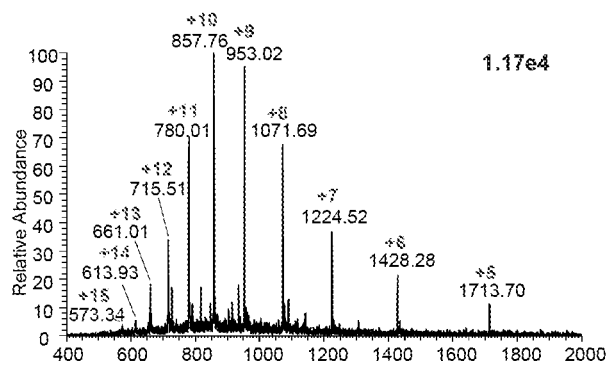
FIGS. 22A-22D. Mass Spectrum of ubiquitin (MW 8559) with 2-NPG matrix solution.
Figure 22B:
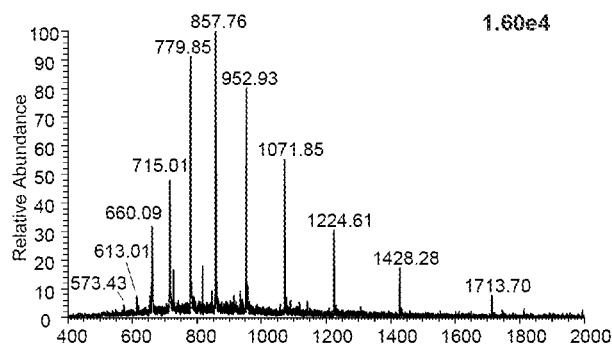
Figure 22C:
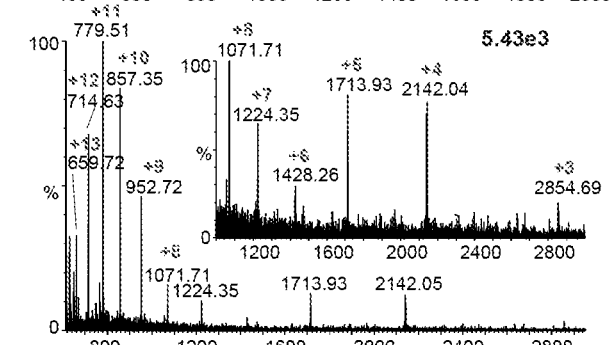
Figure 22D:
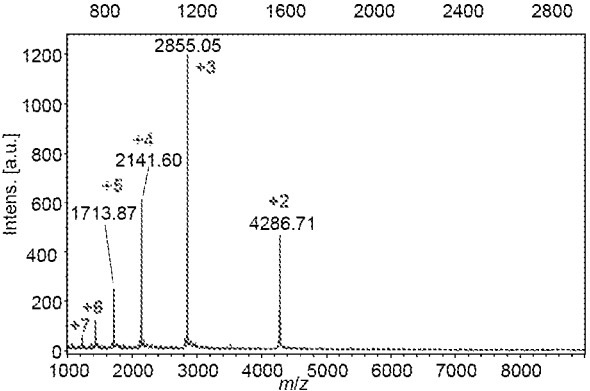

FIGS. 22A-22D. Mass Spectrum of ubiquitin (MW 8559) with 2-NPG matrix solution: FIG. 22A) AP-LSI and FIG. 22B) AP-MAII using the LTQ Velos with a capillary temperature heated to 300° C., FIG. 22C) IP-LSI from the SYNAPT G2 using the IP-MALDI source, and FIG. 22D) from high vacuum MALDI-TOF-TOF Bruker UltrafleXtreme instruments in reflectron mode.

FIGS. 23A and 23B. High vacuum MALDI mass spectrum of Lysozyme (MW 14.3 kDa) with 2-NPG matrix solution acquired in FIG. 23A) reflectron mode and FIG. 23B) linear mode the MALDI-TOF-TOF Bruker UltrafleXtreme instrument.

FIGS. 24A and 24B. High vacuum MALDI mass spectrum of lysozyme (MW 14.3 kDa) acquired in linear mode with FIG. 24A) 2-NPG and FIG. 24B) Sinapinic acid matrix solution using a MALDI-TOF Bruker Autoflex Speed instrument.

Figure 25A:
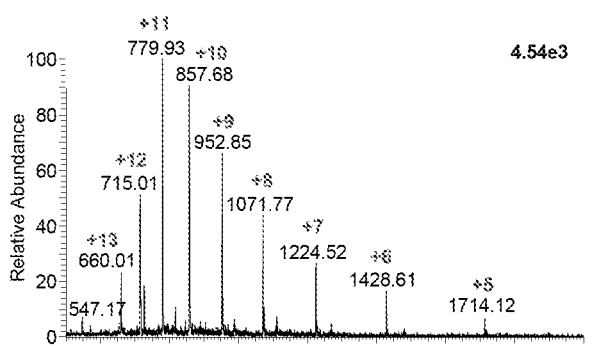
FIGS. 25A-25D. AP-LSI mass spectrum of ubiquitin (MW 8559) with different matrixes solution.
Figure 25B:
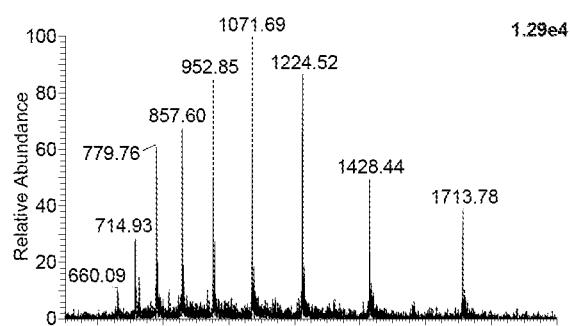
Figure 25C:
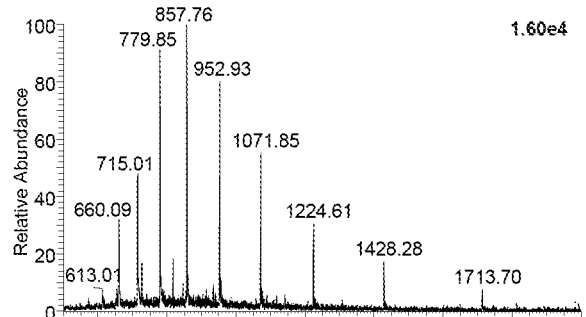
Figure 25D:
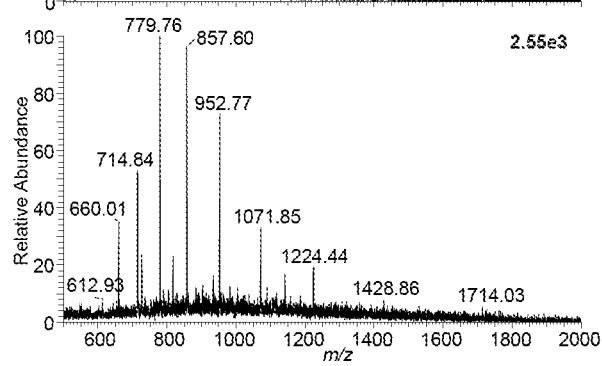

FIGS. 25A-25D. AP-LSI mass spectrum of ubiquitin (MW 8559) with different matrixes solution: FIG. 25A) 2,5-DHB, FIG. 25B) 2,5-DHAP, FIG. 25C) 2-NPG, and FIG. 25D) 4,6-DNPG acquired using the LTQ Velos with the capillary temperature heated to 300° C.

Figure 26A:
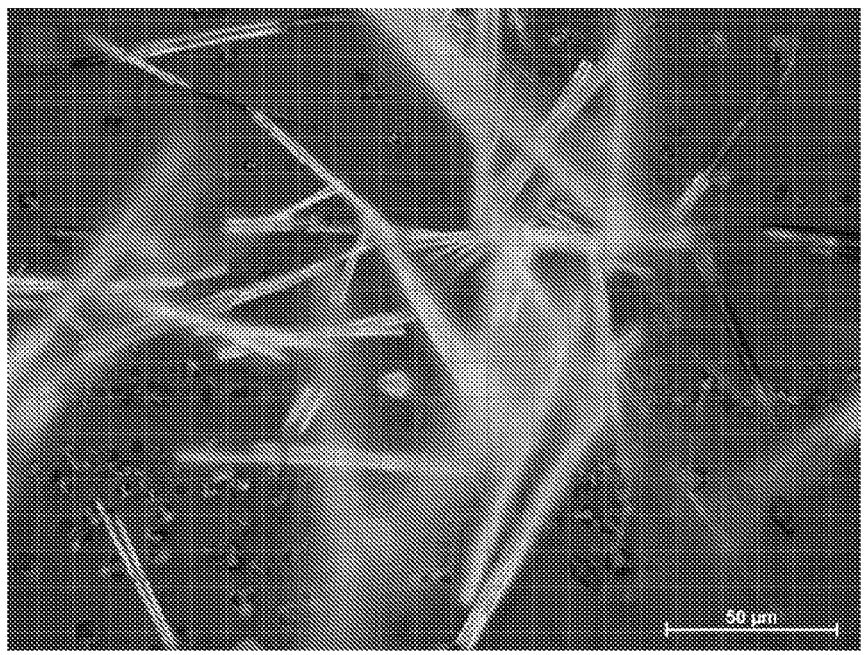
FIGS. 26A and 26B. Photographs of the optical microscopy of a 1 pL dried droplet spot of the 1:1 volume ratio of analyte/matrix mixture of ubiquitin in water with FIG. 26A) 2-NPG and FIG. 26B) 4,6-DNPG matrix solution on a glass plate before laser ablation.
Figure 26B:
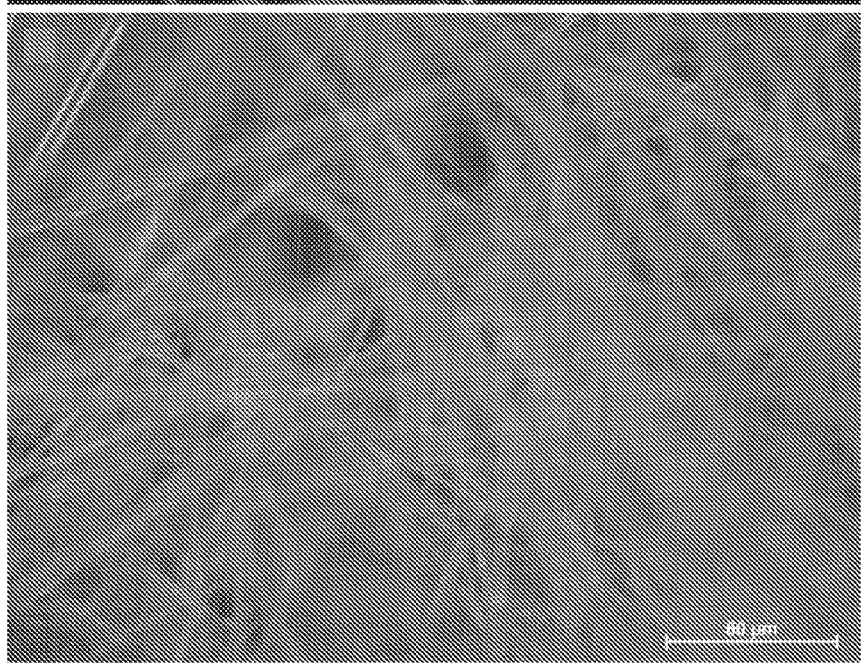

FIGS. 26A and 26B. Photographs of the optical microscopy of a 1 pL dried droplet spot of the 1:1 volume ratio of analyte/matrix mixture of ubiquitin in water with FIG. 26A) 2-NPG and FIG. 26B) 4,6-DNPG matrix solution on a glass plate before laser ablation.

Figure 27A:
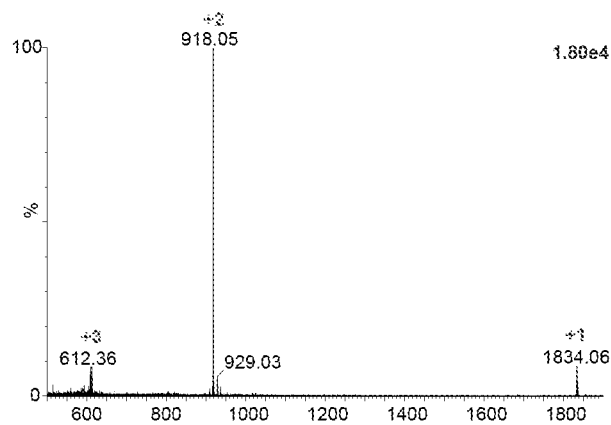
FIGS. 27A, 27B, and 27C. IP-LSI mass spectrum acquired with 4,6-DNPG matrix solution of FIG. 27A) N-acetylated myelin basic protein fragment (MBP) (MW 1833) and FIG. 27B) bovine insulin (MW 5731).
Figure 27B:
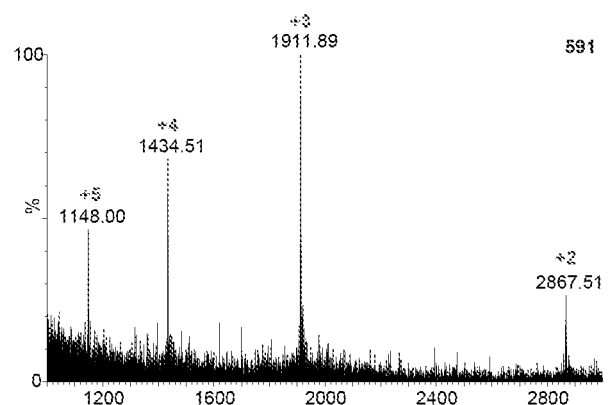
Figure 27C:
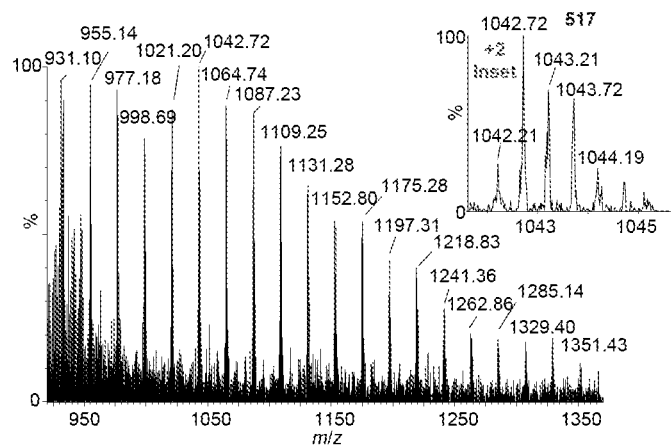
Figures 28A, 28B, 28C, 28D:
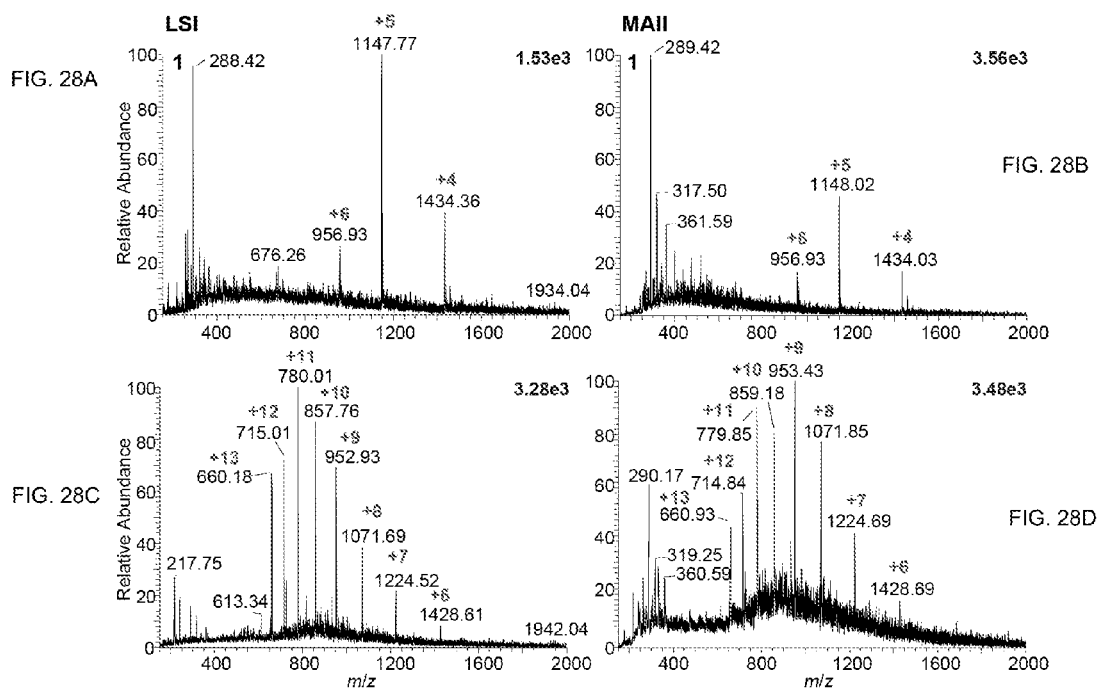
FIGS. 28A-28D. AP-LSI mass spectra of FIG. 28A) bovine insulin (MW 5731) and FIG. 28C) ubiquitin (MW 8559 Da) and AP-MAII mass spectra of FIG. 28B) bovine insulin (MW 5731) and FIG. 28D) ubiquitin (MW 8559 Da) with 4,6-DNPG acquired using the LTQ-Velos with the capillary temperature heated to 300° C.

FIGS. 27A, 27B, and 27C. IP-LSI mass spectrum acquired with 4,6-DNPG matrix solution of FIG. 27A) N-acetylated myelin basic protein fragment (MBP) (MW 1833) and FIG. 27B) bovine insulin (MW 5731). FIG. 27C) Extracted +2 charged state mass spectrum of polyethylene glycol-dimethyl ether (PEGDME) (MW 2000) with +1 charged state in the full mass spectrum. Inset shows +2 charged state isotopic distributions.

FIGS. 28A-28D. AP-LSI mass spectra of FIG. 28A) bovine insulin (MW 5731) and FIG. 28C) ubiquitin (MW 8559 Da) and AP-MAII mass spectra of FIG. 28B) bovine insulin (MW 5731) and FIG. 28D) ubiquitin (MW 8559 Da) with 4,6-DNPG acquired using the LTQ-Velos with the capillary temperature heated to 300° C.

FIGS. 29A, 29B, and 29C. High vacuum MALDI mass spectra of ubiquitin (MW 8559 Da) with different matrixes: FIG. 29A) 2-NPG, FIG. 29B) 2,5-DHB, and FIG. 29C) CHCA acquired in reflectron mode using the MALDI-TOF Bruker Ultraflex instrument.

FIGS. 30A, 30B, and 30C. High vacuum MALDI mass spectra of lysozyme (MW 14.3 kDa) with different matrixes: FIG. 30A) 2-NPG, FIG. 30B) 2,5-DHB, and FIG. 30C) CHCA acquired in linear mode using a MALDI-TOF Bruker Ultraflex instrument FIGS. 31A-31D. High vacuum MALDI mass spectra of bovine insulin (MW 5731) with 2-NPG matrix acquired using the reflectron mode with different pulsed ion extraction (PIE) delay: FIG. 31A) 0, FIG. 31B) 200, FIG. 31C) 400, and FIG. 31D) 600 ns from a MALDI-TOF Bruker UltrafleXtreme instrument.

Figures 32A, 32B, 32C, 32D:
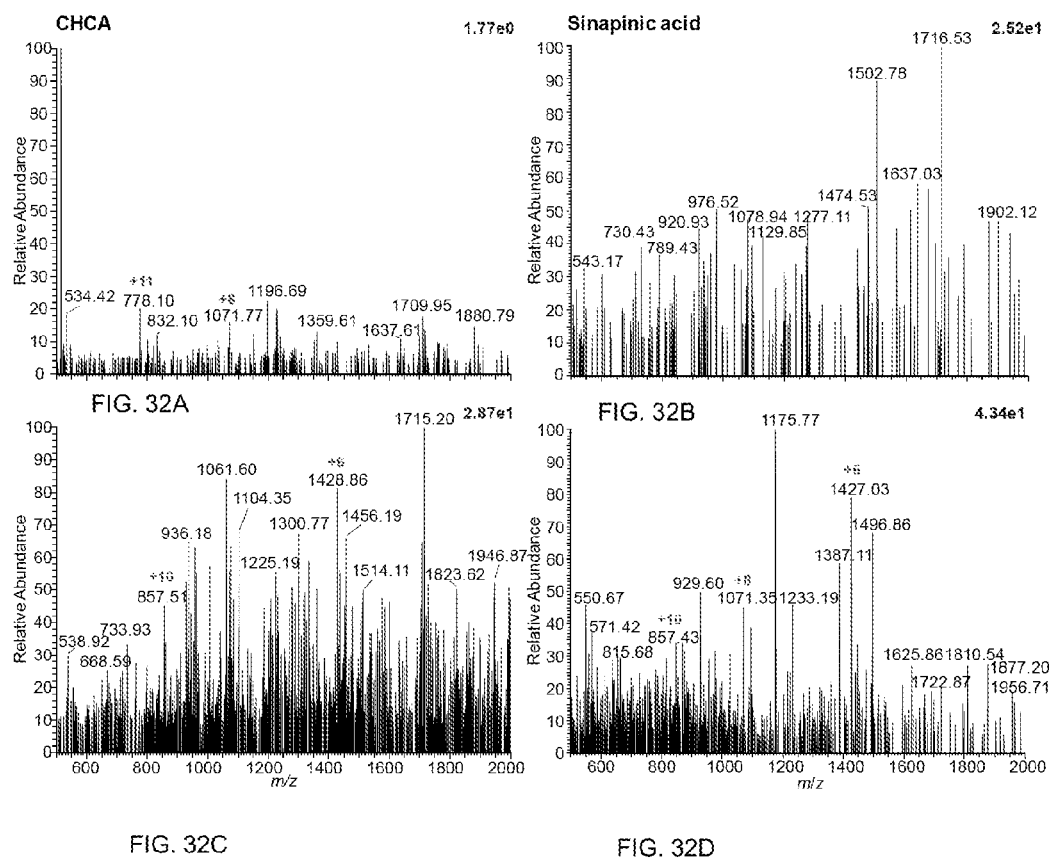
FIGS. 32A-32D. AP-MAII mass spectra of ubiquitin (MW 8559 Da) acquired using the LTQ-Velos mass spectrometer with FIG. 32A) CHCA matrixes with the capillary temperature heated to 300° C.

FIGS. 32A-32D. AP-MAII mass spectra of ubiquitin (MW 8559 Da) with CHCA (FIGS. 32A and 32C) and SA (FIGS. 32B and 32D) matrixes acquired using the LTQ-Velos mass spectrometer with the capillary temperature heated to 300° C. (FIGS. 32A and 32B) and 450° C. (FIGS. 32C and 32D).

Figure 33A:
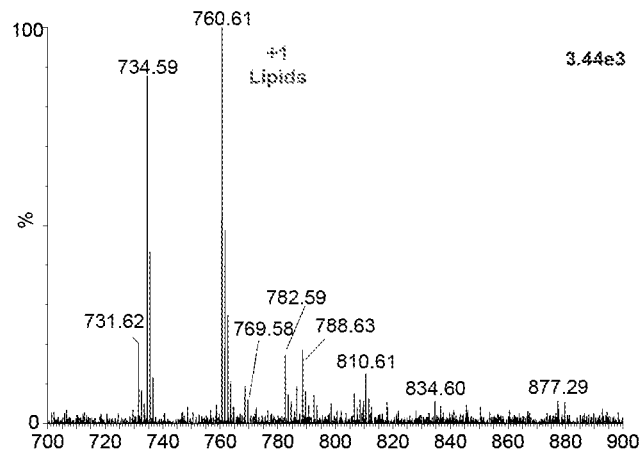
FIGS. 33A, 33B, and 33C. AP-LSI mass spectra of FIG. 33A) lipids from mouse brain tissue section and FIG. 33B) PEG-1000 acquired from the SYNAPT G2 with the source heated to 150° C.
Figure 33B:
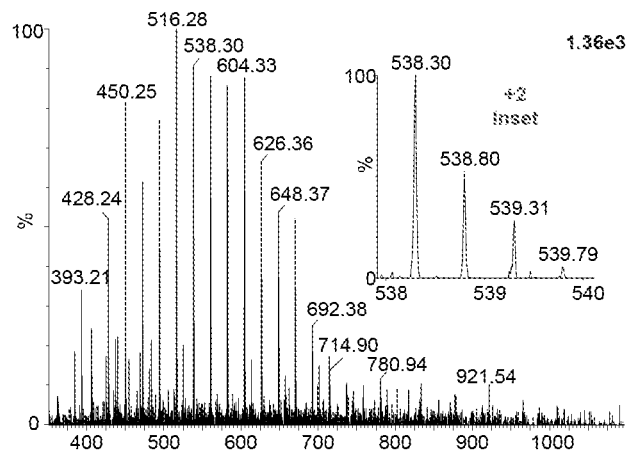
Figure 33C:
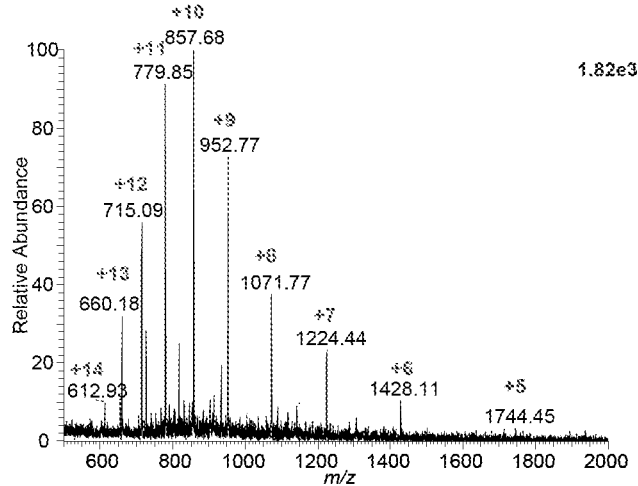

FIGS. 33A, 33B, and 33C. AP-LSI mass spectra of FIG. 33A) lipids from mouse brain tissue section and FIG. 33B) PEG-1000 acquired from the SYNAPT G2 with the source heated to 150° C. and FIG. 33C) ubiquitin (MW 8559 Da) from the LTQ-Velos with the capillary temperature heated to 300° C. using 4,6-DNPG as matrix. Inset shows +2 charged state isotopic distribution of PEG-1000.

FIGS. 34A, 34B, and 34C. High vacuum MALDI mass spectra of ubiquitin (MW 8559 Da) with 2,4-DNPG matrix acquired using the reflectron mode with different laser power: FIG. 34A) 65%, FIG. 34B) 70%, and FIG. 34C) 75% from a MALDI-TOF Bruker UltrafleXtreme instrument.

Figure 35A:
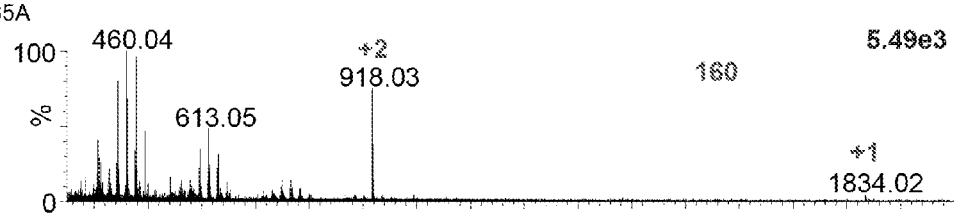
FIGS. 35A, 35B, and 35C. IP-LSI-MS mass spectra of MBP (MW 1833 Da) with 2-NPG matrix acquired using different laser fluence on SYNAPT G2 instrument.
Figure 35B:
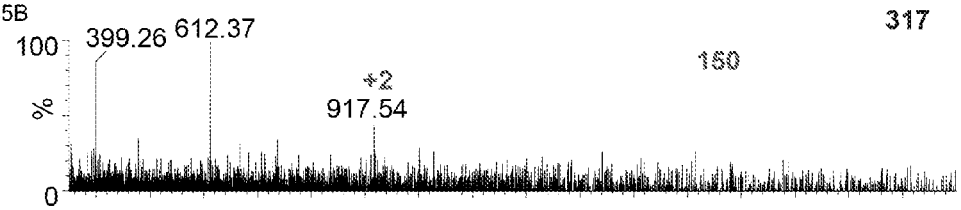
Figure 35C:
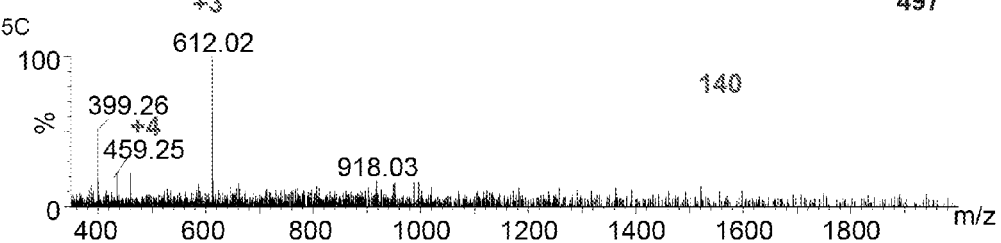

FIGS. 35A, 35B, and 35C. IP-LSI-MS mass spectra of MBP (MW 1833 Da) with 2-NPG matrix acquired using different laser fluence on SYNAPT G2 instrument. FIG. 35A) "160", FIG. 35B) "150", and FIG. 35C) "140".

FIGS. 36A-36E. High vacuum MALDI mass spectra of ubiquitin (MW 8559 Da) with 2-NPG matrix acquired using the reflectron mode with different laser power: FIG. 36A) 45%, FIG. 36B) 50%, FIG. 36C) 55%, FIG. 36D) 60%, and FIG. 36E) 65% from a MALDI-TOF Bruker UltrafleXtreme instrument.

Figure 37:
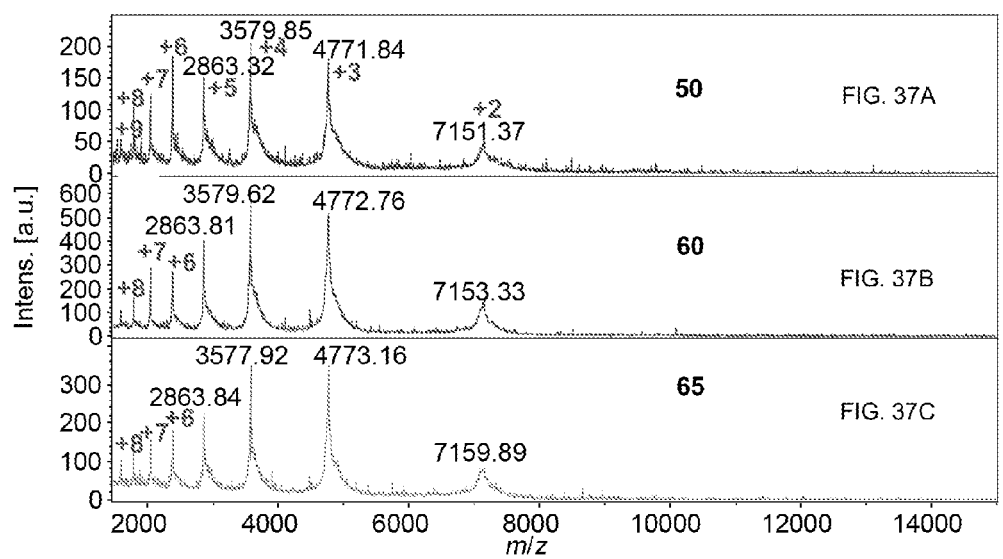
FIGS. 37A, 37B, and 37C. High vacuum MALDI mass spectra of lysozyme (MW 14.3 kDa) with 2-NPG matrix acquired using the reflectron mode with different laser power.
Figure 39A:
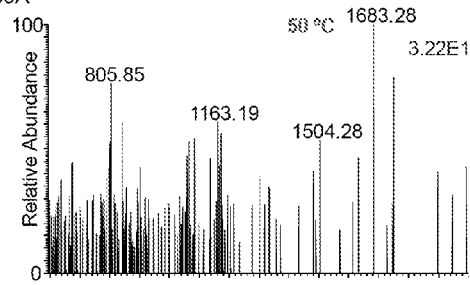
Figure 39B:
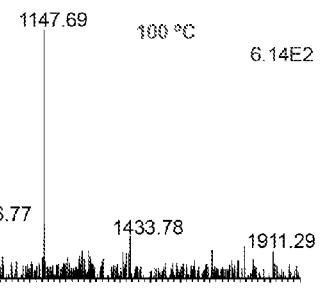
Figure 39C:
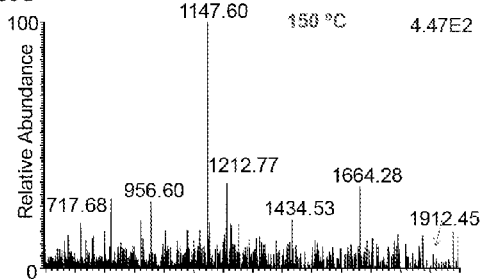
Figure 39D:
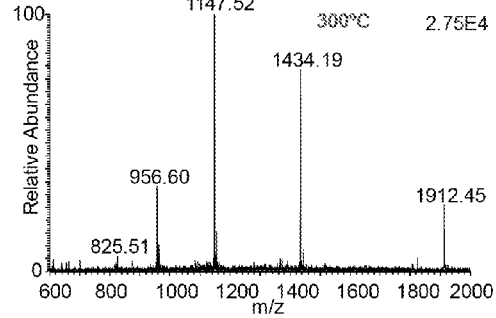
Figure 39E:
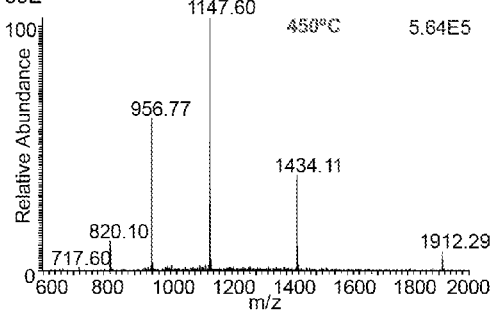

FIGS. 37A, 37B, and 37C. High vacuum MALDI mass spectra of lysozyme (MW 14.3 kDa) with 2-NPG matrix acquired using the reflectron mode with different laser power: FIG. 37A) 50%, FIG. 37B) 60%, and FIG. 37C) 65% from a MALDI-TOF Bruker UltrafleXtreme instrument.

FIGS. 38A and 38B. High vacuum MALDI mass spectra of FIG. 38A) bovine insulin (MW 5731 Da), and FIG. 38B) ubiquitin (MW 8559 Da) with 4,6-DNPG matrix acquired in reflectron mode using a MALDI-TOF Bruker Ultraflex instrument.

LSI is a subset of matrix assisted inlet ionization (MAII) in which a matrix/analyte mixture produces electrospray ionization (ESI)-like mass spectra of the analyte when introduced by dislodging a matrix/analyte into a heated transfer tube linking AP with the first vacuum region of the mass analyzer. Because in MAII the matrix/analyte sample is dislodged by tapping the sample holder against the inlet of the mass spectrometer, the ionization is free of any laser ablation event. MAII therefore permits the study of conditions pertinent to the formation of multiply charged ions. Crucial for the production of highly charged ions is the sample preparation including pH and the proper desolvation conditions for ionization of the analyte molecules during mass spectrometric acquisition. Factors include thermal energy, vacuum assistance, collisions with gases and surfaces for example. We disclose new matrix compounds that produce abundant, highly charged MAII ions. Matrix material composed of linear and aromatic structures produce abundant multiply charged ions. Matrix material that has little or no absorption at the employed laser wavelength is capable of dislodging the matrix/analyte from the surface, especially with the laser aligned in transmission geometry, producing highly charged ions. A variety of different chemical structures including aromatic and nonaromatic matrix compounds indicate the importance of OH and $NH_2$ functionality. The utility for binary matrixes is shown for LSI vacuum to produce abundant, highly charged ions with as little as 5% of a 2-NPG, a potent MAII matrix, added. The solvent-free sample preparation approach can be applied to solubility restricted matrix compounds or to those that are too volatile to be prepared solvent-based. FIG. 39A-39E. MAII-MS of BI with 2-NPG prepared using layer method in 1:1 ratio and acquired at different acquisition temperature of the inlet capillary tube of the LTQ Velos mass spectrometer instrument: (FIG. 39A) 50° C., (FIG. 39B) 100° C., (FIG. 39C) 150° C., (FIG. 39D) 300° C., (FIG. 39E) 450° C.

FIGS. 40A-40H. MAII-MS of Lys with 2-NPG matrix prepared in 1:1 layer method and acquired with different maximum injection times: FIG. 40A) 10, FIG. 40B) 25, FIG. 40C) 50, FIG. 40D) 100, FIG. 40E) 150, FIG. 40F) 200, FIG. 40G) 300, and FIG. 40H) 500 ms at 1 microscan and 450° C. inlet capillary temperature on LTQ-Velos mass spectrometer instrument.

FIGS. 41A-41F. MAII-MS of Lys with 2-NPG matrix prepared in layer method in 1: ratio and acquired with different microscans: FIG. 41A) 1, FIG. 41B) 2, FIG. 41C) 3, FIG. 41D) 5, FIG. 41E) 8 and FIG. 41F) 10 ms at 100 ms maximum injection time and 450° C. inlet capillary temperature on LTQ-Velos mass spectrometer instrument.

FIGS. 42A and 42B. MAII-MS sensitivity study of (FIG. 42A) 10 fmol pL-1 with 2-NPG and (FIG. 42B) 50 fmol with 2,5-DHAP prepared using layer method in 1:1 ratio and blow dried using the Thermo LTQ-Velos mass spectrometer instrument with an inlet capillary temperature of 300° C.:

FIGS. 43A-43D. MAII of Lys with FIG. 43A) 100% CHCA, FIG. 43C) binary mixture of 5%2-NPG and 95% CHCA, FIG. 43B) 100% SA, and FIG. 43D) binary mixture of 5%2-NPG and 95% SA prepared using layer method in 1:2 ratio and acquired at 450° C. inlet capillary temperature on an LTQ-Velos mass spectrometer instrument using microscan of 2 and maximum injection time of 200 ms.

FIGS. 44A and 44B. LSII- and MAII-MS of Lys with binary matrix mixture of 5% 2-NPG and 95% CHCA prepared using layer method in 1:2 ration and acquired at 450° C. inlet capillary temperature on an LTQ-Velos mass spectrometer instrument using microscan of 2 and maximum injection time of 200 ms.

FIGS. 45A-45D. MAII-MS of Lys with binary matrix mixture of 5% 2-NPG and 95% CHCA (FIGS. 45A and 45C) and 5% 2-NPG and 95% SA (FIGS. 45B and 45D) prepared using layer method in 1:2 ratio and acquired at 300° C. (FIGS. 45A and 45B) and 450° C. (FIGS. 45C and 45D) inlet capillary temperature on an LTQ-Velos mass spectrometer instrument using microscan of 2 and maximum injection time of 200 ms.

FIGS. 46A and 46B. LSII-MS of (FIG. 46A) 10 pmol pL-1 CA and (FIG. 46B) a 10 second acquisition of 20 pmol pL-1 BSA with 2-NPG matrix prepared using layer method. Data acquired on the LTQ-Velos mass spectrometer instrument at 300° C. inlet capillary temperature with (FIG. 46A) 2, 200 ms and (FIG. 46B) 10, 100 ms microscans and maximum injection time, respectively.

FIGS. 47A and 47B. (FIG. 47A) LSII-MS and (FIG. 47B) MAII-MS of 20 pmol of BSA with 2-NPG matrix prepared using layer method and acquired on the LTQ-Velos mass spectrometer instrument at 200° C. inlet capillary temperature at 10 microscans and 100 ms maximum injection time. The starred and labeled peaks are believed to be the protonated multiply charged molecules.

FIG. 48. MAII-CID MS/MS of 2 pmol μL-1 of BSA tryptic digest mixed with 4 μL of 2-NPG using layer method on a metal spatula and acquired on the LTQ-Velos mass spectrometer instrument at 325° C. inlet capillary with microscans of 2 and 100 ms maximum injection time. Precursor ion selected was m/z of 642.60 [M+2H]$^{2+}$ and fragment ions produced at a collision energy of 30 and selection window of ±0.9.

FIG. 49. MAII-CID-MS/MS mass spectrum of 1 pmol μL$^{-1}$ Ang II with 2 μL of 2-NPG using layer method on a metal spatula and acquired on the LTQ-Velos mass spectrometer instrument 325° C. inlet capillary temperature with 2 microscans and 100 ms maximum injection time. Precursor ion selected was m/z of 524.01 [M+2H]$^{2+}$ and fragmentation ions produced at a collision energy of 27 and selection window of ±0.9.

FIG. 50. MAII-ETD-MS/MS of 1 pmol μL$^{-1}$ Ang II with 2 μL of 2-NPG using layer method on a metal spatula and acquired on the LTQ-Velos mass spectrometer instrument at 325° C. inlet capillary temperature with 2 microscan and 100 ms maximum injection time. Precursor ion selected was m/z of 524.01 [M+2H]2+ and fragment ions produced at an activation time of 500 ms and selection window of ±0.9.

FIG. 51. MAII (A) full mass spectrum of 5 pmol μL$^{-1}$ BI B chain oxidized (MW 3495 Da) and (B) ETD-MS/MS of the +4 charge state with 2-NPG as matrix prepared using the layer method. and acquired on the LTQ-Velos mass spectrometer instrument at 325° C. inlet capillary temperature with 1 microscan and 50 ms maximum injection time. The ETD activation time was set to 800 ms and 25 V of supplemental activation energy. (C) shows the nearly 100% sequence coverage that was obtained from a single MAII-ETD-MS/MS acquisition in (B).

FIGS. 51A, 51B, and 51C. MAII (FIG. 51A) full mass spectrum of 5 pmol pL$^{-1}$ BI B chain oxidized (MW 3495 Da) and (FIG. 51B) ETD-MS/MS of the +4 charge state with 2-NPG as matrix prepared using the layer method. and acquired on the LTQ-Velos mass spectrometer instrument at 325° C. inlet capillary temperature with 1 microscan and 50 ms maximum injection time. The ETD activation time was set to 800 ms and 25 V of supplemental activation energy. FIG. 51C shows the nearly 100% sequence coverage that was obtained from a single MAII-ETD-MS/MS acquisition in (B).

FIGS. 52A-52D. LSII-IMS-MS of delipified mouse brain tissue acquired using the SYNAPT G2 mass spectrometer instrument with a Nanolockspray source: FIG. 52A) 2-dimensional plot of drift time vs. m/z and extracted mass spectra from the 2-D plot, FIG. 52B) An 8.5 kDa protein contamination, FIG. 52C) endogenous 5 kDa protein and the identified neuropeptide, N-acetylated myelin basic protein (MBP MW 1833), and FIG. 52D) +2 to +4 charged states of peptides detected directly from delipified mouse brain tissue spray coated with a binary matrix of 10% 2-NPG (50 mg in 1 mL ACN:water) and 90% 2,5-DHAP (300 mg in 9 mL ACN:water) matrix solution and added with several 0.5 pL spots of 2,5-DHAP matrix solution on top. Source temperature was set at 150° C.

FIGS. 53A and 53B. LSII-MS obtained directly from delipified mouse brain tissue mounted on a FIG. 53A) CHCA precoated and FIG. 53B) plain glass plate, both spray coated with binary mixture of 10% 2-NPG and 90% 2,5-DHAP matrix solution, and acquired using the LTQ-Velos mass spectrometer with inlet capillary temperature of 350° C., microscan of 2, and maximum injection times of 600 ms.

FIG. 54. LSII-MS images of the different charge states of a 5 kDa protein detected directly from delipified mouse brain tissue on a CHCA precoated glass plate (delipified and spray coated with binary mixture of 10% 2-NPG and 90% 2,5-DHAP matrix solution) acquired using the LTQ-Velos mass spectrometer instrument with an inlet capillary temperature of 350° C. The images showed almost half of the mouse brain tissue slice which acquisitions were done with the correct settings of 2 microscans and 600 ms maximum injection time.

FIG. 55. LSII [M-H]$^-$ ion image of 888.7 from mouse brain tissue using a glass slide pre-coated with matrix. The image was obtained on a Thermo LTQ-Velos mass spectrometer instrument with an inlet capillary temperature of 450° C., microscan of 1, and maximum inject time of 100 ms. Each row was acquired in 0.19 minutes.

FIGS. 56A, 56B, and 56C. LSII-MS of Ubi with FIG. 56A) 100% CHCA, FIG. 56B) 100% NPG, and FIG. 56C) binary matrix mixture of 5% 2-NPG and 95% CHCA using an IR laser at 1064 nm wavelength acquired on the SYNAPT G2 mass spectrometer instrument with source temperature at 150° C.

FIGS. 57A-57D. LSIV-MS at IP of peptides and proteins in water with 2-NPG matrix prepared using the dried droplet method in 1:1 ratio: (FIG. 57A) 1 pmol pL$^{-1}$ N-acetylated myelin basic protein fragment (MBP, MW 1833 Da), (FIG. 57B) 1 pmol pL$^{-1}$ galanin (MW 3158 Da), (FIG. 57C) 1 pmol pL$^{-1}$ bovine insulin (MW 5731 Da), and (FIG. 57D) 2.5 pmol pL$^{-1}$ ubiquitin (MW 8561 Da). Low laser fluence ('140-175') was used for all the acquisitions.

FIGS. 58A-58D. LSIV-IMS-MS at IP of 2.5 pmol pL$^{-1}$ ubiquitin 2-NPG matrix prepared using droplet method in 1:1 ratio and obtained using the SYNAPT G2 mass spectrometer instrument with a MALDI source. Total mass spectra (FIGS. 58A and 58C) and 2-D plot of drift time vs. m/z (FIGS. 58B and 58D) tuned with different quad settings of 500, 1000, 1000 of masses 1, 2, 3 ramping, respectively at low laser power (FIGS. 58A and 58B), and using the auto profile settings of the instrument at high laser power (FIGS. 58C and 58D).

FIGS. 59A-59H. LSIV-IMS-MS at IP of 2.5 pmol pL$^{-1}$ proteins in water with 2-NPG matrix prepared using droplet method and acquired on a SYNAPT G2 mass spectrometer with a MALDI source. The 2-D plots (FIGS. 59A-59D) and the extracted drift times (FIGS. 59E-59H) for each charge state are displayed for (FIGS. 59A and 59E) ubiquitin, (FIGS. 59B and 59F) lysozyme, (FIGS. 59C and 59G) myoglobin, and (FIGS. 59D and 59H) carbonic anhydrase. Low laser fluence was used for all the acquisitions.

FIGS. 60A and 60B. LSIV-MS at IP of 2.5 pmol pL$^{-1}$ angiotensin I (MW 1295) in water using FIG. 60A) binary matrix of 10% 2-NPG and 90% SA and FIG. 60B) 100% SA prepared using droplet method in 1:1 ratio and acquired using the MALDI source of SYNAPT G2 mass spectrometer instrument. Laser fluence used is '200'.

FIGS. 61A-61C. LSIV-MS at IP of 2.5 pmol pL$^{-1}$ BI with FIG. 61A) 100% 2-NPG, FIG. 61B) 100% CHCA, and FIG. 61C) a binary matrix of 10% 2-NPG and 90% CHCA prepared using droplet method in 1:1 ratio and acquired on the SYNAPT G2 mass spectrometer instrument with a MALDI source using an adjusted quad settings preferencing multiply charged ions.

FIGS. 62A-62D. LSIV-MS at IP of 2.5 pmol pL$^{-1}$ ubiquitin in water with binary mixture of 10% 2-NPG and 90% 4-nitroaniline (FIGS. 62A and 62C) and 100% 4-nitroaniline (FIGS. 62B and 62D) prepared using droplet method in 1:1 analyte/matrix volume ratio and spotted 1 pL on a glass plate. Data acquired using LSI (FIGS. 62A and 62B) and MALDI (FIGS. 62C and 62D) settings of the SYNAPT G2 mass spectrometer instrument with a MALDI source.

FIGS. 63A and 63B. LSIV-IMS-MS at IP FIG. 63A) 2-dimensional plot of drift time vs. m/z and FIG. 63B) total mass spectrum of lipids, peptides, and proteins detected directly from delipified mouse brain tissue spotted with 100%-2NPG matrix. The production of multiply charge ions and with gas phase separation, lipids, peptides, and proteins are well separated into charged state families.

FIGS. 64A and 64B. LSIV-IMS-MS at IP 2-D plots of drift time vs. m/z from delipified mouse brain tissue mounted on FIG. 64A) plain glass plate and spray coated with 100% 2-NPG and FIG. 64B) CHCA precoated glass plate and spray coated with 90% 2,5-DHAP and 10% 2-NPG.

FIGS. 65A and 65B. LSIV imaging at IP from an aged delipified mouse brain tissue spray coated with 100% 2-NPG matrix solution showing images of endogenous neuropeptides peptides. FIG. 65A) Total mass spectrum, FIG. 65B) Inset mass spectrum of the +2 peptides with the images of the most abundant signals: (1) m/z 831 and (2) the identified neuropeptide, N-acetylated myelin basic protein fragment m/z 917 and (3) its +1 charged state m/z 1834.

FIGS. 66A-66D. LSIV imaging at IP of endogenous neuropeptides from delipified mouse brain tissue spray coated with 100% 2-NPG matrix solution: FIG. 66A) m/z 795 (+2), FIG. 66B) m/z 831 (+2), and FIG. 66C) m/z 917 (+2), the identified neuropeptide MBP. (FIG. 66D) shows the location of this protein and its abundance in the mouse brain tissue (from Allen mouse brain atlas)

FIG. 67. LSIV-MS at HV of CA with 2-NPG matrix prepared using droplet method in 1:1 ratio and acquired in reflectron mode using a Bruker MALDI-TOF-TOF UltrafleXtreme mass spectrometer at 50% laser power.

FIGS. 68A and 68B. LSIV-MS at HV of Lys with binary mixture of SA and 2-NPG using different composition by volume labeled in FIG. 68A. Data were acquired in positive reflectron mode using the Bruker UltrafleXtreme MALDI-TOF-TOF mass spectrometer instrument. The mass spectrum shown in FIG. 68B is the zoomed-in spectrum using 25% SA and 75% 2-NPG. Charge state observed is up to +12.

FIGS. 69A, 69B, and 69C. LSIV at HV of Lys with FIG. 69A) 100% 2-NPG, FIG. 69B) 100% SA, and FIG. 69C) binary mixture of 50% 2-NPG and 50% SA. Data were acquired in positive reflectron mode using the Bruker UltrafleX Speed MALDI-TOF mass spectrometer instrument.

FIGS. 70A, 70B, and 70C. Collision induced dissociation (CID) of $GD_{1b}$ ganglioside from (FIG. 70A) purchased sample (Sigma Aldrich, St. Louis, Mo.) and (FIG. 70B) directly from mouse brain tissue. The [M-2H]2- peak at m/z 917.5 was selected as the parent ion. In (FIG. 70A), 5 pmol $GD_{1b}$ with 2,5-DHAP matrix, an isotopic width of 0.7, collision energy 25 eV, and activation time of 10 msec were used. The most abundant fragment at m/z 1544 corresponds to the loss of a sialic acid (FIG. 70C). Several characteristic fragments identifying the ganglioside species as $GD_{1b}$ are also present, including m/z 581, corresponding to two attached sialic acids; m/z 1382, the loss of the end group sugars (one sialic acid and one galactose); and m/z 1161, the loss of the end group sugars and the GalNAc attached to the galactose. Similar fragments occur in a mouse brain tissue section spotted with 0.5 pL of 2,5-DHAP (FIG. 70B) (isotopic width 1.0, collision energy 40 eV, activation time 10 msec).

FIGS. 71A and 71B. AP-MAII MS/MS mass spectra of 2 pmol $pL^{-1}$ acetylated angiotensin II (MW 1088) with 2,5-DHAP as matrix using (FIG. 71A) CID and (FIG. 71B) ETD on Thermo LTQ-Velos mass spectrometer instrument at an inlet capillary temperature of 350 ° C.

FIGS. 72A and 72B. AP-MAII MS/MS mass spectra of 2 pmol $pL^{-1}$ oxidized ACTH fragment (1-10) (MW 1315) with 2,5-DHAP as matrix using (FIG. 72A) CID and (FIG. 72B) ETD on Thermo LTQ-Velos mass spectrometer instrument at an inlet capillary temperature of 350° C.

FIGS. 73A and 73B. AP-MAII MS/MS mass spectra in negative mode of 2 pmol $pL^{-1}$ phosphorylated cholecystokinin (MW 1334) with 2,5-DHAP as matrix using (FIG. 73A) CID and (FIG. 73B) ETD on Thermo LTQ-Velos mass spectrometer instrument at an inlet capillary temperature of 350° C.

FIGS. 74A and 74B. A single (FIG. 74A) CID-LSI-MS/MS and (FIG. 74B) ETD-LSII-MS/MS scan of PEGDME-2000 with (I) Full and (II) Inset fragment ion mass spectra using a 2,5-DHAP and LiCl matrix (400:1 salt:polymer molar ratio) on an LTQ-Velos mass spectrometer. The triply charged m/z 727.5 was selected with a ±0.7 mass unit window. (FIG. 74A) CID fragmentation was induced with collision energy of "50". (FIG. 74B) ETD fragmentation was obtained by permitting the reagent gas fluoranthene to react for 500 milliseconds.

FIGS. 75A and 75B. LSIV-CID-MS/MS at IP mass spectra of 2.5 pmol $pL^{-1}$ GFP with 2,5-DHAP prepared using droplet method in 1:1 ratio and acquired on a SYNAPT G2 mass spectrometer with a MALDI source. (FIG. 75A) +1 and (FIG. 75B) +2 fragment ions produced from precursor ions +1 and +2 charge states respectively.

FIGS. 76A and 76B. LSIV-CID-MS/MS at IP mass spectrum of 2.5 pmol $pL^{-1}$ angiotensin I with 2,5-DHAP prepared using droplet method in 1:1 ratio and acquired using the MALDI source of SYNAPT G2 mass spectrometer instrument at "200" laser fluence. Precursor ion selected is 30 3 charged state (m/z 432.95). CID fragment ions produced by FIG. 76A) triwave trap DC bias at '75' and FIG. 76B) trap voltage on at 32 V.

FIGS. 77A and 77B. LSIV-CID-MS/MS at IP of 2.5 pmol $pL^{-1}$ N-acetylated myelin basic protein fragment (MBP) with 2,5-DHAP prepared using droplet method in 1:1 ratio and acquired using the MALDI source of SYNAPT G2 mass spectrometer instrument at "200" laser fluence. Precursor ion selected are +3 (m/z 611.92) and +2 (m/z 917.49) charge states. FIG. 77A) +2, +3 and FIG. 77B) +1 fragment ions from +3 and +2 precursor ions respectively. Trap voltage used are 32 and 58 V for +3 and +2 charge states respectively.

FIGS. 78A, 78B, and 78C. LSII-IMS-MS 2-D plot of drift time vs. m/z of a mixture of 30 pmol of PEG 1000 and 30 pmol of PtBMA 1640 with 4,6-dinitropyrogallol (4,6-DNPG) and LiCl (400:1 salt:analyte molar ratio) as matrix and acquired on a Waters SYNAPT G2 mass spectrometer instrument using the Nanolockspray source. The drift time distributions were created from the drift time integrations of m/z regions (FIG. 78A) 694-702 and (FIG. 78B) 834-836. The source temperature was held at 150° C. with additional 10 V of resistance heating through a wire-coiled home-built desolvation tube device.

FIGS. 79A, 79B, and 79C. (FIG. 79A) A full LSIV-IMS-MS at IP 2-D plot of PEG DME 2000 with 4,6-dinitropyrogallol (4,6-DNPG) and LiCl (400:1 salt:analyte molar ratio) as matrix acquired on a Waters SYNAPT G2 mass spectrometer instrument with a MALDI source. The inset area (FIG. 79B) shows separation of +1 and +2 ions and their integrated drift times at m/z 1109 can be seen in (FIG. 79C).

FIGS. 80A-80D. LSII-MS analysis of polymers on the LTQ-Velos mass spectrometer with 500:1 salt:analyte molar ratios and a 400° C. ion transfer capillary: (FIG. 80A) PEG-1000 using a 2,5-DHAP and NaCl matrix, (FIG. 80B) 4-arm PEG-2000 using LiCl and 2-NPG, (FIG. 80C) Pentaethyritol ethoxylate (PEEO) 800 using a 2,5-DHAP and LiCl matrix, and (FIG. 80D) PtBMA using a 2,5-DHB and Nacl matrix.

FIG. 81. LSII-MS mass spectrum of crude algae extract with 4,6-DNPG matrix acquired using the LTQ-Velos mass spectrometer with an inlet temperature of 450° C.

FIGS. 82A-82D. LSII-MS negative mode analysis of 5 pmol pL$^{-1}$ GD$_{1b}$ ganglioside (MW 1838, 1866 Da) with 2-amino-3-nitrophenol matrix, prepared using the layer method, and acquired on the LTQ-Velos mass spectrometer instrument at (FIG. 82A) 450° C., (FIG. 82B) 400° C., (FIG. 82C) 350° C. and (FIG. 82D) 250° C. inlet capillary temperature.

FIGS. 84A-84L. Single shot LSII acquisitions of mouse brain tissue in negative ion mode spotted with 2,5-DHAP matrix at 50 max inject time and 1-12 microscans (FIGS. 84A-84L, respectively) acquired on a Thermo LTQ-Velos mass spectrometer instrument with an inlet capillary temperature of 450° C.

FIGS. 85A-85H. LSII-MS of BI with 2,5-DHAP matrix prepared using layer method in 1:4 ratio and acquired using the SYNAPT G2 mass spectrometer with a Nanolockspray source acquired at 150° C. source temperature: FIGS. 85A, 85C, 85E, and 85G) TOF mode only with gas flows from API and Trap and FIGS. 85B, 85D, 85F, and 85H) with IMS (additional He and IMS gas flows): (FIGS. 85A and 85B) both API gas and Trap gas on, (FIGS. 85C and 85D) API gas off, (FIGS. 85E and 85F) Trap gas off, and (FIGS. 85G and 85H) both API and Trap gas off.

FIGS. 86A-86D. AP-LSII-IMS-MS 2-D plots of drift time vs. m/z of 5 pmol pL-1 lysozyme acquired with FIG. 86A) 2-NPG matrix using 90° bent tube and FIG. 86B) 2,5-DHAP matrix in straight tube on SYNAPT G2 mass spectrometer using the Nanolockspray source. Extracted drift times of +10 to +14 charge states; FIG. 86C) 2-NPG matrix using 90° bent tube and FIG. 86D) 2,5-DHAP matrix in straight tube on SYNAPT G2 mass spectrometer using the Nanolocksprav source. Analyte/matrix spot was prepared in 1:3 layer method on a glass plate and blow dried.

FIGS. 87A-87F. MAII-MS mass spectra of 2 pmol Ang. I prepared in (1) 1:1 (FIGS. 87A and 87B) and (2) 1:2 (FIGS. 87C-87F) analyte:matrix ratio with I) CHCA (FIGS. 87A, 87C, and 87E) and II) SA (FIGS. 87B, 87D, and 87F) acquired at A) 450° C. (FIGS. 87A-87D) and B) 400° C. (FIGS. 87E and 87F) inlet capillary temperature using an LTQ-Velos mass spectrometer instrument.

FIGS. 88A-88J. MAII-MS mass spectra of 5 pmol of FIGS. 88A and 88F) ang. I, FIGS. 88B and 88G) bovine insulin, FIGS. 88C and 88H) ubiquitin, and FIGS. 88D and 88I) lysozyme with CHCA (FIGS. 88A-88D) and SA (FIGS. 88F-88I) acquired at 450° C. inlet capillary temperature using an LTQ-Velos mass spectrometer instrument. Mass spectra of lyzozyme using binary matrix mixture of 95% CHCA: 5% 2-NPG (FIG. 88E) and 95% SA: 5% 2-NPG (FIG. 88J). Analyte/matrix spot was prepared in 1:2 ratio using layer method on a glass plate and air dried.

FIGS. 89A-89D. LSII-IMS-MS of the neuropeptide, MBP, from FIGS. 89A and 89C) delipified mouse brain tissue and FIGS. 89B and 89D) syntheiszed MBP peptide using 2,5-DHAP matrix at 532 nm (FIGS. 89A and 89B) and 1064 nm wavelengths (FIGS. 89C and 89D). Mass spectra (left panel), 2-D plots of drift time vs. m/z (middle panel) and extracted drift times for +2 and +3 ions (right panel) are displayed.

FIGS. 90-134 show mass spectra obtained with matrix compositions described in FIGS. 135A-135L. Each figure provides the parameters used to generate the data according to the abbreviation key in the Brief Description of the Figures. The data presented in FIGS. 90-134 was acquired using the Thermo LTQ-Velos mass spectrometer instrument with an inlet capillary temperature of 450° C., microscan of 5, and maximum injection time of 20 ms.

FIG. 90. MAII-MS of Ang I (SF) with 2,6-dihydroxybenzoic acid matrix.

FIG. 91. MAII-MS of BI (SB) and Ang I (SF) with 3,4-dihydroxybenzoic acid matrix.

FIG. 92. MAII-MS and LSII-MS of BI (SB) with 5-methylsalisylic acid matrix.

FIG. 93. LSII-MS of BI (SB) with 3-hydroxypicolinic acid matrix.

FIG. 94. MAII-MS of BI (SB) with 2,3-dihydroxyacetophenone matrix.

FIG. 95. MAII-MS of BI (SB) and Ang I (SF) with 2,4-dihydroxyacetophenone matrix.

FIG. 96. MAII-MS of Ubi (SB) with 2,4,6-trihydroxyacetophenone matrix.

FIG. 97. MAII-MS of Ang I (SF) with 3,4-dihydroxybenzenesulfonic acid matrix.

FIG. 98. MAII-MS of Ang I (SF) with 4-nitrocatechol matrix.

FIG. 99. MAII-MS of Ubi (SB) and Ang I (SF) with 2-nitroresorcinol matrix.

FIG. 100. MAII-MS of BI (SB) and Ang I (SF) with 2-nitrophloroglucinol matrix.

FIG. 101. MAII-MS of BI (SB) and Ang I (SF), and LSII-MS of BI (SB) with 2-amino-3-nitrophenol matrix.

FIG. 102. MAII-MS of BI (SB) with 2,4-dinitrophenol matrix.

FIG. 103. MAII-MS of BI (SB) with 3,5-dinitro-benzene-1,2-diol matrix.

FIG. 104. MAII-MS of BI (SB) with 4,6-dinitropyrogallol matrix.

FIG. 105. MAII-MS of Ang I (SF) with 4-nitro-5-[2-nitroethyl]-1,2-benzenediol matrix.

FIG. 106. MAII-MS of Ang I (SF) with chlorohydroquinone matrix.

FIG. 107. MAII-MS of GD1 a (SB) with 1,4-dicyanobenzene matrix.

FIG. 108. MAII-MS and LSII-MS of BI (SB) with salicylamide matrix.

FIG. 109. MAII-MS of BI (SB) and Ang I (SF) with 4-hydroxybenzamide matrix.

FIG. 110. MAII-MS of BI (SB) and Ang I (SF), and LSII of BI (SB) with 3,5-dihydroxybenzamide matrix.

FIG. 111. MAII-MS of Ang I (SF) and GD1a (SB) with 2-hydroxy-5-methylbenzamide matrix.

FIG. 112. MAII-MS of BI (SB) and Ang I (SF) with 5-bromo-2-hydroxybenzohydrazide matrix.

FIG. 113. MAII-MS and LSII-MS of BI (SB) with 3-hydroxy-2-naphthoic hydrazide matrix.

FIG. 114. MAII-MS and LSII-MS of BI (SB), and MAII of GD1a (SB) with 2-amino-3-nitropyridine matrix.

FIG. 115. MAII-MS and LSII-MS of BI (SB) with 2-amino-4-methyl-3-nitropyridine matrix.

FIG. 116. MAII-MS of Ang I (SF) with phenol matrix.

FIG. 117. MAII-MS of BI (SB) and Ang I (SF) with resorcinol matrix.

FIG. 118. MAII-MS of BI (SB) with hydroquinone matrix.

FIG. 119. MAII-MS of Ang I (SF) with phloroglucinol matrix.

FIG. 120. MAII-MS of Ubi (SB) and Ang I (SF) with pyrogallol matrix.

FIG. 121. MAII-MS of Ang I (SF) with 4-trifluoromethyl phenol matrix.

FIG. 122. MAII-MS of Lys (SB) and Ang I (SF) with 1,4-dihydroxy-2,6-dimethoxybenzene matrix.

FIG. 123. MAII-MS of Ubi (SB) and Ang I (SF) with 2,4-dihydroxybenzaldehyde matrix.

FIG. 124. MAII-MS of Ang I (SF) with cis-1,2-cyclohexandediol matrix.

FIG. 125. MAII-MS of Ang I (SF) with 5,5-dimethyl-2-nitrocyclohexane-1,3-dione matrix.

FIG. 126. MAII-MS of BI (SB) with succinic acid matrix.

FIG. 127. MAII-MS of BI (SB) with fumaric acid matrix.

FIG. 128. MAII-MS of BI (SB) with mesaconic acid matrix.

FIG. 129. MAII-MS of BI (SB) with 2,4-hexadienoic acid matrix.

FIG. 130. MAII-MS of Ang I (SF) and GD1a (SB) with cis,cis-2,5-dimethylmuconic acid matrix.

FIG. 131. MAII-MS of Ang I (SF) with trans,trans-muconic acid matrix.

FIG. 132. MAII-MS and LSII-MS of BI (SB) with methyl-4-oxo-2-pentenoate matrix.

FIG. 133. MAII-MS of BI (SB) with N-methylmaleamic acid matrix.

FIG. 134. MAII-MS of Ubi (SB) with 4,4'-azobis(4-cyanovaleric acid) matrix.

Discussion

The endogenous neuropeptide and the standard sample provided identical drift time distributions for charge states +1 to +3 obtained by LSIV-IMS giving further confirmation of the structure present in the tissue. It was noted earlier that the charge state and drift time distribution appearance is nearly identical for the synthetic neuropeptide sample to that observed in LSII or ESI IMS-MS but with the important difference that SCIs are not present under AP conditions even though LSII uses significantly higher laser energy than those used with LSIV. Isomeric beta amyloid peptide mixtures have shown baseline separation using a LSI-IMS-MS (SYNAPT G2) approach, suggesting that even rather small differences in the structures of the peptides would be observed using the IMS-MS approach.

Extractions of drift time distributions (cross-sections) provide exact drift time values of features for a specific m/z. These values can give insight into structures when combined with computer modeling approaches or aid identification when standards are available. Appropriate compute modeling approaches and/or standards are described in Williams et al., J.; Rapid Commun. Mass Spectrom. 2009, 23, 3563-3569; Shvartsburg et al., Proc. Nat. Acad. Sci. of USA 2009, 106, 6495-6500; Scarff et al., Rapid Commun. Mass Spectrom. 2008, 22, 3297-3304; Kim et al., Anal. Chem. 2008, 80, 1928-1936; Trimpin et al., Anal. Chem. 2007, 79, 7965-7974; Tao et al., J. Am. Soc. Mass Spectrom. 2007, 18, 1232-1238; Smith et al., J. Am. Soc. Mass Spectrom. 2007, 18, 2180-2190; Colgrave et al., Int. J. Mass Spectrom. 2003, 229, 209-216; Hoaglund et al., Anal. Chem. 1998, 70, 2236-2242; von Helden et al., Int. J. Mass Spectrom. Ion Processes 1995, 146/147, 349-64; Trimpin & Clemmer, Anal. Chem. 2008, 80, 9073-9083; Dole et al., J. Chem. Phys. 1968, 49, 2240-2249; Iribarne & Thomson, J. Chem. Phys. 1976, 64, 2287-2294; and Karas et al., J. Mass Spectrom 2000, 35, 1-12 each of which is incorporated by reference herein for its teachings regarding the same.

Evaluation of the laser parameters described above suggests that at very low laser energy of 50 and 100 low abundant ions are detected barely above the baseline. At 150, MCIs are observed but in relative low abundance and with essentially no chemical background. At 200 the ion abundances of MCIs increase by a factor of 3 vs. 150, also with essentially no chemical background signals. With increasing laser energy up to 500, matrix signals begin to appear and the relative intensity of the MCIs increases for the lower charge states. The formation of SCIs also becomes much more evident. At the highest laser energy of 500, the doubly charged ions are the base peak but triply charged ions are significantly reduced in abundance.

As stated, only SCIs (Ang I, GFP, ACTH, BI) are observed using the same matrix/analyte samples on a HV commercial MALDI instrument with glass or metal sample plates. Similar results are expected for MALDI sources operated at IP or AP. Higher laser energy was necessary for 2,5-DHAP in comparison to CHCA and 2,5-DHB for the detection of singly charged analyte ions. 2,5-DHAP produced low abundant doubly charged ions for ACTH and BI at high laser energy under vacuum MALDI conditions, whereas the other matrixes only produced SCIs. These results suggest that matrix/analyte clusters are formed under vacuum conditions but MCIs are only observed with proper desolvation conditions, which in this case are produced primarily by the choice of matrix and laser energy.

Also similar to previous studies on a commercial AP-MALDI source on an Orbitrap XL using 2,5-DHAP and reflection geometry, irreproducibility is encountered at relative low threshold laser energy by the inability to observe ions after several laser shots at the same location. Moving to the next spot and increasing the laser energy improves reproducibility. Without being bound by theory, this issue could be related to the laser aligned in reflection geometry and not to IP conditions; in transmission geometry this is not observed because the sample in the path of the laser beam is completely ablated in a single shot.

Exemplary Embodiments

1. A method of producing multiply-charged analyte ions from a matrix/analyte association comprising contacting the matrix/analyte association with a force that generates transfer and receipt of charge between the matrix and analyte; allowing the matrix/analyte association to enter the gas phase of the ion source of a mass spectrometer wherein the gas phase comprises an intermediate pressure zone or a high vacuum zone such that the matrix/analyte association is exposed to a decrease in pressure thereby producing the multiply-charged ions.

2. A method of embodiment 1 wherein the gas phase comprises an intermediate pressure zone with a pressure from about $10^{-3}$ Torr to about 200 Torr.

3. A method of embodiment 1 wherein the gas phase comprises a high vacuum zone with a pressure from about $10^{-9}$ Torr to about $10^{-3}$ Torr.

4. A method of embodiment 1, 2 or 3 wherein the method further comprises heating the ionization region comprising the sample stage on which the matrix/analyte association is contacted with the force.

5. A method of embodiment 1, 2, 3 or 4 wherein the force is applied by contacting the matrix/analyte association with a laser beam.

6. A method of embodiment 1, 2, 3, 4, or 5 wherein the laser beam contacts the matrix-analyte association through transmission or reflection geometry.

7. A method of embodiment 1, 2, 3, 4, 5, or 6 wherein the matrix is an organic composition that comprises a compound of Scheme 1.

8. A method of embodiment 1, 2, 3, 4, 5, 6 or 7 wherein the analyte is an intact, enzymatically digested, oxidized, acetylated, methylated, sulfonated, or phosphorylated protein or peptide.

9. A method of embodiment 8 wherein the oxidation, acetylation or phosphorylation of the protein or peptide is indicative of a disease state.

10. A method of embodiment 8 wherein the analyte is a lipid, a lipid including fragile gangliosides, a carbohydrate, an oligonucleotide, a synthetic polymer, a biofilm, a cell culture, a synthetic surfaces, animal tissue, plant tissue, a drug, a drug metabolite, endogenous metabolite.

11. A method of embodiment 1, 2, 3, 4, 5, 6, 7, 8, 9 or 10 wherein the mass spectrometer is a high vacuum time-of-flight (TOF) and/or TOF/TOF mass spectrometer and the method extends the fragmentation and mass accuracy associated with multiply charged ions on the high performance mass spectrometer.

12. A method of embodiment 1, 2, 3, 4, 5, 6, 7, 8, 9 or 10 wherein the mass spectrometer is a Fourier Transform-Ion Cyclotron Resonance (FT-ICR) mass spectrometer, a Q-TOF mass spectrometer (SYNAPT G2, Waters Corporation, Milford, Mass.) or an Orbitrap mass spectrometer (Thermo Fisher Scientific, Waltham, Mass.) and the method extends the mass range, mass accuracy, and fragmentation of high performance mass spectrometer.

13. A method of embodiment 1, 2, 3, 4, 5, 6, 7, 8, 9 or 10 wherein the mass spectrometer is an ion trap, triple quadrupole, and single quadrupole mass spectrometer and the method extends the mass range, mass accuracy, and fragmentation of the mass spectrometer.

14. A method of gas phase separation of an analyte comprising
contacting a matrix/analyte association with a force that generates transfer and receipt of charge between the matrix and analyte;
allowing the matrix/analyte association to enter the gas phase of the ion source of a mass spectrometer wherein the gas phase comprises an intermediate pressure zone or a high vacuum zone such that the matrix/analyte association is exposed to a decrease in pressure thereby producing the multiply-charged ions and thereby enabling the differentiation of isomers by cross section shape, and permitting cross section analysis using modeling of ions from surfaces using ion mobility spectrometry-mass spectrometry instrumentation.

15. A method of embodiment 14 wherein the ion mobility spectrometry-mass spectrometry instrumentation is a drift tube, a traveling wave or field asymmetry (FAIMS) technology.

16. A method of a preceding embodiment comprising enhancing fragmentation in MS/MS instrumentation through collision induced dissociation, electron transfer dissociation or electron capture dissociation.

17. A method of preparing and analyzing a matrix/analyte association using mass spectrometry and/or ion mobility spectrometry-mass spectrometry comprising
associating a matrix with an analyte to form a matrix/analyte association before or after deposition onto a metal or glass plate;
contacting the matrix/analyte association with a force that dislodges the matrix/analyte association from the plate thereby exposing the matrix/analyte association to an intermediate pressure or high vacuum zone within a mass spectrometer or ion mobility mass spectrometer so that the matrix/analyte association is exposed to a decrease in pressure thereby producing multiply-charged ions that are positively or negatively charged depending on the operation of the mass spectrometer and detector;
acquiring a mass spectrum, fragmentation spectrum or IMS data of the analyte; and
evaluating the mass spectrum, fragmentation spectrum or IMS data to determine a characteristic of the analyte.

18. A method of embodiment 17 wherein the associating of the matrix with the analyte occurs by mixing an analyte solution with a matrix solution to form a matrix/analyte solution in a separate container or on the sample plate and drying the analyte/matrix solution for form the association or bringing a solid analyte including native surfaces into contact with a matrix in which the matrix can be placed below or on top of the analyte surface.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A method of producing multiply-charged analyte ions from a matrix/analyte association comprising
   contacting the matrix/analyte association with a force that generates transfer and receipt of charge between the matrix and analyte;
   allowing the matrix/analyte association to enter the gas phase of an ion source of a mass spectrometer wherein the gas phase comprises an intermediate pressure zone or a high vacuum zone such that the matrix/analyte association is exposed to a decrease in pressure
   thereby producing the multiply-charged analyte ions.

2. A method of claim 1 wherein the gas phase comprises an intermediate pressure zone with a pressure from about $10^{-3}$ Torr to about 200 Torr.

3. A method of claim 1 wherein the gas phase comprises a high vacuum zone with a pressure from about $10^{-9}$ Torr to about $10^{-3}$ Torr.

4. A method of claim 1 wherein the method further comprises heating an ionization region comprising a sample stage on which the matrix/analyte association is contacted with the force.

5. A method of claim 1 wherein the force is a laser beam.

6. A method of claim 5 wherein the laser beam contacts the matrix/analyte association through transmission geometry or through reflection geometry.

7. A method of claim 1 wherein the matrix is an organic composition that comprises a compound of FIGS. 135A-135L.

8. A method of claim 1 wherein the analyte is an intact, enzymatically digested, oxidized, acetylated, methylated, sulfonated, or phosphorylated protein or peptide.

9. A method of claim 8 wherein the oxidation, acetylation or phosphorylation of the protein or peptide is indicative of a disease state.

10. A method of claim 1 wherein the analyte is a lipid, a lipid including fragile gangliosides, a carbohydrate, an oligonucleotide, a synthetic polymer, a biofilm, a cell culture, a synthetic surface, animal tissue, plant tissue, a drug, a drug metabolite, or an endogenous metabolite.

11. A method of claim 1 wherein the mass spectrometer is a high vacuum time-of-flight (TOF) and/or TOF/TOF mass spectrometer and the method extends the fragmentation and mass accuracy associated with multiply charged ions on the mass spectrometer.

12. A method of claim 1 wherein the mass spectrometer is a Fourier Transform-Ion Cyclotron Resonance (FT-ICR) mass spectrometer, a Q-TOF mass spectrometer (SYNAPT G2, Waters Corporation, Milford, Mass.) or an Orbitrap mass spectrometer (Thermo Fisher Scientific, Waltham, Mass.) and the method extends the mass range, mass accuracy, and fragmentation of the mass spectrometer.

13. A method of claim 1 wherein the mass spectrometer is an ion trap, triple quadrupole, and single quadrupole mass spectrometer and the method extends the mass range, mass accuracy, and fragmentation of the mass spectrometer.

14. A method of gas phase separation of an analyte comprising
   contacting a matrix/analyte association with a force that generates transfer and receipt of charge between the matrix and analyte;
   allowing the matrix/analyte association to enter the gas phase of an ion source of a mass spectrometer wherein the gas phase comprises an intermediate pressure zone or a high vacuum zone such that the matrix/analyte association is exposed to a decrease in pressure
   thereby producing multiply-charged ions and enabling the differentiation of isomers by cross section shape, and permitting cross section analysis using modeling of ions from surfaces using ion mobility spectrometry-mass spectrometry instrumentation.

15. A method of claim 14 wherein the ion mobility spectrometry-mass spectrometry instrumentation is a drift tube, a traveling wave or field asymmetry (FAIMS) technology.

16. A method of claim 14 comprising enhancing fragmentation in MS/MS instrumentation through collision induced dissociation, electron transfer dissociation or electron capture dissociation.

17. A method of preparing and analyzing a matrix/analyte association using mass spectrometry and/or ion mobility spectrometry-mass spectrometry comprising associating a matrix with an analyte to form a matrix/analyte association before or after deposition onto a metal or glass plate;
   contacting the matrix/analyte association with a force that dislodges the matrix/analyte association from the plate thereby exposing the matrix/analyte association to an intermediate pressure or high vacuum zone within a mass spectrometer or ion mobility mass spectrometer so that the matrix/analyte association is exposed to a decrease in pressure thereby producing multiply-charged ions that are positively or negatively charged depending on the operation of the mass spectrometer and detector;
   acquiring a mass spectrum, fragmentation spectrum or IMS data of the analyte; and
   evaluating the mass spectrum, fragmentation spectrum or IMS data to determine a characteristic of the analyte.

18. A method of claim 17 wherein the associating of the matrix with the analyte occurs by mixing an analyte solution with a matrix solution to form a matrix/analyte solution in a separate container or on the sample plate and drying the analyte/matrix solution for form the association or bringing a solid analyte including native surfaces into contact with a matrix in which the matrix can be placed below or on top of the analyte surface.

* * * * *